United States Patent
Bungard et al.

(10) Patent No.: US 12,246,008 B2
(45) Date of Patent: Mar. 11, 2025

(54) 4-AMINO OR 4-ALKOXY-SUBSTITUTED ARYL SULFONAMIDE COMPOUNDS WITH SELECTIVE ACTIVITY IN VOLTAGE-GATED SODIUM CHANNELS

(71) Applicant: Merck Sharp & Dohme LLC, Rahway, NJ (US)

(72) Inventors: Christopher J. Bungard, Lansdale, PA (US); Helen Y. Chen, Marlboro, NJ (US); Jason M. Cox, Flemington, NJ (US); Liangqin Guo, Monroe Township, NJ (US); Michael J. Kelly, III, Paoli, PA (US); Ronald M. Kim, Summit, NJ (US); Mark E. Layton, Harleysville, PA (US); Hong Liu, Hillsborough, NJ (US); Jian Liu, Edison, NJ (US); Mehul F. Patel, Blue Bell, PA (US); James J. Perkins, Churchville, PA (US); Deping Wang, Furlong, PA (US); Walter Won, San Diego, CA (US); Younong Yu, East Brunswick, NJ (US); Ting Zhang, Princeton Junction, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 791 days.

(21) Appl. No.: 17/296,601

(22) PCT Filed: Dec. 2, 2019

(86) PCT No.: PCT/US2019/063909
§ 371 (c)(1),
(2) Date: May 25, 2021

(87) PCT Pub. No.: WO2020/117626
PCT Pub. Date: Jun. 11, 2020

(65) Prior Publication Data
US 2022/0000844 A1    Jan. 6, 2022

Related U.S. Application Data

(60) Provisional application No. 62/775,681, filed on Dec. 5, 2018.

(51) Int. Cl.
*A61K 31/433*    (2006.01)
*A61K 31/167*    (2006.01)
(Continued)

(52) U.S. Cl.
CPC .......... *A61K 31/433* (2013.01); *A61K 31/167* (2013.01); *A61K 31/4439* (2013.01);
(Continued)

(58) Field of Classification Search
CPC ................ A61K 31/433; A61K 31/167; A61K 31/4439; A61K 31/505; A61K 31/5377;
(Continued)

(56) References Cited

U.S. PATENT DOCUMENTS

2010/0197655 A1    8/2010    Beaudoin et al.
2012/0010182 A1    1/2012    Brown et al.
2012/0149679 A1    6/2012    Beaudoin et al.

FOREIGN PATENT DOCUMENTS

WO    2003037274 A2    5/2003
WO    2009012242 A2    1/2009
(Continued)

OTHER PUBLICATIONS

Clare et al., Voltage Gated Sodium Channels as Therapeutic Targets, Therapeutic Focus, 2000, 506-520, 5.
Devigili et al., Paroxysmal Itch Caused by Gain of Function Nav1/7 Mutation, Pain, 2014, 1702-1707, 155.
Flaxman et al., Years Lived with Disability (YLDs) for 1160 Sequelae of 289 Diseases and Injuries 1990-2010: A Systematic Analysis for the Global Burden of Disease Study 2010, Lancet, 2012, 2163-2196, 380.
(Continued)

*Primary Examiner* — Bong-Sook Baek
(74) *Attorney, Agent, or Firm* — Sylvia A. Ayler; Catherine D. Fitch

(57) ABSTRACT

Disclosed are compounds of Formula (I), Formula (II), or a salt thereof: Formula (I) Formula (II) which compounds have properties for inhibiting Nav 1.7 ion channels found in peripheral and sympathetic neurons. Also described are pharmaceutical formulations comprising the compounds of Formula (I), Formula (II) or their salts, and methods of treating pain disorders, cough, and itch using the same.

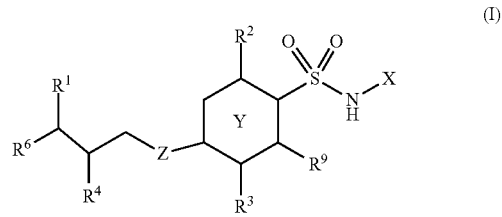

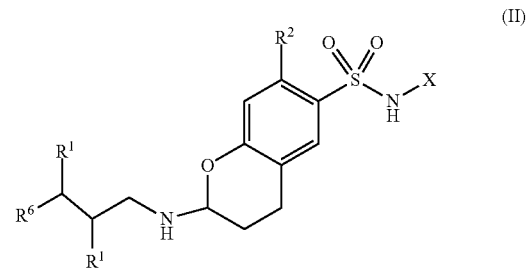

17 Claims, No Drawings

(51) Int. Cl.
*A61K 31/4439* (2006.01)
*A61K 31/505* (2006.01)
*A61K 31/5377* (2006.01)
*C07D 239/42* (2006.01)
*C07D 285/08* (2006.01)
*C07D 417/12* (2006.01)

(52) U.S. Cl.
CPC ........ *A61K 31/505* (2013.01); *A61K 31/5377* (2013.01); *C07D 239/42* (2013.01); *C07D 285/08* (2013.01); *C07D 417/12* (2013.01)

(58) Field of Classification Search
CPC .. C07D 239/42; C07D 285/08; C07D 417/12; C07D 277/52
See application file for complete search history.

(56) References Cited

FOREIGN PATENT DOCUMENTS

| WO | 2010079443 | A1 | 7/2010 | |
|---|---|---|---|---|
| WO | 2012004706 | A2 | 1/2012 | |
| WO | 2012004714 | A2 | 1/2012 | |
| WO | 2012004743 | A1 | 1/2012 | |
| WO | 2013025883 | A1 | 2/2013 | |
| WO | 2013064983 | A1 | 5/2013 | |
| WO | 2013064984 | A1 | 5/2013 | |
| WO | 2013086229 | A1 | 6/2013 | |
| WO | 2013134518 | A1 | 9/2013 | |
| WO | 2015080988 | A1 | 6/2015 | |
| WO | WO-2017106409 | A1 * | 6/2017 | ........... A61K 31/426 |
| WO | 2017/165204 | A1 | 9/2017 | |
| WO | 2018081384 | A1 | 5/2018 | |

OTHER PUBLICATIONS

Ikoma et al., The Neurobiology of Itch, Nature Reviews, 2006, 535-547, 7.
Klinger et al., Sea-Anemone Toxin ATX-II Elicits A-Fiber-Dependent Pain and Enhances Resurgent and Persistent Sodium Currents in large Sensory Neurons, Molecular Pain, 2012, 1-17, 8:69.
Lee et al., A Monoclonal Antibody that Targets a Nav1.7 Channel Voltage Sensor for Pain and Itch Relief, Cell, 2014, 1-12, 157.
McMahon et al., Itching for an Explanation, Trends Neuroscience, 1992, 497-501, 15.
Muroi et al., Selective Inhibition of Vagal Afferent Nerve Pathways Regulating Cough Using Nav 1.7 shRNA Silencing in Guinea Pig Nodose Ganglia, Am. J. Physiol Regul Interg Comp Physiol, 2013, R1017-R1023, 301.
Muroi et al., Targeting Voltage Gated Sodium Channels Nav1.7 Nav 1.8, and Nav 1.9 for Treatment of Pathological Cough, Lung, 2014, 15-20, 192.
Rook et al., Biology of Cardiac Sodium Channel Nav1.5 Expression, Cardiovascular Research, 2012, 12-23, 93.
Schmelz et al., Specific C-Receptors for Itch in Human Skin, J. of Neuroscience, 1997, 8003-8008, 17(20).
Van Loey et al., Itching Following Burns: Epidemiology and Predictors, British J. Dermatology, 2008, 95-100, 158.
Waxman et al., Na, 1.7-Related Small Fiber Neuropathy, Neurology, 2012, 1635-1643, 78 (21).
Wu, Yong-Jin et al., Development of New Benzenesulfonamides As Potent and Selective Nav1.7 Inhibitors for the Treatment of Pain, Journal of Medicinal Chemistry, 2017, 2513-2525, 60.

* cited by examiner

4-AMINO OR 4-ALKOXY-SUBSTITUTED ARYL SULFONAMIDE COMPOUNDS WITH SELECTIVE ACTIVITY IN VOLTAGE-GATED SODIUM CHANNELS

CROSS REFERENCE TO RELATED APPLICATIONS

This application is a U.S. National Phase application under 35 U.S.C. § 371 of PCT Application No. PCT/US2019/063909 filed Dec. 2, 2019, which claims priority from U.S. Ser. No. 62/775,681 filed Dec. 5, 2018.

BACKGROUND

Voltage-gated sodium channels are found in all excitable cells including myocytes of muscle and neurons of the central and peripheral nervous system. There are currently at least nine known members of the family of voltage gated sodium channel (VGSC) alpha subunits. Names for this family include SCNx, SCNAx, and NaVx.x. In patients suffering from chronic pain, abnormal elevation of sensory neuron activity depends, in part, on the activity of sodium channels (NaVs). An increasing body of evidence suggests that NaV1.7, which is preferentially expressed in peripheral sympathetic and sensory neurons, may play a key role in various pain states, including acute, inflammatory and/or neuropathic pain. Local anesthetics, such as lidocaine, produce analgesia via state dependent inhibition of multiple isoforms of NaVs that are present in pain-sensing neurons (nociceptors). Non-selective block of NaVs is accompanied by a loss in other non-noxious sensations (anesthesia) as well as block of channels that control cardiac, motor, respiratory and CNS functions. For this reason, selective inhibition of NaVs that control nociceptor activity yet spare undesired off-target activities is preferred.

In particular, activity at NaV1.7 and a lack of activity at NaV1.6 and NaV1.5 (cardiac isoform) are desirable features. Human "loss of function" mutations in NaV1.7 result in the complete loss of pain in homozygous carriers. Conversely, "gain of function" mutations in NaV1.7 are strongly linked to episodic severe pain disorders. Preclinical genetic evidence in rodents also supports the role of NaV1.7 in pain signaling. Deletion of the SCN9A gene in nociceptive neurons of mice led to a reduction in mechanical and thermal pain thresholds and reduction or abolition of inflammatory pain responses. Preclinical evidence demonstrates that sodium channel-blocking agents can suppress neuronal firing in peripheral and central sensory neurons and it is via this mechanism that they may be useful for relieving pain. In some instances, abnormal or ectopic firing can originate from injured or otherwise sensitized neurons. For example, it has been shown that sodium channels can accumulate in peripheral nerves at sites of axonal injury and may function as generators of ectopic firing. Alterations in either the signaling of, level of, expression of, or distribution of sodium channels, and in particular of Nav1.7 may therefore have a major influence on neuronal excitability and pain-related behaviors. As such identification of subtype selective NaV inhibitors has been desirable, though generally challenging.

In pre-clinical animals, Nav1.7, Nav1.8, and Nav1.9 were determined to be the primary voltage-gated sodium channels expressed in the afferent nerves of the respiratory tract (see Muroi et. al., Lung, 192:15-20 (2014)) and in animal models of cough, suppression of Nav1.7 function resulted in a marked decrease in number of coughs (see Muroi et. al., Am J Physiol Regul integr Comp Physiol, 304:R1017-R0123 (2013)) thus, combined with previous evidence that local anesthetics can be effective antitussive agents, the targeted blockade of Nav1.7 channels is believed to represent a rational approach for the treatment of cough with a preferential side-effect profile as compared to local anesthetics. Local anesthetics undesirably inhibit all voltage gated sodium channels, such as NaV1.5 channels which are found in heart muscle (see Rook et. al., Cardiovascular Research 93:12-23 (2012)).

Pruritus, also commonly known as itch, affects approximately 4% of the global population (see Flaxman et. al., Lancet, 380:2163-2196 (2012)). Pruritus is "an unpleasant sensation that elicits the desire or reflex to scratch" and is regarded as closely related to pain. Theories on the origin of itch implicate the subtle, low-frequency activation of nociceptors (pain-sensing neurons), however, it has been described that some afferents preferentially respond to histamine, which induces itch (see Schmelz et. al., J Neuroscience, 17(20):8003-8008 (1997)). At the same time, it has been found that histamine-responding neurons also respond to capsaicin which produces pain (see McMahon et. al., Trends. Neurosci., 15:497-501 (1992)). Members of the transient receptor potential (TRP) family, and nerve growth factor (NGF) are both known to play a role in itch and pain, and clinically, both maladies are treated with therapeutic agents such as gabapentin and antidepressants—as such, it continues to be accepted that the underlying mechanisms of pain and itch are highly interwoven and complex, and distinguishing pan-selective or itch-selective pathways remains ambiguous (see Ikoma et. al., Nature Reviews Neuroscience, 7:535-547 (2006)).

Itch, both chronic and acute, can arise from many different insults and diseases and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. In skin, pruritogens are released from keratinocytes, lymphocytes, mast cells, and eosinophils during inflammation. These molecules act directly on free nerve endings to induce itch; medicines such as opioids and chloroquine can also trigger itch (see Ikoma et. al., Nature Reviews Neuroscience, 7:535-547 (2006)). Itching following burn is also an extremely serious clinical problem as it hampers the healing process, results in permanent scaring, and negatively impacts quality of life (see Loey et. al., British Journal of Dermatology, 158:95-100 (2008)).

Gain of function mutations of Nav1.7 have been found in approximately 28% of patients with idiopathic small fiber neuropathy (I-SFN); these mutations were found to render dorsal root ganglia neurons hyperexcitable, reducing the threshold of activation and increasing the frequency of evoked firing (see Waxman et. al., Neurology, 78(21):1635-1643 (2012)). Severe, uncontrollable itch has also been genetically linked to a gain-of-function mutation (1739V) in the sodium channel Nav1.7 in man (see Devigili et. al., Pain, 155 (9); pp 1702-7 (2014)). Additionally, the sea-anemone toxin ATX-II has been found to elicit pain and itch in human volunteers after intradermal injection on the forearm; electrophysiology studies revealed that ATX-II enhanced Nav1.7 and Nav1.6 resurgent currents (see Klinger et. al., Molecular Pain, 8:69 (2012)). It has been demonstrated in animal models that selective blockade of Nav1.7 channels can effectively suppress both inflammatory and neuropathic pain, as well as acute and chronic itch, thus blockade of Nav1.7 channels is believed to represent a rational approach to treatment of pain and itch disorders (see Lee et. al., Cell, 157:1-12 (2014)).

Accordingly, it is believed that identification and administration of agents which interact to block $Na_v$ 1.7 voltage-gated sodium ion channels represents a rational approach which may provide treatment or therapy for disorders involving $Na_v$1.7 receptors, for example, but not limited to, those conditions mentioned above (acute pain, preoperative pain, perioperative pain, post-operative pain, neuropathic pain, cough, or itch disorders, as well as those stemming specifically from dysfunction of $Na_v$1.7 voltage-gated sodium ion channels, see Clare et al., Drug Discovery Today, 5: pp 506-520 (2000)).

The present invention claims compounds that are blockers of Nav1.7 and have greater activity of Nav1.7 over Nav1.5 and Nav1.6. Nav1.5 signaling is linked to serious cardiac adverse events associated with changes in cardiac conduction. Nav1.6 signaling is linked to respiratory cessation associated with blockade of phrenic nerve internal Merck data). Selective Nav1.7 inhibitors provide an advantage over other known Nav inhibitors with respect to cardiac, respiratory and CNS liabilities following systemic exposure. Compounds described as Nav1.7 inhibitors with greater activity of Nav1.7 over Nav1.5 have been described, see application WO2010079443, US20100197655, US2012149679, US2012685913, US20120010182, WO2012004706, WO2012004714, WO2012004743, WO2013025883 and WO2013086229. No literature reports have identified selectivity over Nav1.6 as a requirement for safe inhibitors.

Series of aryl-sulfonamide compounds have been described as Nav1.7 blockers with greater activity of Nav1.7 over Nav1.5. Pfizer has described this structural motif in several applications including WO2010079443 (US20100197655), WO2012004706, WO2012004714 and WO2012004743, and Xenon has described a similar series of biaryl-ethers in WO2013064984. A related series of patent application appeared with bicyclic aryl-sulfonamides that have greater activity of Nav1.7 over Nav1.5, see WO2013025883 and WO2013086229. Sulfamides claiming greater activity of Nav1.7 over Nav1.5 have been disclosed by Amgen in WO2013134518. Recently Xenon disclosed a series of O-linked piperidines appended to an aryl-sulfonamide in WO2013064983 that display greater activity of Nav1.7 over Nav1.5. The present invention claims 4-amino or 4-alkoxy-substituted aryl-sulfonamides containing a 4-carbon or 5-carbon aliphatic linker to a 1,2-ethylenediamine or 1,3-propylenediamine, wherein the alkyldiamine or linker is substituted with a hydroxyl or hydroxyalkyl group, and provides novel chemical matter distinct from the prior art that results in potent Nav1.7 inhibitors that display high levels of selectivity over Nav1.5 and Nav1.6. 4-Amine-substituted aryl sulfonamides with activity at Nav1.7 and/or Nav1.3 were disclosed in WO2003037274 and WO2009012242, however no compounds containing alkyl aminoalcohols. Furthermore, compounds described in WO2009012242 were not stated to exhibit greater activity of Nav1.7 over Nav1.5. The compounds to be claimed in this application are highly selective over Nav1.5 and Nav1.6.

There remains a need for additional compounds having high potency for inhibiting Nav 1.7 sodium ion channels and selective activity for $Na_v$ 1.7 over Nav1.5 and Nav1.6 sodium channels providing structural variety to facilitate rational development of therapeutic agents for use as a selective $Na_v$ 1.7 sodium ion channel inhibitor.

SUMMARY OF THE INVENTION

The present invention provides novel chemical matter distinct from the prior art that demonstrates greater activity of Nav1.7 over Nav1.5 and Nav1.6, which will provide improved utility over nonselective Nav inhibitors with respect to serious cardiac and respiratory adverse events associated with Nav1.5 and Nav1.6 following systemic exposure.

In one aspect, the invention provides compounds having selective activity as $Na_v$ 1.7 sodium ion channel inhibitors which have the structure of Formula I or Formula II, or a pharmaceutically acceptable salt thereof:

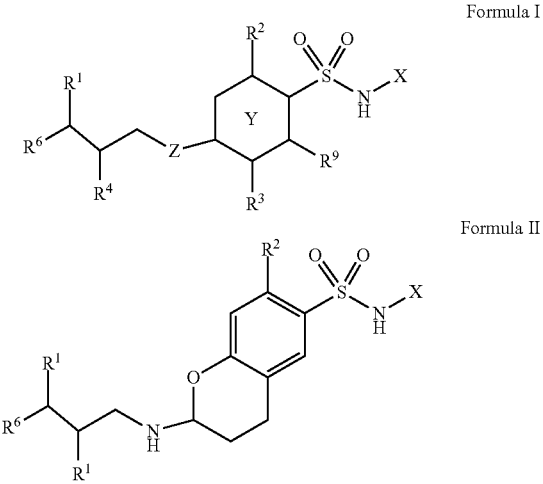

Formula I

Formula II wherein:
X is selected from the group consisting of thiadiazolyl, pyridyl, thiazolyl, and pyrimidinyl, said thiadiazolyl, pyridyl, thiazolyl, and pyrimidinyl, optionally substituted with 1 to 3 groups selected from halogen and $C_{1-6}$ alkyl;
Y is selected from phenyl and pyridyl;
Z is selected from NH and O;
$R^1$ is selected from $C_{1-6}$ alkyl and $(CH_2)_nC_{3-6}$ cycloalkyl;
$R^2$ and $R^3$ are independently selected from the group consisting of hydrogen, halogen, $OC_{1-6}$ alkyl, $C_{1-6}$ alkyl, $C_{3-10}$ heteroaryl, CN, $C_{1-3}$ haloalkyl, and $(CH_2)_nOH$;
R is hydrogen or $C_{1-6}$ alkyl, or two adjacent R groups can combine with the carbon atom to which they are attached to form $C_{3-6}$ cycloalkyl optionally substituted with 1 to 3 groups of halogen or $C_{1-6}$ alkyl;
$R^4$ is selected from the group consisting of $CHR^5NR_2$, $CH_2NHCH(C_{1-6}$ alkyl$)_2$, $CH_2R^5$, $CH_2N(R^5)$ $CH_2CHRNR_2$, $CH_2CH(R^5)(CH_2)_pNR_2$, and $(CH_2)_nC(R)_2(CHR)_pNRR^7$,
$R^5$ is selected from the group consisting of $C_{1-6}$ alkyl, $(CH_2)_nC_{6-10}$ aryl, $C_{3-6}$ cycloalkyl, $(CH_2)_nC_{3-10}$ heterocyclyl, and $OC_{1-6}$ alkyl, said alkyl, aryl, cycloalkyl and heterocyclyl optionally substituted with 1 to 3 groups of halogen, $CF_3$, $C_{1-6}$ alkyl, $C_{3-6}$ cycloalkyl, and $(CH_2)_pNR_2$;

$R^6$ is NHR;

$R^7$ and $R^8$ are independently hydrogen or $C_{1-6}$ alkyl, or when $R^6$ is NHR then R can combine with $R^7$ of $R^4$ when it is $(CH_2)_nC(R)_2(CHR)_pNRR^7$ to form a $C_{6-10}$ heterocyclyl optionally substituted with 1 to 3 groups of $C_{1-6}$ alkyl;

$R^9$ is hydrogen or halogen;

p is 0, 1, or 2, and n is 0, 1, 2, 3, or 4.

An embodiment of this invention is realized when X is unsubstituted or substituted thiadiazolyl. A subembodiment of this aspect of the invention is realized when X is unsubstituted thiadiazolyl.

Another embodiment of this invention is realized when X is unsubstituted or substituted pyridyl. A subembodiment of this aspect of the invention is realized when X is unsubstituted pyridyl. Another subembodiment of this aspect of the invention is realized when X is substituted pyridyl. Still another subembodiment of this aspect of the invention is realized when pyridyl is substituted with one to three groups of fluorine, bromine, chlorine, methyl, ethyl, propryl, and butyl. Still another embodiment of this aspect of the invention is realized when pyridyl is substituted with one to three groups selected from fluorine and methyl, preferably fluorine.

Another embodiment of this invention is realized when X is unsubstituted or substituted thiazolyl. A subembodiment of this aspect of the invention is realized when X is unsubstituted thiazolyl. Another subembodiment of this aspect of the invention is realized when X is substituted thiazolyl. Still another subembodiment of this aspect of the invention is realized when thiazolyl is substituted with one to two groups of fluorine, bromine, chlorine, methyl, ethyl, propryl, and butyl. Still another embodiment of this aspect of the invention is realized when thiazolyl is substituted with one to two groups selected from fluorine and methyl.

Another embodiment of this invention is realized when X is unsubstituted or substituted pyrimidinyl. A subembodiment of this aspect of the invention is realized when X is unsubstituted pyrimidinyl. Another subembodiment of this aspect of the invention is realized when X is substituted pyrimidinyl. Still another subembodiment of this aspect of the invention is realized when pyrimidinyl is substituted with one to three groups of fluorine, bromine, chlorine, methyl, ethyl, propryl, and butyl. Still another embodiment of this aspect of the invention is realized when pyrimidinyl is substituted with one to three groups selected from fluorine and methyl, preferably fluorine.

Another embodiment of this invention is realized when Y is phenyl.

Still another embodiment of this invention is realized when Y is pyridyl.

Another embodiment of this invention is realized when Z is NH.

Still another embodiment of this invention is realized when Z is O.

Another embodiment of this invention is realized when $R^1$ is $C_{1-6}$ alkyl selected from methyl, ethyl, butyl, and pentyl. A subembodiment of this aspect of the invention is realized when $R^1$ is methyl.

Still another embodiment of this invention is realized when $R^1$ is $(CH_2)_nC_{3-6}$ cycloalkyl selected from cylcopropyl, cyclobutyl, cyclopentyl, and cyclohexyl. A subembodiment of this aspect of the invention is realized when $R^1$ is cyclopropyl or $CH_2$ cyclopropyl.

Another embodiment of this invention is realized when $R^2$ is selected from the group consisting of hydrogen, halogen, and $C_{1-6}$ alkyl. A subembodiment of this aspect of the invention is realized when $R^2$ is selected from the group consisting of hydrogen, methyl, and fluorine. Another subembodiment of this aspect of the invention is realized when $R^2$ is hydrogen. Still another subembodiment of this aspect of the invention is realized when $R^2$ is methyl. Yet another subembodiment of this aspect of the invention is realized when $R^2$ is fluorine.

Another embodiment of this invention is realized when $R^3$ is selected from the group consisting of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$. A subembodiment of this aspect of the invention is realized when $R^3$ is selected from the group consisting of hydrogen, fluorine, chlorine, bromine, and $CH_2OH$. A subembodiment of this aspect of the invention is realized when $R^3$ is hydrogen. A subembodiment of this aspect of the invention is realized when $R^3$ is fluorine. A subembodiment of this aspect of the invention is realized when $R^3$ is chlorine. A subembodiment of this aspect of the invention is realized when $R^3$ is bromine. A subembodiment of this aspect of the invention is realized when $R^3$ is $CH_2OH$. Still another subembodiment of this invention is realized when $R^3$ is thiazolyl or oxazolyl. Still another subembodiment of this invention is realized when $R^3$ is CN, $CF_3$, or $CHCF_2$.

Another embodiment of this invention is realized when $R^2$ is fluorine and $R^3$ is selected from the group consisting of of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$. A subembodiment of this aspect of the invention is realized when $R^2$ is fluorine and $R^3$ is selected from the group consisting of of hydrogen, fluorine, chlorine, bromine, methyl, and $CH_2OH$. A subembodiment of this aspect of the invention is realized when $R^2$ is fluorine and $R^3$ is fluorine. A subembodiment of this aspect of the invention is realized when $R^2$ is fluorine and $R^3$ is chlorine. A subembodiment of this aspect of the invention is realized when $R^2$ is fluorine and $R^3$ is bromine. A subembodiment of this aspect of the invention is realized when $R^2$ is fluorine and $R^3$ is, methyl. A subembodiment of this aspect of the invention is realized when $R^2$ is fluorine and $R^3$ is $CH_2OH$.

Another embodiment of this invention is realized when R is hydrogen.

Another embodiment of this invention is realized when R is $C_{1-6}$ alkyl. A subembodiment of this aspect of the invention is realized when R is selected from the group consisting of methyl, ethyl, propyl and butyl. Another subembodiment of this aspect of the invention is realized when R is methyl.

Another embodiment of this invention is realized when two adjacent R groups combine with the carbon atom to which they are attached to form $C_{3-6}$ cycloalkyl, said cycloalkyl optionally substituted with 1 to 3 groups of halogen or $C_{1-6}$ alkyl. A subembodiment of this aspect of the invention is realized when the two R groups combine to form optionally substituted cyclopropyl, cyclobutyl, cyclopentyl, or cyclohexyl. Another subembodiment of this aspect of the invention is realized two R groups combine to form optionally substituted cyclobutyl. Another subembodiment of this aspect of the invention is realized two R groups combine to form optionally substituted cyclopentyl.

Another embodiment of this invention is realized when $R^4$ is $CHR^5NR_2$. A subembodiment of this aspect of the invention is realized when $R^4$ is $CHR^5NH_2$.

Another embodiment of this invention is realized when $R^4$ is $CH_2NHCH(C_{1-6} alkyl)_2$. A subembodiment of this aspect of the invention is realized when $R^4$ is $CH_2NHCH(CH_3)_2$.

Another embodiment of this invention is realized when $R^4$ is $CH_2R^5$.

Another embodiment of this invention is realized when $R^4$ is $CH_2N(R^5)CH_2CHRNR_2$. A subembodiment of this aspect of the invention is realized when $R^4$ is $CH_2N(R^5)CH_2CHRNH_2$.

Another embodiment of this invention is realized when $R^4$ is $CH_2CH(R^5)(CH_2)_pNR_2$. A subembodiment of this aspect of the invention is realized when $R^4$ is $CH_2CH(R^5)(CH_2)_pNH_2$.

Another embodiment of this invention is realized when $R^4$ is $(CH_2)_nC(R)_2(CHR)_pNR_2$. A subembodiment of this aspect of the invention is realized when $R^4$ is $(CH_2)_nC(R)_2(CHR)_pNH_2$.

Another subembodiment of this aspect of the invention is realized when $R^4$ is $(CH_2)_nC(C_{1-6}\ alkyl)_2(CHR)_pNH_2$. Another subembodiment of this aspect of the invention is realized when $R^4$ is $(CH_2)_nC(CH_3)_2(CHR)_pNH_2$. Still another subembodiment of the invention is realized when $(CH_2)_nC(R)_2(CHR)_pNH_2$ of $R^4$ is also represented by $(CH_2)_nC(R^xR^x)_2(CHR)_pNH_2$ where the adjacent $R^x$ groups combine with the carbon atom to which they are attached to form cyclopropyl, cyclobutyl, cyclopentyl, and cyclohexyl optionally substituted with one to three groups selected from $C_{1-6}$ alkyl and halogen.

Another embodiment of this invention is realized when $R^4$ is $(CH_2)_nC(R)_2(CHR)_pNRR^7$.

An embodiment of this invention is realized when $R^5$ is halogen selected from the group consisting of fluorine, chlorine, bromine and iodine.

An embodiment of this invention is realized when $R^5$ is $C_{1-6}$ alkyl. A subembodiment of this aspect of the invention is realized when the alkyl is selected from the group consisting of methyl, ethyl, propyl, butyl and pentyl. Another subembodiment of this aspect of the invention is realized when $C_{1-6}$ alkyl is substituted.

An embodiment of this invention is realized when $R^5$ is $(CH_2)_nC_{6-10}$ aryl. A subembodiment of this aspect of the invention is realized when the aryl is optionally substituted phenyl.

An embodiment of this invention is realized when $R^5$ is optionally substituted $C_{3-6}$ cycloalkyl. A subembodiment of this aspect of the invention is realized when the optionally substituted cycloalkyl is selected from the group consisting of cyclopropyl, cyclobutyl, cyclopentyl, and cyclohexyl. An subembodiment of this invention is realized when $R^5$ is unsubstituted or substituted cyclopropyl. An subembodiment of this invention is realized when $R^5$ is unsubstituted or substituted cyclobutyl. An subembodiment of this invention is realized when $R^5$ is unsubstituted or substituted cyclopentyl. An subembodiment of this invention is realized when $R^5$ is unsubstituted or substituted cyclohexyl.

An embodiment of this invention is realized when $R^5$ is optionally substituted $(CH_2)_nC_{3-10}$ heterocyclyl. A subembodiment of this aspect of the invention is realized when the heterocyclyl is selected from the group consisting of optionally substituted pyridyl, pyrrolidinyl, piperidinyl, morpholinyl, and azabicycloheptanyl. An subembodiment of this invention is realized when $R^5$ is unsubstituted or substituted pyridyl. An subembodiment of this invention is realized when $R^5$ is unsubstituted or substituted pyrrolidinyl. An subembodiment of this invention is realized when $R^5$ is unsubstituted or substituted piperidinyl. An subembodiment of this invention is realized when $R^5$ is unsubstituted or substituted morpholinyl. An subembodiment of this invention is realized when $R^5$ is unsubstituted or substituted azabicycloheptanyl.

Another embodiment of this invention is realized when $R^5$ is $OC_{1-6}$ alkyl, said alkyl optionally substituted with 1 to 3 groups of halogen, $CF_3$, $C_{1-6}$ alkyl and $(CH_2)_pNH_2$.

Another embodiment of this invention is realized when $R^5$ is selected from the group consisting of optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, morpholinyl, and azabicycloheptanyl.

Another embodiment of this invention is realized when $R^6$ is NHR. A subembodiment of this aspect of the invention is realized when $R^6$ is $NH_2$.

Another embodiment of this invention is realized when $R^6$ is NHR and R is combined with $R^7$ of $R^4$ when $R^4$ is $(CH_2)_nC(R)_2(CHR)_pNRR^7$ to form a $C_{6-10}$ heterocyclyl optionally substituted with 1 to 3 groups of $C_{1-6}$ alkyl. A subembodiment of this aspect of the invention is realized when $R^6$ is NHR and R combines with $R^7$ of $R^4$ when $R^4$ is $(CH_2)_nC(R)_2(CHR)_pNRR^7$ to form diazonanyl.

Another embodiment of this invention is realized when $R^9$ is hydrogen.

Still another embodiment this invention is relegalized when $R^9$ is halogen. A subembodiment of this aspect of the invention is realized when $R^9$ is fluorine, bromine, or chlorine.

Another embodiment of this invention is realized when p is 0. Another embodiment of this invention is realized when p is 1. Another embodiment of this invention is realized when p is 2.

Another embodiment of this invention is realized when n is 0. Another embodiment of this invention is realized when n is 1. Another embodiment of this invention is realized when n is 2. Another embodiment of this invention is realized when n is 3. Another embodiment of this invention is realized when n is 4.

In some embodiments, a compound of the invention of Formula I is preferably a compound or a pharmaceutically acceptable salt thereof where Y is a phenyl group as depicted in Formula A1 or a pharmaceutically acceptable salt thereof.

Formula A1

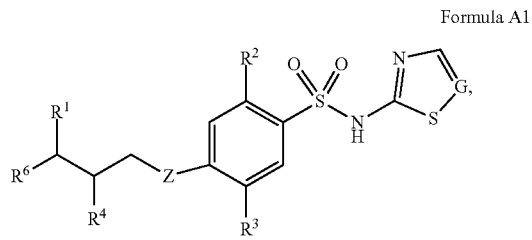

wherein G is N or CH and Z, $R^1$, $R^2$, $R^3$, $R^4$, and $R^6$ are as described herein. A subembodiment of the invention of Formula A1 is realized when G is N. Another subembodiment of the invention of Formula A1 is realized when G is CH. A subembodiment of the invention of Formula A1 is realized when Z is NH. Another subembodiment of the invention of Formula A1 is realized when Z is O. A subembodiment of the invention of Formula A1 is realized when G is N and Z is NH. Another subembodiment of the invention of Formula A1 is realized when G is CH and Z is NH. A subembodiment of the invention of Formula A1 is realized when G is N and Z is O. Another subembodiment of the invention of Formula A1 is realized when G is CH and Z is O.

Still another subembodiment of the invention of Formula A1 is realized when G is N, Z is NH, $R^1$ is $CH_3$, $R^2$ is selected from the group consisting of hydrogen, halogen, and $C_{1-6}$ alkyl and $R^3$ is selected from the group consisting of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$. A further subembodiment of this aspect of the invention of Formula A1 is realized when G is N, Z is NH, $R^1$ is $CH_3$, $R^2$ is fluorine and $R^3$ is selected from the group consisting of of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$. A subembodiment of this aspect of the invention of Formula A1 is realized when G is N, Z is NH, $R^1$ is $CH_3$, $R^2$ is fluorine and $R^3$ is selected from the group consisting of of hydrogen, fluorine, chlorine, bromine, methyl, and $CH_2OH$. A subembodiment of this aspect of the invention of Formula A1 is realized when G is N, Z is NH, $R^1$ is $CH_3$, $R^2$ is fluorine and $R^3$ is fluorine. Another subembodiment of this aspect of the invention of Formula A1 is realized when G is N, Z is NH, $R^1$ is $CH_3$, $R^2$ is fluorine and $R^3$ is chlorine. Another subembodiment of this aspect of the invention of Formula A1 is realized when G is N, Z is NH, $R^1$ is $CH_3$, $R^2$ is fluorine and $R^3$ is bromine. Another subembodiment of this aspect of the invention of Formula A1 is realized when G is N, Z is NH, $R^1$ is $CH_3$, $R^2$ is fluorine and $R^3$ is methyl. Another subembodiment of this aspect of the invention of Formula A1 is realized when G is N, Z is NH, $R^1$ is $CH_3$, $R^2$ is fluorine and $R^3$ is $CH_2OH$.

Yet another subembodiment of the invention of Formula A1 is realized when $R^4$ is selected from the group consisting of $CHR^5NR_2$, $CH_2R^5$, $CH_2N(R^5)CH_2CHRNR_2$, $CH_2CH(R^5)(CH_2)_pNR_2$, $(CH_2)_nC(R)_2(CHR)_pNR_2$, $(CH_2)_nC(R)_2(CH_2)_pN^+H_2R^7$, and $CH_2C(R)_2(CH_2)_pNHC(=N^+H_2)NR_2$.

An aspect of the invention of Formula A1 is realized when $R^4$ is $CHR^5NR_2$, $CH_2R^5$, $CH_2N(R^5)CH_2CHRNR_2$, $CH_2CH(R^5)(CH_2)_pNR_2$, and $(CH_2)_nC(R)_2(CHR)_pNRR^7$.

Another aspect of the invention of Formula A1 is realized when $R^4$ is $CHR^5NR_2$. A subembodiment of this aspect of the invention of Formula A1 is realized when $R^4$ is $CHR^5NH_2$.

Another aspect of this embodiment of the invention of Formula A1 is realized when $R^4$ is $CH_2R^5$. A subembodiment of this aspect of the invention is realized when $R^5$ is optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, and morpholinyl.

Another aspect of this embodiment of the invention of Formula A1 is realized when $R^4$ is $CH_2N(R^5)CH_2CHRNR_2$. Another aspect of this embodiment of the invention of Formula A1 is realized when $R^4$ is $CH_2N(R^5)CH_2CHRNH_2$. A subembodiment of this aspect of the invention of Formula A1 is realized when $R^5$ optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, and morpholinyl. Another subembodiment of this aspect of the invention of Formula A1 is realized when $R^5$ is optionally substituted cyclopropyl, cyclobutyl, cyclopentyl, cyclohexyl, preferably cyclobutyl.

Another aspect of this embodiment of the invention of Formula A1 is realized when $R^4$ is $CH_2CH(R^5)(CH_2)_pNR_2$. Another aspect of this embodiment of the invention of Formula A1 is realized when $R^4$ is $CH_2CH(R^5)(CH_2)_pNH_2$. A subembodiment of this aspect of the invention is realized when $R^5$ is optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, or morpholinyl. Another subembodiment of this aspect of the invention of Formula A1 is realized when $R^5$ is optionally substituted cyclopropyl, cyclobutyl, cyclopentyl, or cyclohexyl, preferably cyclobutyl.

Another aspect of this embodiment of the invention of Formula A1 is realized when $R^4$ is $(CH_2)_nC(R)_2(CHR)_pNRR^7$. A subembodiment of this aspect of the invention of Formula A1 is realized when $(CH_2)_nC(R)_2(CHR)_pNRR^7$ is represented by $(CH_2)_nC(R^xR^x)_2(CHR)_pNH_2$ where the adjacent $R^x$ groups combine with the carbon atom to which they are attached to form cyclopropyl, cyclobutyl, cyclopentyl, pt cyclohexyl optionally substituted with one to three groups selected from $C_{1-6}$ alkyl and halogen. Another subembodiment of this aspect of the invention of Formula A1 is realized when the two $R^x$ groups combine to form optionally substituted cyclobutyl. Another subembodiment of this aspect of the invention of Formula A1 is realized when the two $R^x$ groups combine to form optionally substituted cyclopentyl.

Another aspect of this embodiment of the invention of Formula A1 is realized when $R^4$ is $CH_2NHCH(C_{1-6}$ alkyl$)_2$. A subembodiment of this aspect of the invention of Formula A1 is realized when the alkyl is selected from the group consisting of methyl, ethyl, propy, butyl, preferably methyl.

Another subembodiment of this aspect of the invention of Formula A1 is realized when $R^6$ is $NH_2$.

Another aspect of this embodiment of the invention of Formula A1 is realized when G is N, Z is NH or O, $R^1$ is $CH_3$, $R^2$ is selected from the group consisting of hydrogen, halogen, and $C_{1-6}$ alkyl and $R^3$ is selected from the group consisting of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$, $R^4$ is selected from the group consisting of $(CH_2)_nC(R^xR^x)_2(CHR)_pNH_2$, $CHR^5NR_2$, $CH_2R^5$, $CH_2N(R^5)CH_2CHRNR_2$, $CH_2NHCH(C_{1-6}$ alkyl$)_2$ and $CH_2CH(R^5)(CH_2)_pNR_2$, $R^5$ is selected from the group consisting of optionally substituted $C_{1-6}$ alkyl, $OC_{1-6}$ alkyl, cyclopropyl, cyclobutyl, cyclopentyl, and cyclohexyl, phenyl, pyridyl, pyrrolidinyl, piperidinyl, morpholinyl, and azabicycloheptanyl, and $R^6$ is $NH_2$.

Another aspect of this embodiment of the invention of Formula A1 is realized when G is N, Z is NH, $R^1$ is $CH_3$, $R^2$ is selected from the group consisting of hydrogen and fluorine, $R^3$ is selected from the group consisting of hydrogen, fluorine, chlorine, bromine, methyl, $CH_2OH$, and CN, $R^4$ is selected from the group consisting of $(CH_2)_nC(R^xR^x)_2(CHR)_pNH_2$, $CHR^5NR_2$, $CH_2R^5$, $CH_2N(R^5)CH_2CHRNR_2$, $CH_2NHCH(C_{1-6}$ alkyl$)_2$ and $CH_2CH(R^5)(CH_2)_pNR_2$, $R^5$ is selected from the group consisting of optionally substituted $C_{1-6}$ alkyl, $OC_{1-6}$ alkyl, cyclopropyl, cyclobutyl, cyclopentyl, and cyclohexyl, phenyl, pyridyl, pyrrolidinyl, piperidinyl, morpholinyl, and azabicycloheptanyl, and $R^6$ is $NH_2$.

A subembodiment of this aspect of the invention of Formula A1 is realized when G is N, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $(CH_2)_nC(R^xR^x)_2(CHR)_pNH_2$.

A subembodiment of this aspect of the invention of Formula A1 is realized when G is N, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2NHCH(C_{1-6}$ alkyl$)_2$.

A subembodiment of this aspect of the invention of Formula A1 is realized when G is N, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2CH(R^5)(CH_2)_pNH_2$.

A subembodiment of this aspect of the invention of Formula A1 is realized when G is N, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2R^5$.

A subembodiment of this aspect of the invention of Formula A1 is realized when G is N, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2N(R^5)CH_2CHRNH_2$.

Still another subembodiment of the invention of Formula A1 is realized when G is CH, Z is NH, $R^1$ is $CH_3$, $R^2$ is selected from the group consisting of hydrogen, halogen, and $C_{1-6}$ alkyl and $R^3$ is selected from the group consisting of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$. A further subembodiment of this aspect of the invention of Formula A1 is realized when G is CH, Z is NH, $R^1$ is $CH_3$, $R^2$ is fluorine and $R^3$ is selected from the group consisting of of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$. A subembodiment of this aspect of the invention of Formula A1 is realized when G is N, Z is NH, $R^1$ is $CH_3$, $R^2$ is fluorine and $R^3$ is selected from the group consisting of of hydrogen, fluorine, chlorine, bromine, methyl, and $CH_2OH$. A subembodiment of this aspect of the invention of Formula A1 is realized when G is CH, Z is NH, $R^1$ is $CH_3$, $R^2$ is fluorine and $R^3$ is fluorine. Another subembodiment of this aspect of the invention of Formula A1 is realized when G is CH, Z is NH, $R^1$ is $CH_3$, $R^2$ is fluorine and $R^3$ is chlorine. Another subembodiment of this aspect of the invention of Formula A1 is realized when G is CH, Z is NH, $R^1$ is $CH_3$, $R^2$ is fluorine and $R^3$ is bromine. Another subembodiment of this aspect of the invention of Formula A1 is realized when G is CH, Z is NH, $R^1$ is $CH_3$, $R^2$ is fluorine and $R^3$ is, methyl. Another subembodiment of this aspect of the invention of Formula A1 is realized when G is CH, Z is NH, $R^1$ is $CH_3$, $R^2$ is fluorine and $R^3$ is $CH_2OH$.

Yet another subembodiment of the invention of Formula A1 when G is CH and Z is NH, is realized when $R^4$ is selected from the group consisting of $CHR^5NR_2$, $CH_2NHCH(C_{1-6}$ alkyl$)_2$, $CH_2R^5$, $CH_2N(R^5)CH_2CHRNR_2$, $CH_2CH(R^5)(CH_2)_pNR_2$, and $(CH_2)_nC(R)_2(CHR)_pNRR^7$.

An aspect of the invention of Formula A1 when G is CH and Z is NH, is realized when $R^4$ is $CHR^5NR_2$, $CH_2R^5$, $CH_2N(R^5)CH_2CHRNR_2$, $CH_2CH(R^5)(CH_2)_pNR_2$, or $(CH_2)_nC(R)_2(CHR)_pNRR^7$.

Another aspect of the invention of Formula A1 when G is CH and Z is NH, is realized when $R^4$ is $CHR^5NH_2$.

Another aspect of this embodiment of the invention of Formula A1 when G is CH and Z is NH, is realized when $R^4$ is $CH_2R^5$. A subembodiment of this aspect of the invention is realized when $R^5$ is optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, or morpholinyl. Another subembodiment of this aspect of the invention of Formula A1 is realized when $R^6$ is $NH_2$.

Another aspect of this embodiment of the invention of Formula A1 when G is CH and Z is NH, is realized when $R^4$ is $CH_2N(R^5)CH_2CHRNH_2$. A subembodiment of this aspect of the invention of Formula A1 is realized when $R^5$ is optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, or morpholinyl. Another subembodiment of this aspect of the invention of Formula A1 is realized when $R^5$ is optionally substituted cyclopropyl, cyclobutyl, cyclopentyl, or cyclohexyl, preferably cyclobutyl. Another subembodiment of this aspect of the invention of Formula A1 is realized when $R^6$ is $NH_2$.

Another aspect of this embodiment of the invention of Formula A1 when G is CH and Z is NH, is realized when $R^4$ is $CH_2CH(R^5)(CH_2)_pNH_2$. A subembodiment of this aspect of the invention is realized when $R^5$ is optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, or morpholinyl. Another subembodiment of this aspect of the invention of Formula A1 is realized when $R^5$ is optionally substituted cyclopropyl, cyclobutyl, cyclopentyl, or cyclohexyl, preferably cyclobutyl. Another subembodiment of this aspect of the invention of Formula A1 is realized when $R^6$ is $NH_2$.

Another aspect of this embodiment of the invention of Formula A1 when G is CH and Z is NH, is realized when $R^4$ is $(CH_2)_nC(R)_2(CHR)_pNH_2$. A subembodiment of this aspect of the invention of Formula A1 is realized when $(CH_2)_nC(R)_2(CHR)_pNH_2$ is represented by $(CH_2)_nC(R^xR^x)_2(CHR)_pNH_2$ where the adjacent $R^x$ groups combine with the carbon atom to which they are attached to form cyclopropyl, cyclobutyl, cyclopentyl, or cyclohexyl optionally substituted with one to three groups selected from $C_{1-6}$ alkyl and halogen. Another subembodiment of this aspect of the invention of Formula A1 is realized when the two $R^x$ groups combine to form optionally substituted cyclobutyl. Another subembodiment of this aspect of the invention of Formula A1 is realized when the two $R^x$ groups combine to form optionally substituted cyclopentyl. Another subembodiment of this aspect of the invention of Formula A1 is realized when $R^6$ is $NH_2$.

Another aspect of this embodiment of the invention of Formula A1 when G is CH and Z is NH, is realized when $R^4$ is $CH_2NHCH(C_{1-6}$ alkyl$)_2$. A subembodiment of this aspect of the invention of Formula A1 is realized when the alkyl is selected from the group consisting of methyl, ethyl, propy, and butyl, preferably methyl. Another subembodiment of this aspect of the invention of Formula A1 is realized when $R^6$ is $NH_2$.

Another aspect of this embodiment of the invention of Formula A1 is realized when G is CH, Z is NH, $R^1$ is $CH_3$, $R^2$ is selected from the group consisting of hydrogen, halogen, and $C_{1-6}$ alkyl and $R^3$ is selected from the group consisting of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$, $R^4$ is selected to the group consisting of $CHR^5NR_2$, $(CH_2)_nC(R^xR^x)_2(CHR)_pNH_2$, $(CH_2)_nC(C_{1-6}$ alkyl$)_2(CHR)_pNH_2$, $CH_2CH(R^5)(CH_2)_pNH_2$, $CH_2R^5$, and $CH_2N(R^5)CH_2CHRNH_2$, $R^5$ is selected from the group consisting of optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, morpholinyl, and azabicycloheptanyl and $R^6$ is $NH_2$.

Another aspect of this embodiment of the invention of Formula A1 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, methyl, $CH_2OH$, and CN, $R^4$ is selected to the group consisting of $CHR^5NR_2$, $CH_2R^5$, $CH_2N(R^5)CH_2CHRNR_2$, $CH_2CH(R^5)(CH_2)_pNR_2$, and $(CH_2)_nC(R^xR^x)_2(CHR)_pNH_2$, $R^5$ is selected from the group consisting of optionally substituted $C_{1-6}$ alkyl, $OC_{1-6}$ alkyl, cyclopropyl, cyclobutyl, cyclopentyl, cyclohexyl, phenyl, pyridyl, pyrrolidinyl, piperidinyl, morpholinyl, and spirabicycle azabicycloheptanyl and $R^6$ is $NH_2$.

A subembodiment of this aspect of the invention of Formula A1 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $(CH_2)_nC(R^xR^x)_2(CHR)_pNH_2$.

A subembodiment of this aspect of the invention of Formula A1 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $(CH_2)_nC(C_{1-6}\text{ alkyl})_2(CHR)_pNH_2$.

A subembodiment of this aspect of the invention of Formula A1 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2CH(R^5)(CH_2)_pNH_2$.

A subembodiment of this aspect of the invention of Formula A1 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2R^5$.

A subembodiment of this aspect of the invention of Formula A1 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CHR^5NR_2$.

A subembodiment of this aspect of the invention of Formula A1 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2N(R^5)CH_2CHRNH_2$.

In some embodiments, a compound of the invention of Formula I is preferably a compound or a pharmaceutically acceptable salt thereof where Y is a pyridyl group as depicted in Formula A2:

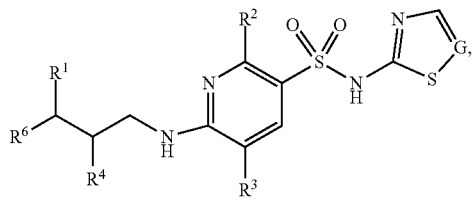

Formula A2 wherein G is N or CH and $R^1$, $R^2$, $R^3$, $R^4$, and $R^6$ are as described herein. A subembodiment of the invention of Formula A2 is realized when G is N. Another subembodiment of the invention of Formula A2 is realized when G is CH.

A subembodiment of this aspect of the invention of Formula A2 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $(CH_2)_nC(R^xR^x)_2(CHR)_pNH_2$.

A subembodiment of this aspect of the invention of Formula A2 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $(CH_2)_nC(C_{1-6}\text{ alkyl})_2(CHR)_pNH_2$.

A subembodiment of this aspect of the invention of Formula A2 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2CH(R^5)(CH_2)_pNH_2$.

A subembodiment of this aspect of the invention of Formula A2 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2R^5$.

A subembodiment of this aspect of the invention of Formula A2 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CHR^5NR_2$.

A subembodiment of this aspect of the invention of Formula A2 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2N(R^5)CH_2CHRNH_2$.

Another subembodiment of this aspect of the invention of Formula A2 is realized when G is N, Z is NH or O, $R^1$ is $CH_3$, $R^2$ is selected from the group consisting of hydrogen and fluorine, $R^3$ is selected from the group consisting of hydrogen, fluorine, chlorine, bromine, methyl, $CH_2OH$, and CN, $R^4$ is selected to the group consisting of $CHR^5NR_2$, $CH_2NHCH(C_{1-6}\text{ alkyl})_2$, $CH_2R^5$, $CH_2N(R^5)CH_2CHRNR_2$, $CH_2CH(R^5)(CH_2)_pNR_2$, and $(CH_2)_nC(R^xR^x)_2(CHR)_pNH_2$, $R^5$ is selected from the group consisting of optionally substituted $C_{1-6}$ alkyl, $OC_{1-6}$ alkyl, cyclopropyl, cyclobutyl, cyclopentyl, and cyclohexyl, phenyl, pyridyl, pyrrolidinyl, piperidinyl, and morpholinyl and $R^6$ is $NH_2$, and wherein the adjacent $R^x$ groups combine with the carbon atom to which they are attached to form cyclopropyl, cyclobutyl, cyclopentyl, and cyclohexyl optionally substituted with one to three groups selected from $C_{1-6}$ alkyl and halogen.

In some embodiments, a compound of the invention of Formula I is preferably a compound or a pharmaceutically acceptable salt thereof where Y is a pyridyl group as depicted in Formula A3:

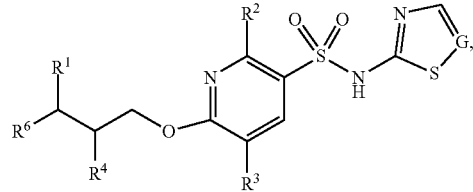

Formula A3 wherein G is N or CH and $R^1$, $R^2$, $R^3$, $R^4$, and $R^6$ are as described herein. A subembodiment of the invention of Formula A3 is realized when G is N. Another subembodiment of the invention of Formula A3 is realized when G is CH.

A subembodiment of this aspect of the invention of Formula A3 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $(CH_2)_nC(R^xR^x)_2(CHR)_pNH_2$.

A subembodiment of this aspect of the invention of Formula A3 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $(CH_2)_nC(C_{1-6}$ alkyl$)_2(CHR)_pNH_2$.

A subembodiment of this aspect of the invention of Formula A3 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2CH(R^5)(CH_2)_pNH_2$.

A subembodiment of this aspect of the invention of Formula A3 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2R^5$.

A subembodiment of this aspect of the invention of Formula A3 is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CHR^5NR_2$.

A subembodiment of this aspect of the invention of Formula A3 is realized when G is N or CH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CH_2N(R^5)CH_2CHRNH_2$.

Another subembodiment of the invention of Formula A3 is realized when G is CH, Z is NH or O, $R^1$ is $CH_3$, $R^2$ is selected from the group consisting of hydrogen and fluorine, $R^3$ is selected from the group consisting of hydrogen, fluorine, chlorine, bromine, methyl, $CH_2OH$, and CN, $R^4$ is selected to the group consisting of $CHR^5NR_2$, $CH_2NHCH(C_{1-6}$ alkyl$)_2$, $CH_2R^5$, $CH_2N(R^5)CH_2CHRNR_2$, $CH_2CH(R^5)(CH_2)_pNR_2$, and $(CH_2)_nC(R^xR^x)_2(CHR)_pNH_2$, $R^5$ is selected from the group consisting of optionally substituted $C_{1-6}$ alkyl, $OC_{1-6}$ alkyl, cyclopropyl, cyclobutyl, cyclopentyl, and cyclohexyl, phenyl, pyridyl, pyrrolidinyl, piperidinyl, and morpholinyl and $R^6$ is $NH_2$, and wherein the adjacent $R^x$ groups combine with the carbon atom to which they are attached to form cyclopropyl, cyclobutyl, cyclopentyl, and cyclohexyl optionally substituted with one to three groups selected from $C_{1-6}$ alkyl and halogen. In some embodiments, a compound of the invention of Formula II is preferably a compound or a pharmaceutically acceptable salt thereof:

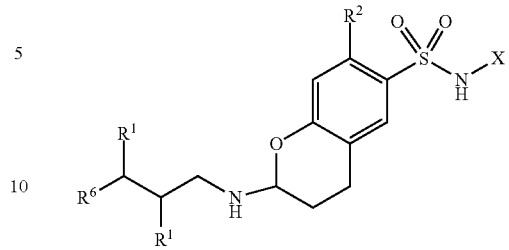

Formula II wherein X, $R^1$, $R^2$, $R^4$ and $R^6$ are as described herein. A subembodiment of this aspect of the invention of Formula II is realized when X is thiadiazolyl or thiazolyl, $R^1$ is $CH_3$, $R^2$ is selected from the group consisting of hydrogen and fluorine, $R^6$ is $NH_2$ and $R^4$ is $(CH_2)_nC(R^xR^x)_2(CHR)_pNH_2$.

Another subembodiment of this aspect of the invention of Formula II is realized when X is thiadiazolyl or thiazolyl, $R^1$ is $CH_3$, $R^2$ is selected from the group consisting of hydrogen and fluorine, $R^6$ is $NH_2$ and $R^4$ is $(CH_2)_nC(C_{1-6}$ alkyl$)_2(CHR)_pNH_2$.

Another subembodiment of this aspect of the invention of Formula II is realized when X is thiadiazolyl or thiazolyl, $R^1$ is $CH_3$, $R^2$ is selected from the group consisting of hydrogen and fluorine, $R^6$ is $NH_2$ and $R^4$ is $CH_2CH(R^5)(CH_2)_pNH_2$.

Another subembodiment of this aspect of the invention of Formula II is realized when X is thiadiazolyl or thiazolyl, $R^1$ is $CH_3$, $R^2$ is selected from the group consisting of hydrogen and fluorine, $R^6$ is $NH_2$ and $R^4$ is $CH_2R^5$.

A subembodiment of this aspect of the invention of Formula II is realized when G is CH, Z is NH, $R^1$ is $CH_3$, $R^2$ is selected from the group consisting of hydrogen and fluorine, $R^3$ is selected from the group consisting of hydrogen, fluorine, chlorine, bromine, and methyl, $R^6$ is $NH_2$ and $R^4$ is $CHR^5NR_2$.

Another subembodiment of this aspect of the invention of Formula II is realized when X is thiadiazolyl or thiazolyl, $R^1$ is $CH_3$, $R^2$ is selected from the group consisting of hydrogen and fluorine, $R^6$ is $NH_2$ and $R^4$ is $CH_2N(R^5)CH_2CHRNH_2$.

Examples of the compounds of the invention are:
4-(((2S)-4-amino-2-((R)-1-aminoethyl)-5,5,5-trifluoropentyl)amino)-5-chloro-2-fluoro-N-(1,2,4-thiadiazol-5-yl)benzenesulfonamide;
4-((5-amino-2-((R)-1-aminoethyl)-4,4-dimethylpentyl)amino)-5-chloro-2-fluoro-N-(1,2,4-thiadiazol-5-yl)benzenesulfonamide;
5-chloro-2-fluoro-N-(1,2,4-thiadiazol-5-yl)-4-((((5R,6S)-5,8,8-trimethyl-1,4-diazonan-6-yl)methyl)amino)benzenesulfonamide;
6-((3R)-3-amino-2-((1-(2-aminoethyl)cyclobutyl)methyl)butoxy)-5-chloro-N-(5-fluorothiazol-2-yl)pyridine-3-sulfonamide;
6-(((3R)-3-amino-2-((1-(2-aminoethyl)cyclobutyl)methyl)butyl)amino)-5-chloro-N-(5-fluorothiazol-2-yl)pyridine-3-sulfonamide;
4-(((2S,3R)-3-amino-2-((1-(2-aminoethyl)cyclobutyl)methyl)butyl)amino)-2,5-difluoro-N-(1,2,4-thiadiazol-5-yl)benzenesulfonamide;
4-(((2R,3R)-3-amino-2-((1-(2-aminoethyl)cyclobutyl)methyl)butyl)amino)-2,5-difluoro-N-(1,2,4-thiadiazol-5-yl)benzenesulfonamide;
4-(((S)-6-amino-2-((R)-1-aminoethyl)-4,4-dimethylhexyl)amino)-5-chloro-2-fluoro-N-(pyrimidin-4-yl)benzenesulfonamide;

6-(((S)-6-amino-2-((R)-1-aminoethyl)-4,4-dimethylhexyl) amino)-N-(1,2,4-thiadiazol-5-yl)-5-(trifluoromethyl)pyridine-3-sulfonamide;

4-(((3R)-3-amino-2-((4,4-dimethylpyrrolidin-2-yl)methyl) butyl)amino)-2,5-difluoro-N-(1,2,4-thiadiazol-5-yl)benzenesulfonamide;

4-(((2S)-4-amino-2-((R)-1-aminoethyl)-4-(1-methylcyclopropyl)butyl)amino)-2,5-difluoro-N-(1,2,4-thiadiazol-5-yl)benzenesulfonamide;

4-(((2S)-6-amino-2-((R)-1-aminoethyl)-4-cyclopropylhexyl)amino)-2-fluoro-N-(1,2,4-thiadiazol-5-yl)benzenesulfonamide;

4-(((3R)-3-amino-2-((1-(2-aminoethyl)cyclobutyl)methyl) pentyl)amino)-2,3,6-trifluoro-N-(1,2,4-thiadiazol-5-yl) benzenesulfonamide;

4-(((3R)-2-((2-azaspiro[3.4]octan-5-yl)methyl)-3-aminobutyl)amino)-2,5-difluoro-N-(1,2,4-thiadiazol-5-yl) benzenesulfonamide;

4-(((S)-6-amino-2-((R)-1-amino-2-methylpropyl)-4,4-dimethylhexyl)amino)-5-chloro-2-fluoro-N-(1,2,4-thiadiazol-5-yl)benzenesulfonamide;

4-(((S)-6-amino-2-((R)-amino(cyclopropyl)methyl)-4,4-dimethylhexyl)amino)-2,5-difluoro-N-(1,2,4-thiadiazol-5-yl)benzenesulfonamide;

4-(((S)-6-amino-2-((R)-1-amino-2-cyclopropylethyl)-4,4-dimethylhexyl)amino)-5-chloro-2-fluoro-N-(1,2,4-thiadiazol-5-yl)benzenesulfonamide;

6-(((S)-6-amino-2-((R)-1-aminoethyl)-4,4-dimethylhexyl) amino)-5-bromo-N-(1,2,4-thiadiazol-5-yl)pyridine-3-sulfonamide;

6-(((S)-6-amino-2-((R)-1-aminoethyl)-4,4-dimethylhexyl) amino)-5-cyano-N-(1,2,4-thiadiazol-5-yl)pyridine-3-sulfonamide;

4-(((S)-6-amino-2-((R)-1-aminoethyl)-4,4-dimethylhexyl) amino)-5-chloro-2-methyl-N-(1,2,4-thiadiazol-5-yl)benzenesulfonamide;

4-(((2S,3R)-3-amino-2-(((1S,2S)-2-(aminomethyl)cyclopropyl)methyl)butyl)amino)-5-chloro-2-fluoro-N-(1,2,4-thiadiazol-5-yl)benzenesulfonamide;

4-(((3R)-3-amino-2-(amino(cyclobutyl)methyl)butyl) amino)-2,5-difluoro-N-(1,2,4-thiadiazol-5-yl)benzenesulfonamide;

4-(((3R)-3-amino-2-((isopropylamino)methyl)butyl) amino)-5-chloro-2-fluoro-N-(1,2,4-thiadiazol-5-yl)benzenesulfonamide;

4-(((3R)-3-amino-2-((((R)-2-aminopropyl)(isopropyl) amino)methyl)butyl)amino)-2,5-difluoro-N-(1,2,4-thiadiazol-5-yl)benzenesulfonamide;

4-(((S)-6-amino-2-((R)-1-aminoethyl)-4,4-dimethylhexyl) amino)-2-fluoro-N-(1,2,4-thiadiazol-5-yl)-5-(thiazol-2-yl)benzenesulfonamide;

2-((2R,3R)-2,7-diamino-5,5-dimethylheptan-3-yl)-7-fluoro-N-(1,2,4-thiadiazol-5-yl)chromane-6-sulfonamide;

4-(((2S,3R)-3-amino-2-((1-(2-(dimethylamino)ethyl)cyclobutyl)methyl)butyl)amino)-2,5-difluoro-N-(1,2,4-thiadiazol-5-yl)benzenesulfonamide;

4-(((3R)-3-amino-2-((2-(aminomethyl)cyclopentyl)methyl) butyl)amino)-2,5-difluoro-N-(1,2,4-thiadiazol-5-yl)benzenesulfonamide;

4-(((3R)-3-amino-2-((2-(aminomethyl)-1-methylcyclobutyl)methyl)butyl)amino)-2,5-difluoro-N-(1,2,4-thiadiazol-5-yl)benzenesulfonamide;

4-(((3R)-3-amino-2-((1-(2-aminoethyl)-3,3-difluorocyclobutyl)methyl)butyl)amino)-5-bromo-2-fluoro-N-(1,2,4-thiadiazol-5-yl)benzenesulfonamide;

4-(((3R)-3-amino-2-((2-(2-aminoethyl)cyclohexyl)methyl) butyl)amino)-2,5-difluoro-N-(1,2,4-thiadiazol-5-yl)benzenesulfonamide;

4-(((S)-6-amino-2-((R)-1-aminoethyl)-4,4-dimethylhexyl) amino)-5-cyano-2-methyl-N-(1,2,4-thiadiazol-5-yl)benzenesulfonamide;

4-(((3R)-2-((5-azaspiro[2.4]heptan-6-yl)methyl)-3-aminobutyl)amino)-2,5-difluoro-N-(1,2,4-thiadiazol-5-yl) benzenesulfonamide;

4-(((3R)-3-amino-2-((1-(aminomethyl)cyclobutyl)methyl) butyl)amino)-2-fluoro-5-methoxy-N-(1,2,4-thiadiazol-5-yl)benzenesulfonamide;

4-(((3R)-3-amino-2-((4,4-dimethylpyrrolidin-3-yl)methyl) butyl)amino)-2,5-difluoro-N-(1,2,4-thiadiazol-5-yl)benzenesulfonamide;

4-(((2S,3R)-3-amino-2-((1-(2-aminoethyl)cyclobutyl) methyl)butyl)amino)-3-chloro-N-(1,2,4-thiadiazol-5-yl) benzenesulfonamide;

4-(((S)-6-amino-2-((R)-1-aminoethyl)-4,4-dimethylhexyl) amino)-2-fluoro-5-(oxazol-2-yl)-N-(1,2,4-thiadiazol-5-yl)benzenesulfonamide;

4-(((2S)-4-amino-2-((R)-1-aminoethyl)-4-cyclopropylbutyl)amino)-2-fluoro-5-(hydroxymethyl)-N-(1,2,4-thiadiazol-5-yl)benzenesulfonamide;

4-(((2S)-5-amino-2-((R)-1-aminoethyl)-4-methoxypentyl) amino)-5-bromo-2-fluoro-N-(1,2,4-thiadiazol-5-yl)benzenesulfonamide;

4-(((2S)-4-amino-2-((R)-1-aminoethyl)hexyl)amino)-2-fluoro-5-methoxy-N-(1,2,4-thiadiazol-5-yl)benzenesulfonamide;

4-(((2S)-4-amino-2-((R)-1-aminoethyl)-6,6,6-trifluorohexyl)amino)-2,5-difluoro-N-(1,2,4-thiadiazol-5-yl)benzenesulfonamide;

4-(((3R)-3-amino-2-((1-aminocyclobutyl)methyl)butyl) amino)-3-fluoro-N-(1,2,4-thiadiazol-5-yl)benzenesulfonamide;

4-((2-((R)-1-aminoethyl)-4-(aminomethyl)hexyl)amino)-2, 5-difluoro-N-(1,2,4-thiadiazol-5-yl)benzenesulfonamide;

4-((3R)-3-amino-2-((1-(2-aminoethyl)cyclobutyl)methyl) butoxy)-2,5-difluoro-N-(1,2,4-thiadiazol-5-yl)benzenesulfonamide;

4-(((3R)-3-amino-2-(((1R,2S)-2-(aminomethyl)-1-methylcyclopentyl)methyl)butyl)amino)-2,5-difluoro-N-(1,2,4-thiadiazol-5-yl)benzenesulfonamide;

4-(((3R)-3-amino-2-(((1S,2R)-2-(aminomethyl)-1-methylcyclopentyl)methyl)butyl)amino)-2,5-difluoro-N-(1,2,4-thiadiazol-5-yl)benzenesulfonamide;

4-(((2S,3R)-3-amino-2-((1-(2-aminoethyl)cyclobutyl) methyl)butyl)amino)-2,3-difluoro-N-(1,2,4-thiadiazol-5-yl)benzenesulfonamide;

4-(((3R)-3-amino-2-(morpholin-3-ylmethyl)butyl)amino)-5-chloro-2-fluoro-N-(1,2,4-thiadiazol-5-yl)benzenesulfonamide;

4-(((2S,3R)-3-amino-2-((1-aminocyclobutyl)methyl)butyl) amino)-5-chloro-2-fluoro-N-(6-fluoropyridin-2-yl)benzenesulfonamide;

4-(((S)-4-amino-2-((R)-1-aminoethyl)-4-methylpentyl) amino)-5-chloro-2-fluoro-N-(4-methylthiazol-2-yl)benzenesulfonamide;

4-(((S)-4-amino-2-((R)-1-aminoethyl)-4-methylpentyl) amino)-2-fluoro-N-(5-fluorothiazol-2-yl)-5-methylbenzenesulfonamide;

4-((4-amino-2-((R)-1-aminoethyl)-5-methylhexyl)amino)-5-bromo-2-fluoro-N-(1,2,4-thiadiazol-5-yl)benzenesulfonamide;

4-(((3R)-3-amino-2-(pyrrolidin-1-ylmethyl)butyl)amino)-5-chloro-2-fluoro-N-(1,2,4-thiadiazol-5-yl)benzenesulfonamide;

4-(((3R)-2-(((1R,3R,4S)-2-azabicyclo[2.2.1]heptan-3-yl)methyl)-3-aminobutyl)amino)-2,5-difluoro-N-(1,2,4-thiadiazol-5-yl)benzenesulfonamide;

or a pharmaceutically acceptable salt of any thereof.

In one aspect the invention provides a pharmaceutical composition comprising at least one compound of Formula I, Formula II, A1, A2, A3, or a salt thereof, and at least one pharmaceutically acceptable excipient adapted for administration to a patient via any pharmaceutically acceptable route, including dosage forms for oral, intravenous, infusion, subcutaneous, transcutaneous, intramuscular, intradermal, transmucosal, or intramucosal routes of administration.

In one aspect this invention provides also a pharmaceutical composition comprising a pharmaceutical carrier, an effective amount of at least one compound of Formula I, Formula II, Formula A1, Formula A2, Formula A3, or a salt thereof, an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

In one aspect the invention provides also a method of treatment, management, alleviation or amelioration of conditions or disease states which can be treated, managed, alleviated or ameliorated by specific inhibition of Nav 1.7 channel activity, the method comprising administering to a patient in need thereof a composition comprising at least one compound of Formula I, Formula II, Formula A1, Formula A2, Formula A3, or a salt thereof, in an amount providing a serum level of at least one said compound sufficient to effect said treatment, management, alleviation or amelioration of said conditions or disease states. In some embodiments, preferably the condition or disease state to be treated, managed, alleviated or ameliorated is acute pain or a chronic pain disorder. In some embodiments, preferably the condition is acute pain.

DETAILED DESCRIPTION OF THE INVENTION

As mentioned above, the invention provides compounds believed to have selective activity as $Na_v$ 1.7 sodium ion channel inhibitors which have the structure of Formula I, Formula II, Formula A1, Formula A2, Formula A3, or a salt thereof as described herein.

Preferred compounds of the invention exhibit a potency ($IC_{50}$) of less than about 500 nanomolar when assayed in accordance with Qube® assay technique described herein, and exhibit at least 50-fold selectivity for $Na_v$ 1.7 sodium channels over $Na_v$ 1.5 and $Na_v$ 1.6 sodium channels, more preferably at least 500-fold selectivity for $Na_v$ 1.7 sodium channels over $Na_v$ 1.5 and $Na_v$ 1.6 sodium channels when functional potency for each channel are compared using the Qube® assay technique described herein.

Compounds of the invention and formulations comprising compounds of the invention are believed to be useful in providing treatment, management, alleviation or amelioration of conditions or disease states which can be treated, managed, alleviated or ameliorated by specific inhibiting of Nav 1.7 channel activity. Examples of disease states which are believed to be desirably affected using such therapy include, but are not limited to, inhibiting acute pain, peri-operative, post-operative and neuropathic pain, for example, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias, pruritis or cough.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the methyl group is emerging from the plane of the paper and the ethyl group is descending into the plane of the paper with the cyclohexene ring in the plane of the paper.

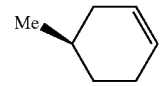

Illus-I

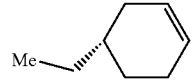

Illus-2

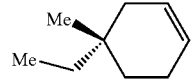

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present.

Components of a composition are typically aliquots of isolated pure material added to the composition, where the purity level of the isolated material added into the composition is the normally accepted purity level for a reagent of the type.

"at least one" used in reference to substituents appended to a compound substrate, for example, a halogen or a moiety appended to a portion of a structure replacing a hydrogen, means that one substituent of the group of substituents specified is present, and more than one of said substituents may be bonded to any of the defined or chemically accessible bonding points of the substrate.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula I, Formula II, Formula A1, Formula A2, or Formula A3 that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula I, Formula II, Formula A1, Formula A2 or Formula A3 to a compound of Formula I, Formula II, Formula A1, Formula A2, Formula A3, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C=O)—" or "R'—C(O)—", or by a structural representation:

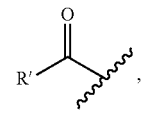

equally, with no differentiation implied using any or all of these representations;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "cycloalkyl" means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term "cycloalkyl" also includes non-aromatic, fused multicyclic ring system comprising up to 20 carbon atoms which may optionally be substituted as defined herein for "alkyl" generally. Suitable multicyclic cycloalkyls are, for example, but are not limited to: 1-decalin; norbornyl; adamanty; and the like;

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

where a structural formula represents bonding between a moiety and a substrate using a the bonding line that terminates in the middle of the structure, for example the following representations:

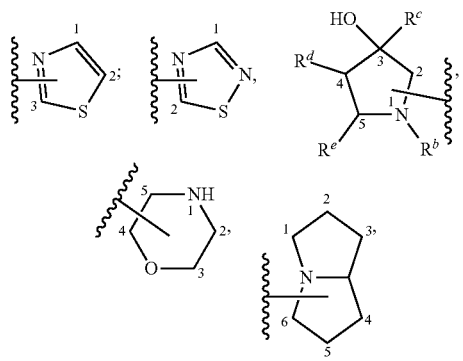

whether or not numbered the structure indicates that unless otherwise defined the moiety may be bonded to the substrate through any of available ring atom, for example, the numbered atoms of the example moieties;

"heterocyclyl" (or heterocycloalkyl) means a non-aromatic saturated monocyclic or multicyclic ring system comprising 3 to 10 ring atoms, preferably 5 to 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiopheneyl and tetrahydrothiopyranyl); and wherein the heteroatoms can be alone or in combination provided that the moiety does not contain adjacent oxygen and/or sulfur atoms present in the ring system; preferred heterocyclyl moieties contain 5 to 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected substituents;

the nitrogen or sulfur atom of the heterocyclyl can be optionally oxidized to the corresponding N-oxide, S-oxide or S,S-dioxide ($SO_2$); non-limiting examples of suitable monocyclic heterocyclyl rings include piperidyl, pyrrolidinyl, piperazinyl, morpholinyl—

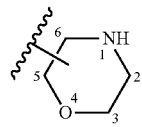

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

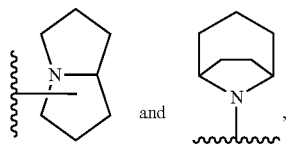

and the like.

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$;

"hydroxyl" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

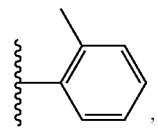

indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5 (1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula I, Formula II, Formula A1, Formula A2, Formula A3, and of the salts, solvates and prodrugs of the compounds of Formula I, Formula II, Formula A1, Formula A2, and Formula A3 are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

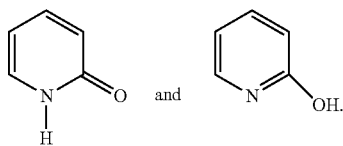 [SMILES: O=c1cccc[nH]1 ; Oc1ccccn1]

In particular, compounds of the invention are presented herein having a portion of their structure represented by the structural drawing A is contemplated as being equivalent to tautomeric form B:

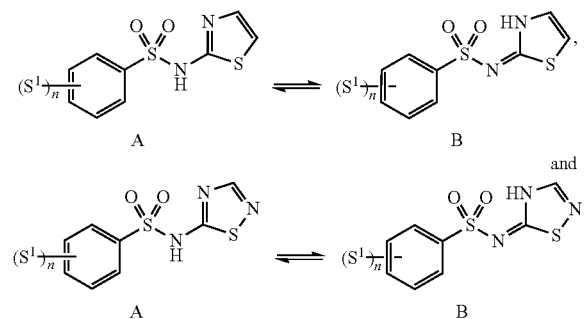

where (S1)n is one to five substituents on the aryl ring, thus, any structural drawing representation where tautomerism is possible is intended to include all tautomeric forms within the scope of the structures represented thereby.

Oxygen and nitrogen atoms in a structure may be represented equivalently as protonated on a lone pair of electrons or in unprotonated form, and both forms are contemplated where either structure is presented, for example, the protonated form A and unprotonated form B of the amine illustrated below:

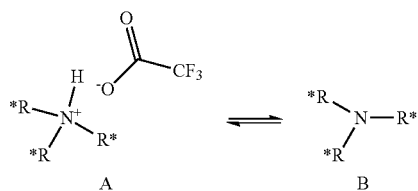

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66 (1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

In general, salts of compounds are intended to be pharmaceutically acceptable salts within the scope of the invention and all acid and base salts are considered equivalent to the free forms of the corresponding compounds for purposes of the invention. Many of the compounds exemplified herein are isolated in the form of a salt, for example, a hydrochloride, acetate trifluoroacetate, formate, or triflate salt. As described in the Examples, herein, such salts may readily be converted to the free-base form of the compound by elution from an appropriate media using an appropriate base solution followed by chromatographic separation on a column of appropriate polarity.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, heterocycl, $R^{XY}$, etc.) appears more than once in any moiety or in any compound of the invention, the selection of moieties defining that variable for each occurrence is independent of its definition at every other occurrence unless specified otherwise in the local variable definition.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by know means also.

Certain isotopically-labeled compounds of the invention (e.g., those labeled with $^3H$, $^{11}C$ and $^{14}C$) are recognized as being particularly useful in compound and/or substrate tissue distribution assays using a variety of known techniques. Tritiated (i.e., $^3H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts. As will be appreciated by the ordinarily skilled artisan, excipients are any constituent which adapts the composition to a particular route of administration or aids the processing of a composition into a dosage form without itself exerting an active pharmaceutical effect. A bulk composition is material that has not yet been formed into individual units for administration As mentioned above, in one aspect the invention provides compositions suitable for use in selectively inhibiting Nav 1.7 sodium channels found in sensory and sympathetic neurons, comprising at least one compound of the invention (as defined herein, for example one or more compounds of Formula I, Formula A1, Formula A2, Formula A3 or a salt thereof) and at least one pharmaceutically acceptable carrier (described below). It will be appreciated that pharmaceutical formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below. Such formulations are believed to have utility in the treatment, management, amelioration or in providing therapy for diseases or conditions related to pain, for example, acute pain, chronic pain, inflammatory pain, or neuropathic pain disorders, or related to pruritic disorders, or cough disorders.

While compositions of the invention may be employed in bulk form, it will be appreciated that for most applications compositions will be incorporated into a dosage form suitable for administration to a patient, each dosage form comprising an amount of the selected composition which contains an effective amount of said one or more compounds of Formula I, Formula II, Formula A1, Formula A2, or Formula A3. Examples of suitable dosage forms include, but are not limited to, dosage forms adapted for: (i) intravenous (IV) infusion, for example, over a prolonged period using an I.V. infusion pump; (ii) a dosage form adapted for intramuscular administration (IM), for example, an injectable solution or suspension, and which may be adapted to form a depot having extended release properties; (iii) a dosage form adapted for drip intravenous administration (IV), for example, a solution or suspension, for example, as an IV solution or a concentrate to be injected into a saline IV bag; or (iv) a dosage form adapted for subcutaneous administration. Other dosage forms which may be contemplated include, but are not limited to: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachets or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; and (vi) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or for example, solution stabilizing or emulsifying agents which may adapt the formulation to a desired route of administration, for example, which provide a formulation for injection, for example, intramuscular or intravenous routes of administration or administration via IV or diffusion pump infusion or other form parenteral administration, or for oral administration, for example, via absorption from the gastrointestinal tract, or for transdermal or transmucosal administration, for example, via adhesive skin "patch" or buccal administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for intravenous administration (IV), for example, but not limited to, administration via drip IV or infusion pump, intramuscular injection (IM), for example, of a bolus which is released over an extended duration, direct IV injection, or adapted to subcutaneous routes of administration. Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in an IV administration, for example, IV drip or infusion pump or injection, or for subcutaneous routes of administration are preferable, a composition of the invention may be formulated for administration via other routes. Examples include aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, MD.

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, NJ 07645-1742, USA), the Physician's Desk Reference, 56th Edition, 2002 (published by Medical Economics company, Inc. Montvale, NJ 07645-1742), or the Physician's Desk Reference, 57th Edition, 2003 (published by Thompson P D R, Montvale, NJ 07645-1742); the disclosures of which is incorporated herein by reference thereto. For convenience, the total daily dosage may be divided and administered in portions during the day as required or delivered continuously.

In another embodiment the present invention is believed to provide for treatment, management, prevention, alleviation or amelioration of conditions or disease states which can be treated, managed, prevented, alleviated or ameliorated by specific inhibition of Nav 1.7 channel activity. Some examples are pain conditions, pruritic conditions and cough conditions. Examples of pain conditions include, but are not limited to, acute pain, perioperative pain, preoperative pain, postoperative pain, neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, pruritic conditions, and cough conditions.

In some embodiments in which it is desired to treat a pain disorder, preferably the disorder is an acute pain, inflammatory pain or neuropathic pain disorder, more preferably an acute pain disorder.

In accordance with the present invention, treatment, alleviation, amelioration, or management of a disease state amenable to treatment by inhibiting $Na_v1.7$ channel activity, for example, one or more of the conditions or disease states mentioned above, comprises administering to a patient in need thereof an effective amount of one or more compounds of the invention, as defined herein, for example, a compound of Formula I, Formula II, Formula A1, Formula A2, Formula A3 or a pharmaceutically acceptable salt thereof. In some embodiments, as mentioned above, it is preferred for the compound of the invention to be present in a pharmaceutical composition.

In general, in whatever form administered, the dosage form administered will contain an amount of at least one compound of the invention, or a salt thereof, which will provide a therapeutically effective serum level of the compound meeting or exceeding the minimum therapeutically effective serum level on a continuous basis throughout the period during which treatment is administered. As mentioned above, a composition of the invention can incorporate additional pharmaceutically active components or be administered simultaneously, contemporaneously, or sequentially with other pharmaceutically active compositions as may be additionally needed in the course of providing treatment.

In one aspect this invention provides also a pharmaceutical composition comprising a pharmaceutical carrier, an effective amount of at least one compound of the invention, for example, a compound of Formula I, Formula II, Formula A1, Formula A2, or Formula A3 and an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

As mentioned above, in one aspect the invention provides compounds having activity as Nav 1.7 sodium ion channel inhibitors which have the structure of Formula I, Formula II, Formula A1, Formula A2, Formula A3 or a salt thereof.

In the examples that follow certain of the exemplified compounds, or salts thereof, are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise, where present, isomers of example compounds were not separated. Unless indicated otherwise, where isomers were separated into fractions containing an excess of a particular isomer, for example, a fraction containing an excess of an optical isomer, which separation may be accomplished, for example, by super critical fluid chromatography, absolute stereochemistry of separated isomers was not determined. For some compounds enantiomers were made in enantiomerically pure form or separated to obtain pure fractions of each enantiomer, and the absolute configuration of each enantiomer was determined, as illustrated herein. Each of those compounds is reported herein structurally with indication of each particular enantiomer using the conventional solid and dashed wedge-bonds at the chiral center and is named in accordance with the specific isomer naming conventions.

Where a reaction scheme appearing in an example employs a compound having one or more stereocenters, the stereocenters can be indicated, for example, with wedges as illustrated below in a', b', c', d', e':

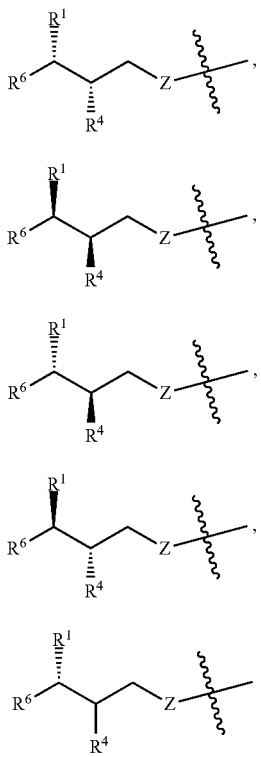

Accordingly, a' and b' illustrate pairs of Cis isomers, c' and d' illustrate pairs of Trans isomers (ii) Cis-isomers and e' illustrate a single isomer. Illustrations of a', b', c', d', and e' are non-limiting examples of the stereocenters encompassed in the instant invention.

When the compound is prepared and separated into pure diastereomers, albeit without determining the absolute configuration of each diastereomer of the compound, the product will be identified in the title using both diastereomer names, e.g., where a' and c' are prepared and separated into pure diastereomers, the title will read "4-(((2S,3R)-3-amino-2-((1-(2-aminoethyl) . . . " and "4-(((2R,3R)-3-amino-2-((1-(2-aminoethyl) . . . ," respectively, or identified in the title as undefined, e. g., where e' are prepared and separated into pure diastereomers, the title will read "4-(((3R)-3-amino-2-((1-(2-aminoethyl) . . . ". In some instances where enantiomeric compounds are prepared the designation (Cis) or (Trans) may be appended to the name to clarify the relationship of the stereo centers present in the two stereoisomers. As will be appreciated, identification of each product in the experimental preparation as: Isomer 1, Isomer 2, Isomer 3, etc., where Isomers 1, 2, and 3 are the same structure with a diastereomeric relationship, each pure diastereomer was prepared and has the properties indicated by the data associated with its report and they were prepared and isolated in increased enantiopurity without determination of the absolute configuration of either compound. In such instances each pure diastereomer is claimed.

The following examples are presented to further illustrate compounds of the invention, but, with reference to the general formula presented above, they are not presented as limiting the invention to these specifically exemplified compounds.

EXAMPLES

Examples of the preparation of compounds of the invention are shown next. In each of the Examples, the identity of the compounds prepared were confirmed by a variety of techniques. In all cases the compounds were analyzed by LC/MS or HPLC.

Where utilized, Prep HPLC was carried out on a Gilson 281 equipped with a Phenomenexd Synergi C18, 100 mm×21.2 mm×5 micron column. Conditions included a flow rate of 25 mL/min., eluted with a 0-40% acetonitrile/water eluent comprising 0.1% v/v TFA.

LC/MS determinations used either an Agilent YMC J'Sphere H-80 (3×50 mm) 5 µm column using mobile phase containing A: 0.1% TFA in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 µm column using mobile phase containing A: 0.0375% TFA in water and B: 0.01875% TFA in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR and high-resolution MS. Proton NMR were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported.

High resolving power accurate mass measurements were acquired by use of a Bruker Daltonics 7T Fourier transform ion cyclotron resonance (FTICR) mass spectrometer. Samples were dissolved in acetonitrile:water:acetic acid (50:50:0.1% v/v), and ionized by use of electrospray ionization (ESI) yielding [M+H]+ and/or [M+Na]+. External calibration was accomplished with oligomers of polypropylene glycol (PPG, average molecular weight 1000 Da).

Throughout the Examples section, the following abbreviations are used to indicate various reagents, substituents and solvents: AcCN=acetonitrile; AcOH=acetic acid; Boc=tert-butoxycarbonyl; Boc₂O or Boc-anhydride=di-tert-butyl carbonate; Bn=Benzyl; DABCO=1,4-diazabicyclo[2.2.2]octane; DAST=diethylaminosulfur trifluoride; DCE=dichloroethane; DCM=dichloromethane; DEAD=diethylazodicarboxylate; DIPEA=diisopropylamine; DMAP=4-dimethylaminopyridine; DMB (2, 4-dimethoxybenzyl-); DMF=dimethylformamide; DMP=Dess-Martin Periodinane; DMS=dimethylsulfide; DMSO=dimethylsulfoxide; DPPA=diphenylphosphoryl azide; dppf=1,1'-bis(diphenylphosphino)ferrocene; EtOAc=ethyl acetate; EtOH=ethanol; Fmoc=fluorenyloxycarbonyl; HATU=1-[Bis(dimethylamino)methylene]-1H-1,2,3-triazolo[4,5-b]pyridinium-3-oxide-hexafluorophosphate; Hex=hexanes; HMPA=hexamethylphosphoramide; HPLC=high-performance liquid chromatography; IPA=isopropyl alcohol; LC/MS or LCMS=liquid chromatography/mass spectrometry; LDA=lithium diisopropylamide; LG=leaving group; LiHMDS=lithium bis(trimethylsilyl)amide;

MeOH=methanol; LRMS=low resolution mass spectrometry; MOM=methoxymethyl; MOMCl=methyl chloromethyl ether; MsCl=methanesulfonyl chloride; NMP=N-methylpyrrolidone; Pd/C=palladium on carbon; Pd₂(dba)₃=tris(dibenzylideneacetone)dipalladium(0); PE=petroleum ether; PG=protecting group; PMP=para-methoxybenzyl; PMBCl=para-methoxybenzyl chloride; Prep-TLC=preparative thin layer chromatography; Py=pyridine; SCX=strong cation exchange; Selectfluor=1-(chloromethyl)-4-fluoro-1,4-diazoniabicyclo[2.2.2]octane ditetrafluoroborate; SFC=Supercritical Fluid Chromatography; TBAF=tetra-n-butylammonium fluoride; TBS=tert-butyldimethylsilyl; TBS-Cl=tert-butyldimethylsilyl chloride; THF=Tetrahydrofuran; TFA=trifluoroacetic acid; TFAA=trifluoroacetic acid anhydride; TsOH=para-toluenesulfonic acid; UV=ultraviolet; Xantphos=4,5-Bis(diphenylphosphino)-9,9-dimethylxanthene.

In general, compounds of the invention can be prepared by the methods outlined in Scheme A. In Scheme A, displacement of a leaving group (LG such as, but not limited to, F) from protected arylsulfonamide intermediates A-1 (PG such as, but not limited to, Boc, DMB, PMB, MOM) by amine $R^1NH_2$ provides compounds A-2. Subsequent removal of PG affords compounds A-3. Alternatively, the amine $R^1NH_2$ can be reacted with unprotected precursors A-1 (PG=H) to provide A-3 directly.

Scheme A

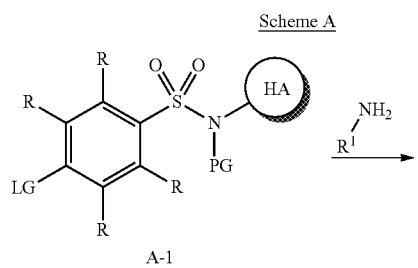

The following examples are provided to more fully illustrate the invention, and are not to be construed as limiting the scope of the invention in any manner.

Intermediate 1

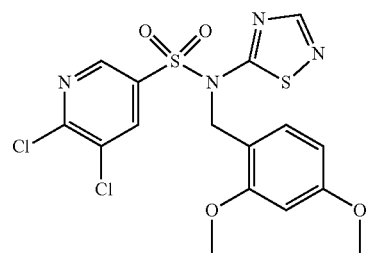 [SMILES: COc1ccc(CN(c2ncns2)S(=O)(=O)c2cnc(Cl)c(Cl)c2)c(OC)c1]

5,6-dichloro-N-(2,4-dimethoxybenzyl)-N-(5-fluorothiazol-2-yl)pyridine-3-sulfonamide To a mixture of N-(2,4-dimethoxybenzyl)-5-fluorothiazol-2-amine (3.0 g, 11 mmol) in THF (30 mL) at −78° C. under N₂ was added LiHMDS (17 mL, 17 mmol) dropwise. After stirring 1 h at −78° C., a solution of 5,6-dichloropyridine-3-sulfonyl chloride (3.3 g, 13 mmol) in THF (20 mL) was added dropwise. After stirring 1 h at −78° C., the mixture was quenched by NH₄Cl aq. and extracted by EtOAc. The organic layer was washed with water, brine, dried over Na₂SO₄, filtered and concentrated to a residue that was purified by column chromatography on silica gel (PE:EA=10:1) to give the title compound. 1H NMR (400 MHz, CD₃OD) δ 8.60 (d, J=2.0 Hz, 1H), 7.95 (d, J=2.0 Hz, 1H), 7.07-6.99 (m, 2H), 6.32-6.26 (m, 1H), 6.24 (d, J=2.0 Hz, 1H), 4.81 (s, 2H), 3.71 (s, 3H), 3.59 (s, 3H). LCMS (ES, m/z): 476.9 [M+H]⁺.

Intermediate 2

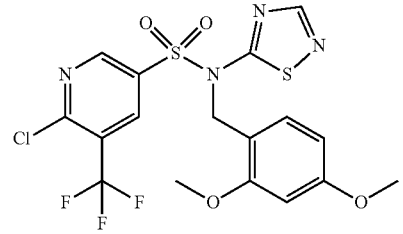 [SMILES: COc1ccc(CN(c2ncns2)S(=O)(=O)c2cnc(Cl)c(C(F)(F)F)c2)c(OC)c1]

6-chloro-N-(2,4-dimethoxybenzyl)-N-(1,2,4-thiadiazol-5-yl)-5-(trifluoromethyl)pyridine-3-sulfonamide Step A: 6-chloro-5-(trifluoromethyl)pyridin-3-amine To a mixture of iron (1.2 g, 22 mmol) and NH₄Cl (1.2 g, 22 mmol) in water (120 mL) and MeOH (80 mL) was added 2-chloro-5-nitro-3-(trifluoromethyl)pyridine (5.0 g, 22 mmol) in MeOH (40 mL). The mixture was stirred at 25° C. for 16 h. The reaction mixture was filtered and the filtrate was extracted with EtOAc. The combined organic layers were washed with brine, dried over Na₂SO₄, filtered and concentrated to a residue that was purified by silica gel chromatography (PE:EtOAc=20:1) to give the title compound. ¹H NMR (CDCl₃, 400 MHz) δ 7.99 (s, 1H), 7.29 (s, 1H), 3.95 (br s, 2H).

Step B: 6-chloro-5-(trifluoromethyl)pyridine-3-sulfonyl chloride A solution of SO₂ was prepared by adding SOCl₂

(17 mL, 0.23 mol) into stirring water (85 mL) containing copper(I) chloride (0.060 g, 0.61 mmol). The solution was then stirred at 20° C. for 16 h. 6-chloro-5-(trifluoromethyl) pyridin-3-amine was added into stirring conc HCl (44 mL, 0.54 mol) portionwise. The mixture was stirred until all solids were dissolved and was then cooled to −5° C. Into the mixture was added dropwise a solution of sodium nitrite (4.42 g, 64.1 mmol) dissolved in water (15 mL) while the temperature was maintained between −5° C. and 0° C. The resulting mixture was stirring for 1 h after the completion of the addition and then added dropwise into the aqueous solution of $SO_2$ while maintaining the temperature below 0° C. The mixture was filtered, and the solid was washed with ice-water and dried in vacuo to give the title compound. $^1$H NMR (CDCl$_3$, 400 MHz) δ 9.18 (d, J=2.3 Hz, 1H), 8.58 (d, J=2.3 Hz, 1H).

Step C: 6-chloro-N-(2,4-dimethoxybenzyl)-N-(1,2,4-thiadiazol-5-yl)-5-(trifluoromethyl)pyridine-3-sulfonamide To a mixture of N-(2,4-dimethoxybenzyl)-1,2,4-thiadiazol-5-amine (5.0 g, 20 mmol) in THF (60 mL) at −78° C. under $N_2$ was added lithium bis(trimethylsilyl)amide (20 mL, 20 mmol) (1M in THF) dropwise. After stirring at −78° C. for 1 h, a solution of 6-chloro-5-(trifluoromethyl)pyridine-3-sulfonyl chloride (5.6 g, 20 mmol) in THF (20 mL) was added to the mixture dropwise. The reaction mixture was stirred at −78° C. for 1 h. The mixture was quenched by saturated aq NH$_4$Cl, and extracted by EtOAc. The combined organic layer was washed with H$_2$O, brine, dried over Na$_2$SO$_4$, filtered and concentrated to a residue that was purified by silica gel chromatography (PE:EtOAc=10:1) to give the title compound. $^1$H NMR (CDCl$_3$, 400 MHz) δ 8.79 (s, 1H), 8.27 (s, 1H), 7.89 (s, 1H), 7.09 (d, J 8.6 Hz, 1H), 6.32 (d, J=7.0 Hz, 1H), 6.10 (s, 1H), 5.38 (s, 2H), 3.75 (s, 3H), 3.53 (s, 3H).

Intermediate 3

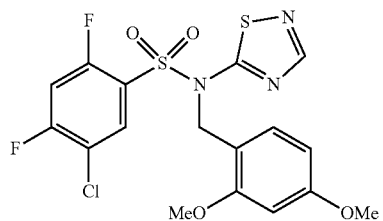 [SMILES: COc1ccc(CN(c2ncns2)S(=O)(=O)c2cc(Cl)c(F)cc2F)c(OC)c1]

5-chloro-N-(2,4-dimethoxybenzyl)-2,4-difluoro-N-(1,2,4-thiadiazol-5-yl)benzenesulfonamide Step A: N-(2,4-dimethoxybenzyl)-1,2,4-thiadiazol-5-amine. A mixture of 1,2,4-thiadiazol-5-amine (0.30 kg, 3.0 mol), 2,4-dimethoxybenzaldehyde. (0.47 kg, 2.8 mol), p-TsOH (4.1 g, 24 mmol), and toluene (9.0 L) under an atmosphere of N$_2$ was heated to reflux overnight with a Dean-Stark trap. The mixture was cooled to room temperature and concentrated under vacuum. The residue was washed with methanol and used crude in the next reaction. To a solution of the crude solid (0.55 kg, 2.2 mol) in THF (5.5 L) under an atmosphere of N$_2$ was added NaBH$_4$ (83 g, 2.2 mol) in several batches at 0° C. The mixture was stirred for 3 h at room temperature, then extracted with ethyl acetate. The organic layers were combined, washed with brine, dried over anhydrous magnesium sulfate and concentrated under vacuum to a residue that was purified via silica gel chromatography (dichloromethane/methanol 100:1) to give the title compound.

Step B: 5-chloro-N-(2,4-dimethoxybenzyl)-2,4-difluoro-N-(1,2,4-thiadiazol-5-yl) benzenesulfonamide. To a mixture of N-(2,4-dimethoxybenzyl)-1,2,4-thiadiazol-5-amine (1.0 g, 4.0 mmol) in THF (20 mL) was added LiHMDS (5.0 mL, 5.0 mmol, 1M) at −78° C. under $N_2$. The mixture was warmed to room temperature and stirred for 1 h. The mixture was cooled to −78° C., then a solution of 5-chloro-2,4-difluorobenzene-1-sulfonyl chloride (1.2 g, 4.8 mmol) in THF (4 mL) was added dropwise. The mixture was stirred at room temperature for additional 1 h, then quenched with saturated NH$_4$Cl and extracted with EtOAc. The combined organic layers were dried with Na$_2$SO$_4$, filtered and concentrated to a residue that was purified by silica gel chromatography (PE:EtOAc=6:1) to give the title compound. 1H NMR (400 MHz, CDCl$_3$) δ 8.22 (s, 1H), 7.73 (t, J=7.6 Hz, 1H), 7.19 (d, J=8.4 Hz, 1H), 6.87 (t, J=8.4 Hz, 1H), 6.35 (dd, J=2.4, 6.0 Hz, 1H), 6.15 (d, J=2.0 Hz, 1H), 5.36 (s, 2H), 3.74 (s, 3H), 3.66 (s, 3H). MS m/z (M+H): 462.0.

Intermediate 4

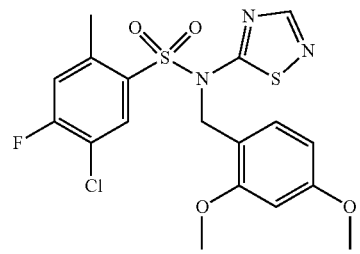 [SMILES: COc1ccc(CN(c2ncns2)S(=O)(=O)c2cc(Cl)c(F)cc2C)c(OC)c1]

5-chloro-N-(2,4-dimethoxybenzyl)-4-fluoro-2-methyl-N-(1,2,4-thiadiazol-5-yl)benzenesulfonamide Step A: 5-chloro-4-fluoro-2-methylbenzenesulfonyl chloride. A mixture of 1-chloro-2-fluoro-4-methylbenzene (4.0 g, 28 mmol) and chlorosulfonic acid (40 mL, 0.60 mol) was stirred at 55° C. for 1 h. The mixture was cooled to 25° C., carefully poured into cold water at 0° C. and then extracted by EtOAc. The combined organic layers were dried over Na$_2$SO$_4$, filtered and concentrated to give the title compound. $^1$H NMR (CDCl$_3$, 400 MHz) δ 8.17 (d, J=7.0 Hz, 1H), 7.23 (d, J=9.0 Hz, 1H), 2.77 (s, 3H).

Step B: 5-chloro-N-(2,4-dimethoxybenzyl)-4-fluoro-2-methyl-N-(1,2,4-thiadiazol-5-yl)benzenesulfonamide. To a mixture of N-(2,4-dimethoxybenzyl)-1,2,4-thiadiazol-5-amine (1.9 g, 7.5 mmol) in THF (40 mL) at −78° C. was added LiHMDS (11 mL, 11 mmol, 1M). The mixture was stirred at −78° C. for 1 h, then a solution of 5-chloro-4-fluoro-2-methylbenzenesulfonyl chloride (2.0 g, 8.2 mmol) in THF (10 mL) was added. The reaction mixture was stirred at −78° C. for 1 h. The mixture was quenched with NH$_4$Cl, and extracted with EtOAc. The combined organic layer was washed with brine, dried over Na$_2$SO$_4$, filtered and concentrated to a residue that was purified by silica gel chromatography (PE:EtOAc=5:1) to give the title compound. $^1$H NMR (CDCl$_3$, 400 MHz) δ 8.25 (s, 1H), 7.89 (d, J=7.0 Hz, 1H), 7.18 (d, J=8.4 Hz, 1H), 6.93 (d, J=9.2 Hz, 1H), 6.35 (dd, J=8.4, 2.2 Hz, 1H), 6.18 (d, J=2.6 Hz, 1H), 5.28 (s, 2H), 3.76 (s, 3H), 3.69 (s, 3H), 2.36 (s, 3H).

Intermediate 5

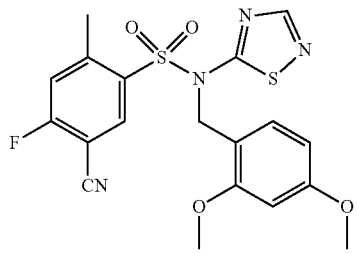 [SMILES: COc1ccc(CN(c2ncns2)S(=O)(=O)c2cc(C#N)c(F)cc2C)c(OC)c1]

5-cyano-N-(2,4-dimethoxybenzyl)-4-fluoro-2-methyl-N-(1,2,4-thiadiazol-5-yl)benzenesulfonamide Step A: 5-bromo-4-fluoro-2-methylbenzenesulfonyl chloride. To solution of 1-bromo-2-fluoro-4-methylbenzene (1.0 g, 5.3 mmol) was added chlorosulfonic acid (6.0 mL, 5.3 mmol) at 0° C. The reaction mixture was stirred at 25° C. for 1 h. The mixture was added slowly to ice water. The the residue was then filtered and the filter cake was washed with water to give the title compound. $^1$H NMR (CDCl$_3$, 400 MHz) δ 8.30 (d, J=6.7 Hz, 1H), 7.20 (d, J=9.0 Hz, 1H), 2.76 (s, 3H).

Step B: 5-bromo-N-(2,4-dimethoxybenzyl)-4-fluoro-2-methyl-N-(1,2,4-thiadiazol-5-yl)benzenesulfonamide. To a mixture of N-(2,4-dimethoxybenzyl)-1,2,4-thiadiazol-5-amine (1.2 g, 4.8 mmol) in THF (20 mL) was added LiHMDS (7.2 mL, 7.2 mmol) dropwise at −78° C. under N$_2$. The mixture was stirred at −78° C. for 1 h, then a solution of 5-bromo-4-fluoro-2-methylbenzenesulfonyl chloride (1.5 g, 5.3 mmol) in THF (10 mL) was added. The mixture was stirred at −78° C. for 1 h. The mixture was quenched by sat. NH$_4$Cl, and extracted by EtOAc. The combined organic layer was washed by sat. NaCl, dried over Na$_2$SO$_4$, filtered and concentrated to a residue that was purified by silica gel chromatography (PE:EtOAc=10/1 to 5/1) to give the title compound. $^1$H NMR (CDCl$_3$, 400 MHz) δ 8.25 (s, 1H), 8.02 (d, J=6.7 Hz, 1H), 7.99-7.84 (m, 1H), 7.18 (d, J=8.6 Hz, 1H), 6.90 (d, J=9.4 Hz, 1H), 6.35 (dd, J=8.6, 2.3 Hz, 1H), 6.17 (d, J=2.3 Hz, 1H), 5.28 (s, 2H), 3.76 (s, 3H), 3.69 (s, 4H), 2.34 (s, 4H).

Step C: 5-cyano-N-(2,4-dimethoxybenzyl)-4-fluoro-2-methyl-N-(1,2,4-thiadiazol-5-yl)benzenesulfonamide. To a mixture of 5-bromo-N-(2,4-dimethoxybenzyl)-4-fluoro-2-methyl-N-(1,2,4-thiadiazol-5-yl)benzenesulfonamide (1.4 g, 2.8 mmol) in DMF (30 mL) under N$_2$ was added dicyanozinc (0.67 g, 5.7 mmol), zinc (0.056 g, 0.85 mmol), DPPF (0.47 g, 0.85 mmol) and Pd$_2$(dba)$_3$ (0.52 g, 0.57 mmol). The reaction mixture was stirred at 110° C. for 14 h under N$_2$. The mixture was diluted H$_2$O and extracted with EtOAc. The combined organic layer was washed with brine, then dried over Na$_2$SO$_4$, filtered and concentrated to give a residue that was purified by prep-TLC (SiO$_2$, PE:EtOAc=3:1) to give the title compound. $^1$H NMR (CDCl$_3$, 400 MHz) δ 8.26 (d, J=6.3 Hz, 1H), 7.98 (s, 1H), 7.22 (d, J=8.6 Hz, 1H), 7.14 (d, J 9.0 Hz, 1H), 6.47 (d, J=2.0 Hz, 1H), 5.01 (s, 2H), 3.82 (d, J=2.7 Hz, 6H), 2.67 (s, 3H).

Intermediate 6

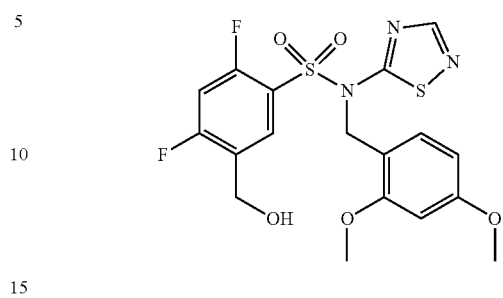

N-(2,4-dimethoxybenzyl)-2,4-difluoro-5-(hydroxymethyl)-N-(1,2,4-thiadiazol-5-yl)benzenesulfonamide Step A: N-(2,4-dimethoxybenzyl)-2,4-difluoro-N-(1,2,4-thiadiazol-5-yl)-5-vinylbenzenesulfonamide. To a mixture of 5-bromo-N-(2,4-dimethoxybenzyl)-2,4-difluoro-N-(1,2,4-thiadiazol-5-yl)benzenesulfonamide (10 g, 20 mmol) in water (80 mL) and toluene (400 mL) was added Pd(dppf)Cl$_2$ (2.9 g, 3.9 mmol), cesium carbonate (39 g, 120 mmol) and potassium trifluoro(vinyl)borate (7.9 g, 59 mmol). The mixture was stirred at 105° C. for 3 h. The mixture was cooled to 25° C., concentrated, diluted by water, and extracted by EtOAc. The organic layer was washed by sat.NaCl, dried over Na$_2$SO$_4$, filtered and concentrated to a residue that was purified by silica gel chromatography (PE:EtOAc=10/1 to 5/1) to give the title compound.

Step B: N-(2,4-dimethoxybenzyl)-2,4-difluoro-5-formyl-N-(1,2,4-thiadiazol-5-yl)benzenesulfonamide. To a solution of N-(2,4-dimethoxybenzyl)-2,4-difluoro-N-(1,2,4-thiadiazol-5-yl)-5-vinylbenzenesulfonamide (6.5 g, 14 mmol) in THF (200 mL) and water (40 mL) were added osmium(VIII) oxide (36 mL, 1.4 mmol) and 4-methylmorpholine 4-oxide (2.0 g, 17 mmol). The mixture was stirred at 20° C. for 1 h. To the stirred mixture was added sodium periodate (15 g, 72 mmol) in portions at 0° C. The mixture was stirred at 20° C. for 2 h. The mixture was filtered, and the filtrate was evaporated to a residue that was dissolved in DCM, washed by sat.Na$_2$SO$_3$, dried over Na$_2$SO$_4$, filtered and concentrated to a residue that was purified by silica gel chromatography (PE:EtOAc=5/1 to 1/1) to give the title compound.

Step C: N-(2,4-dimethoxybenzyl)-2,4-difluoro-5-(hydroxymethyl)-N-(1,2,4-thiadiazol-5-yl)benzenesulfonamide. To a suspension of N-(2,4-dimethoxybenzyl)-2,4-difluoro-5-formyl-N-(1,2,4-thiadiazol-5-yl)benzenesulfonamide (2.5 g, 5.5 mmol) in MeOH (20 mL) and THF (20 mL) was added sodium tetrahydroborate (0.21 g, 5.5 mmol) at 0° C. The reaction mixture was stirred at 0° C. for 1 h. The mixture was quenched by sat. NH$_4$Cl, concentrated. The residue was extracted dissolved in EtOAc, washed with brine, dried over Na$_2$SO$_4$, filtered and concentrated to a residue that was purified by silica gel chromatography (PE:EtOAc=5/1 to 1/1) to give the title compound. $^1$H NMR (CDCl$_3$, 400 MHz) δ 8.20 (s, 1H), 7.85 (t, J=7.9 Hz, 1H), 7.18 (d, J=8.8 Hz, 1H), 6.83 (t, J=9.4 Hz, 1H), 6.36 (dd, J=8.3, 2.2 Hz, 1H), 6.20 (d, J=2.2 Hz, 1H), 5.33 (s, 2H), 4.67 (d, J=5.3 Hz, 2H), 3.80-3.61 (m, 6H). LCMS (ES, m/z): 479.9 [M+H]$^+$.

Intermediate 7

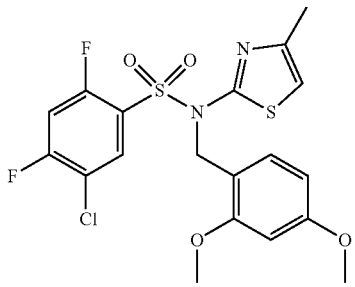 [SMILES: COc1ccc(CN(c2nc(C)cs2)S(=O)(=O)c2cc(Cl)c(F)cc2F)c(OC)c1]

5-chloro-N-(2,4-dimethoxybenzyl)-2,4-difluoro-N-(4-methylthiazol-2-yl)benzenesulfonamide Step A: (Z)-1-(2,4-dimethoxyphenyl)-N-(4-methylthiazol-2-yl)methanimine. A mixture of 4-methylthiazol-2-amine (3.4 g, 0.030 mol) and 2,4-dimethoxybenzaldehyde (5.0 g, 0.030 mol) in toluene (100 mL) was stirred at reflux for 4 h with Dean-Stark apparatus to remove water. The mixture was cooled to room temperature and concentrated in vacuo to give the title compound, which was used directly in the next step.

Step B: N-(2,4-dimethoxybenzyl)-4-methylthiazol-2-amine. To a mixture of (Z)-1-(2,4-dimethoxyphenyl)-N-(4-methylthiazol-2-yl)methanimine (crude product, 0.030 mol) in MeOH (120 mL) at 0° C. was added NaBH$_4$ (5.7 g, 0.15 mol) in small portions. After addition, the reaction was stirred at room temperature for 1 h. The reaction was quenched with water and the MeOH was evaporated in vacuo. The water phase was extracted with ethyl acetate and the combined organic layers were washed with brine, dried over Na$_2$SO$_4$, filtered and concentrated to a residue that was purified by silica gel chromatography (PE:EtOAc=5:1) to give the title compound. 1H NMR (400 MHz CDCl$_3$) δ 7.19 (d, J=8.0 Hz, 1H), 6.44 (d, J=2.4 Hz, 1H), 6.41 (dd, J=8.4, 2.4 Hz, 1H), 6.02 (s, 1H), 4.31 (s, 2H), 3.80 (s, 3H), 3.78 (s, 3H).

Step C: 5-chloro-N-(2,4-dimethoxybenzyl)-2,4-difluoro-N-(4-methylthiazol-2-yl)benzenesulfonamide. To a mixture of N-(2,4-dimethoxybenzyl)-4-methylthiazol-2-amine (1.8 g, 7.0 mmol) in THF (30 mL) at −78° C. under N$_2$ was added LiHMDS (8.4 mL, 8.4 mmol) dropwise. After addition, the mixture was stirred at room temperature for 1 h. The mixture was cooled back to −78° C., and a solution of 5-chloro-2,4-difluorobenzenesulfonyl chloride (2.1 g, 8.4 mmol) in THF (5 mL) was added dropwise. The resulting mixture was stirred at −78° C. for 2 h. The mixture was quenched with water and extracted with ethyl acetate. The combined organic layer was dried over Na$_2$SO$_4$, filtered and evaporated to a residue that was purified by silica gel chromatography (PE:EA=25:1~10:1) to give the title compound. 1H NMR (400 MHz CDCl$_3$) δ 7.94 (t, 1H), 7.21 (d, J=8.4 Hz, 1H), 7.00 (t, J=8.4 Hz, 1H), 6.56 (s, 1H), 6.34~6.40 (m, 2H), 5.15 (s, 2H), 3.76 (s, 3H), 3.73 (s, 3H), 2.26 (s, 3H).

Intermediate 8

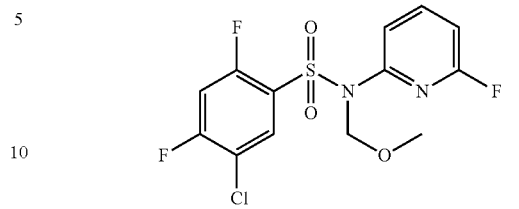

5-chloro-2,4-difluoro-N-(6-fluoropyridin-2-yl)-N-(methoxymethyl)benzene sulfonamide Step A: 5-chloro-2,4-difluoro-N-(6-fluoropyridin-2-yl)benzenesulfonamide. A mixture of 5-chloro-2,4-difluorobenzene-1-sulfonyl chloride (1.3 g, 5.3 mmol), 6-fluoropyridin-2-amine (0.59 mg, 5.3 mmol), pyridine (2.1 g, 26 mmol) and DCM (20 mL) was stirred at room temperature under nitrogen. After 16 h, the mixture was quenched by water and extracted with DCM. The combined organic layers were washed with brine, dried over Na$_2$SO$_4$, filtered and the filtrate was concentrated to give a residue that was purified by silica gel chromatography (PE:EtOAc=5:1) to give the title compound. $^1$H NMR (400 MHz CD$_3$OD) δ 8.16 (t, J=7.6 Hz, 1H), 7.75 (dd, J=16.0, 8.0 Hz, 1H), 7.34 (t, J=9.6 Hz, 1H), 6.89 (dd, J=8.0, 1.2 Hz, 1H), 6.60 (dd, J=8.0, 2.0 Hz, 1H).

Step B: Preparation of 5-chloro-2,4-difluoro-N-(6-fluoropyridin-2-yl)-N-(methoxymethyl)benzenesulfonamide. To a mixture of 5-chloro-2,4-difluoro-N-(6-fluoropyridin-2-yl)benzenesulfonamide (1.0 g, 3.0 mmol) in DCM (20 mL) was added DIEA (1.2 g, 9.0 mmol) and MOMCl (0.60 g, 7.4 mmol). The mixture was stirred at room temperature under nitrogen for 4 h. The mixture was poured into water and extracted with DCM. The combined organic layers were washed with brine, dried over Na$_2$SO$_4$, filtered and the filtrate was concentrated to a residue that was purified by silica gel chromatography (PE:EtOAc=5:1) to give the title compound. $^1$H NMR (400 MHz CD$_3$OD) δ 8.06 (t, J=7.6 Hz, 1H), 7.91 (dd, J=16.0, 8.0 Hz, 1H), 7.35-7.41 (m, 2H), 6.85 (dd, J=8.4, 2.8 Hz, 1H), 5.35 (s, 2H), 3.42 (s, 3H). LCMS (ES, m/z): 367.0 [M+H]$^+$.

Intermediate 9

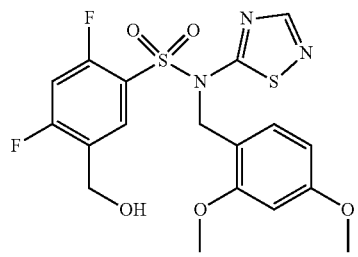 [SMILES: COc1ccc(CN(c2ncns2)S(=O)(=O)c2cc(CO)c(F)cc2F)c(OC)c1]

N-(2,4-dimethoxybenzyl)-2,4-difluoro-5-(hydroxymethyl)-N-(1,2,4-thiadiazol-5-yl)benzenesulfonamide Step A: N-(2,4-dimethoxybenzyl)-2,4-difluoro-N-(1,2,4-thiadiazol-5-yl)-5-vinylbenzenesulfonamide. To a mixture of 5-bromo-N-(2,4-dimethoxybenzyl)-2,4-difluoro-N-(1,2,4-thiadiazol-5-yl)benzenesulfonamide (10 g, 20 mmol) in water (80 mL) and toluene (400 mL) was added Pd(dppf)Cl$_2$ (2.9 g, 3.9 mmol), cesium carbonate (39 g, 120 mmol) and potassium trifluoro(vinyl)borate (7.9 g, 59 mmol). The mixture was stirred at 105° C. for 3 h. The mixture was cooled to 25° C., concentrated, diluted by water, and extracted by EtOAc. The organic layer was washed by sat.NaCl, dried over Na$_2$SO$_4$, filtered and concentrated to a residue that was purified by silica gel chromatography (PE:EtOAc=10/1 to 5/1) to give the title compound.

Step B: N-(2,4-dimethoxybenzyl)-2,4-difluoro-5-formyl-N-(1,2,4-thiadiazol-5-yl)benzenesulfonamide. To a solution of N-(2,4-dimethoxybenzyl)-2,4-difluoro-N-(1,2,4-thiadiazol-5-yl)-5-vinylbenzenesulfonamide (6.5 g, 14 mmol) in THF (200 mL) and water (40 mL) were added osmium(VIII) oxide (36 mL, 1.4 mmol) and 4-methylmorpholine 4-oxide (2.0 g, 17 mmol). The mixture was stirred at 20° C. for 1 h. To the stirred mixture was added sodium periodate (15 g, 72 mmol) in portions at 0° C. The mixture was stirred at 20° C. for 2 h. The mixture was filtered, and the filtrate was evaporated to a residue that was dissolved in DCM, washed by sat.Na$_2$SO$_3$, dried over Na$_2$SO$_4$, filtered and concentrated to a residue that was purified by silica gel chromatography (PE:EtOAc=5/1 to 1/1) to give the title compound.

Step C: N-(2,4-dimethoxybenzyl)-2,4-difluoro-5-(hydroxymethyl)-N-(1,2,4-thiadiazol-5-yl)benzenesulfonamide. To a suspension of N-(2,4-dimethoxybenzyl)-2,4-difluoro-5-formyl-N-(1,2,4-thiadiazol-5-yl)benzenesulfonamide (2.5 g, 5.5 mmol) in MeOH (20 mL) and THF (20 mL) was added sodium tetrahydroborate (0.21 g, 5.5 mmol) at 0° C. The reaction mixture was stirred at 0° C. for 1 h. The mixture was quenched by sat. NH$_4$Cl, concentrated. The residue was extracted dissolved in EtOAc, washed with brine, dried over Na$_2$SO$_4$, filtered and concentrated to a residue that was purified by silica gel chromatography (PE:EtOAc=5/1 to 1/1) to give the title compound. $^1$H NMR (CDCl$_3$, 400 MHz) δ 8.20 (s, 1H), 7.85 (t, J=7.9 Hz, 1H), 7.18 (d, J=8.8 Hz, 1H), 6.83 (t, J=9.4 Hz, 1H), 6.36 (dd, J=8.3, 2.2 Hz, 1H), 6.20 (d, J=2.2 Hz, 1H), 5.33 (s, 2H), 4.67 (d, J=5.3 Hz, 2H), 3.80-3.61 (m, 6H). LCMS (ES, m/z): 479.9 [M+Na]$^+$.

Intermediate 10

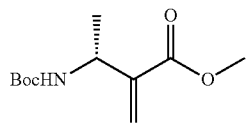 [SMILES: C=C(C(=O)OC)[C@@H](C)NC(=O)OC(C)(C)C]

methyl (R)-3-((tert-butoxycarbonyl)amino)-2-methylenebutanoate

Step A: (Chloromethyl)(methyl)sulfane. To a solution of (methylsulfanyl)methane (0.83 kg, 13 mol) in dichloromethane (8 L) under an inert atmosphere of nitrogen was added sulfurooyl dichloride (1.7 kg, 14 mol) dropwise with stirring at 40° C. over 1 hour. The resulting solution was stirred for 3 h at 40° C. The reaction mixture was cooled to 25° C. and purified by distillation under reduced pressure (10 mm Hg; fraction collected at 50-60° C.) gave the title compound.

Step B: Methyl (3R)-3-[[(tert-butoxy)carbonyl]amino]-2-[(methylsulfanyl)methyl]butanoate. To a solution of diisopropylamine (1.2 kg, 11 mol) in tetrahydrofuran (15 L) under an inert atmosphere of nitrogen at −60° C. was added a solution of n-BuLi (0.71 kg, 11 mol) in Hexane (4.4 L) dropwise with stirring at −60° C. over 20 min. The mixture was stirred at −40° C. for 1 h. To this mixture was added a solution of methyl (3S)-3-[[(tert-butoxy)carbonyl]amino]butanoate (1.0 kg, 4.6 mol) in tetrahydrofuran (1.0 L) dropwise at −78° C. over 30 min. The reaction mixture was then stirred at −78° C. for 1 h. To a solution of NaI (1.7 kg, 11.4 mol) in ethylene glycol dimethyl ether (15 L) under an inert atmosphere of nitrogen in a separate flask was added chloro(methylsulfanyl)methane (1.1 kg, 11 mol) in portions at 25° C. in 30 min. The resulting mixture was stirred for 1 h at 25° C. then was added slowly to the former mixture at −78° C. The combined mixture was maintained at −78° C. to −30° C. for 4 h with stirring. The mixture was washed with NH$_4$Cl and extracted with dichloromethane. The combined organic layers were washed with 1N hydrogen chloride, sodium bicarbonate, sodium sulfite and sodium chloride. The organic layer was dried over anhydrous sodium sulfate, filtered and concentrated under vacuum to a residue that was purified via silica gel chromatography (ethyl acetate/PE 1:10) to give the title compound.

Step C: Methyl (3R)-3-[[(tert-butoxy)carbonyl]amino]-2-(methanesulfinylmethyl)butanoate To a solution of methyl (3R)-3-[[(tert-butoxy)carbonyl]amino]-2-[(methylsulfanyl)methyl]butanoate (1.0 kg, 3.6 mol) in ethanol (20 L) under an inert atmosphere of nitrogen was added peroxol (4.9 kg, 144 mol). The mixture was stirred for 30 min at 25° C. The mixture was diluted with DCM and H$_2$O, then extracted with dichloromethane. The combined organic layers were washed with Na$_2$SO$_3$, sodium chloride, dried over anhydrous sodium sulfate, filtered and concentrated under vacuum to a residue that was purified via silica gel chromatography (ethyl acetate) to give the title compound.

Step D: Methyl (3R)-3-[[(tert-butoxy)carbonyl]amino]-2-methylidenebutanoate A solution of methyl (3R)-3-[[(tert-butoxy)carbonyl]amino]-2-(methanesulfinylmethyl)butanoate (600 g, 2.0 mol) in pyridine (30 L) under an inert atmosphere of nitrogen was stirred at 85° C. for 16 h. The mixture was concentrated under vacuum and diluted with ethyl acetate. The organic layer was washed with water, 1N hydrogen chloride, sodium bicarbonate, then sodium chloride. The organic layer was dried over anhydrous sodium sulfate, filtered and concentrated to a residue that was purified via silica gel chromatography (ethyl acetate/PE 1:20) to give the title compound.

Intermediate 11

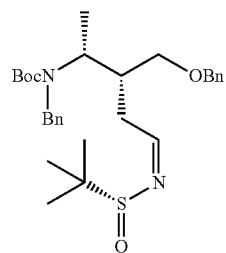 [SMILES: C[C@H]([C@@H](C/C=N\[S@](=O)C(C)(C)C)COCc1ccccc1)N(Cc1ccccc1)C(=O)OC(C)(C)C]

Tert-butyl benzyl((2R,3R,Z)-3-((benzyloxy)methyl)-5-(((R)-tert-butylsulfinyl)imino)pentan-2-yl)carbamate Step A: Benzyl[(1R)-1-phenylethyl]amine. To a solution of (1R)-1-phenylethan-1-amine (2.1 kg, 17 mol) in tetrahydrofuran (21 L) under an inert atmosphere of nitrogen was added benzaldehyde (1.8 kg, 17 mol) followed by the addition of acetic acid (acetyloxy)(sodio)boranyl acetate (7.4 kg, 35 mol), in portions at 0° C. The resulting mixture was stirred for 4 h at 25° C. The reaction was then quenched by the addition of of water and extracted with dichloromethane. The combined organic layers were washed with sodium chloride, dried over anhydrous sodium sulfate, filtered, concentrated in vacuo to give the title compound.

Step B: (3R)-3-[benzyl[(1R)-1-phenylethyl]amino]butanoate. To a solution of benzyl[(1R)-1-phenylethyl]amine (3.0 kg, 14 mol) in tetrahydrofuran (30 L) under an inert atmosphere of nitrogen with stirring at −78° C. was added butyllithium (5.8 L, 14 mol) dropwise. To this mixture was added a solution of methyl (2E)-but-2-enoate (1.7 kg, 17 mol) in tetrahydrofuran (1.7 L) dropwise with stirring at −78° C. The resulting mixture was stirred for 2 h at −78° C. The reaction was then quenched by the addition of satd.NH$_4$Cl and extracted with ethyl acetate. The combined organic layers were washed with sodium chloride, dried over anhydrous sodium sulfate, filtered, concentrated under vacuum to give the title compound.

Step C: Methyl (3R)-3-aminobutanoate. To a solution of methyl (3R)-3-[benzyl[(1R)-1-phenylethyl]amino]butanoate (3.4 kg, 11 mol) in methanol (34 L) under an inert atmosphere of nitrogen was added palladiumdiol (0.34 kg, 0.24 mol). The resulting solution was stirred overnight at 25° C. The solids were filtered out and the filtrate was concentrated under vacuum to give the title compound.

Step D: Methyl (3R)-3-[[(tert-butoxy)carbonyl]amino]butanoate. To a solution of methyl (3R)-3-aminobutanoate (0.99 kg, 8.5 mol) in tetrahydrofuran/H$_2$O=3:1 (14 L) under an inert atmosphere of nitrogen was added sodium carbonate (2700 g, 25.47 mol, 3.00 equiv) followed by a solution of di-tert-butyl dicarbonate (2780 g, 12.74 mol, 1.50 equiv) in tetrahydrofuran (3.3 mL). The resulting mixture was stirred overnight at 25° C. The mixture was diluted with ethyl acetate, washed with sodium chloride, dried over anhydrous sodium sulfate and concentrated under vacuum to a residue that was purified via silica gel chromatography (ethyl acetate/PE 1:50) to give the title compound.

Step E: methyl (R)-2-((R)-1-((tert-butoxycarbonyl)amino)ethyl)pent-4-enoate. To a solution of methyl (3R)-3-[[(tert-butoxy)carbonyl]amino]butanoate (1.1 kg, 4.3 mol) in tetrahydrofuran (16 L) under an inert atmosphere of nitrogen at −78° C. was added LiHMDS (16 L, 13 mol) dropwise with stirring for 30 min at −78° C. To this mixture was added 3-bromoprop-1-ene (0.77 kg, 5.6 mol) dropwise with stirring for 30 min at −78° C. The resulting mixture was stirred for 5 h at −20° C. The mixture was then quenched by the addition of NH$_4$Cl and extracted with ethyl acetate. The combined organic layers were dried over Na$_2$SO$_4$ and concentrated under vacuum to a residue that was purified via silica gel chromatography (ethyl acetate/PE 1:30) to give the title compound.

Step F: Tert-butyl ((2R,3R)-3-(hydroxymethyl)hex-5-en-2-yl)carbamate. To a stirred solution of LiAlH$_4$ (1.591 g, 41.9 mmol) in THF (80 mL) was added methyl methyl (R)-2-((R)-1-((tert-butoxycarbonyl)amino)ethyl)pent-4-enoate (8.3 g, 32.3 mmol), THF (20 mL) at 0° C. under N$_2$. The reaction mixture was stirred for 2 h at 0° C. The reaction mixture was quenched with 1.6 mL of water, 1.6 mL of 15% NaOH and 4.8 mL of water, dried over Na$_2$SO$_4$, filtered and the filtrate was concentrated to afford the title compound, which was used for the next step without purification. $^1$H NMR (CDCl$_3$, 400 MHz) δ 5.89-5.73 (m, 1H), 5.13-4.99 (m, 2H), 4.85 (d, J=7.8 Hz, 1H), 3.77-3.65 (m, 2H), 3.60-3.51 (m, 1H), 2.27-2.11 (m, 2H), 1.43 (s, 9H), 1.21-1.14 (m, 3H).

Step G: Tert-butyl benzyl((2R,3R)-3-((benzyloxy)methyl)hex-5-en-2-yl)carbamate. To a solution of tert-butyl ((2R,3R)-3-(hydroxymethyl)hex-5-en-2-yl)carbamate (7 g, 30.5 mmol) in DMF (150 mL) was added NaH (3.66 g, 92 mmol) at 0° C. The mixture was stirred at 0° C. for 0.5 h. Then (bromomethyl) benzene (14.50 mL, 122 mmol) was added to the mixture, the reaction mixture was stirred at 25° C. for 12 h. The mixture was filtered and concentrated in vacuo. The crude product was purified by chromatography (SiO$_2$, PE:EtOAc=10:1) to give the title compound. LCMS (ES, m/z): 410.3 [M+H]$^+$.

Step H: Tert-butyl benzyl((2R,3R)-3-((benzyloxy)methyl)-5-oxopentan-2-yl)carbamate. To a solution of tert-butyl benzyl((2R,3R)-3-((benzyloxy)methyl)hex-5-en-2-yl)carbamate (1 g, 2.442 mmol) in THF (10 mL) and Water (5 mL) were added NMO (0.429 g, 3.66 mmol), 2-methylpropan-2-ol (9.05 mg, 0.122 mmol) and osmium tetroxide (0.038 mL, 0.122 mmol). The reaction mixture was stirred for 1 h at 25° C. sodium periodate (1.389 g, 6.49 mmol) was added the mixture. The reaction mixture was stirred for 0.5 h at 25° C. The reaction mixture was filtered through celite and washed with EtOAc (50 mL). The filtrate was washed with brine (15 mL) and dried over Na$_2$SO$_4$. Solvent was removed in vacuo to give the title compound, which was used in the next step without further purification. LCMS (ES, m/z): 412.2 [M+H]$^+$.

Step I: Tert-butyl benzyl((2R,3R,Z)-3-((benzyloxy)methyl)-5-(((R)-tert-butylsulfinyl)imino)pentan-2-yl)carbamate. A mixture of tert-butyl benzyl((2R,3R)-3-((benzyloxy)methyl)-5-oxopentan-2-yl)carbamate (7.7 g, 13.10 mmol), (R)-2-methylpropane-2-sulfinamide (3.97 g, 32.7 mmol) and tetraethoxytitanium (7.47 g, 32.7 mmol) in THF (150 mL) was stirred at 50° C. for 12 h. The mixture was diluted by water (50 mL), extracted by EtOAc (2×150 mL), the organic layer was washed with water (50 mL), brine (50 mL), dried over Na$_2$SO$_4$, filtered and the filtrate was concentrated in vacuo to give a residue which was purified by column chromatography on silica gel (PE:EtOAc=10:1) to give the title compound. LCMS (ES, m/z): 537.3 [M+H]$^+$.

Intermediate 12

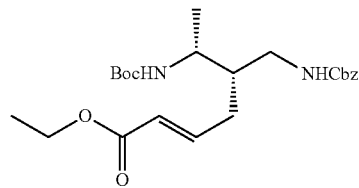 [SMILES: CCOC(=O)/C=C/C[C@@H](CNC(=O)OCc1ccccc1)[C@@H](C)NC(=O)OC(C)(C)C]

Ethyl (5S,6R,E)-5-((((benzyloxy)carbonyl)amino)methyl)-6-((tert-butoxycarbonyl)amino)hept-2-enoate Step A: Tert-butyl N-[(2R,3R)-4-hydroxy-3-(prop-2-en-1-yl)butan-2-yl]carbamate. To a solution of methyl (2R)-2-

[(1R)-1-[[(tert-butoxy)carbonyl]amino]ethyl]pent-4-enoate (0.52 kg, 2.0 mol) in tetrahydrofuran (10 L) under an inert atmosphere of nitrogen was added LAH (116 g, 3.0 equiv) dropwise with stirring at 0° C. The resulting mixture was stirred for 2 h at 0° C. The mixture was then quenched by the addition of water (0.2 L), 15% NaOH (0.2 L), then water (0.2 L). The solids were then filtered away and the filtrate was dried over anhydrous sodium sulfate and concentrated under vacuum to a residue that was purified via silica gel chromatography (ethyl acetate/PE 1:10) to give the title compound.

Step B: Tert-butyl N-[(2R,3S)-3-[(1,3-dioxo-2,3-dihydro-1H-isoindol-2-yl)methyl]hex-5-en-2-yl]carbamate. To a solution of tert-butyl N-[(2R,3R)-4-hydroxy-3-(prop-2-en-1-yl)butan-2-yl]carbamate (0.40 kg, 1.7 mol) in tetrahydrofuran (8 L) under an inert atmosphere of nitrogen was added PPh₃ (0.72 kg, 2.6 mol), DIAD (0.92 kg, 3.9 mol) and 2,3-dihydro-1H-isoindole-1,3-dione (0.26 kg, 1.7 mol). The mixture was stirred for 2 h at room temperature. The mixture was extracted with ethyl acetate and the combined organic layers were washed with sodium chloride and dried over Na₂SO₄. The residue was purified via silica gel chromatography (ethyl acetate/PE 1:15) to give the title compound.

Step C: Tert-butyl ((2R,3S)-3-(aminomethyl)hex-5-en-2-yl)carbamate. To a solution of tert-butyl ((2R,3S)-3-((1,3-dioxoisoindolin-2-yl)methyl)hex-5-en-2-yl)carbamate (0.34 kg, 0.94 mol) in ethanol (4 L) and water (0.8 L) was added hydrazine hydrate (0.30 L, 1.9 mol). The mixture was heated at 60° C. for 2 h. The mixture was cooled, diluted with EtOAc and the solids were filtered off. The filtrate was concentrated and re-dissolved in DCM. The organic layer washed with sat. NaHCO₃, water, brine, dried over MgSO₄, filtered and concentrated to the title compound.

Step D: Benzyl tert-butyl ((2S,3R)-2-allylbutane-1,3-diyl)dicarbamate. To a solution of tert-butyl ((2R,3S)-3-(aminomethyl)hex-5-en-2-yl)carbamate (240 g crude) and DIEA (0.64 L, 3.3 mol) in tetrahydrofuran (2.4 L) at 0° C. was added benzyl carbonochloridate (0.225 L, 1.4 mol) slowly under N₂. The mixture was warmed to r.t and stirred for 1 h. The mixture was cooled to 0° C., quenched with water and diluted with EtOAc. The organic layer was washed with water, brine, and dried over MgSO₄. The residue was purified via silica gel chromatography (ethyl acetate/PE 1:20) to give the title compound.

Step E: Ethyl (5S,6R)-5-((((benzyloxy)carbonyl)amino)methyl)-6-((tert-butoxycarbonyl)amino)hept-2-enoate. To a solution of benzyl tert-butyl ((2S,3R)-2-allylbutane-1,3-diyl)dicarbamate (0.23 kg, 0.64 mol) in dry CH₂Cl₂ (2.6 L) under nitrogen atmosphere was added ethyl acrylate (0.32 kg, 3.2 mol) and the (1,3-Bis(2,4,6-trimethylphenyl)-2-imidazolidinylidene)dichloro(phenylmethylene)(tricyclohexylphosphine)ruthenium (0.14 kg, 0.16 mol). The mixture was stirred overnight at room temperature. The mixture was purified via silica gel chromatography (ethyl acetate/PE 1:20) to give the title compound. LCMS (ES, m/z): 457 [M+Na]⁺. ¹H NMR (300 MHz, Methanol-d4, ppm): δ 7.40-7.26 (m, 5H), 6.99 (dt, J=15.1, 7.4 Hz, 1H), 5.90 (d, J=15.5 Hz, 1H), 5.04 (s, 2H), 4.17 (q, J=7.1 Hz, 2H), 3.70 (d, J=7.1 Hz, 1H), 3.24 (dd, J=13.7, 5.6 Hz, 1H), 3.07 (dd, J=13.9, 7.1 Hz, 1H), 2.32 (dt, J=13.6, 6.4 Hz, 1H), 2.17 (dt, J=14.8, 7.5 Hz, 1H), 1.91-1.83 (m, 1H), 1.45 (s, 9H), 1.28 (t, J=7.1 Hz, 4H), 1.12 (d, J=6.9 Hz, 3H).

Intermediate 13

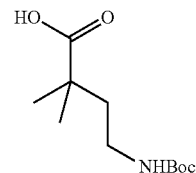

4-((tert-butoxycarbonyl)amino)-2,2-dimethylbutanoic Acid

Step A: Tert-butyl 3,3-dimethyl-2-oxopyrrolidine-1-carboxylate. To a solution of tert-butyl 2-oxopyrrolidine-1-carboxylate (25 g, 135 mmol) in THF (300 mL) was added LiHMDS (351 mL, 351 mmol) at −78° C., and then it was stirred for 1 h at −78° C. under N₂. Then MeI (50.6 mL, 810 mmol) was added to the solution and it was stirred for 12 h at 25° C. The reaction was quenched with sat. NH₄Cl (200 mL) and extracted with EtOAc (3×200 mL). The combined organic layers were washed with brine (300 mL), dried over Na₂SO₄, filtered and the filtrate was concentrated to give the title compound, which was used in the next step directly without further purification.

Step B: 4-((tert-butoxycarbonyl)amino)-2,2-dimethylbutanoic acid. To a solution of tert-butyl 3,3-dimethyl-2-oxopyrrolidine-1-carboxylate (8.2 g, 38.4 mmol) in THF (38.4 ml) and EtOH (38.4 ml) was added 4M NaOH (48.1 ml, 192 mmol) at ambient temperature, and then it was stirred for 16 hours at ambient temperature. Acidified to pH 3.5 using 1M HCl. Extracted with EtOAc (3×200 mL). The combined organic layers were washed with brine (30 mL), dried over Na₂SO₄, filtered and the filtrate was concentrated to afford 4-((tert-butoxycarbonyl)amino)-2,2-dimethylbutanoic acid (INTERMEDIATE 13), which was used in the next step without further purification. LCMS (ES, m/z): 232.1 [M+H]⁺.

Intermediates 14A, 14 B

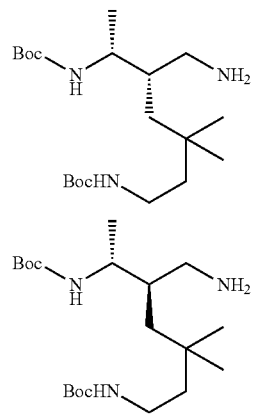

Intermediate 14A: Di-tert-butyl ((5S,6R)-5-(aminomethyl)-3,3-dimethylheptane-1,6-diyl)dicarbamate Intermediate 14B: Di-tert-butyl ((5R,6R)-5-(aminomethyl)-3,3-dimethylheptane-1,6-diyl)dicarbamate Step A: Tert-butyl (4-(methoxy(methyl)amino)-3,3-dimethyl-4-oxobutyl)carbamate. To a solution of INTERMEDIATE 13 (29 g, 125 mmol) and HATU (71.5 g, 188 mmol) in DMF (300 mL) was added N,O-dimethylhydroxylamine hydrochloride (18.35 g, 188 mmol) and DIPEA (109 mL, 627 mmol) at 0° C., and then the mixture was stirred for 24 h at 25° C. under $N_2$. The mixture was concentrated in vacuo. The residue was diluted with EtOAc (200 mL) and washed with 1N HCl (2×20 mL), brine (10 mL), dried over $Na_2SO_4$, filtered and the filtrate was concentrated. The residue was purified by column chromatography ($SiO_2$, PE:EtOAc=5:1) to afford the title compound. LCMS (ES, m/z): 275.2 $[M+H]^+$. $^1$H NMR (400 MHz, $CDCl_3$) δ 4.67 (brs, 1H), 3.66 (s, 3H), 3.15-3.10 (m, 5H), 1.80 (t, J=7.2 Hz, 2H), 1.40 (s, 9H), 1.23 (s, 6H).

Step B: Tert-butyl benzyl(4-(methoxy(methyl)amino)-3,3-dimethyl-4-oxobutyl)carbamate. To a solution of Tert-butyl (4-(methoxy(methyl)amino)-3,3-dimethyl-4-oxobutyl)carbamate (15 g, 54.7 mmol) in DMF (150 mL) at 0° C. was added NaH (4.37 g, 109 mmol) and the mixture was stirred for 0.5 h. Then BnBr (9.75 mL, 82 mmol) was added and the mixture was stirred at 25° C. for 12 h. Then the mixture was quenched by addition of 1N HCl (100 mL), extracted with EtOAc (2×100 mL). The organic layers were washed with water (3×30 mL) and brine (30 mL), dried over $Na_2SO_4$, filtered and the filtrate was concentrated in vacuo. The residue was purified by column chromatography ($SiO_2$, PE:EtOAc=10:1) to afford the title compound. $^1$H NMR (400 MHz, $CDCl_3$) δ 7.26-7.23 (m, 5H), 4.05 (brs, 2H), 3.64 (s, 3H), 3.15-3.05 (m, 5H), 1.80 (brs, 2H), 1.57-1.45 (m, 9H), 1.21 (s, 6H).

Step C: Tert-butyl benzyl(3,3-dimethyl-4-oxobutyl)carbamate. To a stirred solution of $LiAlH_4$ (1.562 g, 41.2 mmol) in THF (200 mL) was added tert-butyl benzyl(4-(methoxy(methyl)amino)-3,3-dimethyl-4-oxobutyl)carbamate (15 g, 41.2 mmol) at 0° C. under $N_2$. The reaction mixture was stirred for 2 h at 0° C. The reaction mixture was quenched with 1 M HCl (10 mL) and dried over $Na_2SO_4$, filtered and the filtrate was concentrated. The residue was purified by column chromatography ($SiO_2$, PE:EtOAc=20:1) to afford the title compound.

Step D: Methyl 6-(benzyl(tert-butoxycarbonyl)amino)-2-((R)-1-((tert-butoxycarbonyl)amino)ethyl)-3-hydroxy-4,4-dimethylhexanoate. To a stirred solution of (R)-methyl 3-((tert-butoxycarbonyl)amino)butanoate (8 g, 36.8 mmol) in THF (200 mL) was added a solution of LDA (46.0 mL, 92 mmol) at −78° C. under $N_2$ atmosphere. After being stirred for 1 h at −78° C., the solution of tert-butyl benzyl (3,3-dimethyl-4-oxobutyl)carbamate (11.25 g, 36.8 mmol) in THF (20 mL) was added to above solution and stirred for 5 h at the same temperature. The mixture was quenched with sat. $NH_4Cl$ (50 mL) and extracted with EA (3×100 mL). The combined organic layers were washed with brine (40 mL), dried over $Na_2SO_4$, filtered and the filtrate was concentrated. The residue was purified by column chromatography ($SiO_2$, PE:EtOAc=5:1 to 3:1) to afford the title compound.

Step E: Methyl (R,Z)-6-(benzyl(tert-butoxycarbonyl)amino)-2-(1-((tert-butoxycarbonyl)amino)ethyl)-4,4-dimethylhex-2-enoate. To a stirred solution of methyl 6-(benzyl (tert-butoxycarbonyl)amino)-2-((R)-1-((tert-butoxycarbonyl)amino)ethyl)-3-hydroxy-4,4-dimethylhexanoate (17 g, 32.5 mmol) in toluene (200 mL) was added Burgess reagent (15.50 g, 65.1 mmol) at 25° C. under $N_2$ atmosphere. And then it was stirred for 4 h at 70° C. The reaction mixture was concentrated and the residue was purified by column chromatography ($SiO_2$, PE:EtOAc=10:1) to afford the title compound.

Step F: Methyl 6-(benzyl(tert-butoxycarbonyl)amino)-2-((R)-1-((tert-butoxycarbonyl)amino)ethyl)-4,4-dimethylhexanoate. A mixture of methyl (R,Z)-6-(benzyl(tert-butoxycarbonyl)amino)-2-(1-((tert-butoxycarbonyl)amino)ethyl)-4,4-dimethylhex-2-enoate (6.6 g, 13.08 mmol) and Pd—C (1.392 g, 1.308 mmol) in MeOH (100 mL) was stirred under $H_2$ (50 psi) at 25° C. for 12 h. The mixture was filtered and the filtrate was concentrated to give the title compound, which was used for the next step without further purification. LCMS (ES, m/z): 507.4 $[M+H]^+$.

Step G: Tert-butyl benzyl((6R)-6-((tert-butoxycarbonyl)amino)-5-(hydroxymethyl)-3,3-dimethylheptyl)carbamate. To a stirred solution of $LiAlH_4$ (0.989 g, 26.1 mmol) in THF (90 mL) was added methyl 6-(benzyl(tert-butoxycarbonyl)amino)-2-((R)-1-((tert-butoxycarbonyl)amino)ethyl)-4,4-dimethylhexanoate (6.6 g, 13.03 mmol) in THF (10 mL) at 0° C. under $N_2$. The reaction mixture was stirred for 1 h at 0° C., then warmed to rt (25° C.) and stirred for 2 h. The reaction mixture was quenched with 1 mL of water, 1 mL of 15% NaOH and 3 mL of water, dried over $Na_2SO_4$, filtered and the filtrate was concentrated to afford the title compound, which was used in the next step without further purification.

Step H: Di-tert-butyl ((6R)-5-(hydroxymethyl)-3,3-dimethylheptane-1,6-diyl)dicarbamate. To a solution of THF (35 mL) and liquid $NH_3$ (80 mL) was added Na (3.00 g, 130 mmol) at −78° C. After 10 min, a solution of tert-butyl benzyl((6R)-6-((tert-butoxycarbonyl)amino)-5-(hydroxymethyl)-3,3-dimethylheptyl)carbamate (6.24 g, 13.04 mmol) in THF (5 mL) was added to the dark blue mixture. The mixture was stirred for 1 h at this temperature. The reaction was quenched by addition of sat. $NH_4Cl$ (100 mL). The mixture was concentrated to remove $NH_3$, extracted with EtOAc (3×100 mL). The combined organic layers were washed with brine (20 mL), dried with $Na_2SO_4$, filtered and concentrated in vacuo. The residue was purified by column chromatography (PE:EtOAc=4:1 to 2:1) on silica gel to give Peak 1, Isomer 1 (less polar on TLC) Peak 2, Isomer 2 (more polar on TLC). Isomer 1: $^1$H NMR (400 MHz, $CDCl_3$) δ 4.54-4.48 (m, 2H), 4.16-4.10 (m, 1H), 3.59-3.55 (m, 1H), 3.24 (t, J=11.2 Hz, 1H), 3.13 (brs, 2H), 1.64 (brs, 2H), 1.45 (s, 18H), 1.40-1.38 (m, 3H), 1.13 (d, J=6.8 Hz, 3H), 0.89 (s, 6H). Isomer 2: $^1$H NMR (400 MHz, $CDCl_3$) δ 4.84-4.81 (m, 1H), 4.47-4.45 (m, 1H), 3.75-3.43 (m, 3H), 3.17-3.08 (m, 2H), 1.49-1.37 (m, 23H), 1.14 (d, J=6.4 Hz, 3H), 0.89 (s, 6H).

Step I: Di-tert-butyl ((6R)-5-((1,3-dioxoisoindolin-2-yl)methyl)-3,3-dimethylheptane-1,6-diyl)dicarbamate. To a stirred solution of Isomer 2, Step H (1.969 g, 13.38 mmol) and $Ph_3P$ (3.51 g, 13.38 mmol) in THF (60 mL) was added DIAD (2.60 mL, 13.38 mmol) and then it was stirred for 16 h at 25° C. under $N_2$. The mixture was concentrated in vacuo. The residue was purified by column chromatography on silica gel (PE:EtOAc=5:1 to 2:1) to give the title compound, which was used in the next step without further purification. LCMS (ES, m/z): 518.3 $[M+H]^+$.

Step J: INTERMEDIATE 14A. To a solution of di-tert-butyl ((6R)-5-((1,3-dioxoisoindolin-2-yl)methyl)-3,3-dimethylheptane-1,6-diyl)dicarbamate (4.1 g, 4.75 mmol) in EtOH (80 mL) was added hydrazine (2 mL, 54.2 mmol). Then the mixture was stirred at 80° C. for 2 h. Lots of white solid were formed during the reaction. The mixture was cooled to room temperature and filtered. The filtrate was concentrated in vacuo. The residue was purified by column chromatography on silica gel (DCM:MeOH=10:1) to give the title compound. LCMS (ES, m/z): 388.2 [M+H]$^+$. $^1$H NMR (400 MHz, CDCl$_3$) δ 5.59 (d, J=7.6 Hz, 1H), 4.55 (brs, 1H), 3.80 (brs, 1H), 3.14-3.10 (m, 2H), 2.90 (dd, J=13.2, 3.6 Hz, 1H), 2.69-2.64 (m, 1H), 1.60 (brs, 1H), 1.44 (s, 20H), 1.27 (d, J=12.6 Hz, 1H), 1.14-1.10 (m, 4H), 0.91 (s, 6H).

Intermediate 14B was prepared according to the procedure of Intermediate 14 A starting with Isomer 1 from Step H. $^1$H NMR (400 MHz, CDCl$_3$) δ 5.23 (d, J=8.8 Hz, 1H), 4.59 (brs, 1H), 3.92 (brs, 1H), 3.14-3.10 (m, 2H), 2.73 (d, J=9.6 Hz, 1H), 2.61-2.55 (m, 1H), 1.53-1.38 (m, 22H), 1.10 (d, J=6.4 Hz, 3H), 1.10-1.09 (m, 1H), 0.91 (s, 6H).

Intermediates 15A, 15B, 15C

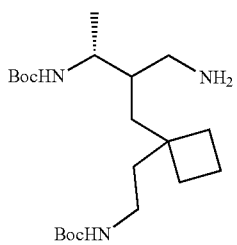 [SMILES: C[C@@H](NC(=O)OC(C)(C)C)C(CN)CC1(CCNC(=O)OC(C)(C)C)CCC1]

Tert-butyl ((2R)-4-amino-3-((1-(2-((tert-butoxycarbonyl)amino)ethyl)cyclobutyl)methyl)butan-2-yl) carbamate Step A: Ethyl 1-(2-(benzyloxy)ethyl)cyclobutane-1-carboxylate. To a solution of ethyl cyclobutanecarboxylate (5 g, 39.0 mmol) in THF (10 mL) was added LDA (21.46 mL, 42.9 mmol) in THF (40 mL) at −78° C. under N$_2$. The mixture was stirred at −78° C. for 20 min under N$_2$ at 0° C. ((2-bromoethoxy)methyl)benzene (9.23 g, 42.9 mmol) in THF (10 mL) was added dropwise slowly at −78° C. under N$_2$. Then the reaction mixture was gradually warmed to 21° C. for 16 h. The reaction was quenched by saturated NH$_4$Cl (50 mL), and extracted by EtOAc (2×100 mL). The organic layer was dried over Na$_2$SO$_4$, then filtered and concentrated to give a residue which was purified by column chromatography (SiO$_2$, PE:EtOAc=50:1~30:1) to give the title compound. $^1$H NMR (CD$_3$OD, 400 MHz) □ 7.30-7.20 (m, 5H), 4.38 (s, 2H), 4.05-3.99 (m, 2H), 3.38 (m, J=6.8 Hz, 2H), 2.39-2.33 (m, 2H), 2.07 (m, J=6.7 Hz, 2H), 1.91-1.83 (m, 4H), 1.13 (m, J=7.0 Hz, 3H).

Step B: (1-(2-(Benzyloxy)ethyl)cyclobutyl)methanol. To a mixture of LiAlH$_4$ (1.15 g, 30.3 mmol) in THF (60 mL) was added ethyl 1-(2-(benzyloxy)ethyl)cyclobutane-1-carboxylate (5.3 g, 20.20 mmol) in THF (10 mL) at 0° C. under N$_2$. Then the mixture was stirred at 0° C. for 0.5 h under N$_2$. The mixture was quenched by water (1.2 mL), 15% NaOH (1.2 mL) and water (3.6 mL), dried over MgSO$_4$. The mixture was stirred at 25° C. for 10 min and filtered. The filtrate was concentrated to purified by silical gel column (PE:EtOAc=5:1) to give the title compound. $^1$H NMR (CD$_3$OD, 400 MHz) □ 7.40-7.29 (m, 5H), 4.53 (s, 2H), 3.59-3.51 (m, 4H), 1.93-1.81 (m, 6H), 1.76-1.70 (m, 2H).

Step C: 1-(2-(Benzyloxy)ethyl)cyclobutane-1-carbaldehyde. To a solution of (1-(2-(benzyloxy)ethyl)cyclobutyl) methanol (10 g, 45.4 mmol) in 200 mL DCM was added DMP (28.9 g, 68.1 mmol) at 0° C. Then the mixture was stirred at 0° C. for 6 h. The reaction was quenched with Na$_2$SO$_3$ (500 mg) and filtered. The residue was purified by column chromatography on silica gel (PE:EtOAc=10:1) to give the title compound. $^1$H NMR (CDCl$_3$, 400 MHz) δ 9.56 (s, 1H), 7.49-7.06 (m, 5H), 4.39 (s, 2H), 3.40 (t, J=6.1 Hz, 2H), 2.39-2.23 (m, 2H), 2.13-2.02 (m, 2H), 1.98-1.74 (m, 4H).

Step D: Methyl (3R)-2-((1-(2-(benzyloxy)ethyl)cyclobutyl)(hydroxy)methyl)-3-((tert-butoxycarbonyl)amino)butanoate. To a stirred solution of LDA (34.5 mL, 69.0 mmol) in THF (30 mL) was added the solution of (R)-methyl 3-((tert-butoxycarbonyl)amino)butanoate (6 g, 27.6 mmol) in THF (60 mL) at −78° C. under argon atmosphere. After being stirred for 1 h at −78° C., the solution of 1-(2-(benzyloxy)ethyl)cyclobutane-1-carbaldehyde (6.03 g, 27.6 mmol) in THF (60 mL) was added to above solution and stirred for 5 h at the same temperature. The reaction was quenched with sat. NH$_4$Cl (100 mL) and extracted with EtOAc (3×100 mL). The combined organic layers were washed with brine (100 mL), dried over Na$_2$SO$_4$, filtered and the filtrate was concentrated. The residue was purified by column chromatography (SiO$_2$, PE:EtOAc=5:1) to afford the title compound.

Step E: Methyl (R,Z)-2-((1-(2-(benzyloxy)ethyl)cyclobutyl)methylene)-3-((tert-butoxycarbonyl)amino)butanoate. To a solution of methyl (3R)-2-((1-(2-(benzyloxy) ethyl)cyclobutyl)(hydroxy)methyl)-3-((tert-butoxycarbonyl)amino)butanoate (9.8 g, 22.50 mmol) in Toluene (100 mL) was added Burgess reagent (26.8 g, 113 mmol) and 4 A MS (10 g) under N$_2$, and the resulting suspension was stirred at 80° C. for 12 h. The mixture was filtered, and the filtration was concentrated by vacuum to give a residue and purified by column chromatography on silic gel (PE:EtOAc=20:1) to afford the title compound and (3R)-methyl 2-(2-(2-(benzyloxy)ethyl) cyclopent-1-en-1-yl)-3-((tert-butoxycarbonyl)amino)butanoate and a mixture of both. Title Compound: LCMS (ES, m/z): 418.2 [M+H]$^+$. $^1$H NMR (CDCl$_3$, 400 MHz) δ 7.30-7.20 (m, 5H), 6.76-6.67 (m, 1H), 5.73-5.61 (m, 1H), 4.65-4.54 (m, 1H), 4.49-4.39 (m, 1H), 4.38-4.27 (m, 2H), 3.63 (s, 3H), 3.50-3.39 (m, 2H), 2.29-2.22 (m, 1H), 2.20-2.07 (m, 4H), 2.06-1.99 (m, 1H), 1.96-1.90 (m, 1H), 1.80-1.74 (m, 1H), 1.50-1.29 (m, 9H), 1.24 (d, J=6.7 Hz, 3H). (3R)-methyl 2-(2-(2-(benzyloxy) ethyl) cyclopent-1-en-1-yl)-3-((tert-butoxycarbonyl)amino) butanoate: $^1$H NMR (CDCl$_3$, 400 MHz) δ7.33 (s, 5H), 5.11-5.00 (m, 1H), 4.51 (d, J=2.0 Hz, 2H), 4.10-3.99 (m, 1H), 3.63 (s, 3H), 3.56-3.45 (m, 3H), 2.53-2.45 (m, 1H), 2.42 (br. s., 1H), 1.81-1.73 (m, 2H), 1.43 (s, 9H), 1.11-1.02 (m, 3H).

Step F: Methyl (3R)-3-((tert-butoxycarbonyl)amino)-2-((1-(2-hydroxyethyl)cyclobutyl)methyl)butanoate. To a stirred solution of methyl (R,Z)-2-((1-(2-(benzyloxy)ethyl)cyclobutyl)methylene)-3-((tert-butoxycarbonyl)amino)butanoate (1 g, 2.395 mmol) and acetic acid (1 mL, 2.395 mmol) in MeOH (50 mL) was added Pd—C (1.274 g, 1.197 mmol) at 50° C. under H$_2$ (50 Psi), which was allowed to stir for 12 h at the same temperature. The reaction was filtered and concentrated to give the title compound, which was used for the next step without purification. LCMS (ES, m/z): 352.1 [M+H]$^+$. $^1$H NMR (CDCl$_3$, 400 MHz) δ 4.80-4.59 (m, 1H), 3.90-3.76 (m, 1H), 3.68 (s, 3H), 3.67-3.57 (m, 2H), 2.62-2.50 (m, 1H), 1.70 (br. s, 10H), 1.45 (br. s, 9H), 1.16-1.05 (m, 3H).

Step G: Methyl (3R)-3-((tert-butoxycarbonyl)amino)-2-((1-(2-(1,3-dioxoisoindolin-2-yl)ethyl)cyclobutyl)methyl) butanoate. DEAD (0.519 mL, 3.28 mmol) was added to a mixture of methyl (3R)-3-((tert-butoxycarbonyl)amino)-2-((1-(2-hydroxyethyl)cyclobutyl)methyl)butanoate (720 mg, 2.186 mmol), isoindoline-1,3-dione (482 mg, 3.28 mmol) and PPh$_3$ (860 mg, 3.28 mmol) in THF (40 mL) under ice-bath. The resulting mixture was stirred at 25° C. for 12 h. The reaction was then diluted with EtOAc (30 mL) and water (30 mL). The aqueous layer was extracted with EtOAc (2×30 mL). The combined organic phase was dried over Na$_2$SO$_4$, filtered and the filtrate was concentrated in vacuo. The residue was purified by column chromatography (SiO$_2$, PE:EtOAc=10:1) to give the title compound. LCMS (ES, m/z): 459.2 [M+H]$^+$.

Step H: Methyl (3R)-3-((tert-butoxycarbonyl)amino)-2-((1-(2-((tert-butoxycarbonyl)amino)ethyl)cyclobutyl) methyl)butanoate. Hydrazine hydrate (1 mL, 2.181 mmol) was added to a solution of methyl (3R)-3-((tert-butoxycarbonyl)amino)-2-((1-(2-(1,3-dioxoisoindolin-2-yl)ethyl)cyclobutyl)methyl)butanoate (1 g, 2.181 mmol) in EtOH (10 mL). The resulting mixture was stirred at 80° C. for 2 h. The mixture was concentrated and DCM (20 mL) was added to the residue. The mixture was filtered and the filtrate was concentrated to give methyl (3R)-2-((1-(2-aminoethyl)cyclobutyl)methyl)-3-((tert-butoxycarbonyl)amino)butanoate which was used in the next step directly. Boc-anhydride (0.877 mL, 3.78 mmol) was added to a mixture of methyl (3R)-2-((1-(2-aminoethyl)cyclobutyl)methyl)-3-((tert-butoxycarbonyl)amino)butanoate (620 mg, 1.888 mmol), and TEA (0.789 mL, 5.66 mmol) in DCM (50 mL) under ice-bath. The resulting mixture was stirred at 25° C. for 12 h. The reaction was then diluted with DCM (30 mL) and water (30 mL). The aqueous layer was extracted with DCM (2×30 mL). The combined organic phase was dried over Na$_2$SO$_4$, filtered and the filtrate was concentrated in vacuo. The residue was purified by column chromatography (SiO$_2$, PE:EtOAc=10:1) to give the title compound. $^1$H NMR (CDCl$_3$, 400 MHz) δ 5.29-5.22 (m, 1H), 4.96-4.85 (m, 1H), 4.65-4.47 (m, 1H), 3.93-3.75 (m, 1H), 3.66 (s, 3H), 3.04 (br. s., 2H), 2.54-2.42 (m, 1H), 2.05-1.92 (m, 1H), 1.89-1.77 (m, 3H), 1.68 (br. s., 5H), 1.50-1.40 (m, 19H), 1.30-1.22 (m, 1H), 1.17-1.06 (m, 3H).

Step I: Tert-butyl ((2R)-4-(1-(2-((tert-butoxycarbonyl) amino)ethyl)cyclobutyl)-3-(hydroxymethyl)butan-2-yl)carbamate. To a stirred solution of LiAlH$_4$ (39.9 mg, 1.050 mmol) in THF (2 mL) was added methyl (3R)-3-((tert-butoxycarbonyl)amino)-2-((1-(2-((tert-butoxycarbonyl) amino)ethyl)cyclobutyl)methyl)butanoate (300 mg, 0.700 mmol) THF (5 mL) at 0° C. under N$_2$. The reaction mixture was stirred for 1 h at 0° C., then warmed to (25° C.) and stirred for 2 h. The reaction mixture was quenched with 0.04 mL of water, 0.04 mL of 15% NaOH and 0.12 mL of water, dried over Na$_2$SO$_4$, filtered and the filtrate was concentrated to afford the title compound, which was used in the next step without further purification. LCMS (ES, m/z): 401.3 [M+H]$^+$.

Step J: Tert-butyl ((2R)-4-(1-(2-((tert-butoxycarbonyl) amino)ethyl)cyclobutyl)-3-((1,3-dioxoisoindolin-2-yl) methyl)butan-2-yl)carbamate. DEAD (0.107 mL, 0.674 mmol) was added to a mixture of Tert-butyl ((2R)-4-(1-(2-((tert-butoxycarbonyl)amino)ethyl)cyclobutyl)-3-(hydroxymethyl)butan-2-yl)carbamate (180 mg, 0.449 mmol), isoindoline-1,3-dione (99 mg, 0.674 mmol) and PPh$_3$ (177 mg, 0.674 mmol) in THF (30 mL) under ice-bath. The resulting mixture was stirred at 25° C. for 2 h. The reaction was then diluted with EtOAc (10 mL) and water (10 mL). The aqueous layer was extracted with EtOAc (2×10 mL). The combined organic phase was dried over Na$_2$SO$_4$, filtered and the filtrate was concentrated in vacuo. The residue was purified by column chromatography (SiO$_2$, PE:EtOAc=10: 1-4:1) to give the title compound as a mixture of diastereomers. LCMS (ES, m/z): 530.4 [M+H]$^+$. The mixture of diastereomers resolved (Column: Chiralpak AD-3 150×4.6 mm I.D., 3 um Mobile phase: A: CO$_2$ B:iso-propanol (0.05% DEA) Gradient: from 5% to 40% of B in 5 min and hold 40% for 2.5 min, then 5% of B for 2.5 min Flow rate: 2.5 mL/min Column temp.: 35° C.) to afford Peak 1 (Isomer 1) and Peak 2 (Isomer 2). Isomer 1: LCMS (ES, m/z): 530.4 [M+H]$^+$. Isomer 2: LCMS (ES, m/z): 552.3 [M+Na]$^+$.

Step K: INTERMEDIATE 15A. Hydrazine hydrate (0.5 mL, 0.393 mmol) was added to a solution of tert-butyl ((2R)-4-(1-(2-((tert-butoxycarbonyl)amino)ethyl)cyclobutyl)-3-((1,3-dioxoisoindolin-2-yl)methyl)butan-2-yl) carbamate as a mixture of diastereomers (260 mg, 0.393 mmol) in EtOH (5 mL). The resulting mixture was stirred at 80° C. for 2 h. The mixture was concentrated and DCM (20 mL) was added to the residue. The mixture was filtered and the filtrate was concentrated to give INTERMEDIATE 15A as a mixture of diastereomers, which was used in the next step without further purification. $^1$H NMR (CDCl$_3$, 400 MHz) δ 5.96-5.70 (m, 1H), 4.64-4.47 (m, 1H), 3.96-3.78 (m, 1H), 3.76-3.64 (m, 1H), 3.07-2.77 (m, 3H), 2.66-2.43 (m, 2H), 1.72 (d, J=8.6 Hz, 10H), 1.47-1.29 (m, 18H), 1.24-1.17 (m, 1H), 1.10-1.01 (m, 3H).

Following a similar procedure as INTERMEDIATE 15A, using Isomer 1 and Isomer 2 from Step J afforded INTERMEDIATE 15B (LCMS (ES, m/z): 400.3 [M+H]$^+$) and INTERMEDIATE 15C (LCMS (ES, m/z): 400.3 [M+H]$^+$) respectively.

Intermediate 16

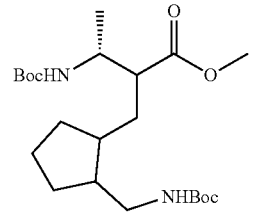 [SMILES: COC(=O)C(CC1CCCC1CNC(=O)OC(C)(C)C)[C@@H](C)NC(=O)OC(C)(C)C]

Methyl (3R)-3-((tert-butoxycarbonyl)amino)-2-((2-(((tert-butoxycarbonyl)amino)methyl)cyclopentyl) methyl)butanoate Step A: Methyl 2-(nitromethyl)cyclopentane-1-carboxylate. A mixture of nitromethane (2.52 g, 41.2 mmol), methyl cyclopent-1-ene-1-carboxylate (4 g, 31.7 mmol) and TBAF (95 mL, 95 mmol) was stirred at 70° C. for 16 h. The resulting reaction mixture was quenched with sat. NH$_4$Cl aq. (20 mL) and then extracted with EtOAc (3×60 mL). The organic layer was washed with brine (3×30 mL), dried over Na$_2$SO$_4$, filtered and the filtrate was concentrated in vacuo. The residue was purified by silica gel column (PE: EtOAc=10:1) to give the title compound.

Step B: Methyl 2-(((tert-butoxycarbonyl)amino)methyl) cyclopentane-1-carboxylate. To a solution of methyl 2-(nitromethyl)cyclopentane-1-carboxylate (200 mg, 1.068 mmol), (Boc)₂O (0.744 mL, 3.21 mmol) and Raney Ni (62.7 mg, 1.068 mmol) in MeOH (10 mL) was stirred for 15 h at 25° C. under H₂ balloon. The reaction mixture was filtered through celite and washed with MeOH (50 mL). The solvent was removed in vacuo and purified by silica gel column (SiO₂, PE:EtOAc=10:1) to give the title compound.

Step C: 2-(((tert-butoxycarbonyl)amino)methyl)cyclopentane-1-carboxylic acid. A 100 mL flask was charged with methyl 2-(((tert-butoxycarbonyl)amino)methyl)cyclopentane-1-carboxylate (190 mg, 0.738 mmol) and lithium hydroxide hydrate (248 mg, 5.91 mmol), which was dissolved in tetrahydrofuran (5.00 mL) and Water (1.00 mL). The mixture was stirred at 25° C. for 15 h. The reaction mixture was concentrated in vacuo and the residue was acidified to pH=3 with 1N HCl. The water phase was extracted with EtOAc (5×10 mL). The combined organic phase was washed with brine (10 mL), dried over Na₂SO₄, and concentrated in vacuo to give the product the title compound, which was used for next step without further purification. ¹H NMR (CDCl₃, 400 MHz) δ=6.31 (s, 1H), 4.89 (s, 1H), 3.34-3.23 (m, 1H), 3.22-3.12 (m, 1H), 3.06 (dd, J=13.9, 8.4, 1H), 2.51-2.35 (m, 1H), 2.35-2.24 (m, 1H), 2.10 (s, 1H), 2.03-1.92 (m, 2H), 1.87 (d, J=7.0 Hz, 1H), 1.76-1.58 (m, 2H), 1.50-1.41 (m, 9H).

Step D: Methyl (3R)-3-((tert-butoxycarbonyl)amino)-2-((2-(((tert-butoxycarbonyl)amino)methyl)cyclopentyl)methyl)butanoate. A mixture of INTERMEDIATE 10 (75 mg, 0.329 mmol), 2-(((tert-butoxycarbonyl)amino)methyl)cyclopentane-1-carboxylic acid (100 mg, 0.329 mmol), potassium hydrogenphosphate (68.7 mg, 0.395 mmol) and Ir[dF(CF₃)ppy]₂(dtbbpy)PF₆ (3.69 mg, 3.29 μmol) in DMF (2 mL) was stirred at 25° C. under N₂, then the mixture was irradiated with a 36 W blue LED lamp and stirred at 25° C. for 16 h. The reaction was quenched by sat.NaHCO₃ (10 mL), extracted with EtOAc (2×30 mL). The combined organic layers were washed with brine (20 mL), dried over Na₂SO₄, filtered and the solvent was removed in vacuo. The residue was purified by prep-TLC (SiO₂, PE:EtOAc=5:1) to give the title compound. LCMS (ES, m/z): 429.2 [M+H]⁺.

Intermediate 17

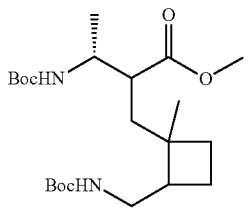 [SMILES: COC(=O)C(CC1(C)CCC1CNC(=O)OC(C)(C)C)[C@@H](C)NC(=O)OC(C)(C)C]

Methyl (3R)-3-((tert-butoxycarbonyl)amino)-2-((2-(((tert-butoxycarbonyl)amino)methyl)-1-methylcyclobutyl)methyl)butanoate Step A: Allyl(tert-butyl)diphenylsilane. A solution of tert-butylchlorodiphenylsilane (20 g, 72.8 mmol) in anhydrous THF (218 mL) was added cautiously to a stirred solution of allylmagnesium chloride (50.9 mL, 102 mmol) at 25° C. under N₂ and the resulting mixture stirred at 55° C. for 15 h. The mixture was cooled to 0° C., quenched with 10% aqueous ammonium chloride solution (1.5 mL/mmol), warmed to 25° C. and partitioned between water and EtOAc (100 mL). The organic phase was separated and the aqueous phase extracted with EtOAc (50 mL). The combined organic layers were washed with brine (50 mL), dried (MgSO₄), filtered and concentrated in vacuo. The products were purified by flash column chromatography (PE:EtOAC=100:1) to give the title compound. ¹H NMR (CDCl₃, 400 MHz) δ 7.62-7.60 (m, 4H), 7.37-7.35 (m, 6H), 5.80-5.74 (m, 1H), 4.93-4.79 (m, 2H), 2.20-2.18 (m, 2H), 1.07 (s, 9H).

Step B: Methyl 2-((tert-butyldiphenylsilyl)methyl)-1-methylcyclobutane-1-carboxylate. A solution of methyl methacrylate (4 g, 40.0 mmol) in dry CH₂Cl₂ (40 mL) was added to a stirred solution of TiCl₄ (4.85 mL, 43.9 mmol) in dry CH₂Cl₂ (68 mL) under N₂ at 20° C. After addition of a solution of allyl(tert-butyl)diphenylsilane (16.14 g, 57.5 mmol) in dry CH₂Cl₂ (40 mL) the reaction mixture was heated at reflux for 4 days. The mixture was hydrolyzed by addition of aq. NH₄Cl (100 mL), the organic layer was separated, the aqueous layer was extracted three times with CH₂Cl₂ (50 mL) and the combined organic layers were dried over MgSO₄, filtered. Evaporation of the solvent in vacuo and flash chromatography (PE EtOAc=50: 1-20:1) of the residue on silica gel afforded the title compound.

Step C: Methyl 2-((tert-butyldifluorosilyl)methyl)-1-methylcyclobutane-1-carboxylate. Boron trifluoride-acetic acid complex (BF₃·2AcOH) (21.91 g, 117 mmol) was added to a solution of methyl 2-((tert-butyldiphenylsilyl)methyl)-1-methylcyclobutane-1-carboxylate (6.34 g, 11.66 mmol) in dry CH₂Cl₂ (250 mL). The mixture was heated at reflux for 8 h, and then poured into aq NaHCO₃ (150 mL). The aqueous layer was extracted with CH₂Cl₂ (3×50 mL). The combined organic layers were dried (MgSO₄), filtered and the solvent was evaporated to give the title compound (3.2 g, 9.68 mmol, 83% yield) and used in the next step without further purification.

Step D: Methyl 2-(hydroxymethyl)-1-methylcyclobutane-1-carboxylate. Methyl 2-((tert-butyldifluorosilyl)methyl)-1-methylcyclobutane-1-carboxylate (3.2 g, 12.10 mmol) was dissolved in THF (80 mL). Then MeOH (80 mL), NaHCO₃ (1.068 g, 12.71 mmol), potassium fluoride (2.250 g, 38.7 mmol) and 30% H₂O₂ (14.84 mL, 145 mmol) were added. The mixture was stirred at 25° C. for 24 h and then washed with H₂O (100 mL). After separation of the organic layer, the aqueous layer was extracted with EtOAc (3×50 mL). The combined organic layers were dried (MgSO₄), filtered and the solvent was evaporated in vacuo. Flash chromatography (silica gel, PE:EtOAc=5:1) of the residue provided the title compound. ¹H NMR (CDCl₃, 400 MHz) δ 3.73-3.68 (m, 3H), 3.68-3.63 (m, 1H), 3.59-3.52 (m, 1H), 2.85-2.73 (m, 1H), 2.42-2.25 (m, 1H), 1.89-1.79 (m, 1H), 1.70-1.59 (m, 2H), 1.37 (s, 3H).

Step E: Methyl 2-formyl-1-methylcyclobutane-1-carboxylate. To a stirred solution of oxalyl dichloride (0.996 ml, 11.38 mmol) in DCM (10 mL) was added DMSO (1.615 mL, 22.76 mmol) at −78° C., which was allowed to stir for 0.5 h at the same temperature. Methyl 2-(hydroxymethyl)-1-methylcyclobutane-1-carboxylate (900 mg, 5.69 mmol) in DCM (10 mL) was added at −78° C., which was allowed to stir for 0.5 h at the same temperature. And then Et₃N (6.34 ml, 45.5 mmol) was added at −78° C., which was allowed to stir for 0.5 h at the same temperature. The reaction was allowed to stir for 1.5 h at 0° C. The reaction was diluted with H₂O (50 mL), extracted by DCM (2×50 mL). The organic layer was washed with H₂O (50 mL), brine (50 mL) and dried over Na₂SO₄, filtered and concentrated in vacuo to give the title compound which was used in the next step without further purification. ¹H NMR (CDCl₃, 400 MHz) δ 9.77 (s, 1H), 3.75 (s, 3H), 3.65-3.57 (m, 1H), 2.49-2.34 (m, 2H), 1.96-1.81 (m, 1H), 1.78-1.66 (m, 1H), 1.36 (s, 3H).

Step F: Methyl (E)-2-((hydroxyimino)methyl)-1-methylcyclobutane-1-carboxylate. To a solution of methyl 2-formyl-1-methylcyclobutane-1-carboxylate (480 mg, 3.07 mmol) in EtOH (10 mL) was added sodium acetate (882 mg, 10.76 mmol) and hydroxylamine hydrochloride (641 mg, 9.22 mmol). The reaction mixture was stirred at 80° C. for 1 h under N$_2$. The mixture was filtered and the filtrate was concentrated in vacuo to give the title compound, which was used the next step without purification. LCMS (ES, m/z): 172.1 [M+H]$^+$.

Step G: Methyl 2-(((tert-butoxycarbonyl)amino)methyl)-1-methylcyclobutane-1-carboxylate. To a solution of methyl (E)-2-((hydroxyimino)methyl)-1-methylcyclobutane-1-carboxylate (600 mg, 2.80 mmol) in EtOH (10 mL) was added Raney-Ni (100 mg, 1.704 mmol) and (Boc)$_2$O (1.302 mL, 5.61 mmol) under H$_2$ balloon at 15° C. The reaction was stirred for 12 h. The mixture was filtered and concentrated in vacuo to give a residue which was purified by column chromatography (SiO$_2$, PE:EtOAc=10:1) to give the title compound. $^1$H NMR (CDCl$_3$, 400 MHz) δ 4.92 (s, 1H), 3.81-3.58 (m, 3H), 3.30-2.98 (m, 2H), 2.69 (dd, J=8.8, 6.6 Hz, 1H), 2.32 (d, J=8.3 Hz, 1H), 1.95-1.79 (m, 1H), 1.70-1.58 (m, 2H), 1.43 (s, 8H), 1.32 (s, 3H).

Step H: 2-(((tert-butoxycarbonyl)amino)methyl)-1-methylcyclobutane-1-carboxylic acid. To a solution of methyl 2-(((tert-butoxycarbonyl)amino)methyl)-1-methylcyclobutane-1-carboxylate (400 mg, 1.554 mmol) in THF (5 mL) and Water (1 mL) was added NaOH (311 mg, 7.77 mmol). The reaction mixture was stirred at 80° C. for 2 hr. The resulting reaction mixture was cooled to ambient temperature before acidifying with 1N HCl (8 mL) then diluted with EtOAc (30 mL), and the organic layer was separated, dried over MgSO$_4$, filtered, and concentrated in vacuo to yield the title compound and was used without any further purification. $^1$H NMR (CDCl$_3$, 400 MHz) δ 5.90 (s, 1H), 4.76 (s, 1H), 3.10 (s, 2H), 2.69 (s, 1H), 2.30 (d, J=8.8 Hz, 1H), 1.84 (q, J=8.8 Hz, 1H), 1.61 (s, 2H), 1.54 (s, 1H), 1.38 (d, J=4.9 Hz, 8H), 1.30 (s, 3H).

Step I: Methyl (3R)-3-((tert-butoxycarbonyl)amino)-2-((2-(((tert-butoxycarbonyl)amino)methyl)-1-methylcyclobutyl)methyl)butanoate. A mixture of INTERMEDIATE 10 (330 mg, 1.439 mmol), 2-(((tert-butoxycarbonyl)amino)methyl)-1-methylcyclobutane-1-carboxylic acid (350 mg, 1.439 mmol), Ir[dF(CF$_3$)ppy]$_2$(dtbbpy)PF$_6$ (16.14 mg, 0.014 mmol) and potassium hydrogenphosphate (301 mg, 1.726 mmol) in DMF (5 mL) was stirred at 25° C. under N$_2$, then the mixture was irradiated with a 36 W blue LED lamp and stirred at 25° C. for 12 h. The reaction was quenched by sat.NaHCO$_3$ (10 mL), extracted with EtOAc (2×50 mL). The combined organic layers were washed with brine (50 mL), dried over Na$_2$SO$_4$, filtered and the solution removed in vacuo. The residue was purified by column chromatography (PE:EtOAc=5:1) to give the title compound.

Intermediate 18

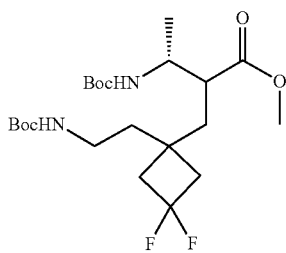 [SMILES: COC(=O)C(CC1(CCNC(=O)OC(C)(C)C)CC(F)(F)C1)[C@@H](C)NC(=O)OC(C)(C)C]

Methyl (3R)-3-((tert-butoxycarbonyl)amino)-2-((1-(2-((tert-butoxycarbonyl)amino)ethyl)-3,3-difluorocyclobutyl)methyl)butanoate Step A: Ethyl 1-(cyanomethyl)-3,3-difluorocyclobutane-1-carboxylate. A mixture of LDA (10.05 mL, 20.10 mmol) in THF (10 mL) was cooled to −78° C. Ethyl 3,3-difluorocyclobutane-1-carboxylate (3 g, 18.28 mmol) in THF (30 mL) was added to the mixture and stirred for 1 h. 2-bromoacetonitrile (3.29 g, 27.4 mmol) in THF (20 mL) was added to the mixture and stirred at −78° C. for 2.5 h. The resulting mixture was quenched with saturated NH$_4$Cl aqueous (30 mL) and extracted with EtOAc (3×30 mL), washed with brine (100 mL), dried over Na$_2$SO$_4$ and filtered. The filtrate was concentrated in vacuo and the residue was purified by flash silica gel chromatography (Biotage, 80 g Agela Silica Flash Column, Eluent of 0-20% EtOAc:PE gradient @ 50 mL/min) to give the product the title compound. $^1$H NMR (CDCl$_3$, 400 MHz) δ 4.27 (q, J=7.0 Hz, 2H), 3.22-3.11 (m, 2H), 2.88 (s, 2H), 2.68-2.60 (m, 2H), 1.32 (t, J=7.0 Hz, 3H).

Step B: Ethyl 1-(2-((tert-butoxycarbonyl)amino)ethyl)-3,3-difluorocyclobutane-1-carboxylate. BOC-Anhydride (3.29 mL, 14.17 mmol) was added to a mixture of ethyl 1-(cyanomethyl)-3,3-difluorocyclobutane-1-carboxylate (1.6 g, 7.09 mmol) and Raney Ni (300 mg, 5.11 mmol) in EtOH (80 mL) under 25° C. The resulting mixture was stirred at 25° C. for 12 h under H$_2$ (15 psi). The reaction was filtered and the filtrate was concentrated in vacuo. The crude product was purified by flash silica gel chromatography (ISCO; 40 g Agela Silica Flash Column, Eluent of 0~20% EtOAc:PE gradient @ 40 mL/min) to give the title compound. $^1$H NMR (CDCl$_3$, 400 MHz) δ 4.18 (q, J=7.2 Hz, 2H), 3.14-3.05 (m, 2H), 3.03-2.94 (m, 2H), 2.55-2.45 (m, 2H), 2.03 (t, J=7.1 Hz, 2H), 1.43-1.37 (m, 9H), 1.27 (t, J=7.2 Hz, 3H).

Step C: 1-(2-((tert-butoxycarbonyl)amino)ethyl)-3,3-difluorocyclobutane-1-carboxylic acid. To a mixture of ethyl 1-(2-((tert-butoxycarbonyl)amino)ethyl)-3,3-difluorocyclobutane-1-carboxylate (1.2 g, 3.51 mmol) in THF (5 mL), Ethanol (5 mL) and H$_2$O (3 mL) was added NaOH (0.422 g, 10.54 mmol). The mixture was stirred at 25° C. for 5 h. The reaction was concentrated and extracted with DCM (2×30 mL). The aqueous phase was adjust to pH=3.0 by 1N HCl and extracted with EtOAc (3×30 mL). The organic layers were dried with Na$_2$SO$_4$, filtered and concentrated in vacuo to give the title compound, which was used in the next step without further purification. $^1$H NMR (CDCl$_3$, 400 MHz) δ 3.17 (s, 2H), 3.03 (q, J=14.0 Hz, 2H), 2.58-2.38 (m, 2H), 2.16-2.05 (m, 2H), 1.48-1.42 (m, 9H).

Step D: Methyl (3R)-3-((tert-butoxycarbonyl)amino)-2-((1-(2-((tert-butoxycarbonyl)amino)ethyl)-3,3-difluorocyclobutyl)methyl)butanoate. A mixture of INTERMEDIATE 10 (388 mg, 1.692 mmol), 1-(2-((tert-butoxycarbonyl)amino)ethyl)-3,3-difluorocyclobutane-1-carboxylic acid (500 mg, 1.611 mmol), Ir[dF(CF$_3$)ppy]$_2$(dtbbpy)PF$_6$ (18.08 mg, 0.016 mmol) and potassium hydrogenphosphate (337 mg, 1.934 mmol) in DMF (15 mL) was stirred at 25° C. under N$_2$, then the mixture was irradiated with a 34 W blue LED lamp and stirred at 25° C. for 12 h. The reaction was detected by TLC (PE:EtOAc=5:1). The reaction was quenched by sat.NaHCO$_3$ (50 mL), extracted with EtOAc (2×30 mL). The combined organic layers were washed with brine (2×50 mL), dried over Na$_2$SO$_4$, filtered and the mixture evaporated in vacuo. The residue was purified by flash silica gel chromatography (Biotage, 12 g Agela Silica Flash Column, Eluent of 5-20% EtOAc:PE gradient @ 30 mL/min) to give the title compound. $^1$H NMR (CDCl$_3$, 400

MHz) δ 3.70 (d, J=2.6 Hz, 3H), 3.14-2.95 (m, 2H), 2.61-2.48 (m, 1H), 2.45-2.35 (m, 1H), 2.33-2.19 (m, 3H), 2.05-1.95 (m, 1H), 1.87-1.65 (m, 4H), 1.44 (s, 18H), 1.12 (dd, J=7.0, 3.5 Hz, 3H).

Intermediate 19

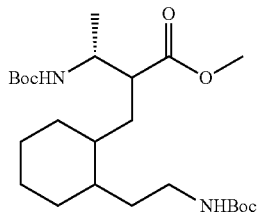

Methyl (3R)-3-((tert-butoxycarbonyl)amino)-2-((2-(2-((tert-butoxycarbonyl)amino)ethyl)cyclohexyl)methyl)butanoate Step A: Octahydroisoquinolin-1 (2H)-one. A solution of isoquinolin-1 (2H)-one (500 mg, 3.44 mmol) and platinum (IV) oxide (391 mg, 1.722 mmol) in AcOH (10 mL) was stirred for 14 h at 50° C. under H$_2$ balloon. The reaction mixture was filtered through celite and washed with MeOH (50 mL). The solvent was removed to give the title compound, which was used for next step without further purification.

Step B: Tert-butyl 1-oxooctahydroisoquinoline-2 (1H)-carboxylate. A solution of octahydroisoquinolin-1 (2H)-one (200 mg, 1.305 mmol), DMAP (175 mg, 1.436 mmol), Et$_3$N (0.400 mL, 2.87 mmol) and Boc$_2$O (1.000 mL, 4.31 mmol) in DCM (10 mL) was stirred for 14 h at 25° C. The solvent was removed and purified by silica gel column (SiO$_2$, PE:EtOAc=1:8) to give the title compound. $^1$H NMR (CDCl$_3$, 400 MHz) δ 3.91-3.79 (m, 1H), 3.47 (m, 1H), 2.68-2.55 (m, 1H), 2.23-2.01 (m, 2H), 1.96-1.84 (m, 1H), 1.80-1.79 (m, 1H), 1.78-1.47 (m, 14H), 1.34-1.24 (m, 2H)

Step C: 2-(2-((tert-butoxycarbonyl)amino)ethyl)cyclohexane-1-carboxylic acid. To a solution of tert-butyl 1-oxooctahydroisoquinoline-2 (1H)-carboxylate (130 mg, 0.513 mmol) in THF (1 mL), Water (0.6 mL) and ethanol (1 mL) was added sodium hydroxide (123 mg, 3.08 mmol) at 0° C., and then it was stirred for 16 h at 25° C. under N$_2$. The organic solvent was evaporated in vacuo and water (2 mL) was added to the mixture. The aqueous layer was extracted with EtOAc (2×10 mL). Then the aqueous phase was acidified to pH 3 using 1M HCl. Then it was extracted with EtOAc (2×15 mL). The combined organic layers were washed with brine (10 mL), dried over Na$_2$SO$_4$, filtered and the filtrate was concentrated in vacuo to afford the title compound and was used in the next step without further purification.

Step D: Methyl (3R)-3-((tert-butoxycarbonyl)amino)-2-((2-(2-((tert-butoxycarbonyl)amino)ethyl)cyclohexyl)methyl)butanoate. A mixture of INTERMEDIATE 10 (67.6 mg, 0.295 mmol), 2-(2-((tert-butoxycarbonyl)amino)ethyl)cyclohexane-1-carboxylic acid (80 mg, 0.295 mmol), potassium phosphate, dibasic (61.6 mg, 0.354 mmol) and Ir[dF(CF$_3$)ppy]$_2$(dtbbpy)PF$_6$ (3.31 mg, 2.95 μmol) in DMF (4 mL) was stirred at 25° C. under N$_2$, then the mixture was irradiated with a 36 W blue LED lamp and stirred at 25° C. for 16 h. The reaction was quenched by sat. NaHCO$_3$ (10 mL), extracted with EtOAc (2×30 mL). The combined organic layers were washed with brine (20 mL), dried over Na$_2$SO$_4$, filtered and concentrated in vacuo. The residue was purified by column chromatography (SiO$_2$, PE:EtOAc=8:1) to give the title compound. LCMS (ES, m/z): 457.3 [M+H]$^+$.

Intermediate 20

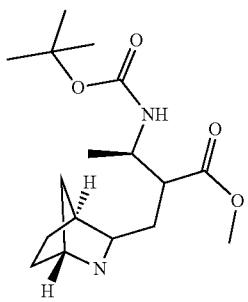

Tert-butyl (1R,3R,4S)-3-((3R)-3-((tert-butoxycarbonyl)amino)-2-(methoxycarbonyl)butyl)-2-azabicyclo[2.2.1]heptane-2-carboxylate In a 40 ml vial was added INTERMEDIATE 10 (1000 mg, 4.36 mmol), potassium hydrogenphosphate (1519 mg, 8.72 mmol), (1r,3s,4s)-2-(tert-butoxycarbonyl)-2-azabicyclo[2.2.1] heptane-3-carboxylic acid (1052 mg, 4.36 mmol), 4,4'-di-t-butyl-2,2'-bipyridine)bis[3,5-difluoro-2-[5-trifluoromethyl-2-pyridinyl-kappan)phenyl-kappac]iridium(iii) hexafluorophosphate (67.4 mg, 0.065 mmol) and then added degassed DMF (25 ml). The resulting mixture was sealed with parafilm and stirred and irradiated with a Merck Photobox 100% power for 18 h with fan at 4700 rpm to keep near ambient temperature. The reaction was quenched by exposure to air. The mixture was diluted with EtOAc, washed with H$_2$O, saturated NaHCO$_3$, brine, dried (Mg$_2$SO$_4$), filtered and the solvent was evaporated under reduced pressure. The residue was purified by column chromatography on silica gel (ISCO 100 gram gold column), eluting with 0-20% ethyl acetate/hexane to give the title compound. LCMS (ES, m/z): 427.0 [M+H]$^+$.

Intermediate 21

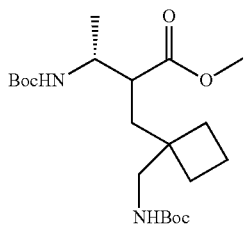 [SMILES: COC(=O)C(CC1(CNC(=O)OC(C)(C)C)CCC1)[C@@H](C)NC(=O)OC(C)(C)C]

Methyl (3R)-3-((tert-butoxycarbonyl)amino)-2-((1-(((tert-butoxycarbonyl)amino)methyl)cyclobutyl)methyl)butanoate Step A: 1-(((tert-butoxycarbonyl)amino)methyl)cyclobutane-1-carboxylic acid. To a solution of (1-(methoxycarbonyl)cyclobutyl)methanaminium chloride (6.0 g, 33.4 mmol) and Et₃N (11.64 ml, 83 mmol) in MeOH (15 ml) and THF (25 ml) was added di-tert-butyl dicarbonate (10.21 g, 46.8 mmol). The mixture was stirred at ambient temperature overnight, followed by addition of H₂O (10 ml) and NaOH (2.67 g, 66.8 mmol). The mixture was heated to 50° C. and stirred for 2 days. After cooled, diluted with diethyl ether (20 mL), washed with H₂O (2×20 mL). The separated aqueous layer was acidified by 5.0 M HCl in H₂O (16.03 ml, 80 mmol) and extracted with diethyl ether, dried (Na₂SO₄), filtered and the solvent was evaporated under reduced pressure to give the title compound. LCMS (ES, m/z): 230.0 [M+H]⁺.

Step B: Methyl (3R)-3-((tert-butoxycarbonyl)amino)-2-((1-(((tert-butoxycarbonyl)amino)methyl)cyclobutyl)methyl)butanoate. In a 40 ml vial was added INTERMEDIATE 10 (1600 mg, 6.98 mmol),1-(((tert-butoxycarbonyl)amino)methyl)cyclobutanecarboxylic acid (2560 mg, 11.17 mmol), potassium hydrogenphosphate (3039 mg, 17.45 mmol), (4,4'-di-t-butyl-2,2'-bipyridine)bis[3,5-difluoro-2-[5-trifluoromethyl-2-pyridinyl-kappan)phenyl-kappac] iridium(iii) hexafluorophosphate (71.9 mg, 0.70 mmol) and then added degassed DMF (2200 ml). The resulting mixture was sealed, stirred and irradiated with a Merck Photobox 100% power for 120 minutes with fan at 4700 rpm to keep near ambient temperature for 16 h. The reaction was quenched by exposure to air. The mixture was diluted with EtOAc, washed with H₂O, sat. NaHCO₃, brine, dried (Mg₂SO₄), filtered and the solvent was evaporated under reduced pressure. The residue was purified by column chromatography on silica gel ISCO 80 gram, eluting with 0-40% EtOAc/hexane to give the title compound. LCMS (ES, m/z): 415.0 [M+H]⁺.

Intermediate 22

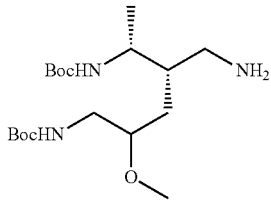 [SMILES: COC(CNC(=O)OC(C)(C)C)C[C@@H](CN)[C@@H](C)NC(=O)OC(C)(C)C]

Di-tert-butyl ((4S,5R)-4-(aminomethyl)-2-methoxy-hexane-1,5-diyl)dicarbamate

Step A: Benzyl tert-butyl ((2S,3R)-2-(oxiran-2-ylmethyl)butane-1,3-diyl)dicarbamate. To a solution of tert-butyl N-[(2R,3S)-3-[(1,3-dioxo-2,3-dihydro-1H-isoindol-2-yl)methyl]hex-5-en-2-yl]carbamate (0.37 g, 1.0 mmol; Step 2 of Intermediate 22) in DCM (8.0 mL) at 0° C. was added MCPBA (0.27 g, 1.6 mmol). The mixture was stirred at 0° C. for 12 h. The mixture was quenched with saturated Na₂CO₃ aqueous and extracted with EtOAc. The combined organic layers were washed with brine, dried over Na₂SO₄, filtered and concentrated in vacuo to a residue that was purified by silica gel chromatography (0-30% EtOAc:PE) to give the title compound. LRMS m/z (M+H): 375.0 found, 375.1 required. ¹H NMR (CDCl₃, 400 MHz) δ 7.89-7.82 (m, 2H), 7.77-7.69 (m, 2H), 4.03-3.79 (m, 1H), 3.77-3.58 (m, 2H), 3.13-2.98 (m, 1H), 2.84-2.76 (m, 1H), 2.56-2.49 (m, 1H), 2.42-2.20 (m, 1H), 1.43 (br s, 9H), 1.28-1.23 (m, 2H), 1.18 (dd, J=12.9, 6.9 Hz, 3H).

Step B: Tert-butyl ((2R,3S)-6-azido-3-((1,3-dioxoisoindolin-2-yl)methyl)-5-hydroxyhexan-2-yl)carbamate. To a mixture of tert-butyl ((2R,3S)-4-(1,3-dioxoisoindolin-2-yl)-3-(oxiran-2-ylmethyl)butan-2-yl)carbamate (2.4 g, 6.41 mmol) in DMF (30 mL) was added sodium azide (4.17 g, 64.1 mmol) and ammonium chloride (3.43 g, 64.1 mmol). The mixture was stirred at 80° C. for 12 h. The resulting mixture was quenched with H₂O (30 mL) and extracted with EtOAc (3×30 mL), washed with brine (50 mL), dried over Na₂SO₄ and filtered. The filtrate was concentrated in vacuo and the residue was purified by normal phase flash chromatography (ISCO®; 24 g SepaFlash® Silica Flash Column, Eluent of 0-40% EtOAc:PE gradient @ 35 mL/min) to give the title compound. LCMS (ES, m/z): 440.0 [M+H]⁺.

Step C: Tert-butyl ((2R,3S)-6-azido-3-((1,3-dioxoisoindolin-2-yl)methyl)-5-methoxyhexan-2-yl)carbamate. Iodomethane (102 mg, 0.719 mmol) was added to the mixture of tert-butyl ((2R,3S)-6-azido-3-((1,3-dioxoisoindolin-2-yl)methyl)-5-hydroxyhexan-2-yl)carbamate (100 mg, 0.240 mmol) and monosilver(I) monosilver(III) monooxide (278 mg, 1.198 mmol) in DMF (5 mL) at 0° C. The mixture was stirred at 25° C. for 12 h. The mixture was quenched by H₂O (30 mL) and extracted by EtOAc (3×30 mL). The combined organic layer was washed by brine (50 mL), dried over Na₂SO₄. The mixture was filtrated and the filtrate was concentrated in vacuo. The residue was purified by prep-TLC (SiO₂, PE:EtOAc=3:1) to afford the title compound. LCMS (ES, m/z): 454.2 [M+H]⁺.

Step D: Di-tert-butyl ((4S,5R)-4-((1,3-dioxoisoindolin-2-yl)methyl)-2-methoxyhexane-1,5-diyl)dicarbamate. A mixture of tert-butyl ((2R,3S)-6-azido-3-((1,3-dioxoisoindolin-2-yl)methyl)-5-methoxyhexan-2-yl)carbamate (40 mg, 0.093 mmol), (Boc)₂O (0.043 mL, 0.185 mmol) and palladium (99 mg, 0.093 mmol) in MeOH (10 mL) was stirred at 25° C. under H₂ balloon for 12 h. The mixture was filtrated to remove the Pd/C and the filtrate was concentrated in vacuo. The residue was purified by prep-TLC (SiO₂, PE:EtOAc=2:1) to give the title compound. LCMS (ES, m/z): 506.3 [M+H]⁺.

Step E: Di-tert-butyl ((4S,5R)-4-(aminomethyl)-2-methoxyhexane-1,5-diyl)dicarbamate. Hydrazine hydrate (14.56 mg, 0.247 mmol) was added to the mixture of Di-tert-butyl ((4S,5R)-4-((1,3-dioxoisoindolin-2-yl)methyl)-2-methoxyhexane-1,5-diyl)dicarbamate (25 mg, 0.049 mmol) in EtOH (5 mL). The mixture was stirred at 80° C. for 2 h. The mixture was concentrated in vacuo and white solid was formed. DCM (30 mL) was added to the residue, the mixture was filtrated and the filtrate was concentrated to give the title compound, which was used in the next step without further purification. LCMS (ES, m/z): 376.1 [M+H]⁺.

Intermediate 23

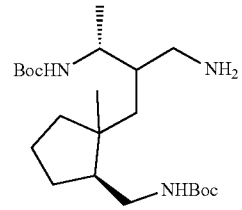

Tert-butyl ((2R)-4-amino-3-(((2S)-2-(((tert-butoxycarbonyl)amino)methyl)-1-methylcyclopentyl)methyl)butan-2-yl)carbamate Step A: (E)-5-bromo-1-nitropent-1-ene. To a solution of 4-bromobutanal (25 g, 99 mmol) in dry THF (250 mL) was added nitromethane (60.6 g, 993 mmol) followed by Et$_3$N (27.7 mL, 199 mmol). The mixture was stirred at 25° C. for 16 h. H$_2$O (50 mL) was added to the mixture and aq. HCl (1N) was used to adjust pH to 4-5. The aqueous phase was extracted with EtOAc (4×150 mL). The EtOAc phase was washed with brine (2×100 mL), dried over Na$_2$SO$_4$, filtered and the filtrate was concentrated to give 5-bromo-1-nitropentan-2-ol, which was used for the next step without further purification. To a solution of 5-bromo-1-nitropentan-2-ol (15 g, 56.6 mmol) in DCM (150 mL) was added MsCl (4.85 mL, 62.3 mmol) followed by Et$_3$N (15.78 mL, 113 mmol) at 0° C. The mixture was stirred at 0° C. for 2 h. H$_2$O (50 mL) was added to the mixture. The aqueous phase was extracted with DCM (4×50 mL). The DCM phase was washed with brine (2×50 mL), dried over Na$_2$SO$_4$, filtered and the filtrate was concentrated in vacuo. The residue was purified by silica gel column (SiO$_2$, PE:EtOAc=30:1) to give the title compound. $^1$H NMR (CDCl$_3$, 400 MHz) δ 7.29-7.17 (m, 1H), 7.02 (d, J=13.6 Hz, 1H), 3.42 (t, J=6.4 Hz, 2H), 2.46 (q, J=7.3 Hz, 2H), 2.14-1.99 (m, 2H).

Step B: (E)-5-iodo-1-nitropent-1-ene. To a solution of (E)-5-bromo-1-nitropent-1-ene (9.1 g, 37.5 mmol) in dry Acetone (100 mL) was added sodium iodide (16.87 g, 113 mmol). The mixture was stirred at 60° C. for 3 h. The mixture was concentrated in vacuo. H$_2$O (40 mL) was added the mixture. The aqueous phase was extracted with EtOAc (4×50 mL). The EtOAc phase was washed with brine (2×50 mL) dried over Na$_2$SO$_4$, filtered and the filtrate was concentrated. The residue was purified by silica gel column (SiO$_2$, PE:EtOAc=30:1) to give the title compound. $^1$H NMR (CDCl$_3$, 400 MHz) δ 7.28-7.16 (m, 1H), 7.03 (d, J=13.6 Hz, 1H), 3.20 (t, J=6.6 Hz, 2H), 2.51-2.36 (m, 2H), 2.08-1.93 (m, 2H).

Step C: (2S)-1-methyl-2-(nitromethyl)cyclopentane-1-carbaldehyde. 1-(diphenyl((trimethylsilyl)oxy)methyl)pyrrolidine (0.945 g, 2.90 mmol) was added to a solution of benzoic acid (1.773 g, 14.52 mmol), propionaldehyde (4.22 g, 72.6 mmol) and (E)-5-iodo-1-nitropent-1-ene (3.5 g, 14.52 mmol) in dry DMSO (25 mL) was stirred at 25° C. for 50 h. H$_2$O (5 mL) was added to the mixture. The aqueous phase was extracted with EtOAc (4×30 mL). The EtOAc phase was washed with sat NaHCO$_3$ (30 mL), brine (2×30 mL) dried over Na$_2$SO$_4$, filtered and the filtrate was concentrated in vacuo. The residue was purified by silica gel column (SiO$_2$, PE:EtOAc=5:1) to give the title compound. $^1$H NMR (CDCl$_3$, 400 MHz) δ 9.51 (d, J=1.1 Hz, 0.3H), 9.47 (s, 0.5H), 4.62-4.52 (m, 0.8H), 4.40-4.32 (m, 0.6H), 4.29-4.21 (m, 0.6H), 3.01-2.89 (m, 0.6H), 2.56-2.42 (m, 0.4H), 2.16-1.99 (m, 2H), 1.73-1.67 (m, 1H), 1.93-1.67 (m, 1H), 1.66-1.50 (m, 2H), 1.26-1.22 (m, 1H), 1.04 (s, 2H).

Step D: (2S)-1-methyl-2-(nitromethyl)cyclopentane-1-carboxylic acid. To a solution (2S)-1-methyl-2-(nitromethyl)cyclopentane-1-carbaldehyde (1.2 g, 7.01 mmol) in Acetone (8 mL) and Water (8 mL) was added successively 2-methylbut-2-ene (13.21 mL, 126 mmol), potassium dihydrogen phosphate (1.908 g, 14.02 mmol) and sodium chlorite (1.522 g, 16.82 mmol). The reaction mixture was stirred for 1 h at 0° C. H$_2$O (10 mL) was added the mixture. The aqueous phase was extracted with EtOAc (4×30 mL). The EtOAc phase was washed with brine (20 mL) dried over Na$_2$SO$_4$, filtered and the filtrate was concentrated in vacuo. The residue was purified by silica gel column (SiO$_2$, PE:EtOAc=8:1) to give the title compound. $^1$H NMR (CDCl$_3$, 400 MHz) δ 4.70-4.58 (m, 1H), 4.46 (dd, J=12.7, 10.0 Hz, 0.3H), 4.27 (dd, J=12.3, 9.9 Hz, 0.7H), 3.06 (dd, J=8.0, 5.5, 10.1 Hz, 0.7H), 2.54-2.44 (m, 0.3H), 2.34-2.18 (m, 1H), 2.13-1.99 (m, 1H), 1.88-1.61 (m, 3H), 1.59-1.49 (m, 1H), 1.38 (s, 1H), 1.17 (s, 2H).

Step E: (2S)-2-(((tert-butoxycarbonyl)amino)methyl)-1-methylcyclopentane-1-carboxylic acid. To a solution of (2S)-1-methyl-2-(nitromethyl)cyclopentane-1-carboxylic acid (170 mg, 0.908 mmol) and Pd—C (30 mg, 0.282 mmol) in MeOH (8 mL) was stirred for 48 h at 25° C. under H$_2$ balloon. Reaction mixture was filtered through celite and washed with MeOH (50 mL). Solvent was removed and purified by silica gel column (PE—MeOH) to give (2S)-2-(aminomethyl)-1-methylcyclopentanecarboxylic acid. Triethylamine (0.231 mL, 1.654 mmol) was added to a mixture of (2S)-2-(aminomethyl)-1-methylcyclopentanecarboxylic acid (130 mg, 0.827 mmol) in Water (2 mL) and Dioxane (2 mL) under ice-bath. The reaction mixture was stirred for 10 min and then di-tert-butyl dicarbonate (0.219 mL, 0.943 mmol) was added dropwise. The reaction mixture was stirred at 20° C. for 16 h. The reaction mixture was diluted with water (10 mL) and EtOAc (10 mL). The organic layer was separated and the aqueous layer was extracted with EtOAc (2×15 mL). EtOAc phrase was washed with 1M HCl (2 mL), birne (2×10 mL), dried over Na$_2$SO$_4$, filtered and the filtrate was concentrated in vacuo and purified by silica gel column (EtOAc) to give the title compound.

Following Steps described previously, (2S)-2-(((tert-butoxycarbonyl)amino)methyl)-1-methylcyclopentane-1-carboxylic acid was converted to INTERMEDIATE 23

The following INTERMEDIATES 24-38 (TABLE 1) were prepared according to the general procedure provided for INTERMEDIATES 1-23. The requisite starting materials are either prepared as described, commercially available, or may be prepared from commercially available reagents using conventional reactions well known in the art without undue experimentation.

TABLE 1

| INTERMEDIATE | Structure | Characterization |
|---|---|---|
| 24 | 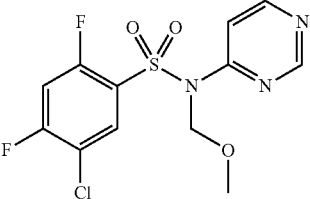 [SMILES: COCN(c1ccncn1)S(=O)(=O)c1cc(Cl)c(F)cc1F] | LCMS (ES, m/z): 350.0 [M + H]$^+$ |

TABLE 1-continued

| INTERMEDIATE | Structure | Characterization |
|---|---|---|
| 25 | 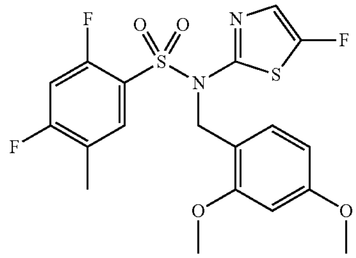 [SMILES: COc1ccc(CN(c2ncc(F)s2)S(=O)(=O)c2cc(C)c(F)cc2F)c(OC)c1] | LCMS (ES, m/z): 481.0 [M + H]⁺ |
| 26 | 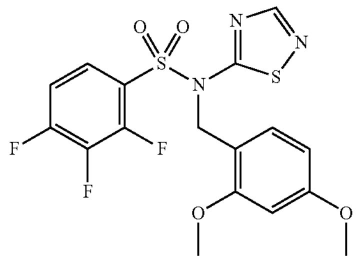 [SMILES: COc1ccc(CN(c2ncns2)S(=O)(=O)c2ccc(F)c(F)c2F)c(OC)c1] | LCMS (ES, m/z): 446.1 [M + H]⁺ |
| 27 | 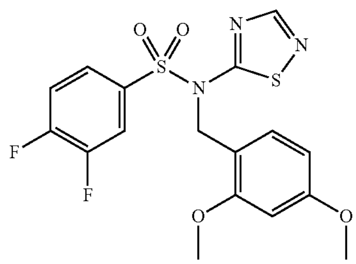 [SMILES: COc1ccc(CN(c2ncns2)S(=O)(=O)c2ccc(F)c(F)c2)c(OC)c1] | LCMS (ES, m/z): 428.1 [M + H]⁺ |
| 28 | 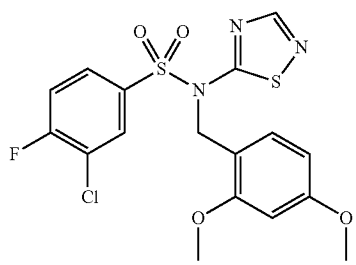 [SMILES: COc1ccc(CN(c2ncns2)S(=O)(=O)c2ccc(F)c(Cl)c2)c(OC)c1] | LCMS (ES, m/z): 444.9 [M + H]⁺ |
| 29 | 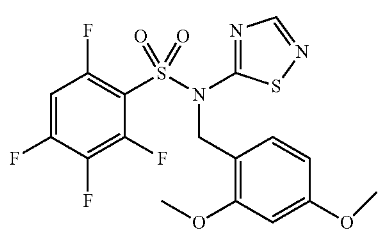 [SMILES: COc1ccc(CN(c2ncns2)S(=O)(=O)c2c(F)cc(F)c(F)c2F)c(OC)c1] | $^1$H NMR (CDCl$_3$, 400 MHz) δ 8.25 (s, 1H), 7.25 (s, 1H), 6.86-6.68 (m, 1H), 6.37 (dd, J = 8.4, 2.2 Hz, 1H), 6.23 (d, J = 2.2 Hz, 1H), 5.42 (s, 2H), 3.74 (d, J = 19.4 Hz, 6H). |
| 30 | 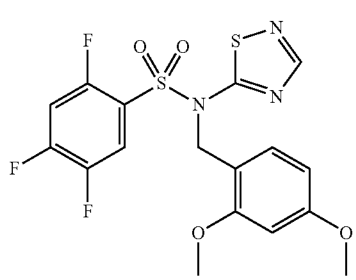 [SMILES: COc1ccc(CN(c2ncns2)S(=O)(=O)c2cc(F)c(F)cc2F)c(OC)c1] | LCMS (ES, m/z): 468.1 [M + Na]⁺ |

TABLE 1-continued

| INTERMEDIATE | Structure | Characterization |
|---|---|---|
| 31 | 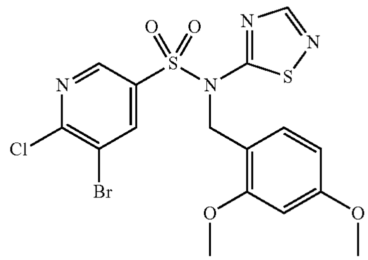 [SMILES: COc1ccc(CN(c2ncns2)S(=O)(=O)c2cnc(Cl)c(Br)c2)c(OC)c1] | ¹H NMR (CDCl₃, 400 MHz) δ 8.59 (d, J = 1.8 Hz, 1H), 8.26 (s, 1H), 7.80 (d, J = 2.0 Hz, 1H), 7.11 (d, J = 8.4 Hz, 1H), 6.43-6.29 (m, 1H), 6.16 (s, 1H), 5.37 (s, 2H), 3.78 (s, 3H), 3.58 (s, 3H). |
| 32 | 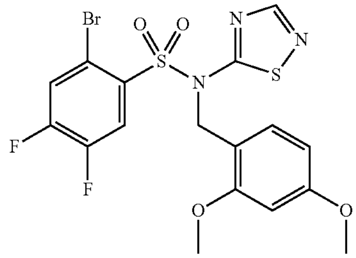 | LCMS (ES, m/z): 494.9 [M + H]⁺ |
| 33 | 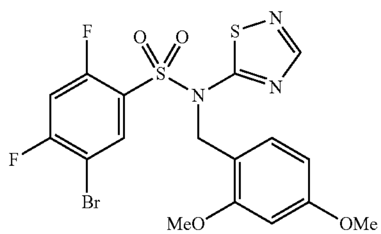 [SMILES: COc1ccc(CN(c2ncns2)S(=O)(=O)c2cc(Br)c(F)cc2F)c(OC)c1] | ¹H NMR (400 MHz, CDCl₃): δ 8.24 (s, 1H), 7.89 (t, J = 7.2 Hz, 1H), 7.21 (d, J = 8.4 Hz, 1H), 6.85 (t, J = 8.4 Hz, 1H), 6.35 (d, J = 8.4 Hz, 1H), 6.16 (d, J = 1.6 Hz, 1H), 5.37 (s, 2H), 2.99 (s, 3H), 3.03 (s, 3H). |
| 34 | 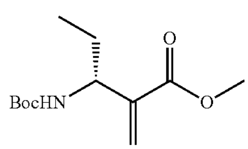 [SMILES: C=C(C(=O)OC)[C@@H](CC)NC(=O)OC(C)(C)C] | LCMS (ES, m/z): 244.1 [M + H]⁺ |
| 35 | 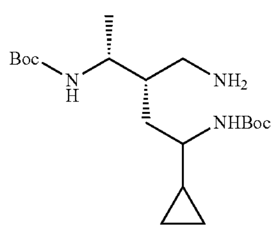 [SMILES: C[C@@H](NC(=O)OC(C)(C)C)[C@H](CN)CC(NC(=O)OC(C)(C)C)C1CC1] | LCMS (ES, m/z): 372.3 [M + H]⁺ |
| 36 | 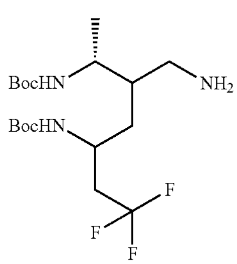 [SMILES: C[C@@H](NC(=O)OC(C)(C)C)C(CN)CC(CC(F)(F)F)NC(=O)OC(C)(C)C] | LCMS (ES, m/z): 414.3 [M + H]⁺ |
| 37 | 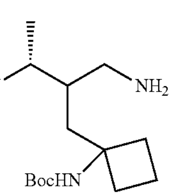 | LCMS (ES, m/z): 372.2 [M + H]⁺ |

TABLE 1-continued

| INTERMEDIATE | Structure | Characterization |
|---|---|---|
| 38 | BocHN, BocHN, NH₂ (ethyl substituent) | LCMS (ES, m/z): 374.3 [M + H]⁺ |

Example 1 (Isomer 1) and Example 2 (Isomer 2)

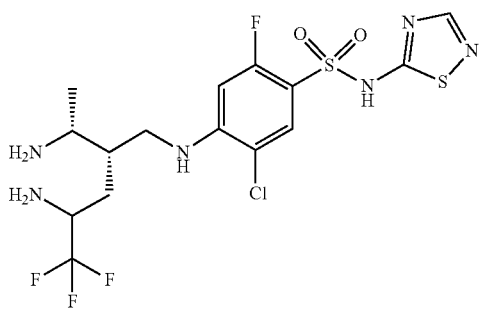 [SMILES: C[C@@H](N)[C@H](CNc1cc(F)c(S(=O)(=O)Nc2ncns2)cc1Cl)CC(N)C(F)(F)F]

4-(((2S)-4-amino-2-((R)-1-aminoethyl)-5,5,5-trifluoropentyl)amino)-5-chloro-2-fluoro-N-(1,2,4-thiadiazol-5-yl)benzenesulfonamide Step A: Tert-butyl benzyl((2R,3R)-3-((benzyloxy)methyl)-5-(((R)-tert-butylsulfinyl)amino)-6,6,6-trifluorohexan-2-yl)carbamate. A mixture of INTERMEDIATE 11 (1 g, 1.943 mmol) and tetrabutylammonium difluorotriphenylsilicate(IV) (2.360 g, 4.37 mmol) in Toluene (25 mL) was stirred for 0.5 h at −78° C. under N₂. Then trimethyl(trifluoromethyl)silane (0.829 g, 5.83 mmol) was added dropwise and the reaction mixture was stirred at 60° C. for 2 h. The mixture was diluted with NH₄Cl (10 mL), extracted with EtOAc (2×20 mL). The organic layer was washed with water (15 mL), brine (15 mL), dried over Na₂SO₄, filtered and filtrate was concentrated. The crude was purified by silica gel column (SiO₂, PE:EtOAc=10:1) to afford the title compound. LCMS (ES, m/z): 585.4 [M+H]⁺.

Step B: Tert-butyl ((2R,3R)-5-(((R)-tert-butylsulfinyl)amino)-6,6,6-trifluoro-3-(hydroxymethyl)hexan-2-yl)carbamate. To a solution of THF (10 mL) and liquid NH₃ (15 mL) was added sodium (450 mg, 19.56 mmol) at −78° C. After 10 min, a solution of tert-butyl benzyl((2R,3R)-3-((benzyloxy)methyl)-5-(((R)-tert-butylsulfinyl)amino)-6,6,6-trifluorohexan-2-yl)carbamate (1144 mg, 1.956 mmol) in THF (5 mL) was added to the dark blue mixture. The mixture was stirred for 1 h at this temperature. The reaction was quenched by addition of sat. NH₄Cl (10 mL). The mixture was concentrated to remove NH₃, extracted with EtOAc (3×20 mL). The combined organic layers were washed with brine (20 mL), dried with Na₂SO₄, filtered and concentrated in vacuo and purified by silica gel column (SiO₂, PE:EtOAc=1:1) to give the title compound. LCMS (ES, m/z): 305.0 [M+H]⁺. ¹H NMR (CDCl₃, 400 MHz) δ 4.87 (d, J=7.0 Hz, 1H), 4.12 (s, 1H), 3.87-3.70 (m, 3H), 3.65 (dd, J=10.8, 4.9 Hz, 1H), 2.01-1.93 (m, 1H), 1.79 (s, 1H), 1.74-1.63 (m, 1H), 1.58 (d, J=6.7 Hz, 1H), 1.43 (s, 9H), 1.26-1.18 (m, 12H).

Step C: Tert-butyl ((2R,3R)-5-(((R)-tert-butylsulfinyl)amino)-6,6,6-trifluoro-3-formylhexan-2-yl)carbamate. A mixture of tert-butyl ((2R,3R)-5-(((R)-tert-butylsulfinyl)amino)-6,6,6-trifluoro-3-(hydroxymethyl)hexan-2-yl)carbamate (120 mg, 0.297 mmol) and DMP (252 mg, 0.593 mmol) in CH₂Cl₂ (6 mL) was stirred at 25° C. for 3 h. The mixture was quenched by sat Na₂S₂O₃ (10 mL), diluted with water (30 mL), extracted by DCM (2×20 mL), dried over Na₂SO₄, filtered and concentrated in vacuo to give the crude product which was purified by prep-TLC (PE:EtOAc=2:1) to give the title compound.

Step D: Tert-butyl ((2R,3R)-5-(((R)-tert-butylsulfinyl)amino)-6,6,6-trifluoro-3-((E)-(hydroxyimino)methyl)hexan-2-yl)carbamate. To a solution of tert-butyl ((2R,3R)-5-(((R)-tert-butylsulfinyl)amino)-6,6,6-trifluoro-3-formylhexan-2-yl)carbamate (75 mg, 0.186 mmol) in EtOH (3 mL) was added sodium acetate (53.5 mg, 0.652 mmol) and hydroxylamine hydrochloride (38.8 mg, 0.559 mmol). The reaction mixture was stirred at 80° C. for 1 h under N₂. The mixture was filtered and the filtrate was concentrated to give the title compound, which was used in the next step without further purification. LCMS (ES, m/z): 418.2 [M+H]⁺.

Step E: Tert-butyl ((2R,3S)-3-(aminomethyl)-5-(((R)-tert-butylsulfinyl)amino)-6,6,6-trifluorohexan-2-yl)carbamate. To a solution of tert-butyl ((2R,3R)-5-(((R)-tert-butylsulfinyl)amino)-6,6,6-trifluoro-3-((E)-(hydroxyimino)methyl)hexan-2-yl)carbamate (80 mg, 0.153 mmol) in EtOH (8 mL) was added Raney Ni (20 mg, 0.153 mmol). The resulting mixture was stirred at 30° C. under H₂ (15 psi) for 40 min. The mixture was filtered, the filtrate was concentrated to give the title compound, which was used in the next step without further purification. LCMS (ES, m/z): 404.4 [M+H]⁺.

Step F: Tert-butyl ((2R,3S)-5-(((R)-tert-butylsulfinyl)amino)-3-(((2-chloro-4-(N-(2,4-dimethoxybenzyl)-N-(1,2,4-thiadiazol-5-yl)sulfamoyl)-5-fluorophenyl)amino)methyl)-6,6,6-trifluorohexan-2-yl)carbamate. A mixture of tert-butyl ((2R,3S)-3-(aminomethyl)-5-(((R)-tert-butylsulfinyl)amino)-6,6,6-trifluorohexan-2-yl)carbamate (70 mg, 0.139 mmol), 5-chloro-N-(2,4-dimethoxybenzyl)-2,4-difluoro-N-(1,2,4-thiadiazol-5-yl)benzenesulfonamide (83 mg, 0.180 mmol) in DMF (10 mL) was added Et₃N (0.097 mL, 0.694 mmol) and the reaction was stirred at 25° C. for 16 h. The mixture was quenched by NH₄Cl (5 mL), extracted by EtOAc (2×20 mL), the organic layer was washed with brine (10 mL), dried over Na₂SO₄, filtered and the filtrate was concentrated by vacuo to give a residue which was purified by prep-TLC (SiO₂, PE:EtOAc=1:1) to give the title compound. LCMS (ES, m/z): 845.3 [M+H]⁺.

Step G: 4-(((2S)-4-amino-2-((R)-1-aminoethyl)-5,5,5-trifluoropentyl)amino)-5-chloro-2-fluoro-N-(1,2,4-thiadiazol-5-yl)benzenesulfonamide. A mixture of tert-butyl ((2R,3S)-5-(((R)-tert-butylsulfinyl)amino)-3-(((2-chloro-4-(N-(2,4-dimethoxybenzyl)-N-(1,2,4-thiadiazol-5-yl)sulfamoyl)-5-fluorophenyl)amino)methyl)-6,6,6-trifluorohexan-2-yl)carbamate (40 mg, 0.047 mmol) and HCl/MeOH (2 mL) in DCM (8 mL) was stirred at 25° C. for 1 h. The mixture was concentrated by vacuo to give a residue which was purified by prep-HPLC (Phenomenex Synergi C18 150*30 mm*4 um using water and acetonitrile as the eluents. Mobile phase A: 0.05% TFA water, mobile phase B: acetonitrile. Gradient: 8-28% B, 0-10.0 min; 100% B, 10.1-12.0 min; 10% B, 12.1-15 min. FlowRate: 25 mL/min.) to give the title compound.

EXAMPLE 1—LCMS (ES, m/z): 491.1 [M+H]⁺. ¹H NMR (MeOD, 400 MHz) δ 8.22 (s, 1H), 7.73 (d, J=7.0 Hz, 1H), 6.67 (d, J=12.5 Hz, 1H), 4.50 (d, J=4.5 Hz, 1H), 3.64-3.34 (m, 3H), 2.43-2.26 (m, 2H), 1.85 (d, J=10.2 Hz, 1H), 1.38 (d, J=6.8 Hz, 3H).

In an analogous manner EXAMPLE 2 (Isomer 2) was prepared from the other diastereomer.

EXAMPLE 2—LCMS (ES, m/z): 491.0 [M+H]⁺. ¹H NMR (MeOD, 400 MHz) δ 8.22 (s, 1H), 7.72 (d, J=7.1 Hz, 1H), 6.72 (d, J=12.6 Hz, 1H), 4.35 (s, 1H), 3.65 (s, 1H), 3.46-3.33 (m, 2H), 2.56 (s, 1H), 2.15 (s, 1H), 2.05 (s, 1H), 1.39 (d, J=6.4 Hz, 3H).

Example 3 (Isomer 1) and Example 4 (Isomer 2)

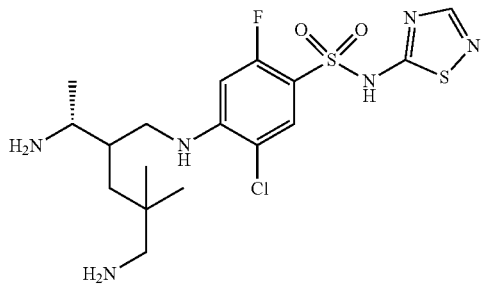 [SMILES: C[C@@H](N)C(CNc1cc(F)c(S(=O)(=O)Nc2ncns2)cc1Cl)CC(C)(C)CN]

4-((5-amino-2-((R)-1-aminoethyl)-4,4-dimethylpentyl)amino)-5-chloro-2-fluoro-N-(1,2,4-thiadiazol-5-yl)benzenesulfonamide Step A: Tert-butyl (2,2-dimethyl-3-oxopropyl)carbamate. To a stirred solution of (COCl)₂ (15.50 mL, 177 mmol) in CH₂Cl₂ (250 mL) was added DMSO (25.1 mL, 354 mmol) at −78° C., which was allowed to stir for 30 min at the same temperature. Tert-butyl (3-hydroxy-2,2-dimethylpropyl)carbamate (18 g, 89 mmol) in CH₂Cl₂ (200 mL) was added at −78° C., which was allowed to stir for 30 min at the same temperature. And then TEA (99 mL, 708 mmol) was added at −78° C., which was allowed to stir for 30 min at the same temperature. The reaction was allowed to stir for 1 h at 0° C. The reaction was diluted with H₂O (200 mL), extracted by CH₂Cl₂ (2×150 mL). The organic layer was washed with water (200 mL) and brine (200 mL) and dried over Na₂SO₄, filtered and concentrated in vacuo. The residue was purified by column chromatography (SiO₂, PE:EtOAc=10:1) to give the title compound. ¹H NMR (CDCl₃, 400 MHz) δ 9.42 (s, 1H), 3.20 (d, J=6.4 Hz, 2H), 1.38 (br s, 9H), 1.05 (s, 6H)

Step B: Methyl 5-((tert-butoxycarbonyl)amino)-2-((R)-1-((tert-butoxycarbonyl)amino)ethyl)-3-hydroxy-4,4-dimethylpentanoate. To a mixture of lithium diisopropylamide (130 mL, 261 mmol) at −78° C. under N₂ was added (R)-methyl 3-((tert-butoxycarbonyl)amino)butanoate (16.19 g, 74.5 mmol) in THF (200 mL) dropwise. And then the mixture was stirred at −78° C. for 1 h. To the mixture was added tert-butyl (2,2-dimethyl-3-oxopropyl)carbamate (15 g, 74.5 mmol) in THF (150 mL) at −78° C. and then stirred at 15° C. for 0.5 h. The mixture was quenched by saturated NH₄Cl aq. (200 mL), and extracted by EtOAc (2×100 mL). The organic layer was washed with water (200 mL) and brine (200 mL), dried over Na₂SO₄, filtered and concentrated in vacuo. The residue was purified by column chromatography (SiO₂) (PE:EtOAc=10: 1-5:1) to give the title compound. ¹H NMR (CDCl₃, 400 MHz) δ 4.10 (d, J=7.0 Hz, 1H), 3.96-3.86 (m, 1H), 3.80-3.66 (m, 3H), 3.59-3.51 (m, 1H), 3.26 (s, 1H), 2.82-2.77 (m, 1H), 1.41 (br s, 18H), 1.21-1.11 (m, 3H), 0.83 (d, J=5.9 Hz, 6H)

Step C: Methyl (R,Z)-5-((tert-butoxycarbonyl)amino)-2-(1-((tert-butoxycarbonyl)amino)ethyl)-4,4-dimethylpent-2-enoate. To a solution of methyl 5-((tert-butoxycarbonyl)amino)-2-((R)-1-((tert-butoxycarbonyl)amino)ethyl)-3-hydroxy-4,4-dimethylpentanoate (18 g, 43.0 mmol) in toluene (240 mL) was added Burgess reagent (35.9 g, 151 mmol) and 4 Å MS (10 g). The reaction was stirred for 12 h at 80° C. The suspension was concentrated and purified by silica gel column chromatography (PE:EtOAc=8:1) to provide the title compound. ¹H NMR (CDCl₃, 400 MHz) δ 6.70-6.65 (m, 1H), 5.06-4.96 (m, 1H), 3.74 (s, 3H), 3.29-3.14 (m, 2H), 1.43 (d, J=4.5 Hz, 18H), 1.36-1.34 (m, 3H), 1.23 (d, J=3.5 Hz, 6H).

Step D: Methyl 5-((tert-butoxycarbonyl)amino)-2-((R)-1-((tert-butoxycarbonyl)amino)ethyl)-4,4-dimethylpentanoate. To a stirred solution of methyl (R,Z)-5-((tert-butoxycarbonyl)amino)-2-(1-((tert-butoxycarbonyl)amino)ethyl)-4,4-dimethylpent-2-enoate in MeOH (200 mL) was added Pd—C (2.391 g, 2.247 mmol) at 15° C. under H₂ balloon, which was allowed to stir for 5 h at 15° C. The reaction was filtered and concentrated to give the title compound which was used for the next step without further purification. ¹H NMR (CDCl₃, 400 MHz) δ 3.84-3.78 (m, 1H), 3.67 (d, J=2.0 Hz, 3H), 3.38-3.18 (m, 1H), 3.04-2.95 (m, 1H), 2.80-2.46 (m, 3H), 1.41 (s, 18H), 1.06 (t, J=6.5 Hz, 3H), 0.81 (d, J=10.2 Hz, 6H).

Step E: Di-tert-butyl ((5R)-4-(hydroxymethyl)-2,2-dimethylhexane-1,5-diyl)dicarbamate. To a solution of calcium chloride (24.81 g, 224 mmol) in EtOH (150 mL) was added NaBH₄ (12.69 g, 335 mmol) at 0° C. Then the mixture was stirred at 15° C. for 0.5 h, methyl 5-((tert-butoxycarbonyl)amino)-2-((R)-1-((tert-butoxycarbonyl)amino)ethyl)-4,4-dimethylpentanoate (9 g, 22.36 mmol) was soluted in dry EtOH (100 mL) and added to the suspension. Then the mixture was stirred at 15° C. for 20 h. The reaction was then quenched by adding citric acid (10% aq.), adjusting the pH of the mixture to 5-6. EtOH was removed in vacuo and the residue was extracted by EtOAc (2×150 mL). The organic layer was dried over Na₂SO₄, then filtered and concentrated to give a residue which was purified by column chrotomagraphy (SiO₂, PE:EtOAc=10: 1-5:1) to give the title compound. ¹H NMR (CDCl₃, 400 MHz) δ 4.00-3.38 (m, 3H), 3.36-3.02 (m, 1H), 2.96-2.84 (m, 2H), 1.37 (d, J=1.6 Hz, 18H), 1.11 (d, J=6.7 Hz, 2H), 1.07-0.96 (m, 3H), 0.82-0.79 (m, 6H).

Step F: Di-tert-butyl ((5R)-4-((1,3-dioxoisoindolin-2-yl)methyl)-2,2-dimethylhexane-1,5-diyl)dicarbamate. DEAD (3.64 mL, 22.96 mmol) in THF (20 mL) was added to a mixture of di-tert-butyl ((5R)-4-(hydroxymethyl)-2,2-dimethylhexane-1,5-diyl)dicarbamate (4.3 g, 11.48 mmol), isoindoline-1,3-dione (2.53 g, 17.22 mmol) and PPh$_3$ (4.52 g, 17.22 mmol) in THF (130 mL) under ice-bath. The resulting mixture was stirred at 15° C. for 15 h. The reaction was then diluted with EtOAc (50 mL) and water (100 mL). The aqueous layer was extracted with EtOAc (2×50 mL). The combined organic phase was dried over Na$_2$SO$_4$, filtered and the filtrate was concentrated in vacuo. The residue was purified by column chromatography (SiO$_2$, PE:EtOAc=20:1-10:1) to give the title compound. $^1$H NMR (CDCl$_3$, 400 MHz) δ 7.86-7.79 (m, 2H), 7.73-7.68 (m, 2H), 3.75-3.42 (m, 3H), 3.05-2.90 (m, 2H), 2.39-2.20 (m, 1H), 1.63-1.27 (m, 18H), 1.20-1.16 (m, 4H), 1.02-0.90 (m, 6H). The diastereometric mixture was was separated by SFC (SFC-1001169-037-01_E1: Column: Chiralpak AD-3 150×4.6 mm I.D., 3 um Mobile phase: A: CO$_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C. t$_1$=2.649, t$_2$=3.037) to give Peak 1, Isomer 1 and Peak 2, Isomer 2.

Step G: Di-tert-butyl ((5R)-4-(aminomethyl)-2,2-dimethylhexane-1,5-diyl)dicarbamate. N$_2$H$_4$·H$_2$O (5 mL, 8.34 mmol) was added to a solution of di-tert-butyl ((5R)-4-((1,3-dioxoisoindolin-2-yl)methyl)-2,2-dimethylhexane-1,5-diyl)dicarbamate (Isomer 1 from Step F) (4.2 g, 8.34 mmol) in EtOH (100 mL). Then the mixture was stirred at 80° C. for 1.5 h. After the reaction was completed the mixture was concentrated by vacuo to give a residue which was diluted with CH$_2$Cl$_2$ (100 mL). The mixture was filtered and the filtrate was concentrated to give the title compound, which was used in the next step without further purification. LCMS (ES, m/z): 374.4 [M+H]$^+$.

Step H: Di-tert-butyl ((5R)-4-(((2-chloro-4-(N-(2,4-dimethoxybenzyl)-N-(1,2,4-thiadiazol-5-yl)sulfamoyl)-5-fluorophenyl)amino)methyl)-2,2-dimethylhexane-1,5-diyl)dicarbamate. A mixture of di-tert-butyl ((5R)-4-(aminomethyl)-2,2-dimethylhexane-1,5-diyl)dicarbamate (2.95 g, 7.90 mmol), INTERMEDIATE 3 (3.65 g, 7.90 mmol) and TEA (1.101 mL, 7.90 mmol) in DMF (70 mL) was stirred at 15° C. for 16 h. The mixture was concentrated in vacuo and purified by column chromatography (SiO$_2$, PE:EtOAc=6:1) to give the title compound. $^1$H NMR (CDCl$_3$, 400 MHz) δ 8.50-8.11 (m, 1H), 7.60 (d, J=7.0 Hz, 1H), 7.14 (d, J=8.4 Hz, 1H), 6.34 (dd, J=8.4, 2.2 Hz, 1H), 6.26 (d, J=2.0 Hz, 1H), 6.18 (br d, J=12.3 Hz, 1H), 5.27-5.17 (m, 2H), 4.39 (br d, J=8.0 Hz, 1H), 3.92 (br s, 1H), 3.72 (d, J=3.3 Hz, 6H), 3.13 (d, J=5.5 Hz, 1H), 2.98-2.88 (m, 3H), 1.42 (s, 18H), 1.23-1.15 (m, 2H), 1.09 (d, J=7.0 Hz, 3H), 0.91 (d, J=13.5 Hz, 6H).

Step I: 4-((5-amino-2-((R)-1-aminoethyl)-4,4-dimethylpentyl)amino)-5-chloro-2-fluoro-N-(1,2,4-thiadiazol-5-yl)benzenesulfonamide. A mixture of di-tert-butyl ((5R)-4-(((2-chloro-4-(N-(2,4-dimethoxybenzyl)-N-(1,2,4-thiadiazol-5-yl)sulfamoyl)-5-fluorophenyl)amino)methyl)-2,2-dimethylhexane-1,5-diyl)dicarbamate (5.2 g, 6.38 mmol) and TFA (15 mL, 195 mmol) in CH$_2$Cl$_2$ (120 mL) was stirred at 20° C. for 1 h. The mixture was concentrated in vacuo to give the crude product which was purified by acidic prep-HPLC (acidic, HCl, Condition: water (0.05% HCl)-ACN, Column: Phenomenex luna C18 250*50 mm*10 um, Begin B: 5 End B: 35 Gradient Time (min): 20 FlowRate (ml/min) 120, 100% B Hold Time (min): 5) to give the title compound.

EXAMPLE 3—LCMS (ES, m/z): 465.1 [M+H]$^+$. $^1$H NMR (CD$_3$OD, 400 MHz) δ 8.21 (s, 1H), 7.72 (d, J=7.1 Hz, 1H), 6.65 (d, J=12.8 Hz, 1H), 3.49-3.40 (m, 2H), 3.18 (dd, J=13.7, 8.6 Hz, 1H), 2.80 (s, 2H), 2.17 (br s, 1H), 1.54-1.49 (m, 1H), 1.44-1.39 (m, 1H), 1.34 (d, J=6.8 Hz, 3H), 1.04-0.98 (m, 6H).

Following the procedure of EXAMPLE 3 steps G through I using Isomer 2 from Step F afforded 4-((5-amino-2-((R)-1-aminoethyl)-4,4-dimethylpentyl)amino)-5-chloro-2-fluoro-N-(1,2,4-thiadiazol-5-yl)benzenesulfonamide (EXAMPLE 4).

EXAMPLE 4—LCMS (ES, m/z): 465.1 [M+H]$^+$. $^1$H NMR (CD$_3$OD, 400 MHz) δ 8.21 (s, 1H), 7.71 (d, J=7.3 Hz, 1H), 6.59 (d, J=12.6 Hz, 1H), 3.51 (dd, J=6.8, 2.6 Hz, 1H), 3.36-3.31 (m, 1H), 3.29-3.24 (m, 1H), 2.85 (s, 2H), 2.26-2.19 (m, 1H), 1.72-1.66 (m, 1H), 1.36-1.30 (m, 4H), 1.07 (d, J=6.6 Hz, 6H).

Example 5

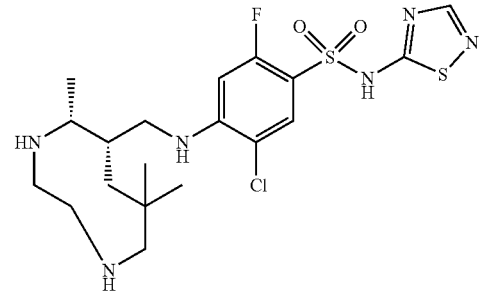 [SMILES: C[C@H]1NCCNCC(C)(C)C[C@H]1CNc1cc(F)c(S(=O)(=O)Nc2ncns2)cc1Cl]

5-chloro-2-fluoro-N-(1,2,4-thiadiazol-5-yl)-4-((((5R,6S)-5,8,8-trimethyl-1,4-diazonan-6-yl)methyl)amino)benzenesulfonamide Step A: Ethyl ((5R)-4-(((4-(N-(1,2,4-thiadiazol-5-yl)sulfamoyl)-2-chloro-5-fluorophenyl)amino)methyl)-5-amino-2,2-dimethylhexyl)glycinate. To a mixture of EXAMPLE 3 (first isomer from above) (200 mg, 0.430 mmol) and ethyl 2-oxoacetate (17.56 mg, 0.172 mmol) in MeOH (3 mL) was added sodium cyanotrihydroborate (54.1 mg, 0.860 mmol). The mixture was stirred at 25° C. for 16 h. The mixture was diluted with NH$_4$Cl (5 mL), extracted with DCM (2×10 mL). The organic layer was washed with water (10 mL), brine (10 mL), dried over Na$_2$SO$_4$, filtered and filtrate was concentrated in vacuo and purified by Prep-HPLC (Mobile phase A: 0.05% ammonia hydroxide v/v; Mobile phase B: acetonitrile. Gradient: 16-36% B, 0-10.0 min; 100% B, 10.1-12.0 min; 10% B, 12.1-15 min.; FlowRate: 25 mL/min) give the title compound. LCMS (ES, m/z): 551.2 [M+H]$^+$.

Step B: ((5R)-4-(((4-(N-(1,2,4-thiadiazol-5-yl)sulfamoyl)-2-chloro-5-fluorophenyl)amino)methyl)-5-amino-2,2-dimethylhexyl)glycine. To a mixture of ethyl ((5R)-4-(((4-(N-(1,2,4-thiadiazol-5-yl)sulfamoyl)-2-chloro-5-fluorophenyl)amino)methyl)-5-amino-2,2-dimethylhexyl)glycinate (50 mg, 0.091 mmol) and NaOH (18.14 mg, 0.454 mmol) in THF (2 mL) and Water (1 mL) was stirred at 25° C. for 2 h. The pH value was adjusted to 2 by 1M HCl solution, concentrated by vacuo to give the title compound, which was used the next step without purification.

Step C: 5-Chloro-2-fluoro-N-(1,2,4-thiadiazol-5-yl)-4-(((((5R)-5,8,8-trimethyl-3-oxo-1,4-diazonan-6-yl)methyl)

amino)benzenesulfonamide. To a mixture of ((5R)-4-(((4-(N-(1,2,4-thiadiazol-5-yl)sulfamoyl)-2-chloro-5-fluorophenyl)amino)methyl)-5-amino-2,2-dimethylhexyl)glycine (45 mg, 0.086 mmol), HATU (65.4 mg, 0.172 mmol) and DIEA (0.045 mL, 0.258 mmol) in DMF (3 mL) was stirred at 25° C. for 16 h. The mixture was diluted with NH$_4$Cl (5 mL), extracted with DCM (2×10 mL). The organic layer was washed with water (10 mL), brine (10 mL), dried over Na$_2$SO$_4$, filtered and filtrate was concentrated and purified by Prep-HPLC (Phenomenex Synergi C18 150*30 mm*4 um using water and acetonitrile as the eluents. Mobile phase A: 0.05% TFA water; Mobile phase B: acetonitrile. Gradient: 10-40% B, 0-10.0 min; 100% B, 10.1-12.0 min; 10% B, 12.1-15 min.; FlowRate: 25 mL/min.) to give the title compound. LCMS (ES, m/z): 505.1 [M+H]$^+$. $^1$H NMR (CD$_3$OD, 400 MHz) δ 8.19 (s, 1H), 7.68 (d, J=7.0 Hz, 1H), 6.57 (d, J=12.9 Hz, 1H), 4.21 (s, 1H), 4.00 (d, J=13.3 Hz, 1H), 3.41 (d, J=13.3 Hz, 1H), 3.20 (s, 1H), 3.13-3.01 (m, 1H), 2.94 (d, J=14.1 Hz, 1H), 2.71 (d, J 13.7 Hz, 1H), 2.27 (s, 1H), 1.70 (d, J=16.0 Hz, 1H), 1.20 (d, J=16.4 Hz, 1H), 1.10 (s, 6H), 0.82 (br s, 3H).

Step D: 5-Chloro-2-fluoro-N-(1,2,4-thiadiazol-5-yl)-4-((((5R,6S)-5,8,8-trimethyl-1,4-diazonan-6-yl)methyl)amino)benzenesulfonamide. To a mixture of 5-chloro-2-fluoro-N-(1,2,4-thiadiazol-5-yl)-4-((((5R)-5,8,8-trimethyl-3-oxo-1,4-diazonan-6-yl)methyl)amino)benzenesulfonamide (22 mg, 0.044 mmol) and BF$_3$·OEt$_2$ (0.039 mL, 0.305 mmol) in THF (2 mL) was added NaBH$_4$ (8.24 mg, 0.218 mmol) at 0° C. The mixture was stirred at 25° C. for 1 h. The mixture was added MeOH (1 mL) and purified by Prep-HPLC (Mobile phase A: 0.05% TFA water; Mobile phase B: acetonitrile. Gradient: 25-45% B, 0-10.0 min; 100% B, 10.1-12.0 min; 10% B, 12.1-15 min.; Flow-Rate: 25 mL/min.) to give the title compound. LCMS (ES, m/z): 490.9 [M+H]$^+$. $^1$H NMR (CD$_3$OD, 400 MHz) δ 8.20 (s, 1H), 7.69 (d, J=7.0 Hz, 1H), 6.58 (d, J=12.5 Hz, 1H), 3.26-3.10 (m, 4H), 3.03-2.91 (m, 1H), 2.87 (s, 2H), 2.65 (q, J=14.1 Hz, 2H), 2.16 (s, 1H), 1.94 (d, J=14.9 Hz, 1H), 1.10-0.98 (m, 7H), 0.87 (s, 3H).

Example 6 (Isomer 1) and Example 7 (Isomer 2)

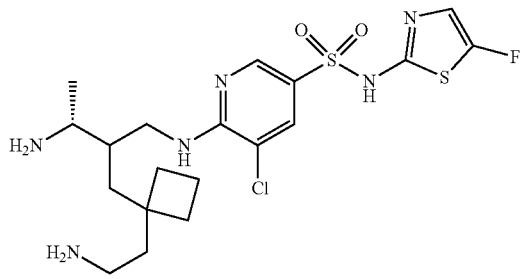 [SMILES: C[C@@H](N)C(CNc1ncc(S(=O)(=O)Nc2ncc(F)s2)cc1Cl)CC1(CCN)CCC1]

6-((3R)-3-amino-2-((1-(2-aminoethyl)cyclobutyl)methyl)butoxy)-5-chloro-N-(5-fluorothiazol-2-yl)pyridine-3-sulfonamide Step A: Tert-butyl ((2R)-4-(1-(2-((tert-butoxycarbonyl)amino)ethyl)cyclobutyl)-3-(((3-chloro-5-(N-(2,4-dimethoxybenzyl)-N-(5-fluorothiazol-2-yl)sulfamoyl)pyridin-2-yl)oxy)methyl)butan-2-yl)carbamate. To a mixture of tert-butyl ((2R)-4-(1-(2-((tert-butoxycarbonyl)amino)ethyl)cyclobutyl)-3-(hydroxymethyl)butan-2-yl)carbamate (60 mg, 0.154 mmol) and Intermediate 18 (229 mg, 0.479 mmol) in DMF (5 mL) was added LiHMDS (0.386 mL, 0.386 mmol) at 0° C. under N$_2$. The mixture was stirred at 0° C. for 1 h. The reaction was quenched by addition of sat. NH$_4$Cl (5 mL), extracted with EtOAc (2×10 mL). The combined organic layers were washed with brine (5 mL), dried over Na$_2$SO$_4$, filtered and concentrated. The crude product was purified by prep-TLC (SiO$_2$, PE:EtOAc=3:1) to give the title compound as a mixture of diastereomers. The mixture of diastereomers was resolved (Column: Chiralpak IC-3 150×4.6 mm I.D., 3 um Mobile phase: A: CO$_2$ B:ethanol (0.05% DEA) Gradient: from 5% to 40% of B in 5.5 min and hold 40% for 3 min, then 5% of B for 1.5 min Flow rate: 2.5 mL/min Column temperature: 40° C.) to give Peak 1, Isomer 1 and Peak 2 Isomer 2. LCMS (ES, m/z): 864.3 [M+H]$^+$ for both isomers.

Step B: 6-((3R)-3-amino-2-((1-(2-aminoethyl)cyclobutyl)methyl)butoxy)-5-chloro-N-(5-fluorothiazol-2-yl)pyridine-3-sulfonamide. A mixture of Isomer 1 from Step A (100 mg, 0.119 mmol) in CH$_2$Cl$_2$ (5 mL) and TFA (2 mL) was stirred at 20° C. for 1 h. After the reaction was complete, the mixture was concentrated in vacuo to give the crude product which was purified by acidic prep-HPLC (Phenomenex Synergi C18 150*30 mm*4 um using water and acetonitrile as the eluents. Mobile phase A: water (0.1% TFA)-ACN; mobile phase B: acetonitrile. Gradient: 8-38% B, 0-11.0 min; 100% B, 11.1-12.0 min; 10% B, 12.1-15 min. Flow-Rate: 25 mL/min.) to give the title compound.

EXAMPLE 6—LCMS (ES, m/z): 492.1 [M+H]$^+$. $^1$H NMR (CD$_3$OD, 400 MHz) δ 8.56 (d, J=1.8 Hz, 1H), 8.17 (d, J=1.8 Hz, 1H), 7.04 (s, 1H), 4.68-4.60 (m, 1H), 4.40-4.31 (m, 1H), 3.63-3.54 (m, 1H), 3.01-2.89 (m, 2H), 2.41-2.31 (m, 1H), 2.05-1.88 (m, 7H), 1.88-1.73 (m, 2H), 1.69-1.57 (m, 1H), 1.47-1.35 (m, 3H).

Following the similar procedure with Isomer 2 from Step A in EXAMPLE 6 afforded EXAMPLE 7.

EXAMPLE 7—$^1$H NMR (CD$_3$OD, 400 MHz) δ 8.56 (s, 1H), 8.22-8.12 (m, 1H), 7.10-6.99 (m, 1H), 4.51 (d, J=3.5 Hz, 2H), 3.59-3.51 (m, 1H), 3.02-2.87 (m, 2H), 2.49-2.40 (m, 1H), 2.06-1.96 (m, 3H), 1.96-1.89 (m, 4H), 1.89-1.82 (m, 1H), 1.79-1.70 (m, 1H), 1.64-1.55 (m, 1H), 1.39 (d, J=6.8 Hz, 3H).

Example 8 (Isomer 1) and Example 9 (Isomer 2)

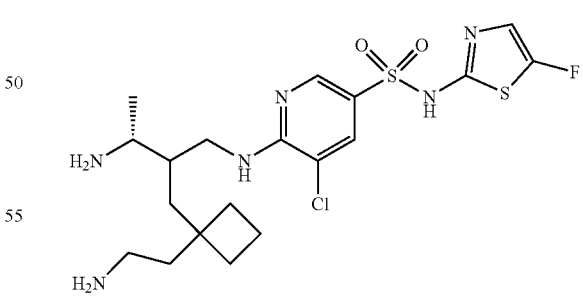

6-(((3R)-3-amino-2-((1-(2-aminoethyl)cyclobutyl)methyl)butyl)amino)-5-chloro-N-(5-fluorothiazol-2-yl)pyridine-3-sulfonamide Step A: Tert-butyl ((2R)-4-(1-(2-((tert-butoxycarbonyl)amino)ethyl)cyclobutyl)-3-(((3-chloro-5-(N-(2,4-dimethoxybenzyl)-N-(5-fluorothiazol-2-yl)sulfamoyl)pyridin-2- yl)amino)methyl)butan-2-yl)carbamate. To a mixture of INTERMEDIATE 15A (400 mg, 1.001 mmol) and INTERMEDIATE 1 (575 mg, 1.201 mmol) in DMSO (5 mL) was added TEA (0.419 mL, 3.00 mmol) at 20° C. under $N_2$. The mixture was stirred at 80° C. for 2 h. The reaction was quenched by addition of sat. $NH_4Cl$ (5 mL), extracted with EtOAc (2×10 mL). The combined organic layers were washed with brine (5 mL), dried over $Na_2SO_4$, filtered and concentrated. The crude product was purified by prep-TLC ($SiO_2$, PE:EtOAc=3:1) to give the title compound as a mixture of diastereomers. The mixture of diastereomers (110 mg, 0.131 mmol) was resolved (Column: Chiralpak AD-3 150×4.6 mm I.D., 3 um Mobile phase: A: $CO_2$ B: isopropanol (0.05% DEA) Gradient: from 5% to 40% of B in 5 min and hold 40% for 2.5 min, then 5% of B for 2.5 min Flow rate: 2.5 mL/min Column temp.: 35° C.) to give Peak 1, Isomer 1 and Peak 2 Isomer 2. LCMS (ES, m/z): 841.3 $[M+H]^+$.

Step B: 6-(((3R)-3-amino-2-((1-(2-aminoethyl)cyclobutyl)methyl)butyl)amino)-5-chloro-N-(5-fluorothiazol-2-yl)pyridine-3-sulfonamide. A mixture of Isomer 1 from Step A (100 mg, 0.119 mmol) in $CH_2Cl_2$ (5 mL) and TFA (2 mL) was stirred at 20° C. for 1 h. After the reaction was complete, the mixture was concentrated in vacuo to give the crude product which was purified by acidic prep-HPLC (Phenomenex Synergi C18 150*30 mm*4 um using water and acetonitrile as the eluents. Mobile phase A: water (0.1% TFA)-ACN; mobile phase B: acetonitrile. Gradient: 9-39% B, 0-10.0 min; 100% B, 10.1-12.0 min; 10% B, 12.1-15 min. FlowRate: 25 mL/min) to give the title compound.

EXAMPLE 8—LCMS (ES, m/z): 491.1 $[M+H]^+$. $^1$H NMR ($CD_3OD$, 400 MHz) δ 8.51-8.43 (m, 1H), 7.99-7.92 (m, 1H), 7.06-6.98 (m, 1H), 3.77-3.68 (m, 1H), 3.49-3.36 (m, 2H), 2.95-2.82 (m, 2H), 2.23-2.15 (m, 1H), 2.09-1.73 (m, 8H), 1.68-1.61 (m, 1H), 1.53-1.44 (m, 1H), 1.37-1.27 (m, 3H).

Following the similar procedure with Isomer 2 from EXAMPLE 8, Step A, afforded EXAMPLE 9.

EXAMPLE 9—$^1$H NMR ($CD_3OD$, 400 MHz) δ 8.46 (br. s., 1H), 7.95-7.85 (m, 1H), 7.00 (br. s., 1H), 3.72-3.61 (m, 1H), 3.40 (br. s., 2H), 2.95 (br. s., 2H), 2.42-2.29 (m, 1H), 2.11 (d, J=6.7 Hz, 2H), 2.06-1.73 (m, 6H), 1.60-1.39 (m, 2H), 1.30 (d, J=5.1 Hz, 3H).

Example 10

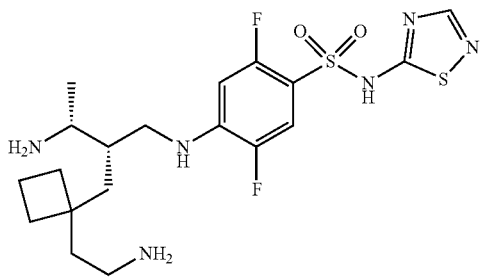 [SMILES: C[C@@H](N)[C@H](CNc1cc(F)c(S(=O)(=O)Nc2ncns2)cc1F)CC1(CCN)CCC1]

4-(((2S,3R)-3-amino-2-((1-(2-aminoethyl)cyclobutyl)methyl)butyl)amino)-2,5-difluoro-N-(1,2,4-thiadiazol-5-yl)benzenesulfonamide Step A: Tert-butyl (2-(1-(((2S,3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)cyclobutyl)ethyl)carbamate. To a mixture of INTERMEDIATE 15C (40 mg, 0.100 mmol), INTERMEDIATE 30 (53.5 mg, 0.120 mmol) in DMF (4 mL) was added $Et_3N$ (0.070 mL, 0.501 mmol) and the reaction was stirred at 25° C. for 16 h. The mixture was quenched by $NH_4Cl$ (5 mL), extracted by EtOAc (2×20 mL), the organic layer was washed with brine (10 mL), dried over $Na_2SO_4$, filtered and the filtrate was concentrated in vacuo to give a residue which was purified by prep-TLC ($SiO_2$, PE:EtOAc=2:1) to afford the title compound. LCMS (ES, m/z): 825.4 $[M+H]^+$.

Step B: 4-(((2S,3R)-3-amino-2-((1-(2-aminoethyl)cyclobutyl)methyl)butyl)amino)-2,5-difluoro-N-(1,2,4-thiadiazol-5-yl)benzenesulfonamide. To a solution of tert-butyl (2-(1-(((2S,3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)cyclobutyl)ethyl)carbamate (80 mg, 0.097 mmol) in 4 mL DCM was added TFA (1 mL, 12.98 mmol). The mixture was stirred at 25° C. for 1.5 h. The mixture was concentrated in vacuo and the residue was purified by prep-HPLC (acidic, TFA, Condition: water (0.1% TFA)-ACN, Column: Phenomenex Synergi C18 150*30 mm*4 um, Begin B: 5 End B: 30 Gradient Time (min): 11, FlowRate (mL/min): 25, 100% B Hold Time (min): 2) to afford the title compound. LCMS (ES, m/z): 475.2 $[M+H]^+$. $^1$H NMR (400 MHz, $CD_3OD$) δ 8.18 (s, 1H), 7.44 (dd, J=10.9, 6.1 Hz, 1H), 6.52 (dd, J=12.0, 6.7 Hz, 1H), 3.54 (dd, J=6.8, 3.1 Hz, 1H), 3.20 (d, J=6.6 Hz, 2H), 2.99-2.88 (m, 2H), 2.17 (br s, 1H), 2.01-1.85 (m, 8H), 1.63-1.42 (m, 2H), 1.30 (d, J=6.6 Hz, 3H).

Example 11

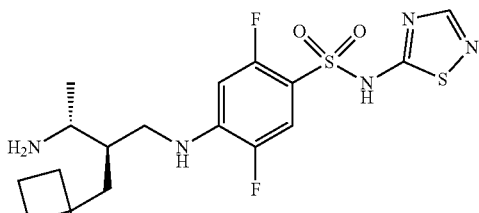

4-(((2R,3R)-3-amino-2-((1-(2-aminoethyl)cyclobutyl)methyl)butyl)amino)-2,5-difluoro-N-(1,2,4-thiadiazol-5-yl)benzenesulfonamide In an analogous fashion to EXAMPLE 10, using INTERMEDIATE 15B, EXAMPLE 11 was prepared. LCMS (ES, m/z): 475.2 $[M+H]^+$. $^1$H NMR (400 MHz, $CD_3OD$) δ 8.17 (br s, 1H), 7.45 (dd, J=10.7, 5.6 Hz, 1H), 6.58 (br s, 1H), 3.52 (br s, 1H), 3.34 (s, 1H), 3.16-3.07 (m, 1H), 2.87 (t, J=8.5 Hz, 2H), 2.14 (br s, 1H), 2.00-1.83 (m, 8H), 1.62-1.47 (m, 2H), 1.33 (d, J=6.6 Hz, 3H).

Example 12

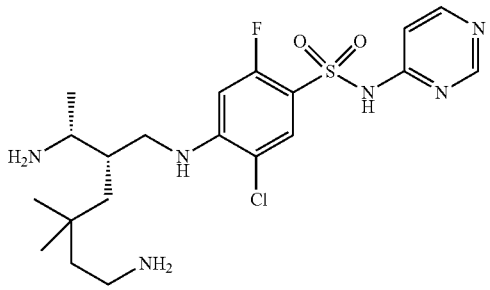 [SMILES: C[C@@H](N)[C@H](CNc1cc(F)c(S(=O)(=O)Nc2ccncn2)cc1Cl)CC(C)(C)CCN]

4-(((S)-6-amino-2-((R)-1-aminoethyl)-4,4-dimethylhexyl)amino)-5-chloro-2-fluoro-N-(pyrimidin-4-yl)benzenesulfonamide Step A: Di-tert-butyl ((5S,6R)-5-(((2-chloro-5-fluoro-4-(N-(methoxymethyl)-N-(pyrimidin-4-yl)sulfamoyl)phenyl)amino)methyl)-3,3-dimethylheptane-1,6-diyl)dicarbamate. A mixture of INTERMEDIATE 14A (45 mg, 0.116 mmol), INTERMEDIATE 24 (48.7 mg, 0.139 mmol) and Et₃N (0.081 mL, 0.581 mmol) in DMF (5 mL) was stirred at 25° C. for 16 h. The mixture was concentrated in vacuo and purified by prep-TLC (SiO₂) (PE:EtOAc=2:1) to give the title compound. LCMS (ES, m/z): 717.4 [M+H]⁺.

Step B: 4-(((S)-6-amino-2-((R)-1-aminoethyl)-4,4-dimethylhexyl)amino)-5-chloro-2-fluoro-N-(pyrimidin-4-yl)benzenesulfonamide. A mixture of di-tert-butyl ((5S,6R)-5-(((2-chloro-5-fluoro-4-(N-(methoxymethyl)-N-(pyrimidin-4-yl)sulfamoyl)phenyl)amino)methyl)-3,3-dimethylheptane-1,6-diyl)dicarbamate (30 mg, 0.042 mmol) and TFA (1 mL) in DCM (5 mL) was stirred at 25° C. for 20 mins. The mixture was concentrated in vacuo to give a residue which was purified by prep-HPLC (Phenomenex Synergi C18 150*30 mm*4 um using water and acetonitrile as the eluents. Mobile phase A: 0.05% TFA water; mobile phase B: acetonitrile. Gradient: 0-27% B, 0-10.0 min; 100% B, 10.1-12.0 min; 10% B, 12.1-15 min. FlowRate: 25 mL/min.) to give the title compound. LCMS (ES, m/z): 473.2 [M+H]⁺. ¹H NMR (MeOD, 400 MHz) δ 8.59 (s, 1H), 8.33 (d, J=6.1 Hz, 1H), 7.89 (d, J=7.2 Hz, 1H), 7.05 (d, J=5.9 Hz, 1H), 6.55 (d, J=12.9 Hz, 1H), 3.49 (s, 1H), 3.28 (d, J=7.6 Hz, 2H), 3.01-2.91 (m, 2H), 2.17 (s, 1H), 1.66-1.57 (m, 2H), 1.50 (d, J=14.7 Hz, 1H), 1.32 (d, J=6.8 Hz, 3H), 1.25 (dd, J=15.0, 6.0 Hz, 1H), 0.98 (s, 6H).

Example 13

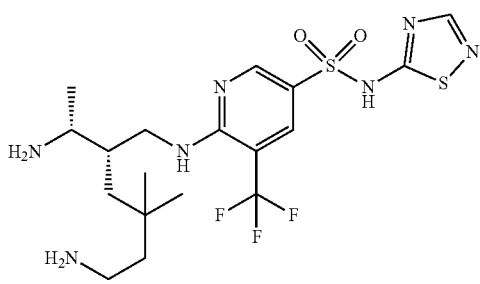 [SMILES: C[C@@H](N)[C@H](CNc1ncc(S(=O)(=O)Nc2ncns2)cc1C(F)(F)F)CC(C)(C)CCN]

6-(((S)-6-amino-2-((R)-1-aminoethyl)-4,4-dimethylhexyl)amino)-N-(1,2,4-thiadiazol-5-yl)-5-(trifluoromethyl)pyridine-3-sulfonamide Step A: Di-tert-butyl ((5S,6R)-5-(((5-(N-(2,4-dimethoxybenzyl)-N-(1,2,4-thiadiazol-5-yl)sulfamoyl)-3-(trifluoromethyl)pyridin-2-yl)amino)methyl)-3,3-dimethylheptane-1,6-diyl)dicarbamate. To a mixture of INTERMEDIATE 14A (60 mg, 0.155 mmol), INTERMEDIATE 2 (92 mg, 0.186 mmol) and TEA (0.065 mL, 0.464 mmol) in DMSO (3 mL). The reaction was stirred at 80° C. for 3 h. The mixture was concentrated in vacuo. The residue was purified by prep-TLC (SiO₂, PE:EtOAc=5:1) to give the title compound. LCMS (ES, m/z): 846.3 [M+H]⁺.

Step B: 6-(((S)-6-amino-2-((R)-1-aminoethyl)-4,4-dimethylhexyl)amino)-N-(1,2,4-thiadiazol-5-yl)-5-(trifluoromethyl)pyridine-3-sulfonamide. To a mixture of Di-tert-butyl ((5S,6R)-5-(((5-(N-(2,4-dimethoxybenzyl)-N-(1,2,4-thiadiazol-5-yl)sulfamoyl)-3-(trifluoromethyl)pyridin-2-yl)amino)methyl)-3,3-dimethylheptane-1,6-diyl)dicarbamate (100 mg, 0.118 mmol) in DCM (5 mL) was added TFA (1 mL, 12.98 mmol) at 0° C. under N₂. The mixture was stirred at 20° C. for 1 h. Then the mixture was concentrated in vacuo and purified by PREP-HPLC (Phenomenex Synergi C18 150*30 mm*4 um; Condition water (0.05% HCl)-ACN Begin B 6; End B 26 Gradient Time (min) 10; 100% B Hold Time (min) 2 FlowRate (mL/min) 25) to give the title compound. LCMS (ES, m/z): 496.2 [M+H]⁺. ¹H NMR (CD₃OD, 400 MHz) δ 8.73 (d, J=1.5 Hz, 1H), 8.23 (s, 1H), 8.07 (s, 1H), 3.90-3.74 (m, 1H), 3.42-3.32 (m, 2H), 3.11-2.94 (m, 2H), 2.44-2.27 (m, 1H), 1.74 (br. s., 2H), 1.55-1.43 (m, 1H), 1.33 (d, J=6.8 Hz, 3H), 1.27-1.17 (m, 1H), 1.17-1.09 (m, 3H), 1.08-1.01 (m, 3H).

Example 14 (Isomer 1), Example 15 (Isomer 2), Example 16 (Isomer 3), Example 17 (Isomer 4)

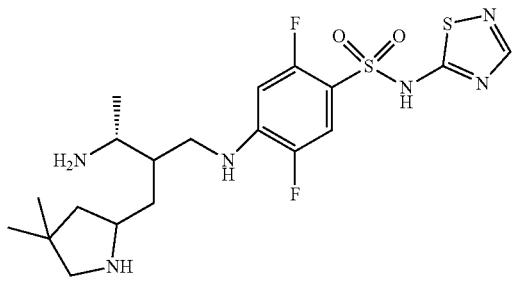 [SMILES: C[C@@H](N)C(CNc1cc(F)c(S(=O)(=O)Nc2ncns2)cc1F)CC1CC(C)(C)CN1]

4-(((3R)-3-amino-2-((4,4-dimethylpyrrolidin-2-yl)methyl)butyl)amino)-2,5-difluoro-N-(1,2,4-thiadiazol-5-yl)benzenesulfonamide Step A: Tert-butyl 2-((3R)-3-((tert-butoxycarbonyl)amino)-2-(methoxycarbonyl)butyl)-4,4-dimethylpyrrolidine-1-carboxylate. A mixture of Intermediate 7 (134 mg, 0.583 mmol), (S)-1-(tert-butoxycarbonyl)-4,4-dimethylpyrrolidine-2-carboxylic acid (135 mg, 0.555 mmol), potassium phosphate, dibasic (116 mg, 0.666 mmol) and Ir[dF(CF₃)ppy]₂(dtbbpy)PF₆ (6.23 mg, 5.55 μmol) in DMF (4 mL) was stirred at 25° C. under N₂, then the mixture was irradiated with a 36 W blue LED lamp and stirred at 25° C. for 12 h. The reaction was quenched by sat.NaHCO₃ (10 mL), extracted with EtOAc (2×10 mL). The combined organic layers were washed with brine (30 mL), dried over Na$_2$SO$_4$, filtered and the solvent removed in vacuo. The residue was purified by normal phase chromatography (ISCO, 12 g RediSep Gold column, 0%-15% EtOAc/PE, 30 min, dry loaded) to give the title compound. LCMS (ES, m/z): 429.1 [M+H]$^+$.

Step B: Tert-butyl 2-((3R)-3-((tert-butoxycarbonyl)amino)-2-(hydroxymethyl)butyl)-4,4-dimethylpyrrolidine-1-carboxylate. To a mixture of LiAlH$_4$ (65.1 mg, 1.715 mmol) in THF (2 mL) was added tert-butyl 2-((3R)-3-((tert-butoxycarbonyl)amino)-2-(methoxycarbonyl)butyl)-4,4-dimethylpyrrolidine-1-carboxylate (245 mg, 0.572 mmol) in 3 mL THF at 0° C. The reaction mixture was stirred at 0° C. for 1 h. The reaction was detected by TLC. The starting material was consumed completely. The reaction was quenched with 0.07 mL water and 0.07 mL 15% NaOH aq followed by 0.21 mL water and dried over MgSO$_4$. The mixture was filtered, solvent removed in vacuo and the residue purified by normal phase chromatography (ISCO, 12 g RediSep Gold column, 15%-30% EtOAc/PE, 30 min, dry loaded) to give the title compound. LCMS (ES, m/z): 401.2 [M+H]$^+$.

Step C: Tert-butyl 2-((3R)-3-((tert-butoxycarbonyl)amino)-2-((1,3-dioxoisoindolin-2-yl)methyl)butyl)-4,4-dimethylpyrrolidine-1-carboxylate. DIAD (0.039 mL, 0.200 mmol) in THF (2 mL) was added to a solution of isoindoline-1,3-dione (17.63 mg, 0.120 mmol), tert-butyl 2-((3R)-3-((tert-butoxycarbonyl)amino)-2-(hydroxymethyl)butyl)-4,4-dimethylpyrrolidine-1-carboxylate (40 mg, 0.100 mmol) and Ph$_3$P (39.3 mg, 0.150 mmol) in THF (4 mL) at 0° C. The resulting mixture was warmed to and stirred at 40° C. for 6 h. The mixture was concentrated in vacuo to give the title compound which was purified by Prep-HPLC (Column YMC-Actus Pro C18 150*30 5 u, Condition water (0.1% TFA)-ACN Begin B 55, End B 85 Gradient Time (min) 11, 100% B Hold Time (min) 1.1 FlowRate (mL/min) 40. LCMS (ES, m/z): 530.4 [M+H]$^+$.

Step D: Tert-butyl 2-((3R)-2-(aminomethyl)-3-((tert-butoxycarbonyl)amino)butyl)-4,4-dimethylpyrrolidine-1-carboxylate. Hydrazine hydrate (1 mL, 0.132 mmol) was added to a solution of tert-butyl 2-((3R)-3-((tert-butoxycarbonyl)amino)-2-((1,3-dioxoisoindolin-2-yl)methyl)butyl)-4,4-dimethylpyrrolidine-1-carboxylate (70 mg, 0.132 mmol) in EtOH (10 mL), then the mixture was stirred 2 h at 80° C. The solvent was removed in vacuo to give the title compound which was used in the next step without purification. LCMS (ES, m/z): 400.6 [M+H]$^+$.

Step E: Tert-butyl 2-((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)-4,4-dimethylpyrrolidine-1-carboxylate. To a mixture of tert-butyl 2-((3R)-2-(aminomethyl)-3-((tert-butoxycarbonyl)amino)butyl)-4,4-dimethylpyrrolidine-1-carboxylate (63 mg, 0.158 mmol) and triethylamine (0.066 mL, 0.473 mmol) in DMF (3 mL) was added Intermediate 1 (77 mg, 0.173 mmol) under N$_2$ at 25° C. The reaction was stirred for 12 h at 25° C. concentrated in vacuo to give a residue which was purified by prep-TLC (SiO$_2$, PE:EtOAc=2.5:1) to give the title compound as a mixture of isomers. The mixture of isomers were separated by SFC (SFC-1004443-063-01_G$_1$: Column: Lux Cellulose-2 150×4.6 mm I.D., 3 um Mobile phase: A: CO$_2$ B:Methanol (0.05% DEA) Gradient: from 5% to 40% of B in 5.5 min and hold 40% for 3 min, then 5% of B for 1.5 min Flow rate: 2.5 mL/min Column temperature: 40° C. t$_1$=4.352 min, t$_2$=4.761 min) to give Peak 1 (P$_1$) as a mixture of three isomers and Peak 2 (P$_2$) as a single isomer. The three isomers in Peak 1 (P$_1$) were further separated by SFC (SFC-1004443-068-O1P$_1$_G$_1$: Column: ChiralPak AS-3 150×4.6 mm I.D., 3 um Mobile phase: A: CO$_2$ B: IPA (0.05% DEA) Gradient: from 5% to 40% of B in 5.5 min and hold 40% for 3 min, then 5% of B for 1.5 min Flow rate: 2.5 mL/min Column temperature: 40° C. t$_1$=3.211 min, t$_2$=3.575 min, t$_3$=3.704 min) to give Peak 1-1 (P$_{1-1}$), Peak 1-2 (P$_{1-2}$) and Peak 1-3 (P$_{1-3}$). LCMS (ES, m/z): 825.4 [M+H]$^+$.

Step F: 4-(((3R)-3-Amino-2-((4,4-dimethylpyrrolidin-2-yl)methyl)butyl)amino)-2,5-difluoro-N-(1,2,4-thiadiazol-5-yl)benzenesulfonamide. To a solution of tert-butyl 2-((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)-4,4-dimethylpyrrolidine-1-carboxylate (Peak 1-1 from Step E) (90 mg, 0.11 mmol) in CH$_2$Cl$_2$ (4 mL) was added TFA (1 mL, 12.98 mmol) at 30° C. The mixture was stirred for 1 h at 30° C. The solvent was removed in vacuo and the residue purified by prep-HPLC (Column YMC-Actus Pro C18 150*30 5 u; conditions water (0.1% TFA)-ACN Begin B 20; End B 50 Gradient Time (min) 11; 100% B Hold Time (min) 1.1 FlowRate (mL/min) 40) to give the title compound.

(EXAMPLE 14)—LCMS (ES, m/z): 475.3 [M+H]$^+$. $^1$H NMR (CD$_3$OD, 400 MHz) δ 8.19 (s, 1H), 7.45 (dd, J=11.1, 6.3 Hz, 1H), 6.65 (dd, J=12.0, 6.7 Hz, 1H), 3.96-3.86 (m, 1H), 3.65-3.57 (m, 1H), 3.38 (dd, J=13.7, 6.0 Hz, 1H), 3.23 (dd, J=13.8, 7.8 Hz, 1H), 3.07 (s, 2H), 2.17 (s, 1H), 2.05 (dd, J=13.0, 6.4 Hz, 1H), 1.97 (td, J=14.1, 7.2 Hz, 1H), 1.82 (ddd, J=14.0, 8.0, 6.2 Hz, 1H), 1.61-1.53 (m, 1H), 1.33 (d, J=6.8 Hz, 3H), 1.19 (s, 3H), 1.11 (s, 3H).

To a solution of tert-butyl 2-((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)-4,4-dimethylpyrrolidine-1-carboxylate (Peak 1-2 from Step E) (95 mg, 0.11 mmol) in CH$_2$Cl$_2$ (4 mL) was added TFA (1 mL, 12.98 mmol) at 30° C. The mixture was stirred for 1 h at 30° C. The solvent was removed in vacuo and the residue purified by prep-HPLC (Column YMC-Actus Pro C18 150*30 5 u; conditions water (0.1% TFA)-ACN Begin B 20; End B 50 Gradient Time (min) 11; 100% B Hold Time (min) 1.1 FlowRate (mL/min) 40) to give the title compound (EXAMPLE 15).

EXAMPLE 15—LCMS (ES, m/z): 475.3 [M+H]$^+$. $^1$H NMR (CD$_3$OD, 400 MHz) δ 8.19 (s, 1H), 7.45 (dd, J=11.1, 6.3 Hz, 1H), 6.59 (dd, J=12.0, 6.7 Hz, 1H), 4.03-3.93 (m, 1H), 3.61-3.55 (m, 1H), 3.36-3.31 (m, 1H), 3.29-3.23 (m, 1H), 3.07 (s, 2H), 2.09 (s, 1H), 2.04 (dd, J=12.8, 6.6 Hz, 1H), 1.93-1.87 (m, 2H), 1.62-1.54 (m, 1H), 1.30 (d, J=6.8 Hz, 3H), 1.19 (s, 3H), 1.13 (s, 3H).

To a solution of tert-butyl 2-((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)-4,4-dimethylpyrrolidine-1-carboxylate (Peak 1-3 from Step E) (50 mg, 0.11 mmol) in CH$_2$Cl$_2$ (4 mL) was added TFA (1 mL, 12.98 mmol) at 30° C. The mixture was stirred for 1 h at 30° C. The solvent was removed in vacuo and the residue purified by prep-HPLC (Column YMC-Actus Pro C18 150*30 5 u; conditions water (0.1% TFA)-ACN Begin B 20; End B 50 Gradient Time (min) 11; 100% B Hold Time (min) 1.1 FlowRate (mL/min) 40) to give the title compound (EXAMPLE 16).

EXAMPLE 16—LCMS (ES, m/z): 475.3 [M+H]$^+$. $^1$H NMR (CD$_3$OD, 400 MHz) δ 8.18 (s, 1H), 7.43 (dd, J=11.0, 6.4 Hz, 1H), 6.66 (dd, J=12.0, 6.7 Hz, 1H), 3.92-3.82 (m, 1H), 3.60-3.52 (m, 1H), 3.40 (dd, J=13.8, 5.8 Hz, 1H), 3.23 (dd, J=13.7, 7.9 Hz, 1H), 3.10-3.03 (m, 2H), 2.15 (s, 1H), 2.06 (dd, J=13.0, 6.6 Hz, 1H), 1.99-1.90 (m, 1H), 1.88-1.79 (m, 1H), 1.56-1.47 (m, 1H), 1.34 (d, J=6.8 Hz, 3H), 1.17 (s, 3H), 1.14 (s, 3H).

To a solution of tert-butyl 2-((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)-butyl)-4,4-dimethylpyrrolidine-1-carboxylate (Peak 2 from Step E) (100 mg, 0.11 mmol) in $CH_2Cl_2$ (4 mL) was added TFA (1 mL, 12.98 mmol) at 30° C. The mixture was stirred for 1 h at 30° C. The solvent was removed in vacuo and the residue purified by prep-HPLC (Column YMC-Actus Pro C18 150*30 5 u; conditions water (0.1% TFA)-ACN Begin B 20; End B 50 Gradient Time (min) 11; 100% B Hold Time (min) 1.1 FlowRate (m/min) 40) to give the title compound (EXAMPLE 17).

EXAMPLE 17—LCMS (ES, m/z): 475.3 $[M+H]^+$. $^1H$ NMR ($CD_3OD$, 400 MHz) δ 8.19 (s, 1H), 7.45 (dd, J=11.1, 6.3 Hz, 1H), 6.65 (dd, J=12.1, 6.8 Hz, 1H), 3.99-3.89 (m, 1H), 3.63-3.54 (m, 1H), 3.36-3.31 (m, 1H), 3.29-3.22 (m, 1H), 3.13-3.05 (m, 2H), 2.19 (s, 1H), 2.10-2.00 (m, 2H), 1.77 (ddd, J=14.9, 9.0, 5.8 Hz, 1H), 1.57 (dd, J=12.9, 10.9 Hz, 1H), 1.31 (d, J=6.8 Hz, 3H), 1.19 (s, 3H), 1.15 (s, 3H).

Example 18

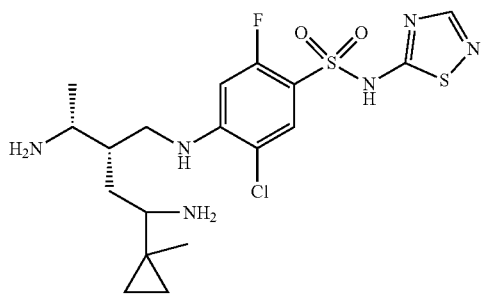 [SMILES: C[C@@H](N)[C@H](CNc1cc(F)c(S(=O)(=O)Nc2ncns2)cc1Cl)CC(N)C1(C)CC1]

4-(((2S)-4-amino-2-((R)-1-aminoethyl)-4-(1-methylcyclopropyl)butyl)amino)-2,5-difluoro-N-(1,2,4-thiadiazol-5-yl)benzenesulfonamide Step A: Tert-butyl benzyl((2R,3R)-3-((benzyloxy)methyl)-5-(((R)-tert-butylsulfinyl)amino)-6-methylhept-6-en-2-yl)carbamate. To a mixture of INTERMEDIATE 11 (3.5 g, 6.80 mmol) in THF (30 mL) was added prop-1-en-2-ylmagnesium bromide (68.0 mL, 34.0 mmol) at 0° C. The mixture was stirred for 1 h at 25° C. under $N_2$. The mixture was diluted by $NH_4Cl$ (30 mL), extracted with EtOAc (2×30 mL), the filtrate was washed with brine (30 mL), dried over $Na_2SO_4$, filtered and the filtrate was concentrated in vacuo to give a residue which was purified by column chromatography on silica gel (PE:EtOAc=10: 1-2:1) to give the title compound.

Step B: Tert-butyl ((2R,3R)-5-amino-3-((benzyloxy)methyl)-6-methylhept-6-en-2-yl)(benzyl)carbamate. To a mixture of tert-butyl benzyl((2R,3R)-3-((benzyloxy)methyl)-5-(((R)-tert-butylsulfinyl)amino)-6-methylhept-6-en-2-yl)carbamate (2.7 g, 4.85 mmol) in MeOH (10 mL) was added HCl-MeOH (2 mL, 8.00 mmol) at 0° C. The mixture was stirred at 15° C. for 1 h. The mixture was concentrated to give the title compound which was used in the next step directly. LCMS (ES, m/z): 453.4 $[M+H]^+$.

Step C: Tert-butyl benzyl((2R,3R)-3-((benzyloxy)methyl)-5-((tert-butoxycarbonyl)amino)-6-methylhept-6-en-2-yl)carbamate. To a mixture of tert-butyl ((2R,3R)-5-amino-3-((benzyloxy)methyl)-6-methylhept-6-en-2-yl)(benzyl)carbamate (2.2 g, 4.37 mmol) and TEA (2.439 mL, 17.50 mmol) in DCM (30 mL) was added $Boc_2O$ (3.05 mL, 13.12 mmol). The mixture was stirred at 25° C. for 16 h. The solvent was removed in vacuo and the residue purified by column chromatography on silica gel ($SiO_2$, PE:EtOAc=20: 1-5:1) to give the title compound. LCMS (ES, m/z): 553.5 $[M+H]^+$.

Step D: (3R,4R)—$N_4$-benzyl-3-((benzyloxy)methyl)-1-(1-methylcyclopropyl)pentane-1,4-diamine. To a mixture of diiodomethane (1.168 mL, 14.47 mmol) in DCE (12 mL) was added diethylzinc (7.24 mL, 7.24 mmol) at 0° C. The resulting mixture was stirred at 0° C. for 30 min. Then tert-butyl benzyl((2R,3R)-3-((benzyloxy)methyl)-5-((tert-butoxycarbonyl)amino)-6-methylhept-6-en-2-yl)carbamate (1 g, 1.809 mmol) in DCE (3 mL) was added to the above mixture at 0° C. The resulting mixture was stirred at 40° C. for 16 h. The mixture was quenched by sat. $NH_4Cl$ (10 mL). The mixture was extracted with DCM (3×15 mL). The combined DCM was dried over $Na_2SO_4$, filtered and the filtrate was concentrated in vacuo to the title compound, which was used in the next steps directly. LCMS (ES, m/z): 367.3 $[M+H]^+$.

Step E: Tert-butyl benzyl((2R,3R)-3-((benzyloxy)methyl)-5-((tert-butoxycarbonyl)amino)-5-(1-methylcyclopropyl)pentan-2-yl)carbamate. To a mixture of (3R,4R)—$N_4$-benzyl-3-((benzyloxy)methyl)-1-(1-methylcyclopropyl)pentane-1,4-diamine (700 mg, 0.955 mmol) and TEA (0.799 mL, 5.73 mmol) in DCM (20 mL) was added $Boc_2O$ (0.887 mL, 3.82 mmol). The mixture was stirred at 25° C. for 16 h. The mixture was extracted by DCM (2×30 mL), the organic layer was washed with water (20 mL), brine (20 mL), dried over $Na_2SO_4$, filtered and the filtrate was concentrated in vacuo. The residue was purified by column chromatography on silica gel ($SiO_2$, PE:EtOAc=10:1-2:1) to give the title compound. LCMS (ES, m/z): 589.4 $[M+H]^+$.

Step F: Di-tert-butyl ((3R,4R)-3-(hydroxymethyl)-1-(1-methylcyclopropyl)pentane-1,4-diyl)dicarbamate. To a solution of THF (6 mL) and liquid $NH_3$ (8 mL) was added sodium (284 mg, 12.35 mmol) at −78° C. After 10 min, a solution of tert-butyl benzyl((2R,3R)-3-((benzyloxy)methyl)-5-((tert-butoxycarbonyl)amino)-5-(1-methylcyclopropyl)pentan-2-yl)carbamate (700 mg, 0.618 mmol) in THF (2 mL) was added to the dark blue mixture. The mixture was stirred for 0.5 h at −78° C. The reaction was quenched by addition of sat $NH_4Cl$ (20 mL). The mixture was concentrated to remove $NH_3$, extracted with EtOAc (2×20 mL). The combined organic layers were washed with brine (10 mL), dried with $Na_2SO_4$, filtered and the filtrate was concentrated in vacuo. The residue was purified by column chromatography on silica gel (PE:EtOAc=10: 1-5:1) to give the title compound. LCMS (ES, m/z): 409.3 $[M+H]^+$.

Step G: Di-tert-butyl ((3S,4R)-3-((1,3-dioxoisoindolin-2-yl)methyl)-1-(1-methylcyclopropyl)pentane-1,4-diyl)dicarbamate. To a solution of di-tert-butyl ((3R,4R)-3-(hydroxymethyl)-1-(1-methylcyclopropyl)pentane-1,4-diyl)dicarbamate (100 mg, 0.220 mmol), triphenylphosphine (115 mg, 0.440 mmol) and isoindoline-1,3-dione (64.7 mg, 0.440 mmol) in THF (5 mL) was added DEAD (0.070 mL, 0.440 mmol) at 0° C. under $N_2$. Then the mixture was stirred at 25° C. for 16 h. The mixture was concentrated in vacuo and purified by column chromatography on silica gel ($SiO_2$, PE:EtOAc=5: 1-1:1) to give the title compound. LCMS (ES, m/z): 516.3 $[M+H]^+$.

Step H: Di-tert-butyl ((3S,4R)-3-(aminomethyl)-1-(1-methylcyclopropyl)pentane-1,4-diyl)dicarbamate. To a solution of di-tert-butyl ((3S,4R)-3-((1,3-dioxoisoindolin-2-yl)methyl)-1-(1-methylcyclopropyl)pentane-1,4-diyl)dicarbamate (120 mg, 0.198 mmol) in EtOH (6 mL) was added hydrazine hydrate (46.6 mg, 0.791 mmol). Then the mixture was stirred at 80° C. for 2 h. The mixture was cooled to 20° C. and filtered. The filtrate was concentrated in vacuo to give a residue which was diluted with DCM (20 mL). The mixture was filtered and the filtrate was concentrated in vacuo to give the title compound, which was used in the next step without further purification. LCMS (ES, m/z): 386.3 [M+H]$^+$.

Step I: Di-tert-butyl ((3S,4R)-3-(((4-(N-(2,4-dimethoxybenzyl)-N-(1,2,4-thiadiazol-5-yl)sulfamoyl)-2,5-difluorophenyl)amino)methyl)-1-(1-methylcyclopropyl)pentane-1,4-diyl)dicarbamate. A mixture of di-tert-butyl ((3S,4R)-3-(aminomethyl)-1-(1-methylcyclopropyl)pentane-1,4-diyl)dicarbamate (32 mg, 0.071 mmol), INTERMEDIATE 30 (34.6 mg, 0.078 mmol) and TEA (0.049 mL, 0.353 mmol) in DMF (1 mL) was stirred at 25° C. for 16 h. The mixture was concentrated in vacuo and purified by prep-TLC (PE:EtOAc=2:1) to give the title compound. LCMS (ES, m/z): 811.3 [M+H]$^+$.

Step J: 4-(((2S)-4-amino-2-((R)-1-aminoethyl)-4-(1-methylcyclopropyl)butyl)amino)-2,5-difluoro-N-(1,2,4-thiadiazol-5-yl)benzenesulfonamide A mixture of di-tert-butyl ((3S,4R)-3-(((4-(N-(2,4-dimethoxybenzyl)-N-(1,2,4-thiadiazol-5-yl)sulfamoyl)-2,5-difluorophenyl)amino)methyl)-1-(1-methylcyclopropyl)pentane-1,4-diyl)dicarbamate (55 mg, 0.068 mmol) in DCM/TFA (3 mL, 5:1) was stirred for 1 h at 25° C. The solvent was removed in vacuo and the mixture purified by prep-HPLC (Column Phenomenex Synergi C18 150*30 mm*4 um; Condition water (0.1% TFA)-ACN, Begin B 4%, End B 34%; Gradient Time (min) 10, 100% B Hold Time (min) 2) to give the title compound. LCMS (ES, m/z): 461.0 [M+H]$^+$. $^1$H NMR (CD$_3$OD, 400 MHz) δ 8.19 (s, 1H), 7.44 (dd, J=11.2, 6.4 Hz, 1H), 6.64 (dd, J=12.1, 6.8 Hz, 1H), 3.58 (dd, J=6.8, 3.7 Hz, 1H), 3.34 (br d, J=7.0 Hz, 1H), 3.28-3.20 (m, 1H), 2.63 (dd, J=7.7, 6.4 Hz, 1H), 2.33-2.23 (m, 1H), 2.05-1.95 (m, 1H), 1.91-1.81 (m, 1H), 1.36 (d, J=6.6 Hz, 3H), 1.05 (s, 3H), 0.63-0.43 (m, 4H).

Example 19 (Isomer 1) and Example 20 (Isomer 2)

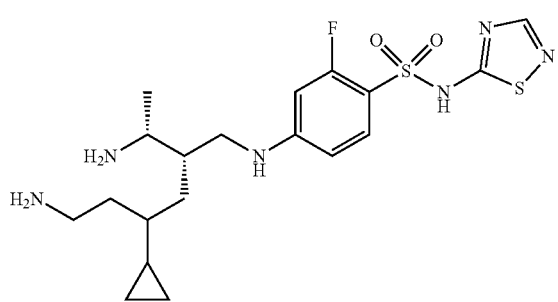 [SMILES: C[C@@H](N)[C@H](CNc1ccc(S(=O)(=O)Nc2ncns2)c(F)c1)CC(CCN)C1CC1]

4-(((2S)-6-amino-2-((R)-1-aminoethyl)-4-cyclopropylhexyl)amino)-2-fluoro-N-(1,2,4-thiadiazol-5-yl)benzenesulfonamide Step A: Ethyl (5S,6R)-5-((((benzyloxy)carbonyl)amino)methyl)-6-(((tert-butoxycarbonyl)amino)-3-vinylheptanoate.

To a mixture of CuI (3.07 g, 16.11 mmol) in THF (20 mL) was added vinyl magnesium bromide (32.22 mL, 32.22 mmol) at −40° C. The mixture was stirred at −40° C. for 30 min. Intermediate 6 (2 g, 4.6 mmol) in THF (10 mL) was added to the mixture at −78° C. for 1 h, and stirred at 0° C. for 1 h. The resulting mixture was quenched with NH$_4$Cl (30 mL), extracted with EtOAc (2×50 mL), washed with brine (30 mL), dried over Na$_2$SO$_4$ and filtered. The filtrate was concentrated in vacuo. The residue was purified by column chromatography on silica gel (SiO$_2$, PE:EtOAc=10: 1-2:1) to give the product the title compound.

Step B: Ethyl (5S,6R)-5-((((benzyloxy)carbonyl)amino)methyl)-6-((tert-butoxycarbonyl)amino)-3-cyclopropylheptanoate. To a mixture of 1-methylurea (7.4 g, 99.89 mmol) in H$_2$O (60 mL) at 0° C. was added NaNO$_2$ (7.6 g, 110.15 mmol). Concentrated aq HCl (13.35 mL, 0.26 mol) was added to the mixture dropwise. The mixture was stirred for 30 min at 0° C. The precipitate formed was filtered off, washed with H$_2$O (20 mL), and dried in vacuo to afford N-Methyl-N-nitrosourea. N-Methyl-N-nitrosourea (8.5 g, 82.5 mmol) was introduced into an Erlenmeyer flask containing Et$_2$O (200 mL) and 40% aq KOH (60 mL) previously cooled to 0° C. in an ice bath. The mixture was left to stand for 30 min at this temperature, carefully shaking it several times. The organic phase contained the generated CH$_2$N$_2$ in Et$_2$O (0.4 M, 200 mL). To a mixture of ethyl (5S,6R)-5-((((benzyloxy)carbonyl)amino)methyl)-6-((tert-butoxycarbonyl)amino)-3-vinylheptanoate (1.14 g, 2.46 mmol) and Pd(OAc)$_2$ (55.33 mg, 246.44 μmol) in Et$_2$O (30 mL) at 0° C. was added CH$_2$N$_2$ (200 mL, 0.4 M). The mixture was stirred at 0° C. for 1 h. The mixture was filtered and the filtrate was concentrated in vacuo. The residue was purified by column chromatography on silica gel (PE:EtOAc=10: 1-3:1) to give the title compound. LCMS (ES, m/z): 477.3 [M+H]$^+$.

Step C: Benzyl tert-butyl ((2S,3R)-2-(2-cyclopropyl-4-hydroxybutyl)butane-1,3-diyl)dicarbamate. To a stirred solution of LiAlH$_4$ (119.45 mg, 3.15 mmol) in THF (10 mL) was added ethyl (5S,6R)-5-((((benzyloxy)carbonyl)amino)methyl)-6-((tert-butoxycarbonyl)amino)-3-cyclopropylheptanoate (1 g, 2.10 mmol) THF (5 mL) at 0° C. under N$_2$. The reaction mixture was stirred for 1 h at 0° C. The reaction mixture was quenched with 0.12 mL of water, 0.12 mL of 15% NaOH and 0.36 mL of water, dried over Na$_2$SO$_4$, filtered and the filtrate was concentrated in vacuo to afford the title compound and was used for the next step without further purification.

Step D: Benzyl tert-butyl ((2S,3R)-2-(2-cyclopropyl-4-(1,3-dioxoisoindolin-2-yl)butyl)butane-1,3-diyl)dicarbamate. To a solution of benzyl tert-butyl ((2S,3R)-2-(2-cyclopropyl-4-hydroxybutyl)butane-1,3-diyl)dicarbamate (900 mg, 1.97 mmol), Phthalimide (578.95 mg, 3.93 mmol) and PPh$_3$ (1.03 g, 3.93 mmol) in THF (20 mL) was added DEAD (622.99 mmL, 3.93 mmol) at 0° C. under N$_2$. Then the mixture was stirred at 30° C. for 16 h. The mixture was concentrated in vacuo and purified by column chromatography on silica gel (SiO$_2$, PE:EtOAc=5: 1-1:1) to give the diastereo mixture title compound. The Diastereo mixture was resolved by SFC (Column: Chiralpak AD-3 150×4.6 mm I.D., 3 um Mobile phase: A: CO$_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C.) to give the faster eluting isomer (Peak 1) LCMS (ES, m/z): 586.4 [M+H]$^+$ and the slower eluting isomer (Peak 2). LCMS (ES, m/z): 586.4 [M+H]$^+$.

Step E: Benzyl tert-butyl ((2S,3R)-2-(4-amino-2-cyclopropylbutyl)butane-1,3-diyl)dicarbamate. To a solution of benzyl tert-butyl ((2S,3R)-2-(2-cyclopropyl-4-(1,3-dioxoisoindolin-2-yl)butyl)butane-1,3-diyl)dicarbamate (Peak 1 from Step D) (700 mg, 1.242 mmol) in EtOH (10 mL) was added hydrazine hydrate (293 mg, 4.97 mmol). Then the mixture was stirred at 80° C. for 2 h. The mixture was cooled to 20° C. and filtered. The filtrate was concentrated in vacuo to give a residue which was diluted with DCM (10 mL). The mixture was filtered and the filtrate was concentrated to give the title compound, which was used in the next step without further purification. LCMS (ES, m/z): 434.4 [M+H]$^+$.

Step F: Di-tert-butyl ((5S,6R)-5-((((benzyloxy)carbonyl)amino)methyl)-3-cyclopropylheptane-1,6-diyl)dicarbamate. To a solution of benzyl tert-butyl ((2S,3R)-2-(4-amino-2-cyclopropylbutyl)butane-1,3-diyl)dicarbamate (520 mg, 1.139 mmol) and TEA (0.476 mL, 3.42 mmol) in $CH_2Cl_2$ (10 mL) was added $Boc_2O$ (0.529 mL, 2.279 mmol). Then the mixture was stirred at 30° C. for 16 h. The mixture was concentrated in vacuo to give a residue which was purified by column chromatography on silica gel (PE:EtOAc=10: 1-2:1) to give the title compound. LCMS (ES, m/z): 556.4 [M+H]$^+$.

Step G: Di-tert-butyl ((5S,6R)-5-(aminomethyl)-3-cyclopropylheptane-1,6-diyl)dicarbamate. To a solution of di-tert-butyl ((5S,6R)-5-((((benzyloxy)carbonyl)amino)methyl)-3-cyclopropylheptane-1,6-diyl)dicarbamate (600 mg, 1.068 mmol) in EtOAc (10 mL) was added 10% Pd—C (227 mg, 0.214 mmol). The reaction mixture was stirred at 30° C. for 1 h under $H_2$ balloon. The reaction mixture was filtered through celite and the filtrate was concentrated to give the title compound, which was used in the next step without further purification. LCMS (ES, m/z): 400.3 [M+H]$^+$.

Step H: Di-tert-butyl ((5S,6R)-5-(((2-bromo-4-(N-(2,4-dimethoxybenzyl)-N-(1,2,4-thiadiazol-5-yl)sulfamoyl)-5-fluorophenyl)amino)methyl)-3-cyclopropylheptane-1,6-diyl)dicarbamate. A mixture of di-tert-butyl ((5S,6R)-5-(aminomethyl)-3-cyclopropylheptane-1,6-diyl)dicarbamate. (450 mg, 1.014 mmol), INTERMEDIATE 33 (565 mg, 1.115 mmol) and TEA (0.706 mL, 5.07 mmol) in DMF (8 mL) was stirred at 30° C. for 16 h. The mixture was concentrated in vacuo and purified by column chromatography on silica gel ($SiO_2$, PE:EtOAc=10: 1-2:1) to give the title compound. LCMS (ES, m/z): 885.3 [M+H]$^+$.

Step I: Di-tert-butyl ((5S,6R)-3-cyclopropyl-5-(((4-(N-(2,4-dimethoxybenzyl)-N-(1,2,4-thiadiazol-5-yl)sulfamoyl)-3-fluorophenyl)amino)methyl)heptane-1,6-diyl)dicarbamate. To a solution of di-tert-butyl ((5S,6R)-5-(((2-bromo-4-(N-(2,4-dimethoxybenzyl)-N-(1,2,4-thiadiazol-5-yl)sulfamoyl)-5-fluorophenyl)amino)methyl)-3-cyclopropylheptane-1,6-diyl)dicarbamate (690 mg, 0.779 mmol) in MeOH (15 mL) was added DIPEA (1.360 mL, 7.79 mmol) and 10% Pd—C (166 mg, 0.156 mmol). The reaction mixture was stirred at 30° C. for 1 h under $H_2$ balloon. The reaction mixture was filtered through celite and the filtrate was concentrated in vacuo. The residue was purified by column chromatography silica gel ($SiO_2$, PE:EtOAc=2:1) to give the title compound. LCMS (ES, m/z): 807.3 [M+H]$^+$.

Step J: 4-(((2S)-6-amino-2-((R)-1-aminoethyl)-4-cyclopropylhexyl)amino)-2-fluoro-N-(1,2,4-thiadiazol-5-yl)benzenesulfonamide. A mixture of: di-tert-butyl ((5S,6R)-3-cyclopropyl-5-(((4-(N-(2,4-dimethoxybenzyl)-N-(1,2,4-thiadiazol-5-yl)sulfamoyl)-3-fluorophenyl)amino)methyl)heptane-1,6-diyl)dicarbamate (1.65 g, 2.045 mmol) in DCM/TFA (15 mL, 4:1) was stirred for 1 h at 30° C. The mixture was concentrated in vacuo. MeOH (20 mL) was added to the mixture, the mixture was filtered and the filtrate was concentrated in vacuo to give the crude product. To the crude product in MeOH (10 mL) was added 4M HCl-MeOH (10 mL). Then the mixture was concentrated and purified by prep-HPLC (HCl) to give EXAMPLE 19.

EXAMPLE 19—LCMS (ES, m/z): 457.2 [M+H]$^+$. $^1$H NMR (CD$_3$OD, 400 MHz) δ 8.19 (s, 1H), 7.60 (t, J=8.6 Hz, 1H), 6.54-6.40 (m, 2H), 3.56 (dd, J=7.0, 3.9 Hz, 1H), 3.30-3.10 (m, 3H), 3.02 (dt, J=11.8, 5.3 Hz, 1H), 2.25 (dd, J=8.3, 3.9 Hz, 1H), 2.04-1.87 (m, 1H), 1.81-1.66 (m, 1H), 1.63-1.47 (m, 2H), 1.30 (d, J=7.0 Hz, 3H), 0.88 (dd, J=8.3, 4.4 Hz, 1H), 0.62-0.42 (m, 3H), 0.28-0.06 (m, 2H).

In an analogus fashion the slower eluting isomer (Peak 2) from EXAMPLE 19, Step D, can be carried through steps E-J to afford the other diastereomer EXAMPLE 20.

EXAMPLE 20—LCMS (ES, m/z): 457.2 [M+H]$^+$. $^1$H NMR (CD$_3$OD, 400 MHz) δ 8.20 (s, 1H), 7.61 (t, J=8.4 Hz, 1H), 6.54-6.40 (m, 2H), 3.56-3.50 (m, 1H), 3.32-3.24 (m, 1H), 3.14-3.06 (m, 3H), 2.20-2.14 (m, 1H), 1.82-1.78 (m, 2H), 1.75-1.66 (m, 1H), 1.47-1.43 (m, 1H), 1.31 (d, J=6.8 Hz, 3H), 1.11-1.09 (m, 1H), 0.65-0.52 (m, 3H), 0.29-0.27 (m, 1H), 0.15-0.13 (m, 1H).

Example 21 (Isomer 1) and Example 22 (Isomer 2)

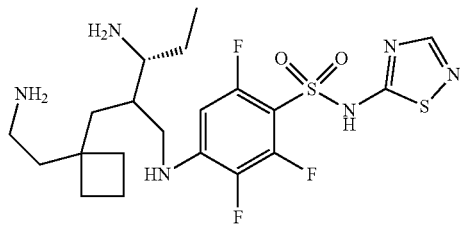 [SMILES: CC[C@@H](N)C(CNc1cc(F)c(S(=O)(=O)Nc2ncns2)c(F)c1F)CC1(CCN)CCC1]

4-(((3R)-3-amino-2-((1-(2-aminoethyl)cyclobutyl)methyl)pentyl)amino)-2,3,6-trifluoro-N-(1,2,4-thiadiazol-5-yl)benzenesulfonamide Step A: Methyl (3R)-3-((tert-butoxycarbonyl)amino)-2-((1-(2-((tert-butoxycarbonyl)amino)ethyl)cyclobutyl)methyl)pentanoate. A mixture of INTERMEDIATE 34 (300 mg, 1.233 mmol), 1-(2-((tert-butoxycarbonyl)amino)ethyl)cyclobutane-1-carboxylic acid (306 mg, 1.258 mmol), Ir[dF(CF$_3$)ppy]$_2$(dtbbpy)PF$_6$ (13.83 mg, 0.012 mmol) and potassium hydrogenphosphate (258 mg, 1.480 mmol) in DMF (3 mL) was stirred at 25° C. under N$_2$, then the mixture was irradiated with a 34 W blue LED lamp and stirred at 25° C. for 12 h. The reaction was quenched by sat.NaHCO$_3$ (10 mL) in 0° C., extracted with EtOAc (2×50 mL). The combined organic layers were washed with brine (50 mL), dried over Na$_2$SO$_4$, filtered and the solution removed by evaporation. The residue was purified by column chromatography (SiO$_2$, PE:EtOAc=2:1~1:1) to give the title compound. LCMS (ES, m/z): 443.4 [M+H]$^+$.

Step B: Tert-butyl ((3R)-1-(1-(2-((tert-butoxycarbonyl)amino)ethyl)cyclobutyl)-2-(hydroxymethyl)pentan-3-yl)carbamate. To a stirred solution of aluminum(III) lithium hydride (51.5 mg, 1.356 mmol) in THF (3 mL) was added methyl (3R)-3-((tert-butoxycarbonyl)amino)-2-((1-(2-((tert-butoxycarbonyl)amino)ethyl)cyclobutyl)methyl)pentanoate (300 mg, 0.678 mmol) in THF (3 mL) at 0° C. under N$_2$. The reaction mixture was stirred for 2 h at 0° C. The reaction mixture was quenched with 0.05 mL of water, 0.05 mL of 15% NaOH and 0.15 mL of water, dried over Na$_2$SO$_4$, filtered and the filtrate was concentrated to afford the title compound, which was used in the next step without further purification. LCMS (ES, m/z): 415.1 [M+H]⁺.

Step C: Tert-butyl ((3R)-1-(1-(2-((tert-butoxycarbonyl) amino)ethyl)cyclobutyl)-2-((1,3-dioxoisoindolin-2-yl) methyl)pentan-3-yl)carbamate. (E)-diethyl diazene-1,2-dicarboxylate (294 mg, 1.688 mmol) in THF (2 mL) was added to a solution of isoindoline-1,3-dione (149 mg, 1.013 mmol), triphenylphosphine (266 mg, 1.013 mmol) and tert-butyl ((3R)-1-(1-(2-((tert-butoxycarbonyl)amino)ethyl)cyclobutyl)-2-(hydroxymethyl)pentan-3-yl)carbamate (350 mg, 0.844 mmol) in THF (3 mL) at 0° C. The resulting mixture was stirred at 20° C. for 12 h. The reaction was diluted with EtOAc (10 mL) and water (10 mL). The aqueous layer was extracted with EtOAc (2×10 mL). The combined organic phase was washed with water (10 mL) and brine (10 mL), dried over Na$_2$SO$_4$, filtered and the filtrate was concentrated in vacuo. The residue was purified by normal phase chromatography (ISCO, 12 g RediSep Gold column, 0-30% EtOAc/PE, 20 min, dry loaded) to give the title compound. LCMS (ES, m/z): 544.4 [M+H]⁺.

Step D: Tert-butyl ((3R)-1-amino-2-((1-(2-((tert-butoxycarbonyl)amino)ethyl)cyclobutyl)methyl)pentan-3-yl)carbamate. Tert-butyl ((3R)-1-(1-(2-((tert-butoxycarbonyl) amino)ethyl)cyclobutyl)-2-((1,3-dioxoisoindolin-2-yl) methyl)pentan-3-yl)carbamate (400 mg, 0.736 mmol) in EtOH (5 mL) was added hydrazine hydrate (37.6 mg, 0.736 mmol) 25° C. The resulting mixture was stirred for 2 h at 80° C. The mixture was concentrated by vacuo to give a residue which was diluted with DCM/MeOH (40/1) (10 mL) and filtered, the filtrate was concentrated by vacuo to give the title compound. LCMS (ES, m/z): 414.5 [M+H]⁺.

Step E: Tert-butyl ((3R)-1-(1-(2-((tert-butoxycarbonyl) amino)ethyl)cyclobutyl)-2-(((4-(N-(2,4-dimethoxybenzyl)-N-(1,2,4-thiadiazol-5-yl)sulfamoyl)-2,3,5-trifluorophenyl) amino)methyl)pentan-3-yl)carbamate. To a solution of tert-butyl ((3R)-1-amino-2-((1-(2-((tert-butoxycarbonyl)amino) ethyl)cyclobutyl)methyl)pentan-3-yl)carbamate (280 mg, 0.677 mmol) and INTERMEDIATE 29 (345 mg, 0.745 mmol) in DMF (5 mL) was added TEA (0.283 mL, 2.031 mmol) under N$_2$. The reaction was stirred at 20° C. for 15 h. The mixture was quenched with H$_2$O (10 mL), extracted with EtOAc (3×10 mL) and washed with saturated brine (10 mL). The organic layers were dried over Na$_2$SO$_4$, filtered and the filtrate was concentrated. The residue was purified by Prep-TLC (SiO$_2$, PE:EtOAc=2:1) to afford the title compound as a diastereometric mixture. The diastereometric mixture was separated by SFC (Instrument SFC-14; Method Column AD (250 mm*30 mm, 5 um); Condition 0.1% NH$_3$H$_2$O IPA Begin B 30%; End B 30% Gradient Time (min); 100% B Hold Time (min) Flow Rate (mL/min) 50 mL/min; Injections 80) to afford the faster eluting isomer 1 (Peak 1) and the slower eluting isomer (Peak 2). LCMS (ES, m/z): 879.5 [M+H]⁺.

Step F: 4-(((3R)-3-amino-2-((1-(2-aminoethyl)cyclobutyl)methyl)pentyl)amino)-2,3,6-trifluoro-N-(1,2,4-thiadiazol-5-yl)benzenesulfonamide. To a solution of tert-butyl ((3R)-1-(1-(2-((tert-butoxycarbonyl)amino)ethyl) cyclobutyl)-2-(((4-(N-(2,4-dimethoxybenzyl)-N-(1,2,4-thiadiazol-5-yl)sulfamoyl)-2,3,5-trifluorophenyl)amino) methyl)pentan-3-yl)carbamate (Peak 1 from Step E) (100 mg, 0.117 mmol) in DCM (5 mL) was added TFA (1 mL) under N$_2$. The reaction was stirred at 20° C. for 1 h. The mixture was concentrated. The residue was purified by Prep-HPLC (Method Column Phenomenex Synergi C18 150*30 mm*4 um; Condition water (0.1% TFA)-ACN Begin B 5; End B 35 Gradient Time (min) 10; 100% B Hold Time (min) 2 Flow Rate (mL/min) 25; Injections 2) to give EXAMPLE 21.

EXAMPLE 21—LCMS (ES, m/z): 507.3 [M+H]⁺. ¹H NMR (CD$_3$OD, 400 MHz) δ 8.21 (s, 1H), 6.42 (dd, J=13.0, 5.5 Hz, 1H), 3.40-3.32 (m, 1H), 3.28-3.08 (m, 1H), 3.00-2.77 (m, 3H), 2.08-2.05 (m, 1H), 2.00-1.73 (m, 9H), 1.72-1.39 (m, 3H), 1.06 (t, J=7.5 Hz, 3H).

In an analogous manner EXAMPLE 22, was prepared from Peak 2, Step E OF EXAMPLE 22 to afford the other diastereomer.

EXAMPLE 22—LCMS (ES, m/z): 507.3 [M+H]⁺. ¹H NMR (CD$_3$OD, 400 MHz) δ 8.22 (s, 1H), 6.36 (dd, J=5.8, 12.5 Hz, 1H), 3.30-3.12 (m, 3H), 3.05-2.77 (m, 2H), 2.29-2.11 (m, 1H), 2.09-1.76 (m, 9H), 1.72-1.43 (m, 3H), 1.06 (t, J=7.5 Hz, 3H).

Example 23 (Isomer 1), Example 24 (Isomer 2), Example 25 (Isomer 3), Example 26 (Isomer 4)

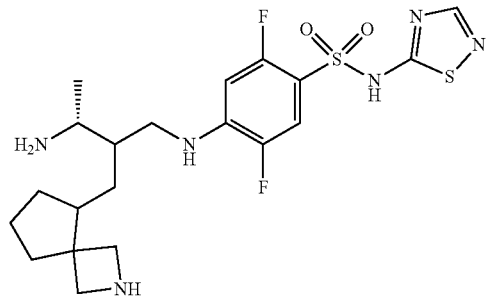 [SMILES: C[C@@H](N)C(CNc1cc(F)c(S(=O)(=O)Nc2ncns2)cc1F)CC1CCCC12CNC2]

4-(((3R)-2-((2-azaspiro[3.4]octan-5-yl)methyl)-3-aminobutyl)amino)-2,5-difluoro-N-(1,2,4-thiadiazol-5-yl)benzenesulfonamide Step A: Tert-butyl 5-hydroxy-2-azaspiro[3.4]octane-2-carboxylate. A mixture of NaBH$_4$ (1.753 g, 46.3 mmol) in MeOH (200 mL) was stirred at 0° C. for 5 min, then a solution of tert-butyl 5-oxo-2-azaspiro[3.4]octane-2-carboxylate (8.7 g, 38.6 mmol) in MeOH (70 mL) was added to the mixture at 0° C. The mixture was stirred at 0° C. under N$_2$ for 4 h. Sat. NH$_4$Cl (100 mL) was added to the mixture and extracted by EtOAc (3×100 mL), washed by brine (40 mL), dried over Na$_2$SO$_4$, filtered and the filtrate was concentrated in vacuo, the residue was purified by column chromatography (SiO$_2$, PE:EtOAc=4:1) to give the title compound.

Step B: Tert-butyl 5-bromo-2-azaspiro[3.4]octane-2-carboxylate. To a solution of tert-butyl 5-hydroxy-2-azaspiro [3.4]octane-2-carboxylate (5 g, 22.00 mmol) in DCM (150 mL) at 25° C. under N$_2$ was added perbromomethane (10.94 g, 33.0 mmol) and triphenylphosphine (8.65 g, 33.0 mmol), then the mixture was stirred at 25° C. for 3 h. The reaction mixture was concentrated in vacuo, the residue was purified by column chromatography (SiO$_2$, PE:EtOAc=10:1) to give title compound. ¹H NMR (CDCl$_3$, 400 MHz) δ 4.41-4.39 (t, J=3.6 Hz, 1H), 4.06-4.04 (d, J=8.8 Hz, 1H), 3.77-3.75 (d, J=9.2 Hz, 1H), 3.68-3.61 (m, 2H), 2.17-2.12 (br, s 3H), 1.94-1.92 (br, s, 2H), 1.70-1.68 (br, s, 1H), 1.44 (s, 9H).

Step C: Tert-butyl 5-((3R)-3-((tert-butoxycarbonyl) amino)-2-(methoxycarbonyl)butyl)-2-azaspiro[3.4]octane-2-carboxylate. A mixture of tert-butyl 5-bromo-2-azaspiro

[3.4]octane-2-carboxylate (500 mg, 1.723 mmol), INTERMEDIATE 10 (415 mg, 1.809 mmol), TMS$_3$SiH (42.8 mg, 0.172 mmol) and Na$_2$CO$_3$ (365 mg, 3.45 mmol) in MeOH (10 mL) was stirred at 25° C. under N$_2$, then catalyst (19.33 mg, 0.017 mmol) was added to the mixture under N$_2$. The mixture was then irradiated with a 34 W blue LED lamp and stirred at 25° C. for 12 h. The reaction mixture was diluted with brine (10 mL), extracted with EtOAc (3×20 mL), washed with brine (20 mL), dried over Na$_2$SO$_4$ and filtered, the filtrate was concentrated in vacuo, the residue was purified by column chromatography (SiO$_2$, PE:EtOAc=5:1) to give the title compound. LCMS (ES, m/z): 341.2 [M+H]$^+$.

Step D: Tert-butyl 5-((3R)-3-((tert-butoxycarbonyl) amino)-2-(hydroxymethyl)butyl)-2-azaspiro[3.4]octane-2-carboxylate. To a suspension of LiAlH$_4$ (17.23 mg, 0.454 mmol) in THF (2.5 mL) at 0° C. was added a solution of tert-butyl 5-((3R)-3-((tert-butoxycarbonyl)amino)-2-(methoxycarbonyl)butyl)-2-azaspiro[3.4]octane-2-carboxylate (100 mg, 0.227 mmol) in THF (0.5 mL). Then the mixture was stirred at 25° C. for 1.5 h. Water (0.1 mL), aqueous NaOH (0.1 mL, 15%) and water (0.2 mL) was added to the mixture, then diluted with EtOAc (10 mL), MgSO$_4$ (0.5 g) was added to the mixture and the mixture was stirred at 25° C. for 10 min. The result mixture was filtered and the filtrate was concentrated in vacuo, the residue was purified by column chromatography (SiO$_2$, PE:EtOAc=4:1) to give the title compound. LCMS (ES, m/z): 413.1 [M+H]$^+$.

Step E: Tert-butyl 5-((3R)-3-((tert-butoxycarbonyl) amino)-2-((1,3-dioxoisoindolin-2-yl)methyl)butyl)-2-azaspiro[3.4]octane-2-carboxylate. To a mixture of tert-butyl 5-((3R)-3-((tert-butoxycarbonyl)amino)-2-(hydroxymethyl)butyl)-2-azaspiro[3.4]octane-2-carboxylate (200 mg, 0.485 mmol) in THF (3.5 mL) at 25° C. was added triphenylphosphine (254 mg, 0.970 mmol), isoindoline-1,3-dione (143 mg, 0.970 mmol) and a solution of DEAD (0.154 mL, 0.970 mmol) in THF (0.5 mL). Then the mixture was stirred at 25° C. for 4 h. The reaction mixture was concentrated in vacuo. The residue was purified by column chromatography (SiO$_2$, PE:EtOAc=5:1) to give the title compound as a mixture of diastereomers. LCMS (ES, m/z): 542.3 [M+H]$^+$. The mixture of diastereomers was separated by SFC (Chiralpak AD-3 150×4.6 mm I.D., 3 um Mobile phase: A: CO$_2$ B:ethanol (0.05% DEA) Gradient: from 5% to 40% of B in 5.5 min and hold 40% for 3 min, then 5% of B for 1.5 min Flow rate: 2.5 mL/min Column temp.: 40° C.) to give the first peak as a single diastereomer (Peak 1, Isomer 1), the second peak as a mixture of two diastereomers (Peak 2, Isomer 2 and Isomer 3) and the third peak as a single diastereomer (Peak 3, Isomer 4).

Step F: Tert-butyl 5-((3R)-2-(aminomethyl)-3-((tert-butoxycarbonyl)amino)butyl)-2-azaspiro[3.4]octane-2-carboxylate. To a solution of tert-butyl 5-((3R)-3-((tert-butoxycarbonyl)amino)-2-((1,3-dioxoisoindolin-2-yl)methyl) butyl)-2-azaspiro[3.4]octane-2-carboxylate (Step E, Peak 1) (110 mg, 0.203 mmol) in EtOH (7 mL) was added hydrazine hydrate (1 mL, 20.16 mmol). Then the mixture was stirred at 80° C. for 2 h. The mixture was concentrated in vacuo and diluted with DCM (15 mL), then the white solid was filtered, the filtrate was concentrated in vacuo, the residue was purified by prep-TLC (MeOH:DCM=1:10) to give the title compound as Isomer 1. LCMS (ES, m/z): 412.3 [M+H]$^+$. A similar procedure was used for the Peak 2 (Isomers 2 and 3) and Peak 3 (Isomer 4) from Step E to afford the respective diastereoisomeric title compounds.

Step G: Tert-butyl 5-((3R)-3-((tert-butoxycarbonyl) amino)-2-(((4-(N-(2,4-dimethoxybenzyl)-N-(1,2,4-thiadiazol-5-yl)sulfamoyl)-2,5-difluorophenyl)amino)methyl) butyl)-2-azaspiro[3.4]octane-2-carboxylate. To a solution of tert-butyl 5-((3R)-2-(aminomethyl)-3-((tert-butoxycarbonyl)amino)butyl)-2-azaspiro[3.4]octane-2-carboxylate (First diastereomer from Step F, Isomer 1) (40 mg, 0.097 mmol) and Intermediate 1 (47.6 mg, 0.107 mmol) in DMF (3 mL) was added triethylamine (0.034 mL, 0.243 mmol) at 25° C., then the mixture was stirred at 25° C. under N$_2$ for 12 h. Brine (3 mL) was added to the mixture and extracted by EtOAc (3×5 mL), washed with brine (5 mL), dried over Na$_2$SO$_4$, filtered and the filtrate was concentrated under vacuo, the residue was purified by prep-TLC (PE:EtOAc=2:1) to give the title compound in Step G (Isomer 1). LCMS (ES, m/z): 859.5 [M+H]$^+$. $^1$H NMR Isomer 1 (CDCl$_3$, 400 MHz) δ 8.16 (s, 1H), 7.39 (dd, J=10.7, 6.3 Hz, 1H), 7.15 (d, J=8.4 Hz, 1H), 6.37 (dd, J=8.5, 2.3 Hz, 1H), 6.32 (d, J=2.2 Hz, 1H), 6.33-6.30 (m, 1H), 6.17 (dd, J=12.0, 6.5 Hz, 1H), 5.24 (d, J=4.0 Hz, 2H), 4.51 (br d, J=7.9 Hz, 1H), 4.00-3.90 (m, 1H), 3.83-3.81 (m, 2H), 3.76 (s, 6H), 3.52 (d, J=8.6 Hz, 1H), 3.15-3.03 (m, 2H), 2.02-1.87 (m, 2H), 1.83-1.64 (m, 7H), 1.46 (d, J=4.0 Hz, 18H), 1.27-1.24 (m, 1H), 1.16 (d, J=6.8 Hz, 3H).

A similar procedure isomer 1, Step G, was used to prepare the other diastereomers (Isomer 2, Isomer 3, and Isomer 4) from Steps E and F, with the Isomer 2 and Isomer 3 diastereomeric mixture from Steps E and F being separated by prp-TLC to give Peak 1 (Isomer 2) and Peak 2 (Isomer 3). $^1$H NMR Isomer 2 (CDCl$_3$, 400 MHz) δ 8.15 (s, 1H), 7.43-7.35 (m, 1H), 7.18-7.10 (m, 1H), 6.37 (dd, J=8.5, 2.3 Hz, 1H), 6.32 (d, J=2.4 Hz, 1H), 6.13 (br dd, J=12.0, 6.5 Hz, 1H), 4.39 (br d, J=9.3 Hz, 1H), 4.05-3.97 (m, 1H), 3.84-3.79 (m, 2H), 3.76 (d, J=1.8 Hz, 6H), 3.68 (d, J=8.4 Hz, 1H), 3.54 (d, J=8.8 Hz, 1H), 3.30-3.17 (m, 1H), 2.98-2.86 (m, 1H), 1.96-1.70 (m, 6H), 1.65-1.54 (m, 4H), 1.47 (d, J=3.7 Hz, 18H), 1.23 (br d, J=7.9 Hz, 1H), 1.14 (d, J=6.8 Hz, 3H). $^1$H NMR Isomer 3 (CDCl$_3$, 400 MHz) δ 8.15 (s, 1H), 7.41 (dd, J=10.8, 6.2 Hz, 1H), 7.15 (d, J=8.4 Hz, 1H), 6.37 (dd, J=2.3, 8.5 Hz, 1H), 6.32 (d, J=2.4 Hz, 1H), 6.23 (dd, J=11.8, 6.5 Hz, 1H), 4.46 (br d, J=7.7 Hz, 1H), 3.96-3.88 (m, 1H), 3.84 (s, 1H), 3.76 (s, 6H), 3.74 (s, 2H), 3.50-3.47 (m, 1H), 3.20-3.09 (m, 1H), 3.08-2.97 (m, 1H), 1.92-1.76 (m, 6H), 1.64-1.53 (m, 3H), 1.43 (d, J=1.8 Hz, 18H), 1.22 (d, J=6.8 Hz, 3H), 1.19-1.05 (m, 2H). $^1$H NMR Isomer 4 (CDCl$_3$, 400 MHz) δ 8.16 (s, 1H), 7.40 (dd, J=10.6, 6.2 Hz, 1H), 7.15 (d, J=8.4 Hz, 1H), 6.37 (dd, J=8.5, 2.3 Hz, 1H), 6.32 (d, J=2.2 Hz, 1H), 6.23 (dd, J=11.8, 6.5 Hz, 1H), 4.53 (br s, 1H), 3.88-3.80 (m, 2H), 3.76 (s, 6H), 3.75-3.73 (m, 1H), 3.65-3.58 (m, 1H), 3.56-3.48 (m, 2H), 3.19-2.97 (m, 2H), 1.96-1.68 (m, 6H), 1.64-1.56 (m, 3H), 1.43 (d, J=7.9 Hz, 18H), 1.23-1.15 (m, 1H), 1.23-1.15 (m, 1H), 1.12 (d, J=6.8 Hz, 3H).

Step H: 4-(((3R)-2-((2-azaspiro[3.4]octan-5-yl)methyl)-3-aminobutyl)amino)-2,5-difluoro-N-(1,2,4-thiadiazol-5-yl) benzenesulfonamide. To a solution of Tert-butyl 5-((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)-2-azaspiro[3.4]octane-2-carboxylate (Step G, Isomer 1) (45 mg, 0.054 mmol) in DCM (2 mL) was added TFA (0.5 mL) at 25° C., then the mixture was stirred at 25° C. for 1 h. The mixture was concentrated in vacuo and the residue was purified by prep-HPLC (Waters XSELECT C18 150*30 mm*5 um is using water using water (0.1% TFA) and acetonitrile as the eluents. Mobile phase A: acetonitrile, mobile phase B: water, Gradient: 3-33% B, 0-10 min; 100% B, 10.1-12.1 min; 10%

B 12.2-15 min. FlowRate: 25 mL/min.) to give the title compound from Step H (EXAMPLE 23; Isomer 1). LCMS (ES, m/z): 412.3 [M+H]+. 1H NMR (CD3OD, 400 MHz) δ 8.20 (s, 1H), 7.44 (dd, J=11.2, 6.4 Hz, 1H), 6.62 (dd, J=12.3, 6.6 Hz, 1H), 4.17 (d, J=11.0 Hz, 1H), 3.97 (d, J=10.5 Hz, 1H), 3.81 (d, J=11.0 Hz, 1H), 3.71 (d, J=11.0 Hz, 1H), 3.59 (br dd, J=6.8, 2.4 Hz, 1H), 3.49-3.39 (m, 1H), 3.12 (dd, J=13.8, 9.0 Hz, 1H), 2.07 (br s, 1H), 2.04-1.97 (m, 2H), 1.97-1.87 (m, 1H), 1.86-1.75 (m, 1H), 1.69-1.58 (m, 3H), 1.43-1.37 (m, 1H), 1.36 (d, J=7.0 Hz, 3H), 1.26-1.15 (m, 1H).

A similar procedure for Isomer 1, Step H, was used to afford EXAMPLE 24 (Isomer 2) EXAMPLE 25 (Isomer 3) and EXAMPLE 26 (Isomer 4).

EXAMPLE 24 (Isomer 2): 1H NMR (CD3OD, 400 MHz) δ 8.20 (s, 1H), 7.45 (dd, J=11.0, 6.1 Hz, 1H), 6.62 (dd, J=12.1, 6.8 Hz, 1H), 4.19 (d, J=10.5 Hz, 1H), 3.97 (d, J=10.5 Hz, 1H), 3.80 (d, J=11.0 Hz, 1H), 3.71 (d, J=10.5 Hz, 1H), 3.56 (br dd, J=3.3, 6.8 Hz, 1H), 3.34 (br d, J=6.6 Hz, 2H), 2.07-1.99 (m, 4H), 1.94-1.84 (m, 1H), 1.75-1.54 (m, 3H), 1.35 (s, 3H), 1.33-1.26 (m, 2H).

EXAMPLE 25 (Isomer 3) 1H NMR (CD3OD, 400 MHz) δ 8.19 (s, 1H), 7.44 (dd, J=11.0, 6.6 Hz, 1H), 6.57 (dd, J=12.1, 6.8 Hz, 1H), 4.24 (d, J=11.0 Hz, 1H), 4.08 (d, J=10.5 Hz, 1H), 3.80 (d, J=10.5 Hz, 1H), 3.70 (br d, J=11.0 Hz, 1H), 3.58 (br dd, J=3.7, 6.8 Hz, 1H), 3.33 (br s, 1H), 3.24-3.12 (m, 1H), 2.12-1.79 (m, 6H), 1.73-1.55 (m, 2H), 1.38 (d, J=6.6 Hz, 3H), 1.33-1.19 (m, 2H).

EXAMPLE 26 (Isomer 4). 1H NMR (CD3OD, 400 MHz) δ 8.19 (s, 1H), 7.45 (dd, J=11.2, 6.4 Hz, 1H), 6.54 (dd, J=12.3, 7.0 Hz, 1H), 4.21 (d, J=11.0 Hz, 1H), 4.01 (d, J=10.5 Hz, 1H), 3.84 (d, J=11.0 Hz, 1H), 3.73 (d, J=11.0 Hz, 1H), 3.61-3.52 (m, 1H), 3.49-3.41 (m, 1H), 3.22-3.13 (m, 1H), 2.15-2.02 (m, 4H), 1.92 (dt, J=8.6, 13.3 Hz, 1H), 1.77-1.63 (m, 2H), 1.52 (br t, J=11.2 Hz, 1H), 1.39-1.30 (m, 2H), 1.29 (d, J=6.6 Hz, 3H).

Example 27

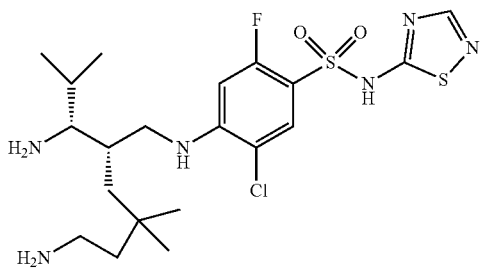 [SMILES: CC(C)[C@@H](N)[C@H](CNc1cc(F)c(S(=O)(=O)Nc2ncns2)cc1Cl)CC(C)(C)CCN]

4-(((S)-6-amino-2-((R)-1-amino-2-methylpropyl)-4,4-dimethylhexyl)amino)-5-chloro-2-fluoro-N-(1,2,4-thiadiazol-5-yl)benzenesulfonamide bis(2,2,2-trifluoroacetate)

Step A: (S)-ethyl 3-((tert-butoxycarbonyl)amino)-4-methylpentanoate. To a stirred solution of Boc-D-Val-OH (5.0 g, 23.01 mmol) and ethyl acetate (115 ml) at 0° C. was added N-methylmorpholine (2.78 ml, 25.3 mmol) followed by isobutyl chloroformate (3.17 ml, 24.2 mmol). After 1 hour, the reaction mixture was washed with H2O, brine, dried (MgSO4), and filtered into a round bottom flask. After cooling to 0° C., the mixed anhydride was treated with an ethereal solution of diazomethane (prep shown below). After 1 hour, the cooling bath was removed and the excess diazomethane removed by purging the solution with nitrogen for 30 minutes. Concentration in vacuo provided crude (R)-tert-butyl (1-diazo-4-methyl-2-oxopentan-3-yl)carbamate as yellow oil. The crude material was dissolved in ethanol (37.2 ml) and treated sequentially with triethylamine (1.244 ml, 8.92 mmol) and silver benzoate (0.511 g, 2.231 mmol) to affect vigorous gas evolution and afford a black precipitate. After 1 hour, the reaction mixture was concentrated in vacuo. The residue was suspended in 20 ml CH2Cl2, filtered and the filtrate was purified by column chromatography on silica gel, eluting with a gradient of 0-100% EtOAc/hexanes to provide (S)-ethyl 3-((tert-butoxycarbonyl)amino)-4-methylpentanoate. LCMS (ES, m/z): 260.2 [M+H]+. Preparation of diazomethane: To a rapidly stirred mixture of 40 ml Et2O and 50 ml 40% aq KOH in a 250 ml erlenmeyer flask at 0° C. was added 1-methyl-3-nitro-1-nitrosoguanidine (10.16 g, 34.5 mmol) in 2 portions, 5 minutes apart. The mixture was stirred for 30 minutes and then placed in −78° C. bath to freeze aqueous layer (about 20 minutes). The organic layer was decanted and added to the mixed anhydride above.

Step B: (3R)-ethyl 3-((tert-butoxycarbonyl)amino)-4-methyl-2-((methylthio)methyl)pentanoate. To a stirred solution of (S)-ethyl 3-((tert-butoxycarbonyl)amino)-4-methylpentanoate (1.7 g, 6.56 mmol) in THF (18.03 ml) at −78° C. under nitrogen was added lithium diisopropylamide (8.19 ml, 16.39 mmol) dropwise over 20 minutes. The mixture was stirred at −78° C. for 1 hour. In a another flask, to a solution of sodium iodide (2.456 g, 16.39 mmol) in DME (14.75 ml) was added chloromethyl methyl sulfide (1.373 ml, 16.39 mmol) dropwise. The sulfide mixture was stirred at room temperature for 30 minutes. The mixture was filtered, and the resulting solution was added dropwise to the enolate solution. The reaction mixture was stirred at −78° C. for 4 hours under nitrogen atmosphere. The resulting reaction mixture was quenched with sat. NH4Cl and then diluted with EtOAC. The organic layer was separated, dried over MgSO4, filtered, and concentrated in vacuo. The residue was purified by column chromatography on silica gel, eluting with a gradient of 0-100% EtOAc/hexanes to provide (3R)-ethyl 3-((tert-butoxycarbonyl)amino)-4-methyl-2-((methylthio)methyl)pentanoate. LCMS (ES, m/z): 320.2 [M+H]+.

Step C: (3R)-ethyl 3-((tert-butoxycarbonyl)amino)-4-methyl-2-((methylsulfinyl)methyl)pentanoate. To a stirred solution of ((3R)-ethyl 3-((tert-butoxycarbonyl)amino)-4-methyl-2-((methylthio)methyl)pentanoate (1.5 g, 4.70 mmol) in EtOH (23.48 ml) was added H2O2 (4.11 ml, 47.0 mmol) and then the mixture was stirred for 1 hour at ambient temperature. The mixture was diluted with water and then was extracted with dichloromethane. The combined organic fractions were washed with brine, dried (Na2SO4), filtered and the solvent was evaporated under reduced pressure to provide crude (3R)-ethyl 3-((tert-butoxycarbonyl)amino)-4-methyl-2-((methylsulfinyl)methyl)pentanoate, which was used in the next reaction without further purification. LCMS (ES, m/z): 336.2 [M+H]+.

Step D: (R)-ethyl 3-((tert-butoxycarbonyl)amino)-4-methyl-2-methylenepentanoate. (3R)-ethyl 3-((tert-butoxycarbonyl)amino)-4-methyl-2-((methylsulfinyl)methyl)pentanoate (1.5 g, 4.47 mmol) was dissolved in pyridine (8.94 ml) and the mixture was stirred at 85° C. overnight under nitrogen atmosphere. The resulting reaction mixture was concentrated in vacuo. The residue was purified by column chromatography on silica gel, eluting with a gradient of 0-100% EtOAc/hexanes to provide (R)-ethyl 3-((tert-butoxycarbonyl)amino)-4-methyl-2-methylenepentanoate. LCMS (ES, m/z): 272.2 [M+H]+.

Step E: Ethyl 6-((tert-butoxycarbonyl)amino)-2-((R)-1-((tert-butoxycarbonyl)amino)-2-methylpropyl)-4,4-dimethylhexanoate. To a 20 ml vial was added (R)-ethyl 3-((tert-butoxycarbonyl)amino)-4-methyl-2-methylenepentanoate (0.45 g, 1.658 mmol), 4-((tert-butoxycarbonyl)amino)-2,2-dimethylbutanoic acid (0.499 g, 2.156 mmol), potassium phosphate, dibasic (0.722 g, 4.15 mmol), and Ir[dF(CF$_3$)ppy]$_2$(dtbbpy)PF$_6$ (0.019 g, 0.017 mmol). To the mixture was added degassed DMF (8.29 ml). The vial was capped and sealed with parafilm, stirred and irradiated with a Merck Photoreactor (100% power for 90 minutes with fan at 4700 rpm). The reaction was quenched by exposure to air. The mixture diluted with EtOAc, washed with H$_2$O, sat. NaHCO$_3$, brine, dried (MgSO$_4$), filtered and the solvent was evaporated under reduced pressure. The residue was purified by column chromatography on silica gel, eluting with a gradient of 0-100% EtOAc/hexanes to provide ethyl 6-((tert-butoxycarbonyl)amino)-2-((R)-1-((tert-butoxycarbonyl)amino)-2-methylpropyl)-4,4-dimethylhexanoate as a mixture of diastereomers. LCMS (ES, m/z): 459.5 [M+H]+.

Step F: Di-tert-butyl ((6R)-5-(hydroxymethyl)-3,3,7-trimethyloctane-1,6-diyl)dicarbamate. To a solution of ethyl 6-((tert-butoxycarbonyl)amino)-2-((R)-1-((tert-butoxycarbonyl)amino)-2-methylpropyl)-4,4-dimethylhexanoate (640 mg, 1.395 mmol) and THF (4652 µl) at 0° C. was added LAH (1047 µl, 2.093 mmol). The reaction was stirred for 2 hours at 0° C. To the mixture was added 50 ml Et$_2$O followed by 20 ml sat aqueous Rochelle's salt and the mixture was stirred for 30 minutes. The organic portion was separated, washed with brine, dried (MgSO$_4$) and then concentrated. The residue was purified by column chromatography on silica gel, eluting with a gradient of 0-100% EtOAc/hexanes to provide di-tert-butyl ((6R)-5-(hydroxymethyl)-3,3,7-trimethyloctane-1,6-diyl)dicarbamate. LCMS (ES, m/z): 417.5 [M+H]+.

Step G: Di-tert-butyl ((6R)-5-((1,3-dioxoisoindolin-2-yl)methyl)-3,3,7-trimethyloctane-1,6-diyl)dicarbamate. (E)-diisopropyl diazene-1,2-dicarboxylate (230 µl, 1.162 mmol) was added to a solution of di-tert-butyl ((6R)-5-(hydroxymethyl)-3,3,7-trimethyloctane-1,6-diyl)dicarbamate (440 mg, 1.056 mmol), isoindoline-1,3-dione (171 mg, 1.162 mmol)), and triphenylphosphine (416 mg, 1.584 mmol) and the resulting reaction heated at 50° C. for 1 hour, LCMS shows the reaction is complete. The solvent was evaporated under reduced pressure. The residue was purified by column chromatography on silica gel, eluting with gradient of 0-100% EtOAc/hexanes to provide di-tert-butyl ((6R)-5-((1,3-dioxoisoindolin-2-yl)methyl)-3,3,7-trimethyloctane-1,6-diyl)dicarbamate. LCMS (ES, m/z): 546.5 [M+H]+.

Step H: Di-tert-butyl ((6R)-5-(aminomethyl)-3,3,7-trimethyloctane-1,6-diyl)dicarbamate. Hydrazine hydrate (0.769 ml, 15.81 mmol) was added to a solution of di-tert-butyl ((6R)-5-((1,3-dioxoisoindolin-2-yl)methyl)-3,3,7-trimethyloctane-1,6-diyl)dicarbamate (0.575 g, 1.054 mmol) in EtOH (5.27 ml) and the reaction was heated at 50° C. for 1.5 hours. A white precipitate had formed. The reaction was filtered, rinsing the solid with EtOH and then the filtrate concentrated in vacuo. Added 50 ml sat aq NaHCO$_3$ and then extracted with EtOAc. The organic portion was separated, washed with brine, dried (MgSO$_4$) and then concentrated to give di-tert-butyl ((6R)-5-(aminomethyl)-3,3,7-trimethyloctane-1,6-diyl)dicarbamate. LCMS (ES, m/z): 416.4 [M+H]+.

Step I: Di-tert-butyl ((5S,6R)-5-(((2-chloro-4-(N-(2,4-dimethoxybenzyl)-N-(1,2,4-thiadiazol-5-yl)sulfamoyl)-5-fluorophenyl)amino)methyl)-3,3,7-trimethyloctane-1,6-diyl)dicarbamate. To a solution of di-tert-butyl ((6R)-5-(aminomethyl)-3,3,7-trimethyloctane-1,6-diyl)dicarbamate (225 mg, 0.541 mmol) in DMF (2706 µl) was added 5-chloro-N-(2,4-dimethoxybenzyl)-2,4-difluoro-N-(1,2,4-thiadiazol-5-yl)benzenesulfonamide (250 mg, 0.541 mmol) and DIEA (284 µl, 1.624 mmol). The reaction mixture was stirred at room temperature overnight in a capped vial. The resulting reaction mixture was diluted with EtOAc and then washed with H$_2$O, brine, dried over MgSO$_4$, filtered, and concentrated in vacuo. The residue was purified by column chromatography on silica gel, eluting with a gradient of 0-100% EtOAc/hexanes to provide the major diastereomer di-tert-butyl ((5S,6R)-5-(((2-chloro-4-(N-(2,4-dimethoxybenzyl)-N-(1,2,4-thiadiazol-5-yl)sulfamoyl)-5-fluorophenyl)amino)methyl)-3,3,7-trimethyloctane-1,6-diyl)dicarbamate and the minor diastereomer. LCMS (ES, m/z): 416.4 [M+H]+.

Step J: Di-tert-butyl ((5S,6R)-5-(((2-chloro-4-(N-(2,4-dimethoxybenzyl)-N-(1,2,4-thiadiazol-5-yl)sulfamoyl)-5-fluorophenyl)amino)methyl)-3,3,7-trimethyloctane-1,6-diyl)dicarbamate. To a solution of di-tert-butyl ((5S,6R)-5-(((2-chloro-4-(N-(2,4-dimethoxybenzyl)-N-(1,2,4-thiadiazol-5-yl)sulfamoyl)-5-fluorophenyl)amino)methyl)-3,3,7-trimethyloctane-1,6-diyl)dicarbamate (140 mg, 0.163 mmol) in CH$_2$Cl$_2$ (816 µl) was added TFA (629 µl, 8.16 mmol). The reaction mixture was stirred at room temperature for 45 minutes and then added MeOH, stirred for 15 minutes. Filtered to remove solids and then the solvent was removed in vacuo. The residue was dissolved in 1 ml DMSO and then was purified by preparative HPLC Reverse phase (C-18), 5 uM, 20×100 mm, eluting with Acetonitrile/Water+ 0.05% TFA, 20 minute gradient (1-40%), 20 ml/min, 1 run. The fractions that contained product were combined, concentrated, azeotroped with MeOH and then dried in vacuo to provide 4-(((S)-6-amino-2-((R)-1-amino-2-methylpropyl)-4,4-dimethylhexyl)amino)-5-chloro-2-fluoro-N-(1,2,4-thiadiazol-5-yl)benzenesulfonamide bis(2,2,2-trifluoroacetate). LCMS (ES, m/z): 507.3 [M+H]+. $^1$H NMR (600 MHz, DMSO-d6) δ 8.38 (s, 1H), 7.84 (s, 2H), 7.64 (s, 2H), 7.57 (d, J=7.5 Hz, 1H), 6.58 (d, J=13.0 Hz, 1H), 6.51 (s, 1H), 3.20 (m, 1H), 3.05 (m, 1H), 2.71 (m, 3H), 2.15 (m, 1H), 1.99 (m, 1H), 1.44-1.26 (m, 3H), 1.22-1.07 (m, 2H), 0.95 (m, 6H), 0.77 (m, 6H).

Example 28

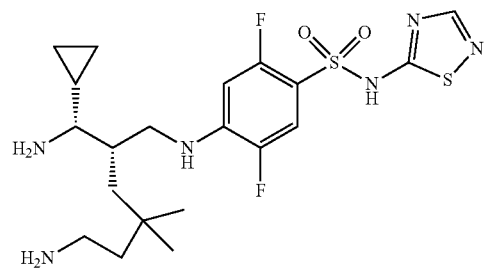 [SMILES: CC(C)(CCN)C[C@@H](CNc1cc(F)c(S(=O)(=O)Nc2ncns2)cc1F)[C@H](N)C1CC1]

4-(((S)-6-amino-2-((R)-amino(cyclopropyl)methyl)-4,4-dimethylhexyl)amino)-2,5-difluoro-N-(1,2,4-thiadiazol-5-yl)benzenesulfonamide Di-tert-butyl ((1R)-2-(aminomethyl)-1-cyclopropyl-4,4-dimethylhexane-1,6-diyl)dicarbamate was prepared by the same method as in EXAMPLE 27 starting from (R)-2-((tert-butoxycarbonyl)amino)-2-cyclopropylacetic acid. LCMS (ES, m/z): 414.4 [M+H]$^+$.

Step A: Di-tert-butyl ((1R,2S)-1-cyclopropyl-2-(((4-(N-(2,4-dimethoxybenzyl)-N-(1,2,4-thiadiazol-5-yl)sulfamoyl)-2,5-difluorophenyl)amino)methyl)-4,4-dimethylhexane-1,6-diyl)dicarbamate. To a solution of di-tert-butyl ((1R)-2-(aminomethyl)-1-cyclopropyl-4,4-dimethylhexane-1,6-diyl)dicarbamate (111 mg, 0.269 mmol) in DMF (1122 μl) was added N-(2,4-dimethoxybenzyl)-2,4,5-trifluoro-N-(1,2,4-thiadiazol-5-yl)benzenesulfonamide (100 mg, 0.224 mmol) and DIEA (118 μl, 0.673 mmol). The reaction mixture was stirred at room temperature overnight in a capped vial. The resulting reaction mixture was diluted with EtOAc and then washed with H$_2$O, brine, dried over MgSO$_4$, filtered, and concentrated in vacuo. The residue was purified by column chromatography on silica gel, eluting with a gradient of 0-100% EtOAc/hexanes to provide di-tert-butyl ((1R,2S)-1-cyclopropyl-2-(((4-(N-(2,4-dimethoxybenzyl)-N-(1,2,4-thiadiazol-5-yl)sulfamoyl)-2,5-difluorophenyl)amino)methyl)-4,4-dimethylhexane-1,6-diyl)dicarbamate. The other diastereomer was not collected. LCMS (ES, m/z): 839.5 [M+H]$^+$.

Step B: 4-(((S)-6-amino-2-((R)-amino(cyclopropyl)methyl)-4,4-dimethylhexyl)amino)-2,5-difluoro-N-(1,2,4-thiadiazol-5-yl)benzenesulfonamide bis(2,2,2-trifluoroacetate). To a solution of di-tert-butyl ((1R,2S)-1-cyclopropyl-2-(((4-(N-(2,4-dimethoxybenzyl)-N-(1,2,4-thiadiazol-5-yl)sulfamoyl)-2,5-difluorophenyl)amino)methyl)-4,4-dimethylhexane-1,6-diyl)dicarbamate (85 mg, 0.101 mmol) in CH$_2$Cl$_2$ (507 μl) was added TFA (390 μl, 5.07 mmol). The reaction mixture was stirred at room temperature for 45 minutes and then added MeOH, stirred for 15 minutes. The reaction mixture was filtered to remove solids and then the solvent was removed in vacuo. The residue was dissolved in 1 ml DMSO and then was purified by preparative HPLC Reverse phase (C-18), 5 uM, 20×100 mm, eluting with Acetonitrile/Water+0.05% TFA, 20 minute gradient (1-40%), 20 ml/min, 1 run. The fractions that contained product were combined, concentrated, azeotroped with MeOH and then dried in vacuo to provide 4-(((S)-6-amino-2-((R)-amino(cyclopropyl)methyl)-4,4-dimethylhexyl)amino)-2,5-difluoro-N-(1,2,4-thiadiazol-5-yl)benzenesulfonamide bis(2,2,2-trifluoroacetate). LCMS (ES, m/z): 489.3 [M+H]$^+$. $^1$H NMR (600 MHz, DMSO-d6) δ 8.39 (s, 1H), 7.92 (s, 2H), 7.72 (s, 3H), 7.34 (dd, J=10.9, 6.5 Hz, 1H), 6.71 (s, 1H), 6.56 (dd, J=12.4, 6.6 Hz, 1H), 3.36-3.24 (m, 1H), 3.09-2.95 (m, 1H), 2.74 (m, 2H), 2.09 (s, 1H), 1.54 (d, J=12.0 Hz, 1H), 1.44-1.35 (m, 2H), 1.22-1.11 (m, 1H), 1.02 (t, J=7.0 Hz, 2H), 0.78 (m, 6H), 0.59 (m, 1H), 0.50 (m, 1H), 0.38 (m, 1H), 0.31 (m, 1H).

Example 29

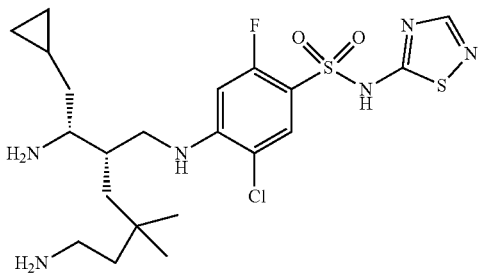 [SMILES: CC(C)(CCN)C[C@@H](CNc1cc(F)c(S(=O)(=O)Nc2ncns2)cc1Cl)[C@H](N)CC1CC1]

4-(((S)-6-amino-2-((R)-1-amino-2-cyclopropylethyl)-4,4-dimethylhexyl)amino)-5-chloro-2-fluoro-N-(1,2,4-thiadiazol-5-yl)benzenesulfonamide bis(2,2,2-trifluoroacetate)

Di-tert-butyl ((6R)-5-(aminomethyl)-7-cyclopropyl-3,3-dimethylheptane-1,6-diyl)dicarbamate was prepared by the same method as EXAMPLE 27 starting from Boc-D-cyclopropylalanine-DCHA. LCMS (ES, m/z): 428.4 [M+H]$^+$.

Step A: di-tert-butyl ((5S,6R)-5-(((2-chloro-4-(N-(2,4-dimethoxybenzyl)-N-(1,2,4-thiadiazol-5-yl)sulfamoyl)-5-fluorophenyl)amino)methyl)-7-cyclopropyl-3,3-dimethylheptane-1,6-diyl)dicarbamate. To a solution of di-tert-butyl ((6R)-5-(aminomethyl)-7-cyclopropyl-3,3-dimethylheptane-1,6-diyl)dicarbamate (255 mg, 0.595 mmol) in DMF (2706 μl) was added 5-chloro-N-(2,4-dimethoxybenzyl)-2,4-difluoro-N-(1,2,4-thiadiazol-5-yl)benzenesulfonamide (250 mg, 0.541 mmol) and DIPEA (284 μl, 1.624 mmol). The reaction mixture was stirred at room temperature overnight in a capped vial. The resulting reaction mixture was diluted with EtOAc and then washed with H$_2$O, brine, dried over MgSO$_4$, filtered, and concentrated in vacuo. The residue was purified by column chromatography on silica gel, eluting with a gradient of 0-100% EtOAc/hexanes to provide the major diastereomer di-tert-butyl ((5S,6R)-5-(((2-chloro-4-(N-(2,4-dimethoxybenzyl)-N-(1,2,4-thiadiazol-5-yl)sulfamoyl)-5-fluorophenyl)amino)methyl)-7-cyclopropyl-3,3-dimethylheptane-1,6-diyl)dicarbamate and the minor diastereomer. LCMS (ES, m/z): 869.5 [M+H]$^+$.

Step B: 4-(((S)-6-amino-2-((R)-1-amino-2-cyclopropylethyl)-4,4-dimethylhexyl)amino)-5-chloro-2-fluoro-N-(1,2,4-thiadiazol-5-yl)benzenesulfonamide bis(2,2,2-trifluoroacetate). To a solution of di-tert-butyl ((5S,6R)-5-(((2-chloro-4-(N-(2,4-dimethoxybenzyl)-N-(1,2,4-thiadiazol-5-yl)sulfamoyl)-5-fluorophenyl)amino)methyl)-7-cyclopropyl-3,3-dimethylheptane-1,6-diyl)dicarbamate (140 mg, 0.161 mmol) in CH$_2$Cl$_2$ (805 μl) was added TFA (620 μl, 8.05 mmol). The reaction mixture was stirred at room temperature for 45 minutes and MeOH was then added, and the mixture was stirred for 15 minutes. The reaction was filtered to remove solids and then the solvent was removed in vacuo. The residue was dissolved in 1 ml DMSO and then was purified by preparative HPLC Reverse phase (C-18), 5 uM, 20×100 mm, eluting with Acetonitrile/Water+0.05% TFA, 20 minute gradient (1-40%), 20 ml/min, 1 run. The fractions that contained product were combined, concentrated, azeotroped with MeOH and then dried in vacuo to provide 4-(((S)-6-amino-2-((R)-1-amino-2-cyclopropylethyl)-4,4-dimethylhexyl)amino)-5-chloro-2-fluoro-N-(1,2,4-thiadiazol-5-yl)benzenesulfonamide bis(2,2,2-trifluoroacetate).

LCMS (ES, m/z): 519.3 [M+H]+. 1H NMR (600 MHz, DMSO-d6) δ 8.40 (s, 1H), 7.86 (s, 2H), 7.71 (s, 2H), 7.57 (d, J=7.2 Hz, 1H), 6.53 (d, J=12.8 Hz, 2H), 3.23-3.04 (m, 3H), 2.74 (m, 2H), 2.14 (s, 1H), 1.62-1.53 (m, 1H), 1.46-1.37 (m, 3H), 1.34 (dt, J=14.7, 7.6 Hz, 1H), 1.01 (m, 2H), 0.82 (m, 6H), 0.74 (m, 1H), 0.44 (m, 1H), 0.37 (m, 1H), 0.13-0.06 (m, 1H).

Example 30

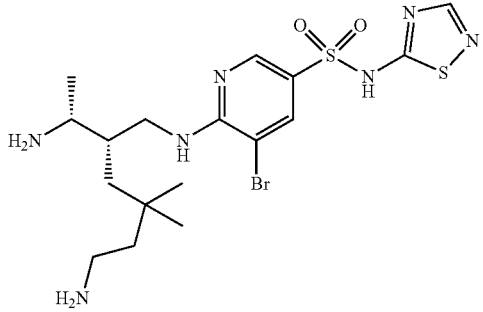 [SMILES: C[C@@H](N)[C@H](CNc1ncc(S(=O)(=O)Nc2ncns2)cc1Br)CC(C)(C)CCN]

6-(((S)-6-amino-2-((R)-1-aminoethyl)-4,4-dimethylhexyl)amino)-5-bromo-N-(1,2,4-thiadiazol-5-yl)pyridine-3-sulfonamide Step A: Di-tert-butyl ((5S,6R)-5-(((3-bromo-5-(N-(2,4-dimethoxybenzyl)-N-(1,2,4-thiadiazol-5-yl)sulfamoyl)pyridin-2-yl)amino)methyl)-3,3-dimethyl heptane-1,6-diyl)dicarbamate. To a vial containing INTERMEDIATE 31 (305 mg, 0.603 mmol) and INTERMEDIATE 14A (252 mg, 0.650 mmol) was added DMF (2 mL), followed by DIPEA (325 µL, 1.861 mmol). The reaction mixture was then capped and stirred at room temperature. After 16 h at ambient temperature the reaction mixture was suspended in EtOAc, washed with saturated NaHCO₃, then H₂O, then brine; organics dried over Na₂SO₄, filtered and concentrated in vacuo. The resulting residue was purified by silica gel chromatography (0-40% EtOAc/Hex; 40 g ISCO) to afford the title compound. LCMS (ES, m/z): 858.5 [M+H]+.

Step B: 6-(((S)-6-amino-2-((R)-1-aminoethyl)-4,4-dimethylhexyl)amino)-5-bromo-N-(1,2,4-thiadiazol-5-yl)pyridine-3-sulfonamide bis(2,2,2-trifluoroacetate). To a vial containing crude di-tert-butyl ((5S,6R)-5-(((3-bromo-5-(N-(2,4-dimethoxybenzyl)-N-(1,2,4-thiadiazol-5-yl)sulfamoyl)pyridin-2-yl)amino)methyl)-3,3-dimethylheptane-1,6-diyl)dicarbamate (22.5 mg, 0.026 mmol) was added TFA (400 µL, 5.19 mmol), followed by DCM (1 mL) The reaction mixture was then stirred at room temperature. After ~30 min the reaction mixture was diluted with MeOH, stirred ~5 minutes, then filtered (syringe filter), to the filtrate was added 0.5 mL DMSO, then partially concentrated. The resulting residue was then dissolved/diluted to ~1.75 mL with DMSO & purified by mass guided reverse phase chromatography 5-35% MeCN/water with 0.1% TFA modifier to afford the title compound. LCMS (ES, m/z): 507.9 [M+H]+. 1H NMR (500 MHz, DMSO-d6) δ 8.41 (d, J=2.0 Hz, 1H), 8.16 (s, 1H), 7.94 (d, J=2.0 Hz, 1H), 7.65 (s, 6H), 7.42-7.38 (m, 1H), 3.59-3.53 (m, 1H), 3.25-3.06 (m, 2H), 2.86-2.77 (m, 2H), 2.08 (s, 1H), 1.59-1.50 (m, 2H), 1.39-1.30 (m, 1H), 1.14 (d, J=6.7 Hz, 3H), 1.01 (s, 3H), 0.99-0.92 (m, 1H), 0.89 (s, 3H).

Example 31

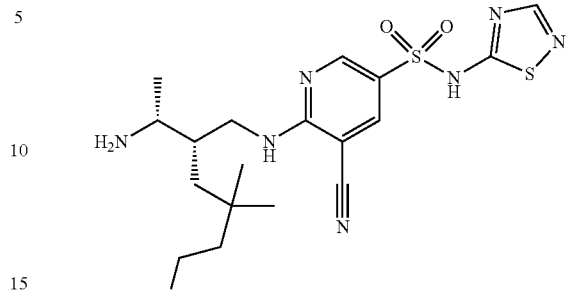

6-(((S)-6-amino-2-((R)-1-aminoethyl)-4,4-dimethylhexyl)amino)-5-cyano-N-(1,2,4-thiadiazol-5-yl)pyridine-3-sulfonamide Step A: Di-tert-butyl ((5S,6R)-5-(((3-cyano-5-(N-(2,4-dimethoxybenzyl)-N-(1,2,4-thiadiazol-5-yl)sulfamoyl)pyridin-2-yl)amino)methyl)-3,3-dimethylheptane-1,6-diyl)dicarbamate. To a microwave vial containing di-tert-butyl ((5S,6R)-5-(((3-bromo-5-(N-(2,4-dimethoxybenzyl)-N-(1,2,4-thiadiazol-5-yl)sulfamoyl)pyridin-2-yl)amino)methyl)-3,3-dimethylheptane-1,6-diyl)dicarbamate (72 mg, 0.084 mmol) was added zinc cyanide (10.6 mg, 0.090 mmol), then tBuXPhos G3=methanesulfonato(2-di-t-butylphosphino-2',4',6'-tri-i-propyl-1,1'-biphenyl)(2'-amino-1,1'-biphenyl-2-yl)palladium(II) (30.7 mg, 0.039 mmol). This mixture was then capped under an atmosphere of nitrogen. THF (0.500 mL) was then added followed by water (2.0 mL). The reaction mixture was then heated overnight at 65° C. sealed under an atmosphere of nitrogen. After 12 hours the reaction mixture was then cooled to room temperature, then suspended in EtOAc and saturated NaHCO₃, then filtered (syringe filter). The organic layer of the filtrate was separated. The aqueous layer was then re-extracted with EtOAc. The combined organics were dried over Na₂SO₄, filtered & concentrated. The resulting residue was then dissolved in MeOH/DMSO and purified by reverse phase chromatography (50-100% MeCN/H2O; 0.1% TFA in AQ; 20 min gradient; Waters 30×150 mm Sunfire 5 micron C18 column; Flow=40 mL/min) to afford the title compound that was used in the next step without further purification. LCMS (ES, m/z): 803.5 [M+H]+.

Step B: 6-(((S)-6-amino-2-((R)-1-aminoethyl)-4,4-dimethylhexyl)amino)-5-cyano-N-(1,2,4-thiadiazol-5-yl)pyridine-3-sulfonamide bis(2,2,2-trifluoroacetate). To a vial containing di-tert-butyl ((5S,6R)-5-(((3-cyano-5-(N-(2,4-dimethoxybenzyl)-N-(1,2,4-thiadiazol-5-yl)sulfamoyl)pyridin-2-yl)amino)methyl)-3,3-dimethylheptane-1,6-diyl)dicarbamate (29 mg, 0.036 mmol) was added TFA (400 µL, 5.19 mmol), followed by DCM (1 mL). The reaction mixture was then stirred at room temperature open to the atmosphere. After 30 minutes at room temperature the reaction mixture was then diluted with MeOH, stirred ~5 minutes, then filtered (syringe filter), to the filtrate was added 0.5 mL DMSO, then partially concentrated in vacuo. The resulting residue was then dissolved/diluted to ~1.75 mL with DMSO & purified by mass guided reverse phase chromatography 5-35% MeCN/water with 0.1% TFA modifier to afford the title compound. LCMS (ES, m/z): 453.0 [M+H]+. 1H NMR (500 MHz, DMSO-d6) δ 8.62 (d, J=2.4 Hz, 1H), 8.16 (d, J=2.3 Hz, 1H), 8.08-8.02 (m, 2H), 7.72-7.56 (m, 7H), 3.59-3.53 (m, 1H), 3.17-3.04 (m, 2H), 2.84-2.75 (m, 2H), 2.07 (s, 1H), 1.58-1.50 (m, 2H), 1.39-1.30 (m, 1H), 1.13 (d, J=6.7 Hz, 3H), 1.00 (s, 3H), 0.98-0.91 (m, 1H), 0.89 (s, 3H).

Example 32

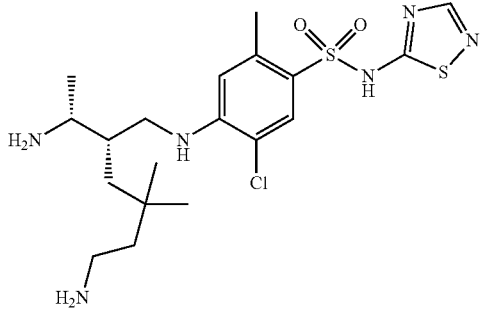 [SMILES: Cc1cc(NC[C@H](CC(C)(C)CCN)[C@@H](C)N)c(Cl)cc1S(=O)(=O)Nc1ncns1]

4-(((S)-6-amino-2-((R)-1-aminoethyl)-4,4-dimethylhexyl)amino)-5-chloro-2-methyl-N-(1,2,4-thiadiazol-5-yl)benzenesulfonamide Step A: Di-tert-butyl ((5S,6R)-5-(((2-chloro-4-(N-(2,4-dimethoxybenzyl)-N-(1,2,4-thiadiazol-5-yl)sulfamoyl)-5-methylphenyl)amino)methyl)-3,3-dimethylheptane-1,6-diyl)dicarbamate. To a vial containing INTERMEDIATE 4 (28.3 mg, 0.062 mmol) & INTERMEDIATE 14A (28 mg, 0.072 mmol) was added DMF (0.8 mL), followed by DIPEA (40 µl, 0.229 mmol). The reaction mixture was then capped and stirred at room temperature. After 3 days at ambient temperature the reaction mixture was diluted with MeOH, then concentrated to yield crude di-tert-butyl ((5S,6R)-5-(((2-chloro-4-(N-(2,4-dimethoxybenzyl)-N-(1,2,4-thiadiazol-5-yl)sulfamoyl)-5-methylphenyl)amino)methyl)-3,3-dimethylheptane-1,6-diyl)dicarbamate, which was used as is for next step without further purification. LCMS (ES, m/z): 825.5 [M+H]⁺.

Step B: 4-(((S)-6-amino-2-((R)-1-aminoethyl)-4,4-dimethylhexyl)amino)-5-chloro-2-methyl-N-(1,2,4-thiadiazol-5-yl)benzenesulfonamide bis(2,2,2-trifluoroacetate). To a vial containing crude di-tert-butyl ((5S,6R)-5-(((2-chloro-4-(N-(2,4-dimethoxybenzyl)-N-(1,2,4-thiadiazol-5-yl)sulfamoyl)-5-methylphenyl)amino)methyl)-3,3-dimethylheptane-1,6-diyl)dicarbamate (51 mg, 0.062 mmol) was added TFA (400 µl, 5.19 mmol) followed by DCM (0.8 ml). The reaction mixture was then stirred at room temperature. After 1 h the reaction mixture was diluted with MeOH, stirred ~5 minutes, then filtered (syringe filter), to the filtrate was added 0.5 mL DMSO, then partially concentrated. The resulting residue was then dissolved/diluted to ~1.75 mL with DMSO & purified by mass guided reverse phase chromatography 10-45% MeCN/water with 0.1% TFA modifier to afford the title compound. LCMS (ES, m/z): 474.9 [M+H]⁺. ¹H NMR (500 MHz, DMSO-d6) δ 8.11 (s, 1H), 7.69-7.65 (m, 7H), 6.55 (s, 1H), 6.10 (s, 1H), 3.21-3.09 (m, 3H), 2.82-2.76 (m, 2H), 2.45 (s, 3H), 2.04 (s, 1H), 1.52-1.37 (m, 3H), 1.15 (d, J=6.7 Hz, 3H), 0.99 (dd, J=14.7, 7.0 Hz, 1H), 0.93 (s, 3H), 0.88 (s, 3H).

Example 33

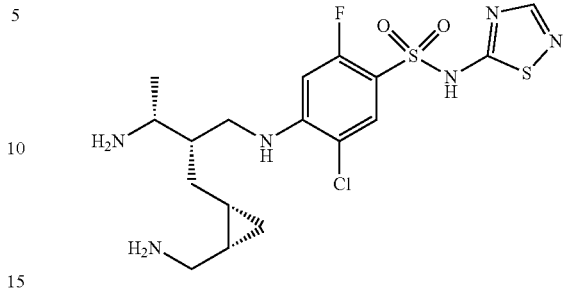

4-(((2S,3R)-3-amino-2-((((1S,2S)-2-(aminomethyl)cyclopropyl)methyl)butyl)amino)-5-chloro-2-fluoro-N-(1,2,4-thiadiazol-5-yl)benzenesulfonamide Step A: Methyl (R,Z)-2-((R)-1-((tert-butoxycarbonyl)amino)ethyl)-6-((tert-butyldimethylsilyl)oxy)hex-4-enoate. Into a 5000-mL 4-necked round-bottom flask purged and maintained with an inert atmosphere of nitrogen, was placed a solution of methyl (R)-3-((tert-butoxycarbonyl)amino)butanoate (50 g, 230.14 mmol, 1.00 equiv) in tetrahydrofuran (1000 mL). This was followed by the addition of LiHMDS (690 mL, 3.00 equiv) dropwise with stirring at −78° C. The mixture was stirred for 2 hrs at −78° C. To this was added a solution of [(2Z)-4-bromobut-2-en-1-yl]oxy(tert-butyl)dimethylsilane (183.2 g, 690.64 mmol, 3.00 equiv) in tetrahydrofuran (200 mL) dropwise with stirring at −78° C. The resulting solution was stirred for 3 h at room temperature. The reaction was then quenched by the addition of 1000 mL of sodium bicarbonate. The resulting solution was extracted with 3×800 mL of ethyl acetate and the organic layers combined. The resulting mixture was washed with 1×1000 mL of brine. The mixture was dried over anhydrous magnesium sulfate and concentrated under vacuum. The residue was applied onto a silica gel column with ethyl acetate/petroleum ether (1:20). The crude product was purified by Prep-SFC with the following conditions: Column: (R,R)-WHELK-01-Kromasil (5*25 cm, 5 um); mobile phase: 30% MeOH (0.1% DEA), 70% CO₂; Detector: 210 nm. the title compound. LCMS (ES, m/z): 402 [M+H]⁺. ¹H-NMR (400 MHz, Chloroform-d, ppm): δ 5.60 (dddd, J=11.0, 6.2, 5.4, 1.4 Hz, 1H), 5.47-5.31 (m, 1H), 5.22 (d, J=9.6 Hz, 1H), 4.20 (dt, J=6.4, 2.0 Hz, 2H), 3.91 (q, J=10.5 Hz, 1H), 3.68 (s, 3H), 2.62-2.47 (m, 1H), 2.50-2.37 (m, 1H), 2.29 (dt, J=13.8, 6.7 Hz, 1H), 1.43 (s, 9H), 1.13 (d, J=6.8 Hz, 3H), 0.90 (d, J=7.6 Hz, 11H), 0.08 (d, J=12.6 Hz, 7H).

Step B: Methyl (R,Z)-2-((R)-1-((tert-butoxycarbonyl)amino)ethyl)-6-hydroxyhex-4-enoate. To methyl (R,Z)-2-((R)-1-((tert-butoxycarbonyl)amino)ethyl)-6-((tert-butyldimethylsilyl)oxy)hex-4-enoate (5 g, 12.45 mmol) in THF (62.2 ml) at 0 C was added TBAF (18.700 ml, 18.70 mmol), and stirred at RT for 2 hr. The reaction mixture was partitioned between EtOAc and saturated sodium bicarbonate solution. Solvent was removed in vacuo and the residue was purified via normal phase silica gel chromatography with 0-50% EtOAc in hexanes to afford the title compound. LCMS (ES, m/z): 288.3 [M+H]⁺.

Step C: Methyl (2R,3R)-2-((2-(azidomethyl)cyclopropyl)methyl)-3-((tert-butoxycarbonyl)amino)butanoate. To methyl (R,Z)-2-((R)-1-((tert-butoxycarbonyl)amino)ethyl)-6-hydroxyhex-4-enoate (472 mg, 1.566 mmol), diphenylphosphoryl azide (675 µl, 3.13 mmol), and triphenylphosphine (1027 mg, 3.92 mmol) in THF (1.04E+04 µl) was added diisopropyl azodicarboxylate (776 µl, 3.92 mmol). The reaction was heated to 50° C. and stirred for 1 h before partitioned between Et$_2$O and water. The organic layer was dried over MgSO$_4$ and filtered. Solvent was removed in vacuo and the residue was purified via normal phase silica gel chromatography with 0-30% EtOAc in hexanes to afford the title compound as a mixture of diasteromers. LCMS (ES, m/z): 327.3 [M+H]$^+$.

Step D: Methyl (2R,3R)-3-((tert-butoxycarbonyl)amino)-2-((2-(((tert-butoxycarbonyl)amino)methyl)cyclopropyl)methyl)butanoate. Methyl (2R,3R)-2-((2-(azidomethyl)cyclopropyl)methyl)-3-((tert-butoxycarbonyl)amino) butanoate (450 mg, 1.379 mmol) was dissolved in THF (7958 µl) and water (398 µl). The reaction vessel was evacuated via vacuum pump and then refilled with N$_2$. Trimethylphosphine in toluene (2757 µl, 2.76 mmol) was added and the reaction was stirred at rt under N$_2$ for 2 h. Solvent was removed and residue was dissolved in Et$_2$O (100 mL). The solution was washed with water (30 mL), then brine (10 mL), dried over MgSO$_4$, filtered and concentrated to yield a colorless substance. The crude residue was dissolved in DCM 8 ml, treated with Boc-Anhydride (541 mg, 2.48 mmol) and Et$_3$N (242 µl, 1.738 mmol) stirred at RT for 1 h. Solvent was removed in vacuo and the residue was purified via normal phase silica gel chromatography with 0-30% EtOAc in hexanes to afford the title compound as a mixture of diasteromers. LCMS (ES, m/z): 401.4 [M+H]$^+$.

Step E: Tert-butyl ((2R,3R)-4-((1R,2R)-2-(((tert-butoxycarbonyl)amino)methyl)cyclopropyl)-3-(hydroxymethyl)butan-2-yl)carbamate and tert-butyl ((2R,3R)-4-((1S,2S)-2-(((tert-butoxycarbonyl)amino)methyl)cyclopropyl)-3-(hydroxymethyl)butan-2-yl)carbamate. To a flask containing (2R,3R)-methyl 3-((tert-butoxycarbonyl)amino)-2-((2-(((tert-butoxycarbonyl)amino)methyl)cyclopropyl)-methyl)butanoate, as mixture of cyclopropane diastereomers (400 mg, 0.999 mmol) was added anhydrous THF (9987 µl). The reaction mixture was capped and stirred under N$_2$ at 0° C. (ice water bath). LAH (1498 µl, 1.498 mmol) was added and the reaction was stirred at 0° C. for 1 h. While cold, the reaction was quenched with the addition of H$_2$O (0.8 mL), 10N NaOH (2 mL), and H$_2$O (3.2 mL), diluted with EtOAc (80 mL) and then warmed to RT and stirred for 10 min. The aqueous layer was collected and extracted with EtOAc. The combined organic layer was dried over MgSO$_4$, filtered over celite. Solvent was removed in vacuo and the residue was purified via normal phase chromatography with 0-40% EtOAc in hexanes to afford the fast-eluting isomer (tert-butyl ((2R,3R)-4-((1R,2R)-2-(((tert-butoxycarbonyl)amino)methyl)cyclopropyl)-3-(hydroxymethyl)butan-2-yl)carbamate) and the slow-eluting isomer (tert-butyl ((2R,3R)-4-((1S,2S)-2-(((tert-butoxycarbonyl)amino)methyl)cyclopropyl)-3-(hydroxymethyl)butan-2-yl)carbamate). LCMS (ES, m/z): 373.4 [M+H]$^+$ for both isomers.

Step F: Tert-butyl ((2R,3S)-4-((1S,2S)-2-(((tert-butoxycarbonyl)amino)methyl)cyclopropyl)-3-((1,3-dioxoisoindolin-2-yl)methyl)butan-2-yl)carbamate. To tert-butyl ((2R,3R)-4-((1S,2S)-2-(((tert-butoxycarbonyl)amino)methyl)cyclopropyl)-3-(hydroxymethyl)butan-2-yl)carbamate (59 mg, 0.158 mmol), phthalimide (23.30 mg, 0.158 mmol), and triphenylphosphine (62.3 mg, 0.238 mmol) in THF (1056 µl) was added diisopropyl azodicarboxylate (47.1 µl, 0.238 mmol). The reaction was heated to 50° C. and stirred for 1 h before cooled down and partitioned between Et$_2$O and water. The organic layer was dried over MgSO$_4$, concentrated and purified on normal phase chromatography 0-50% EtOAc/hexane to yield the title compound. LCMS (ES, m/z): 502.4 [M+H]$^+$.

Step G: Tert-butyl ((2R,3S)-4-amino-3-(((1S,2S)-2-(((tert-butoxycarbonyl)amino)methyl)cyclopropyl)methyl) butan-2-yl)carbamate. To tert-butyl ((2R,3S)-4-((1S,2S)-2-(((tert-butoxycarbonyl)amino)methyl)cyclopropyl)-3-((1,3-dioxoisoindolin-2-yl)methyl)butan-2-yl)carbamate (77 mg, 0.154 mmol) dissolved in EtOH (768 µl) was added hydrazine hydrate (105 µl, 2.149 mmol). The mixture was stirred at 50° C. for 1.5 h before diluted with DCM and filtered. The filtrate was concentrated in vacuo, redissolved in DCM, and washed with water. The organic layer was dried over MgSO$_4$, filtered and concentrated to provide the title compound that was used without further purification. LCMS (ES, m/z): 372.4 [M+H]$^+$.

Step H: 4-(((2S,3R)-3-amino-2-(((1S,2S)-2-(aminomethyl)cyclopropyl)methyl)butyl)amino)-5-chloro-2-fluoro-N-(1,2,4-thiadiazol-5-yl)benzenesulfonamide. To INTERMEDIATE 3 (17 mg, 0.037 mmol) and Tert-butyl ((2R,3S)-4-amino-3-(((1S,2S)-2-(((tert-butoxycarbonyl)amino)methyl)cyclopropyl)methyl)butan-2-yl)carbamate (13.67 mg, 0.037 mmol) in DMF (184 µl) was added DIPEA (32.1 µl, 0.184 mmol). The reaction was stirred at ambient temperature overnight, before diluted with EtOAc (10×), washed with water then brine, dried over MgSO$_4$ and filtered. Solvent was removed in vacuo and the crude was then dissolved in 1 mL DCM/1 mL TFA and stirred for 1 h. The solvent was removed in vacuo and the residue was dissolved in a DMSO/water=1, filtered and purified via reverse-phase chromatography with 0-100% AcCN in Water (0.05% TFA) to afford the title compound. LCMS (ES, m/z): 463.3 [M+H]$^+$. $^1$H NMR (500 MHz, Methanol-d$_4$) δ 8.20 (s, 1H), 7.71 (d, J=7.1 Hz, 1H), 6.58 (d, J=12.7 Hz, 1H), 3.58-3.49 (m, 2H), 3.31-3.21 (m, 2H), 2.75 (dd, J=13.0, 9.3 Hz, 1H), 2.18 (dd, J=8.8, 3.7 Hz, 1H), 1.89 (dd, J=10.1, 3.1 Hz, 1H), 1.30 (d, J=6.8 Hz, 3H), 1.21-1.08 (m, 3H), 1.03 (td, J=8.1, 5.0 Hz, 1H), 0.30 (q, J=5.1 Hz, 1H).

Example 34 (Isomer 1), Example 35 (Isomer 2)

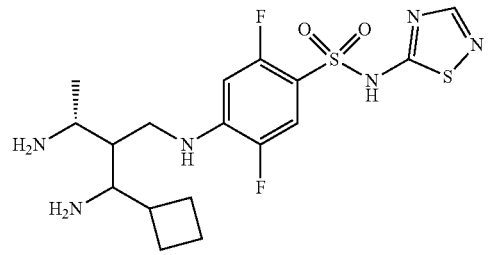 [SMILES: C[C@@H](N)C(CNc1cc(F)c(S(=O)(=O)Nc2ncns2)cc1F)C(N)C1CCC1]

4-(((3R)-3-amino-2-(amino(cyclobutyl)methyl)butyl)amino)-2,5-difluoro-N-(1,2,4-thiadiazol-5-yl)benzenesulfonamide Step A: (E)-N-(cyclobutylmethylene)-2-methylpropane-2-sulfinamide. To a stirred solution of cyclobutanecarboxaldehyde (1.388 g, 16.50 mmol) in DCM (50 ml) were added the 2-methylpropane-2-sulfinamide (1 g, 8.25 mmol), magnesium sulfate (4.97 g, 41.3 mmol), and pyridinium p-toluenesulfonate (0.104 g, 0.413 mmol). The reaction mixture was left to stir overnight at RT under N$_2$ atmosphere. The resulting reaction mixture was filtered and then the filtrate was concentrated in vacuo. The residue was purified by flash chromatography (80 g ISCO cartridge) using 0-25% EtOAc/Hex to give the title compound. LCMS (ES, m/z): 188.1 [M+H]⁺.

Step B: methyl (3R)-3-((tert-butoxycarbonyl)amino)-2-(((tert-butylsulfinyl)amino)(cyclobutyl)methyl)butanoate. To a mixture of 2M lithium diisopropylamide (12.08 ml, 24.16 mmol) in THF and THF (50 ml) was added slowly a solution of (R)-methyl 3-((tert-butoxycarbonyl)amino)butanoate (1.5 g, 6.90 mmol)) in THF at −78° C. under N₂ atmosphere. The mixture was stirred at −78° C. for 1 hr under N₂ atmosphere. Then was added slowly a solution of (E)-N-(cyclobutylmethylene)-2-methylpropane-2-sulfinamide (1.422 g, 7.59 mmol) in THF (3 ml) at −78° C. under N₂ atmosphere. The reaction mixture was stirred at −78° C. for an additional 1 hr under N₂ atmosphere. The resulting reaction mixture was quenched with sat. NH₄Cl and diluted with EtOAC. The organic layer was separated, dried over MgSO₄, filtered, and concentrated in vacuo. The residue was purified by flash chromatography (40 g ISCO cartridge) using 0-25% EtOAc/Hex to yield the title compound. LCMS (ES, m/z): 405.4 [M+H]⁺.

Step C: Tert-butyl ((2R)-4-cyclobutyl-4-(1,1-dimethylethylsulfinamido)-3-(hydroxymethyl)butan-2-yl)carbamate. To a solution of (3R)-methyl 3-((tert-butoxycarbonyl)amino)-2-(cyclobutyl(1,1-dimethylethylsulfinamido)methyl)butanoate (1.1 g, 2.72 mmol) in THF (5 ml) was added lithium chloride (0.576 g, 13.59 mmol) and methanol (0.550 ml, 13.59 mmol) at 0° C. and stirred under N₂ atmosphere for 15 min. Then was added lithium borohydride (6.80 ml, 13.59 mmol) slowly at 0° C. The reaction mixture was stirred under N₂ atmosphere overnight at room temperature. The resulting reaction mixture was diluted with EtOAc and sat. NH₄Cl. The organic layer was separated, dried over MgSO₄, filtered, and concentrated in vacuo. The residue was purified by flash chromatography (40 g ISCO cartridge) using 0-10% EtOAc/Hex to yield the title compound. LCMS (ES, m/z): 377.4 [M+H]⁺.

Step D: Tert-butyl ((2R)-4-cyclobutyl-4-(1,1-dimethylethylsulfinamido)-3-((1,3-dioxoisoindolin-2-yl)methyl)butan-2-yl)carbamate. To a solution of tert-butyl ((2R)-4-cyclobutyl-4-(1,1-dimethylethylsulfinamido)-3-(hydroxymethyl)butan-2-yl)carbamate (708 mg, 1.880 mmol) in THF (50 ml) was added phthalimide (415 mg, 2.82 mmol), triphenylphosphine (740 mg, 2.82 mmol), and DIAD (0.548 ml, 2.82 mmol) at 0° C. The reaction mixture was stirred at room temperature under N₂ atmosphere overnight. The resulting reaction mixture was concentrated in vacuo. The residue was purified by flash chromatography (80 g ISCO cartridge) using 0-50% EtOAc/Hex to yield the the separated diastereomeric title compound (faster eluting Peak, Isomer 1; slower eluting Peak, Isomer 2). LCMS (ES, m/z): 506.3 [M+H]⁺ Isomer 1; LCMS (ES, m/z): 506.3 [M+H]⁺ Isomer 2.

Step E: Tert-butyl ((2R,3S,4R)-3-(aminomethyl)-4-((tert-butylsulfinyl)amino)-4-cyclobutylbutan-2-yl)carbamate. To a solution of tert-butyl ((2R,3R,4S)-4-((tert-butylsulfinyl)amino)-4-cyclobutyl-3-((1,3-dioxoisoindolin-2-yl)methyl)butan-2-yl)carbamate (Isomer 1) (165 mg, 0.326 mmol) in Ethanol (5 ml) was added hydrazine hydrate (0.158 ml, 3.26 mmol). The reaction was stirred at 50° C. for 3 h. The resulting reaction mixture was filtered washing with CH₂Cl₂. The filtrate was concentrated in vacuo. The residue was diluted with CH₂Cl₂ and H₂O. The organic layer was extracted two times with CH₂Cl₂. The combined organic layers were dried over MgSO₄, filtered, and concentrated in vacuo. The residue was carried onto the next step without any further purification. LCMS (ES, m/z): 376.4 [M+H]⁺.

Step F: Tert-butyl ((2R,3S,4R)-4-((tert-butylsulfinyl)amino)-4-cyclobutyl-3-(((4-(N-(2,4-dimethoxybenzyl)-N-(1,2,4-thiadiazol-5-yl)sulfamoyl)-2,5-difluorophenyl)amino)methyl)butan-2-yl)carbamate. To a solution of INTERMEDIATE 30 (120 mg, 0.269 mmol) in DMF (2 ml) was added tert-butyl ((2R,3S,4R)-3-(aminomethyl)-4-((tert-butylsulfinyl)amino)-4-cyclobutylbutan-2-yl)carbamate (101 mg, 0.269 mmol) and DIPEA (0.141 ml, 0.808 mmol). The reaction mixture was stirred in a capped vial overnight at room temperature. The resulting residue was diluted with EtOAc and then washed with H₂O three times. The resulting organic layer was separated, dried over MgSO₄, filtered, and concentrated in vacuo. The residue was carried onto the next step without further purification. LCMS (ES, m/z): 801.5 [M+H]⁺.

Step G: 4-(((3R)-3-amino-2-(amino(cyclobutyl)methyl)butyl)amino)-2,5-difluoro-N-(1,2,4-thiadiazol-5-yl)benzenesulfonamide. To a solution of tert-butyl ((2R,3S,4R)-4-cyclobutyl-3-(((4-(N-(2,4-dimethoxybenzyl)-N-(1,2,4-thiadiazol-5-yl)sulfamoyl)-2,5-difluorophenyl)amino)methyl)-4-(1,1-dimethylethylsulfinamido)butan-2-yl)carbamate (86 mg, 0.107 mmol) in DCM (1 ml) was added TFA (1 ml, 12.98 mmol). The mixture was left in a capped vial at room temperature for 1 hr. The resulting mixture was concentrated in vacuo. The residue was then dissolved in MeOH (1 ml) and then added 4M solution of HCl (1 ml, 4.00 mmol) in dioxane. The mixture was stirred at room temperature for 30 min. The resulting mixture was concentrated in vacuo. The residue was purified by reverse phase HPLC (50 g C18 column) using ACN+0.05% TFA and H₂O+0.05% TFA to yield the title compound (EXAMPLE 34).

EXAMPLE 34—LCMS (ES, m/z): 447.3 [M+H]⁺. ¹H NMR (500 MHz, Methanol-d₄) δ 8.20 (s, 1H), 7.51 (dd, J=10.9, 6.3 Hz, 1H), 6.72 (dd, J=11.7, 6.6 Hz, 1H), 3.53-3.45 (m, 2H), 3.38 (dd, J=6.6, 3.0 Hz, 2H), 2.77-2.74 (m, 1H), 2.32-2.26 (m, 1H), 2.13 (d, J=8.3 Hz, 2H), 2.08-1.96 (m, 3H), 1.86 (d, J=8.0 Hz, 1H), 1.48 (d, J=6.7 Hz, 3H).

Following a similar procedure for EXAMPLE 34, Steps E-G of EXAMPLE 34, using Isomer 2 from Step D afforded EXAMPLE 35 4-(((3R)-3-amino-2-(amino(cyclobutyl)methyl)butyl)amino)-2,5-difluoro-N-(1,2,4-thiadiazol-5-yl)benzenesulfonamide, Isomer 2).

EXAMPLE 35—¹H NMR (500 MHz, Methanol-d4) δ 8.19 (s, 1H), 7.52 (dd, J=11.0, 6.3 Hz, 1H), 6.60 (dd, J=11.7, 6.7 Hz, 1H), 3.62 (t, J=6.8 Hz, 1H), 3.51 (d, J=10 Hz, 1H), 3.44-3.33 (m, 2H), 2.83-2.75 (m, 1H), 2.20-2.10 (m, 3H), 2.06-1.81 (m, 4H), 1.46 (d, J=6.8 Hz, 3H).

Example 36 (Isomer 1), Example 37 (Isomer 2)

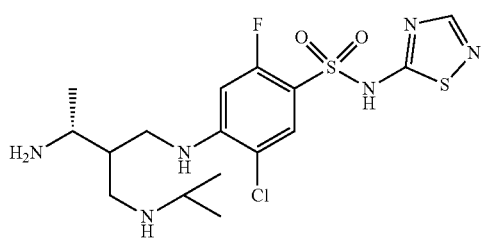 [SMILES: CC(C)NCC(CNc1cc(F)c(S(=O)(=O)Nc2ncns2)cc1Cl)[C@@H](C)N]

4-(((3R)-3-amino-2-((isopropylamino)methyl)butyl)amino)-5-chloro-2-fluoro-N-(1,2,4-thiadiazol-5-yl)benzenesulfonamide Step A: (R)-tert-butyl (3-carbamoylbut-3-en-2-yl)carbamate. To a solution of INTERMEDIATE 10, HATU (3.65 g, 9.59 mmol), ammonium chloride (0.560 g, 10.46 mmol) in DMF (87 ml) were added triethylamine (3.65 ml, 26.2 mmol). The mixture was stirred at RT overnight. DMF was removed in vacuo and the residue was purified via reverse-phase chromatography with 0-20%-100% AcCN in water to afford the title compound. LCMS (ES, m/z): 215.2 [M+H]$^+$.

Step B: (R)-tert-butyl (3-cyanobut-3-en-2-yl)carbamate. To (R)-tert-butyl (3-carbamoylbut-3-en-2-yl)carbamate (1000 mg, 4.67 mmol) in THF was added pyridine (3775 µl, 46.7 mmol) and trifluoroacetic anhydride (3296 µl, 23.34 mmol). The mixture was stirred at RT for 2 hrs. Solvent was removed in vacuo and the residue was purified via normal phase chromatography with 0-30% EtOAc in hexanes to afford the title compound. LCMS (ES, m/z): 197.2 [M+H]$^+$.

Step C: Tert-butyl ((3R)-3-((tert-butoxycarbonyl)amino)-2-cyanobutyl)(isopropyl)carbamate. To (R)-tert-butyl (3-cyanobut-3-en-2-yl)carbamate, (96 mg, 0.489 mmol) was added isopropylamine (84 µl, 0.978 mmol), stirred at 40 C for 3 h. The reaction was then Cooled to RT and diluted with 1 mL DCM. BOC-Anhydride (341 µl, 1.468 mmol) was added and the reaction was stirred at RT overnight. The solvent was removed in vacuo and the residue was purified via normal phase chromatography with 0-20% EtOAc in hexanes to afford the title compound as a 1:1 mixture of diastereomers. LCMS (ES, m/z): 356.4 [M+H]$^+$.

Step D: Tert-butyl ((3R)-2-(aminomethyl)-3-((tert-butoxycarbonyl)amino)butyl)(isopropyl)carbamate. To a mixture of tert-butyl ((3R)-3-((tert-butoxycarbonyl)amino)-2-cyanobutyl)(isopropyl)carbamate (as a mixture of diastereomers) (51 mg, 0.143 mmol) in THF (2050 µl) was added borane-methyl sulfide complex, 2.0 M in THF (717 µl, 1.435 mmol) at 0° C. Then the mixture was stirred at 20° C. for 20 h. The reaction was cooled to 0 C and MeOH (5.1 mL) was added. The mixture was heated at 80° C. for 3 h. Solvent was removed in vacuo to yield the title compound, which was used in the next step without purification. LCMS (ES, m/z): 360.7 [M+H]$^+$.

Step E: Tert-butyl ((3R)-3-((tert-butoxycarbonyl)amino)-2-(((2-chloro-4-(N-(2,4-dimethoxybenzyl)-N-(1,2,4-thiadiazol-5-yl)sulfamoyl)-5-fluorophenyl)amino)methyl)butyl)(isopropyl)carbamate. To tert-butyl ((3R)-2-(aminomethyl)-3-((tert-butoxycarbonyl)amino)butyl)(isopropyl)carbamate (66 mg, 0.143 mmol) and INTERMEDIATE 3 (66.1 mg, 0.143 mmol) in DMF (1430 µl) was added DIPEA (125 µl, 0.715 mmol). The reaction was stirred at RT for 16 h, before diluted with EtOAc (10×), washed with water then brine, dried over (MgSO$_4$) and filtered. Solvent was removed in vacuo and the residue was purified via normal phase chromatography with 0-30% EtOAc in hexanes the title compound as separate diastereomers (fast-eluting Peak, Isomer 1 slow-eluting Peak, Isomer 2). LCMS (ES, m/z): 801.5 [M+H]$^+$.

Step F: 4-(((3R)-3-amino-2-((isopropylamino)methyl)butyl)amino)-5-chloro-2-fluoro-N-(1,2,4-thiadiazol-5-yl)benzenesulfonamide. Tert-butyl ((3R)-3-((tert-butoxycarbonyl)amino)-2-(((2-chloro-4-(N-(2,4-dimethoxybenzyl)-N-(1,2,4-thiadiazol-5-yl)sulfamoyl)-5-fluorophenyl)amino)methyl)butyl)(isopropyl)carbamate (Isomer 2) (38 mg, 0.047 mmol) was dissolved in DCM (237 µl)/TFA (237 µl), and stirred at RT for 1 h. Solvent was removed in vacuo and the residue re-dissolved in DMSO:water=1:1, filtered and purified via reverse-phase chromatography with 0-100% AcCN in Water (0.05% TFA) to afford the title compound (EXAMPLE 36).

EXAMPLE 36—LCMS (ES, m/z): 451.3 [M+H]$^+$. $^1$H NMR (500 MHz, Methanol-d$_4$) δ 8.19 (s, 1H), 7.72 (d, J=7.1 Hz, 1H), 6.67 (d, J=12.4 Hz, 1H), 3.69 (qd, J=6.9, 3.0 Hz, 1H), 3.50 (dd, J=14.4, 6.5 Hz, 1H), 3.47-3.33 (m, 3H), 3.13 (dd, J=13.2, 8.3 Hz, 1H), 2.58 (dd, J=7.2, 3.4 Hz, 1H), 1.38 (m, 9H).

Following a similar procedure for EXAMPLE 36, Step F of EXAMPLE 36, using Isomer 1 from Step E afforded EXAMPLE 37 (4-(((3R)-3-amino-2-((isopropylamino)methyl)butyl)amino)-5-chloro-2-fluoro-N-(1,2,4-thiadiazol-5-yl)benzenesulfonamide; Isomer 1).

Example 37—LCMS (ES, m/z): 451.3 [M+H]$^+$. $^1$H NMR (499 MHz, Methanol-d4) δ 8.19 (s, 1H), 7.72 (d, J=7.0 Hz, 1H), 6.68 (d, J=12.3 Hz, 1H), 3.78-3.73 (m, 1H), 3.50 (dd, J=13.7, 4.9 Hz, 1H), 3.44-3.38 (m, 1H), 3.35 (d, J=9.2 Hz, 1H), 3.32-3.28 (m, 1H), 3.18 (d, J=5.5 Hz, 1H), 2.56 (brs, 1H), 1.35 (m, 9H).

Example 38 (Isomer 1), Example 39 (Isomer 2)

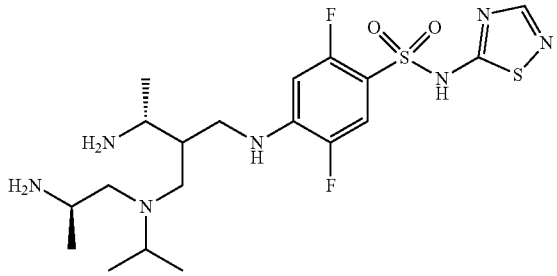 [SMILES: CC(C)N(CC(CNc1cc(F)c(S(=O)(=O)Nc2ncns2)cc1F)[C@@H](C)N)C[C@@H](C)N]

4-(((3R)-3-amino-2-((((R)-2-aminopropyl)(isopropyl)amino)methyl)butyl)amino)-2,5-difluoro-N-(1,2,4-thiadiazol-5-yl)benzenesulfonamide Step A: Methyl (3R)-3-((tert-butoxycarbonyl)amino)-2-((isopropylamino) methyl)butanoate. To a solution of INTERMEDIATE 10 (1.40 g, 6.11 mmol) in CH$_2$Cl$_2$ (20 ml) was added propan-2-amine (2.099 ml, 24.43 mmol) and 12 (0.155 g, 0.611 mmol). The mixture was stirred at RT overnight. To this mixture was added 10 ml Na$_2$S$_2$O$_3$ saturated aqueous solution. The mixture was stirred for 10 min and partitioned between EtOAc and H$_2$O. The layers were separated, dried over Na$_2$SO$_4$, filtered and concentrated in vacuo to give the crude the title compound which was used in the next step without further purification. LCMS (ES, m/z): 289.0 [M+H]$^+$.

Step B: Methyl (3R)-2-(((((benzyloxy)carbonyl)(isopropyl)amino)methyl)-3-((tert-butoxycarbonyl)amino)butanoate. To a solution of (3R)-methyl 3-((tert-butoxycarbonyl)amino)-2-((isopropylamino)methyl)butanoate (1760 mg, 6.10 mmol) and Et$_3$N (1.701 ml, 12.21 mmol) in THF (15 ml) was added CBZ-Cl (1.307 ml, 9.15 mmol). The mixture was stirred at RT for 5 h and patitioned between ethyl acetate and H$_2$O, dried over Na$_2$SO$_4$, filtered and concentrated in vacuo. The residue was purified by column chromatography on silica gel, eluting with 0-3% MeOH/DCM to give the title compound. LCMS (ES, m/z): 423.0 [M+H]$^+$.

Step C: Benzyl ((3R)-3-((tert-butoxycarbonyl)amino)-2-(hydroxymethyl) butyl)(isopropyl)carbamate. To a solution of (3R)-methyl 2-((((benzyloxy)carbonyl)(isopropyl)amino)methyl)-3-((tert-butoxycarbonyl)amino)butanoate (1.9 g, 4.50 mmol) in THF (25 ml) at 0° C. was added LAH (1.0M in THF) (6.75 ml, 6.75 mmol). The mixture was stirred at 0° C. for 30 min and worked up with $H_2O$. The filtration through a pad of the celite removed the solid. After washing with diethyl ether, the separated ether layer was dried over $Na_2SO_4$, filtered and concentrated in vacuo to give the crude title compound that was used in the next step without further purification. LCMS (ES, m/z): 395.0 $[M+H]^+$.

Step D: Benzyl ((3R)-3-((tert-butoxycarbonyl)amino)-2-((1,3-dioxoisoindolin-2-yl)methyl)butyl)(isopropyl)carbamate. To a solution of benzyl ((3R)-3-((tert-butoxycarbonyl)amino)-2-(hydroxymethyl)butyl)(isopropyl)carbamate (300 mg, 0.760 mmol) and phthalimide (224 mg, 1.521 mmol) in $CH_2Cl_2$ (3 ml) and THF (3.00 ml) was added $Ph_3P$ (399 mg, 1.521 mmol) and DIAD (0.296 ml, 1.521 mmol). The mixture was stirred at ambient temperature for 3 h and concentrated in vacuo. The residue was purified by column chromatography on silica gel, eluting with 0-4% MeOH/DCM to give the title compound. LCMS (ES, m/z): 524.0 $[M+H]^+$.

Step E: benzyl ((3R)-2-(aminomethyl)-3-((tert-butoxycarbonyl)amino) butyl)(isopropyl)carbamate. To a solution of benzyl ((3R)-3-((tert-butoxycarbonyl)amino)-2-((1,3-dioxoisoindolin-2-yl)methyl)butyl)(isopropyl)carbamate (303 mg, 0.579 mmol) in 2-propanol (20 ml) was added hydrazine (0.363 ml, 11.57 mmol). The mixture was heated to 50° C. and stirred for 4 h. The mixture was filtered through a pad of the celite, washed with MeOH, and the combined filtrate was concentrated in vacuo to give the crude title compound that was used without further purification. LCMS (ES, m/z): 394.0 $[M+H]^+$.

Step F: benzyl ((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino) methyl)butyl)(isopropyl)carbamate. To a solution of INTERMEDIATE 30 (387 mg, 0.869 mmol) and benzyl ((3R)-2-(aminomethyl)-3-((tert-butoxycarbonyl)amino)butyl)(isopropyl)carbamate (228 mg, 0.579 mmol) in DMF (8 ml) was added DIPEA (0.101 ml, 0.579 mmol). The mixture was stirred at ambient temperature overnight, partitioned between ethyl acetate and $H_2O$, dried over $Na_2SO_4$, filtered and concentrated in vacuo. The residue was purified by preparative TLC, eluting with 1.5% MeOH/DCM, to give the more polar diastereomer title compound (Isomer 1) and the less polar diastereomer title compound (Isomer 2). The Isomer 1 was submitted for next step. LCMS (ES, m/z): 819.0 $[M+H]^+$.

Step G: Tert-butyl ((2R)-4-((4-(N-(2,4-dimethoxybenzyl)-N-(1,2,4-thiadiazol-5-yl)sulfamoyl)-2,5-difluorophenyl)amino)-3-((isopropylamino)methyl)butan-2-yl)carbamate. Benzyl ((3R)-3-((tert-butoxycarbonyl)amino)-2-(((4-(N-(2,4-dimethoxybenzyl)-N-(1,2,4-thiadiazol-5-yl)sulfamoyl)-2,5-difluorophenyl)amino)methyl)butyl)(isopropyl) carbamate (Isomer 1 from Step F) (220 mg, 0.269 mmol) and 10% Pd—C (57.2 mg, 0.537 mmol) were combined in THF (2 ml) and MeOH (2 ml). The mixture was stirred under $H_2$ balloon for 1 h and filtrate through a pad of celite to remove Pd/C. After washing with MeOH, the combined filtered was concentrated in vacuo to give tert-butyl the title compound which was used in the next step without further purification. LCMS (ES, m/z): 685.0 $[M+H]^+$.

Step H: 4-(((3R)-3-amino-2-((((R)-2-aminopropyl)(isopropyl)amino) methyl)butyl)amino)-2,5-difluoro-N-(1,2,4-thiadiazol-5-yl)benzenesulfonamide. Tert-butyl ((2R)-4-((4-(N-(2,4-dimethoxybenzyl)-N-(1,2,4-thiadiazol-5-yl)sulfamoyl)-2,5-difluorophenyl)amino)-3-((isopropylamino)methyl)butan-2-yl)carbamate (30 mg, 0.044 mmol) and (R)-tert-butyl (1-oxopropan-2-yl)carbamate (22.76 mg, 0.131 mmol) was dissolved in $CH_2Cl_2$ (1.0 ml) and THF (1.0 ml), followed by addition of sodium triacetoxyborohydride (37.1 mg, 0.175 mmol). The mixture was stirred at rt overnight and added TFA (2 ml, 26.0 mmol). The mixture was stirred at rt for 2 h and concentrated in vacuo. The residue was purified by column chromatography on C18 reverse, eluting with 0-100% water with 0.05% TFA/0.0.5 TFA $CH_3CN$ to give the title compound EXAMPLE 38.

EXAMPLE 38—LCMS (ES, m/z): 492.1 $[M+H]^+$. $^1H$ NMR (500 MHz, Methanol-d4) δ 8.23 (s, 1H), 7.47 (dd, J=11.1, 6.3 Hz, 1H), 6.65-6.58 (m, 1H), 3.60 (tt, J=6.8, 3.4 Hz, 1H), 3.39-3.35 (m, 1H), 3.27 (dd, J=13.9, 8.2 Hz, 1H), 3.13-3.00 (m, 1H), 2.80-2.68 (m, 1H), 2.55 (tt, J=13.8, 8.3 Hz, 2H), 2.43 (dd, J=13.4, 9.6 Hz, 1H), 2.19 (d, J=4.1 Hz, 1H), 1.35 (dt, J=6.2, 2.9 Hz, 6H), 1.31 (d, J=6.8 Hz, 1H), 1.15 (dd, J=22.7, 6.7 Hz, 3H), 1.05 (dd, J=14.0, 6.5 Hz, 3H).

EXAMPLE 39 was prepared from Isomer 2, Step F of EXAMPLE 38 in the same fashion as EXAMPLE 38. LCMS (ES, m/z): 492.2 $[M+H]^+$.

Example 39—$^1H$ NMR (500 MHz, Methanol-d4) δ 8.23 (s, 1H), 7.47 (dd, J=11.1, 6.3 Hz, 1H), 7.41-7.25 (m, 5H), 6.60 (dt, J=12.0, 6.5 Hz, 1H), 3.85 (d, J=13.4 Hz, 1H), 3.65-3.57 (m, 2H), 3.55-3.49 (m, 1H), 3.48-3.40 (m, 1H), 3.29 (d, J=6.0 Hz, 1H), 3.20 (dd, J=13.9, 7.8 Hz, 1H), 2.74-2.66 (m, 1H), 2.62 (dt, J=10.3, 4.4 Hz, 2H), 2.55 (dd, J=13.4, 8.3 Hz, 1H), 1.27 (ddd, J=12.8, 6.8, 2.2 Hz, 6H).

Example 40

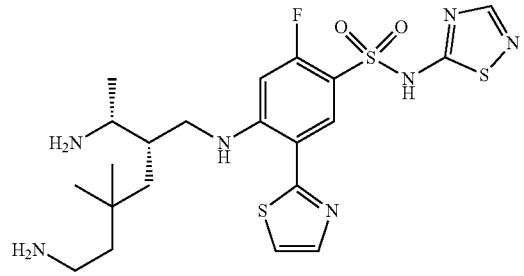 [SMILES: C[C@@H](N)[C@H](CNc1cc(F)c(S(=O)(=O)Nc2ncns2)cc1-c1nccs1)CC(C)(C)CCN]

4-(((S)-6-amino-2-((R)-1-aminoethyl)-4,4-dimethylhexyl)amino)-2-fluoro-N-(1,2,4-thiadiazol-5-yl)-5-(thiazol-2-yl)benzenesulfonamide Step A: Di-tert-butyl ((5S,6R)-5-(((4-(N-(2,4-dimethoxybenzyl)-N-(1,2,4-thiadiazol-5-yl)sulfamoyl)-5-fluoro-2-(thiazol-2-yl)phenyl)amino)methyl)-3,3-dimethylheptane-1,6-diyl)dicarbamate. To a pressure tube charged with di-tert-butyl ((5S,6R)-5-(((2-bromo-4-(N-(2,4-dimethoxybenzyl)-N-(1,2,4-thiadiazol-5-yl)sulfamoyl)-5-fluorophenyl)amino)methyl)-3,3-dimethylheptane-1,6-diyl)dicarbamate (40 mg, 0.046 mmol), 2-(tributylstannyl)thiazole (17.13 mg, 0.046 mmol), $Pd(Ph_3P)_4$ (52.9 mg, 0.046 mmol), and toluene (1.5 ml), purged with $N_2$ for 5 min and sealed. The mixture was heated to 85° C., stirred overnight and then at 100° C. for 1 h, cooled to ambient temperature and filtered through a pad of the celite to remove the solid. After washing with ethyl acetate, the combined filtrate was concentrated in vacuo. The residue was purified by column chromatography on silica gel (40 g Gold ISCO), eluting with 0-4% MeOH/DCM to give the title compound. LCMS (ES, m/z): 878.2 [M+H]⁺.

Step B: 4-(((S)-6-amino-2-((R)-1-aminoethyl)-4,4-dimethylhexyl)amino)-2-fluoro-N-(1,2,4-thiadiazol-5-yl)-5-(thiazol-2-yl)benzenesulfonamide. To a solution of di-tert-butyl ((5S,6R)-5-(((4-(N-(2,4-dimethoxybenzyl)-N-(1,2,4-thiadiazol-5-yl)sulfamoyl)-5-fluoro-2-(thiazol-2-yl)phenyl)amino)methyl)-3,3-dimethylheptane-1,6-diyl)dicarbamate (20 mg, 0.023 mmol) in CH₂Cl₂ (1 ml) was added TFA (1 ml, 12.98 mmol). The mixture was stirred at RT for 2 h and concentrated in vacuo. The residue was purified by column chromatography on C18 reverse, eluting with 0-100% water with 0.05% TFA/0.0.5 TFA CH₃CN to give the title compound. LCMS (ES, m/z): 528.1 [M+H]⁺. ¹H NMR (500 MHz, Methanol-d4) δ 8.23 (s, 1H), 8.20 (d, J=7.5 Hz, 1H), 7.87 (d, J=3.4 Hz, 1H), 7.59 (d, J=3.4 Hz, 1H), 6.67 (d, J=13.2 Hz, 1H), 3.65-3.53 (m, 1H), 3.42 (d, J=6.7 Hz, 2H), 3.06-2.93 (m, 2H), 2.24 (dt, J=6.5, 3.2 Hz, 1H), 1.70-1.62 (m, 2H), 1.58 (dd, J=14.8, 2.6 Hz, 1H), 1.41 (d, J=6.9 Hz, 1H), 1.38 (d, J=6.8 Hz, 3H), 1.03 (d, J=4.1 Hz, 6H).

Example 41 (Isomer 1), Example 42 (Isomer 2)

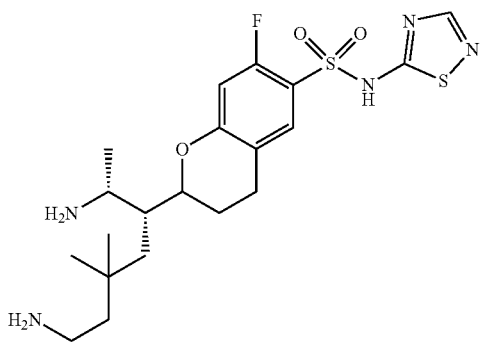 [SMILES: C[C@@H](N)[C@@H](CC(C)(C)CCN)C1CCc2cc(S(=O)(=O)Nc3ncns3)c(F)cc2O1]

2-((2R,3R)-2,7-diamino-5,5-dimethylheptan-3-yl)-7-fluoro-N-(1,2,4-thiadiazol-5-yl)chromane-6-sulfonamide Step A: Di-tert-butyl ((5R,6R)-5-formyl-3,3-dimethylheptane-1,6-diyl)dicarbamate. To a solution of oxalyl chloride (0.137 ml, 1.569 mmol) in 2 mL of anhydrous DCM at −78° C. was added dropwise DMSO (0.186 ml, 2.62 mmol). The reaction was stirred for 10 min. before adding dropwise a solution of di-tert-butyl ((5R,6R)-5-(hydroxymethyl)-3,3-dimethylheptane-1,6-diyl)dicarbamate (0.5081 g, 1.308 mmol) in anhydrous DCM (6 mL). The internal temperature was maintained below −70° C. during the addition. The flask containing the substrate was rinsed with 1.0 mL of anhydrous DCM and the rinsate was added to the reaction. The resulting white slurry was stirred for approximately 5 min. before adding Hunig's Base (0.914 ml, 5.23 mmol) dropwise. The reaction was stirred for 10 min. before removing the dry ice/acetone bath and allowing the reaction to warm to ambient temperature. After 1 h 20 min., the reaction was recooled to −5° C. (ice/brine bath) and saturated NH₄Cl was added. The reaction was warmed to ambient temperature before partitioning the mixture between brine and DCM. The organic layer was collected, dried over Na₂SO₄, filtered, and concentrated in vacuo. The residue was purified by (SiO₂, 0-65% EtOAc/hexanes; ninhydrin stain to view fractions) to give the title compound. LCMS (ES, m/z): 387.3 [M+H]⁺. ¹H NMR (500 MHz, Chloroform-d) δ 9.69 (d, J=2.1 Hz, 1H), 4.68 (d, J=7.5 Hz, 1H), 4.45 (bs, 1H), 4.01 (d, J=6.3 Hz, 1H), 3.12 (m, 2H), 2.70 (m, 1H), 1.80 (dd, J=14.4, 8.4 Hz, 1H), 1.58 (s, 2H), 1.44 (d, J=3.5 Hz, 18H), 1.41-1.32 (m, 2H), 1.10 (d, J=6.9 Hz, 3H), 0.87 (d, J=7.2 Hz, 6H).

Step B: Di-tert-butyl ((5R,6R)-5-(1-hydroxyallyl)-3,3-dimethylheptane-1,6-diyl)dicarbamate. To a solution of di-tert-butyl ((5R,6R)-5-formyl-3,3-dimethylheptane-1,6-diyl)dicarbamate (0.4267 g, 1.104 mmol) in anhydrous THF (5.52 ml) at 0° C. was added dropwise 1 M vinylmagnesium bromide in THF (1.656 ml, 1.656 mmol). After 3.5 h, the reaction was quenched with addition of saturated NH₄Cl and the mixture was extracted with EtOAc. The organic layer was washed with brine, dried over Na₂SO₄, filtered, and concentrated in vacuo. The residue was purified by chromatography (SiO₂, 0-40% EtOAc/hexanes; ninhydrin stain to view fractions) to give the title compound. LCMS (ES, m/z): 415.3 [M+H]⁺.

Step C: Di-tert-butyl ((5R,6R)-5-(3-(5-(N-(2,4-dimethoxybenzyl)-N-(1,2,4-thiadiazol-5-yl)sulfamoyl)-2,4-difluorophenyl)propanoyl)-3,3-dimethylheptane-1,6-diyl)dicarbamate. To a flask charged with di-tert-butyl ((5R,6R)-5-(1-hydroxyallyl)-3,3-dimethylheptane-1,6-diyl)dicarbamate (0.3175 g, 0.766 mmol), and INTERMEDIATE 33 (0.2631 g, 0.520 mmol) was added anhydrous toluene (2.60 ml). The mixture was sparged with N₂ for 5 min. before adding t-buxphos palladacycle (0.018 g, 0.026 mmol) followed by N,N-dicyclohexylmethylamine (0.167 ml, 0.779 mmol). The resulting yellow solution was sparged with N₂ for another 1 min., sealed, and then heated conventionally in a heating block at 90° C. for 4 h. The mixture was partitioned between EtOAc and saturated NH₄Cl. The organic layer was washed with brine, dried over Na₂SO₄, filtered, and concentrated in vacuo. The residue was purified by chromatography 2x (SiO₂, 0-50% EtOAc/hexanes) to give the title compound. LCMS (ES, m/z): 841.2 [M+H]⁺.

Step D: Di-tert-butyl ((5R,6R)-5-(3-(5-(N-(2,4-dimethoxybenzyl)-N-(1,2,4-thiadiazol-5-yl)sulfamoyl)-2,4-difluorophenyl)-1-hydroxypropyl)-3,3-dimethylheptane-1,6-diyl)dicarbamate. To a mixture of di-tert-butyl ((5R,6R)-5-(3-(5-(N-(2,4-dimethoxybenzyl)-N-(1,2,4-thiadiazol-5-yl)sulfamoyl)-2,4-difluorophenyl)propanoyl)-3,3-dimethylheptane-1,6-diyl)dicarbamate (71.6 mg, 0.085 mmol) in anhydrous MeOH (0.5 mL) at 0° C. was added NaBH₄ (12.90 mg, 0.341 mmol) in one portion. The reaction mixture became a grey mixture. After 50 min., the reaction was cooled to 0° C. and quenched with addition of water and saturated NH₄Cl. The mixture was extracted with EtOAc (2x). The combined organic layers were washed with brine, dried over Na₂SO₄, filtered, and concentrated in vacuo. The residue was purified by chromatography 2x (SiO₂, 0-100% EtOAc/hexanes) to give the title compound. LCMS (ES, m/z): 843.2 [M+H]⁺.

Step E: Di-tert-butyl ((5R,6R)-5-(6-(N-(2,4-dimethoxybenzyl)-N-(1,2,4-thiadiazol-5-yl)sulfamoyl)-7-fluorochroman-2-yl)-3,3-dimethylheptane-1,6-diyl)dicarbamate. To a solution of di-tert-butyl ((5R,6R)-5-(3-(5-(N-(2,4-dimethoxybenzyl)-N-(1,2,4-thiadiazol-5-yl)sulfamoyl)-2,4-difluorophenyl)-1-hydroxypropyl)-3,3-dimethylheptane-1,6-diyl)dicarbamate (43.2 mg, 0.051 mmol) in anhydrous THF (1710 μl) at 0° C. was added dropwise 1 M KOt-Bu in THF (71.8 μl, 0.072 mmol). The reaction became a yellow solution. After 30 min., the reaction was quenched with sat. NH₄Cl and the mixture was extracted with EtOAc (2x). The organic layers were combined, washed with brine, dried over Na₂SO₄, filtered, and concentrated in vacuo to afford the title compound, which was used in the next step without further purification. LCMS (ES, m/z): 823.2 [M+H]⁺.

Step F: 2-((2R,3R)-2,7-diamino-5,5-dimethylheptan-3-yl)-7-fluoro-N-(1,2,4-thiadiazol-5-yl)chromane-6-sulfonamide. To a solution of di-tert-butyl ((5R,6R)-5-(6-(N-(2,4-dimethoxybenzyl)-N-(1,2,4-thiadiazol-5-yl)sulfamoyl)-7-fluorochroman-2-yl)-3,3-dimethylheptane-1,6-diyl) dicarbamate (41.9 mg, 0.051 mmol) in anhydrous DCM (510 μl) was added TFA (196 μl, 2.55 mmol) at ambient temperature. The reaction turned dark purple. After 25 min., MeOH (1 mL) was added to the reaction, resulting in formation of a white precipitate. The reaction was stirred for 5 min., before filtering the mixture through a microfilter (0.45 micron). The filtrate was concentrated in vacuo and redissolved in 2 mL of 2:1:1 CH₃CN/DMSO/water and purified directly on HPLC (Sunfire column C18 OBD, 30×150 mm, 10 uM; flow rate=30 mL/min.; 5%-50% AcCN+0.05% TFA/water+0.05% TFA over 12 min.; collect at 220 nM, monitor at 254 nM) to give the title compound as separate diastereomers. First eluting peak, Isomer 1 (EXAMPLE 41).

EXAMPLE 41—LCMS (ES, m/z): 472.2 [M+H]⁺. ¹H NMR (500 MHz, Methanol-d₄) δ 8.22 (d, J=7.0 Hz, 1H), 7.67 (t, J=7.6 Hz, 1H), 6.74 (d, J=11.2 Hz, 1H), 4.53 (d, J=10.4 Hz, 1H), 3.59-3.43 (m, 1H), 3.10-2.83 (m, 4H), 2.09-1.88 (m, 3H), 1.77-1.53 (m, 3H), 1.53-1.39 (m, 4H), 1.03 (d, J=5.3 Hz, 6H).

Second eluting peak, Isomer 2 (EXAMPLE 42).

EXAMPLE 42—LCMS (ES, m/z): 472.2 [M+H]⁺. ¹H NMR (500 MHz, Methanol-d₄) δ 8.22 (s, 1H), 7.67 (d, J=7.9 Hz, 1H), 6.74 (d, J=11.2 Hz, 1H), 4.24 (dd, J=9.7, 4.9 Hz, 1H), 3.69 (tt, J=6.8, 3.4 Hz, 1H), 3.07-2.82 (m, 4H), 2.27-2.11 (m, 2H), 2.06-1.87 (m, 1H), 1.75 (dd, J=15.0, 6.7 Hz, 1H), 1.71-1.57 (m, 2H), 1.55-1.46 (m, 1H), 1.42 (d, J=6.9 Hz, 3H), 1.09-0.95 (m, 6H).

Example 43

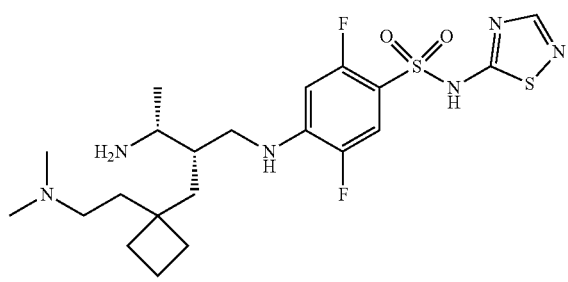 [SMILES: C[C@@H](N)[C@H](CNc1cc(F)c(S(=O)(=O)Nc2ncns2)cc1F)CC1(CCN(C)C)CCC1]

4-(((2S,3R)-3-amino-2-((1-(2-(dimethylamino)ethyl) cyclobutyl)methyl)butyl)amino)-2,5-difluoro-N-(1,2, 4-thiadiazol-5-yl)benzenesulfonamide Step A: Methyl (2R,3R)-2-((1-(2-(((benzyloxy)carbonyl) amino)ethyl)cyclobutyl)methyl)-3-((tert-butoxycarbonyl) amino)butanoate. In a 40 ml vial was added 1-(2-(((benzyloxy)carbonyl)amino)ethyl)cyclobutane-1-carboxylic acid (2.58 g, 9.29 mmol), INTERMEDIATE 10 (1.99 g, 8.68 mmol), potassium hydrogen phosphate (3.02 g, 17.36 mmol), and (IR[DF(CF₃)PPY]₂(DTBPY))PF₆ catalyst (0.179 g, 0.160 mmol). The vial was evacuated and filled with N₂ (3×) before adding anhydrous DMF (20 mL) which had been sparged with N₂ prior to use. The resulting mixture was sealed and sonicated to ensure both starting material substrates had dissolved. With stirring, the vial was irradiated in a Merck photoreactor (100% LED, 450 nM) for 18 h. The resulting dark brown reaction was quenched by exposure to air. The mixture was filtered to remove insoluble solids and the solids were washed well with EtOAc. The filtrate was partitioned between EtOAc and water. The organic layer was collected, washed with saturated NH₄Cl, brine, dried over Na₂SO₄, filtered, and concentrated in vacuo. The crude was purified by chromatography (SiO₂, 0-50% EtOAc/hexanes) to give the diastereometric mixture. The diastereomers were separated using SFC (10% EtOH/ CO₂, Chiral-pak AD-H column, 50×250 mm). First eluting peak, Isomer 1: Methyl (2R,3R)-2-((1-(2-(((benzyloxy)carbonyl)amino)ethyl)cyclobutyl)methyl)-3-((tert-butoxycarbonyl)amino)butanoate. LCMS (ES, m/z): 463.4 [M+H]⁺. ¹H NMR (500 MHz, Chloroform-d) δ 7.43-7.28 (m, 5H), 5.27 (d, J=8.0 Hz, 1H), 5.10 (s, 2H), 4.86 (s, 1H), 3.83 (bs, 1H), 3.68 (s, 3H), 3.10 (bs, 2H), 2.51 (bs, 1H), 2.04-1.56 (m, 10H), 1.44 (s, 9H), 1.21 (d, 3H). Second eluting peak, Isomer 2: Methyl (2S,3R)-2-((1-(2-(((benzyloxy)carbonyl) amino)ethyl)cyclobutyl)methyl)-3-((tert-butoxycarbonyl) amino)butanoate. LCMS (ES, m/z): 463.4 [M+H]⁺. ¹H NMR (500 MHz, Chloroform-d) δ 7.45-7.30 (m, 5H), 5.11 (s, 2H), 4.80 (d, J=31.3 Hz, 2H), 3.82 (s, 1H), 3.67 (s, 3H), 3.29-2.94 (m, 2H), 2.49 (s, 1H), 2.11-1.92 (m, 1H), 1.92-1.53 (m, 9H), 1.45 (s, 9H), 1.12 (d, J=6.4 Hz, 3H).

Step B: Tert-butyl ((2R,3S)-4-(1-(2-(((benzyloxy)carbonyl)amino)ethyl)cyclobutyl)-3-(hydroxymethyl)butan-2-yl) carbamate. To a solution of methyl (2R,3R)-2-((1-(2-(((benzyloxy)carbonyl)amino)ethyl)cyclobutyl)methyl)-3-((tert-butoxycarbonyl)amino)butanoate (1.1972 g, 2.59 mmol) in anhydrous THF (21.2 ml) at 0° C. was added LAH (1.0 M in THF) (7 ml, 7.00 mmol). The resulting mixture was stirred at 0° C. for 1.5 h. The reaction was diluted with ether and cooled to 0° C. Water (0.3 mL) was slowly added to the reaction, followed by 15% aqueous NaOH (0.3 mL), and water (0.9 mL). The reaction was warmed to ambient temperature and stirred for 15 min. before adding solid Na₂SO₄. The mixture was stirred for another 15 min. and the mixture was filtered to remove the insoluble salts. The filtrate was concentrated in vacuo to give the crude title compound, which was used without further purification. LCMS (ES, m/z): 435.4 [M+H]⁺.

Step C: Tert-butyl ((2R,3S)-4-(1-(2-(((benzyloxy)carbonyl)amino)ethyl)cyclobutyl)-3-((1,3-dioxoisoindolin-2-yl) methyl)butan-2-yl)carbamate. To a solution of tert-butyl ((2R,3R)-4-(1-(2-(((benzyloxy)carbonyl)amino)ethyl)cyclobutyl)-3-(hydroxymethyl)butan-2-yl)carbamate (1.126 g, 2.59 mmol) in anhydrous THF (23 ml) was added phthalimide (0.572 g, 3.89 mmol), Ph₃P (1.019 g, 3.89 mmol) and DIAD (0.755 ml, 3.89 mmol) at 0° C. After addition, the reaction was warmed to ambient temperature. After stirring for 35 min., the reaction was quenched with water/brine and the mixture was extracted with EtOAc. The organic layer was dried over Na₂SO₄, filtered, and concentrated in vacuo. The residue was purified by chromatography (SiO₂, 0-50% EtOAc/hexanes) to give the title compound. LCMS (ES, m/z): 564.4 [M+H]⁺.

Step D: Tert-butyl ((2R,3S)-4-amino-3-((1-(2-(((benzyloxy)carbonyl)amino)ethyl)cyclobutyl)methyl)butan-2-yl) carbamate. To solution of tert-butyl ((2R,3S)-4-(1-(2-(((benzyloxy)carbonyl)amino)ethyl)cyclobutyl)-3-((1,3-dioxoisoindolin-2-yl)methyl)butan-2-yl)carbamate (1.2601 g, 2.235 mmol) in anhydrous ethanol (20 ml) was added hydrazine (0.702 ml, 22.35 mmol). The mixture was heated to 60° C. After 15 min., the reaction became a very thick white slurry. After 2 h, the reaction was cooled to ambient temperature after 3 h, and filtered to remove the insoluble white solids. The solids were washed well with EtOH. The filtrate was concentrated in vacuo and the resulting white residue was resuspended in AcCN. The insoluble solids were removed by vacuum filtration. The filtrate was concentrated in vacuo to give the crude title compound, which was used without further purification. LCMS (ES, m/z): 434.4 [M+H]$^+$.

Step E: Tert-butyl ((2R,3S)-4-(1-(2-(((benzyloxy)carbonyl)amino)ethyl)cyclobutyl)-3-(((4-(N-(2,4-dimethoxybenzyl)-N-(1,2,4-thiadiazol-5-yl)sulfamoyl)-2,5-difluorophenyl)amino)methyl)butan-2-yl)carbamate. To a vial containing INTERMEDIATE 30 (0.996 g, 2.235 mmol) and tert-butyl ((2R,3S)-4-amino-3-((1-(2-(((benzyloxy)carbonyl)amino)ethyl)cyclobutyl)methyl)butan-2-yl)carbamate (0.969 g, 2.235 mmol) was added anhydrous DMF (20 ml), followed by DIPEA (1.171 ml, 6.71 mmol). The reaction mixture was then capped and stirred at ambient temperature for 20 h. The reaction was partitioned between EtOAc and saturated NaHCO$_3$. The organic layer was washed with water and brine. The aqueous layers were combined and back-extracted with EtOAc. The organic layers were combined, dried over Na$_2$SO$_4$, filtered, and concentrated in vacuo. The residue was purified by chromatography (SiO$_2$, 0-30% EtOAc/hexanes) to give the title compound. LCMS (ES, m/z): 859.5 [M+H]$^+$.

Step F: Tert-butyl ((2R,3S)-4-(1-(2-aminoethyl)cyclobutyl)-3-(((4-(N-(2,4-dimethoxybenzyl)-N-(1,2,4-thiadiazol-5-yl)sulfamoyl)-2,5-difluorophenyl)amino)methyl)butan-2-yl)carbamate. To a degassed mixture of tert-butyl ((2R,3S)-4-(1-(2-(((benzyloxy)carbonyl)amino)ethyl)cyclobutyl)-3-(((4-(N-(2,4-dimethoxybenzyl)-N-(1,2,4-thiadiazol-5-yl)sulfamoyl)-2,5-difluorophenyl)amino)methyl)butan-2-yl)carbamate (0.2165 g, 0.252 mmol), 10% Pd—C (30 mg, 0.282 mmol) and 20% Pd(OH)$_2$—C (30 mg, 0.214 mmol) was added anhydrous MeOH (2.5 ml) under N$_2$ followed by 3N HCl in MeOH (0.042 ml, 0.126 mmol). The reaction was degassed 3× and hydrogenated under H$_2$ balloon. After 30 min., an additional 50 uL of 3 N HCl in MeOH was added to the reaction followed by another 50 uL of 3 N HCl in MeOH after 1.5 h to drive the reaction to completion. After 2 h, another 20 mg of 10% Pd/C and 20 mg of 20% Pd(OH)$_2$ were added to the reaction. After a total of 3 h, the reaction was filtered through a 0.45 micron filter to remove catalyst and washed well with MeOH. To the filtrate was added DIPEA (0.132 ml, 0.756 mmol), and the resulting solution was concentrated in vacuo. The residue was purified by reverse-phase chromatography (C18, 0-100% AcCN/water) to afford the title compound. LCMS (ES, m/z): 725.5 [M+H]$^+$.

Step G: Tert-butyl ((2R,3S)-4-((4-(N-(2,4-dimethoxybenzyl)-N-(1,2,4-thiadiazol-5-yl)sulfamoyl)-2,5-difluorophenyl)amino)-3-((1-(2-(dimethylamino)ethyl)cyclobutyl)methyl)butan-2-yl)carbamate. To a solution of tert-butyl ((2R,3S)-4-(1-(2-aminoethyl)cyclobutyl)-3-(((4-(N-(2,4-dimethoxybenzyl)-N-(1,2,4-thiadiazol-5-yl)sulfamoyl)-2,5-difluorophenyl)amino)methyl)butan-2-yl)carbamate (47.9 mg, 0.066 mmol) in anhydrous methanol (661 µl) was added formaldehyde (52.0 µl, 0.661 mmol) followed by sodium cyanoborohydride (20.76 mg, 0.330 mmol). The mixture was stirred for approx. 1.5 h at which point the reaction was partitioned between EtOAc and saturated NaHCO$_3$. The organic layer was collected, washed with brine, dried over Na$_2$SO$_4$, filtered, and concentrated in vacuo to afford the title compound, which was used without further purification. LCMS (ES, m/z): 753.5 [M+H]$^+$.

Step H: 4-(((2S,3R)-3-amino-2-((1-(2-(dimethylamino)ethyl)cyclobutyl)methyl)butyl)amino)-2,5-difluoro-N-(1,2,4-thiadiazol-5-yl)benzenesulfonamide. To a solution of tert-butyl ((2R,3S)-4-((4-(N-(2,4-dimethoxybenzyl)-N-(1,2,4-thiadiazol-5-yl)sulfamoyl)-2,5-difluorophenyl)amino)-3-((1-(2-(dimethylamino)ethyl)cyclobutyl)methyl)butan-2-yl)carbamate (49.7 mg, 0.066 mmol) in anhydrous CH$_2$Cl$_2$ (1 mL) was added 4.0 M HCl in dixone (0.083 mL, 0.330 mmol) dropwise at ambient temperature. The mixture was stirred at ambient temperature for 15 min. DIPEA (0.115 mL, 0.660 mmol) was added to the reaction before concentrating in vacuo. The residue was dissolved in 2:1:1 AcCN/DMSO/water and purified by HPLC (Sunfire column C18 OBD, 30×150 mm, 10 uM; flow rate=30 mL/min.; 5%-90% AcCN+0.05% TFA/water+0.05% TFA over 10 min.; collect at 220 nM, monitor at 254 nM) to afford the title compound. LCMS (ES, m/z): 503.3 [M+H]$^+$. $^1$H NMR (500 MHz, Methanol-d$_4$) δ 8.21 (s, 1H), 7.44 (dd, J=10.8, 6.1 Hz, 1H), 6.56 (dd, J=11.9, 6.6 Hz, 1H), 3.63-3.47 (m, 1H), 3.36-3.28 (m, 3H), 3.27-3.02 (m, 4H), 2.91 (s, 6H), 2.22 (bs, 1H), 2.08-1.83 (m, 9H), 1.56 (m, 1H), 1.32 (d, J=6.7 Hz, 3H).

The following compounds were prepared according to the general procedure provided in the examples and procedures herein using known or prepared starting materials, as described in the reaction schemes and examples herein. The requisite starting materials are either prepared as described in the intermediates section, commercially available, or may be prepared from commercially available reagents using conventional reactions well known in the art without undue experimentation.

TABLE 2

| EXAMPLE | Structure | Isomer | LCMS (ES, m/z): [M + H]$^+$ |
|---|---|---|---|
| 44 | 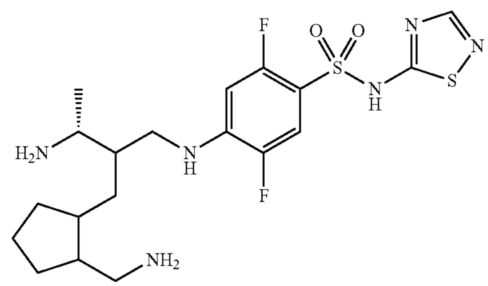 [SMILES: C[C@@H](N)C(CNc1cc(F)c(S(=O)(=O)Nc2ncns2)cc1F)CC1CCCC1CN] | 1 | 475.2 |

TABLE 2-continued
| EXAMPLE | Structure | Isomer | LCMS (ES, m/z): [M + H]+ |
|---|---|---|---|
| 45 | 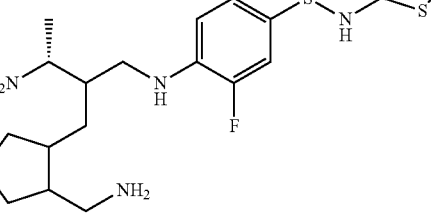 | 2 | 475.2 |
| 46 | 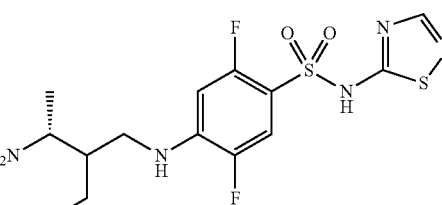 | 3 | 475.2 |
| 47 | 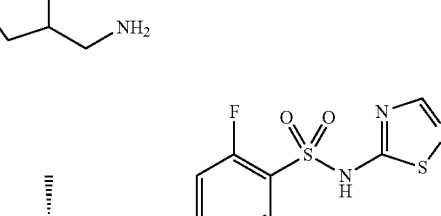 | 4 | 475.2 |
| 48 | 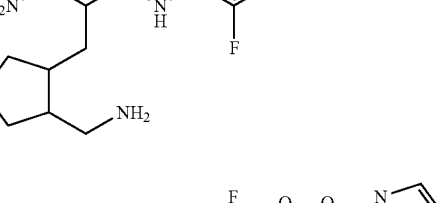 | 1 | 474.9 |
| 49 | 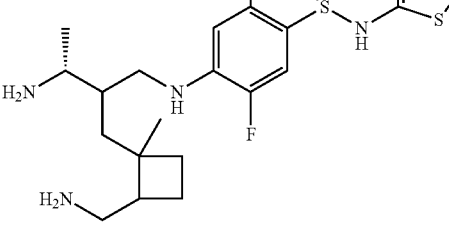 | 2 | 475.0 |

TABLE 2-continued

| EXAMPLE | Structure | Isomer | LCMS (ES, m/z): [M + H]+ |
|---|---|---|---|
| 50 | 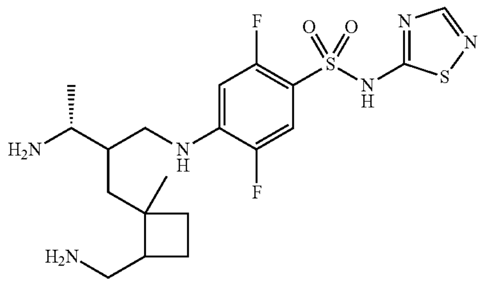 [SMILES: C[C@@H](N)C(CNc1cc(F)c(S(=O)(=O)Nc2ncns2)cc1F)CC1(C)CCC1CN] | 3 | 475.0 |
| 51 | 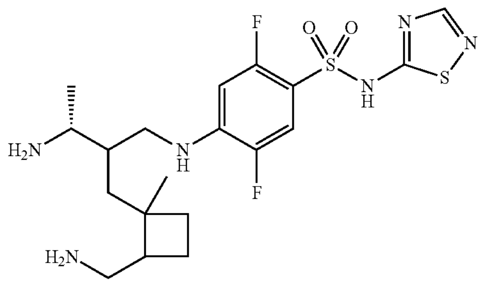 [SMILES: C[C@@H](N)C(CNc1cc(F)c(S(=O)(=O)Nc2ncns2)cc1F)CC1(C)CCC1CN] | 4 | 475.0 |
| 52 | 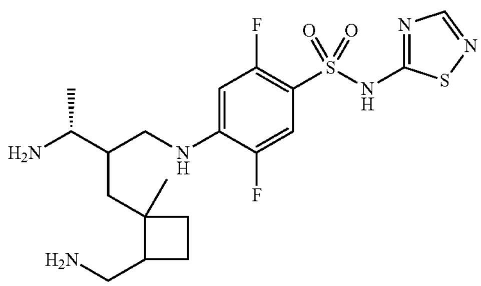 [SMILES: C[C@@H](N)C(CNc1cc(F)c(S(=O)(=O)Nc2ncns2)cc1F)CC1(C)CCC1CN] | 5 | 475.0 |
| 53 | 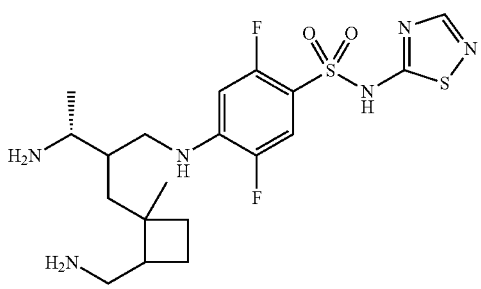 [SMILES: C[C@@H](N)C(CNc1cc(F)c(S(=O)(=O)Nc2ncns2)cc1F)CC1(C)CCC1CN] | 6 | 475.0 |
| 54 | 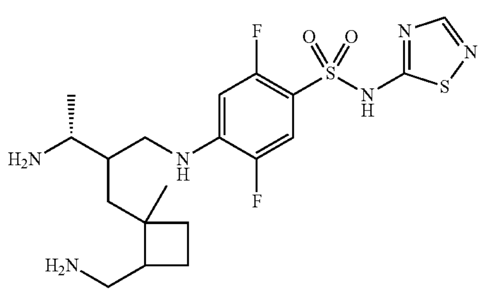 [SMILES: C[C@@H](N)C(CNc1cc(F)c(S(=O)(=O)Nc2ncns2)cc1F)CC1(C)CCC1CN] | 7 | 475.0 |

TABLE 2-continued

| EXAMPLE | Structure | Isomer | LCMS (ES, m/z): [M + H]+ |
|---|---|---|---|
| 55 | 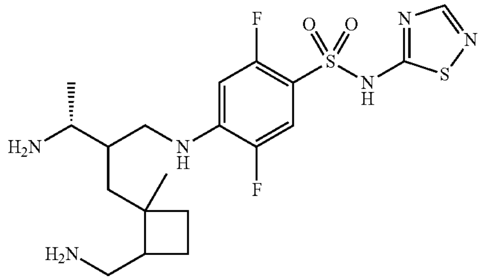 [SMILES: C[C@@H](N)C(CNc1cc(F)c(S(=O)(=O)Nc2ncns2)cc1F)CC1(C)CCC1CN] | 8 | 475.0 |
| 56 | 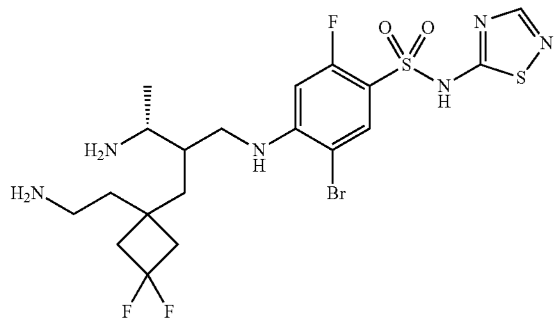 [SMILES: C[C@@H](N)C(CNc1cc(F)c(S(=O)(=O)Nc2ncns2)cc1Br)CC1(CCN)CC(F)(F)C1] | 1 | 573.2 |
| 57 | 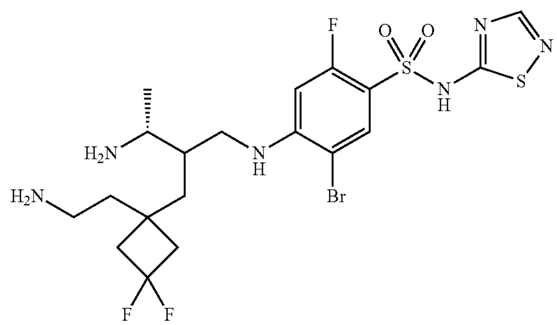 [SMILES: C[C@@H](N)C(CNc1cc(F)c(S(=O)(=O)Nc2ncns2)cc1Br)CC1(CCN)CC(F)(F)C1] | 2 | 573.2 |
| 58 | 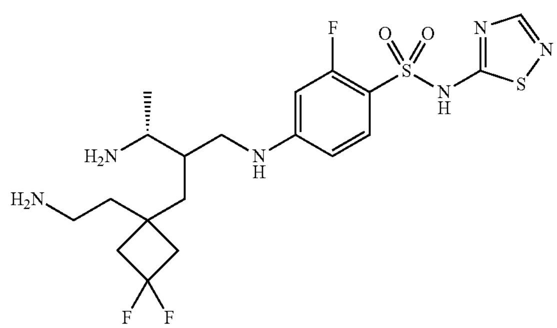 [SMILES: C[C@@H](N)C(CNc1ccc(S(=O)(=O)Nc2ncns2)c(F)c1)CC1(CCN)CC(F)(F)C1] | 1 | 493.3 |
| 59 | 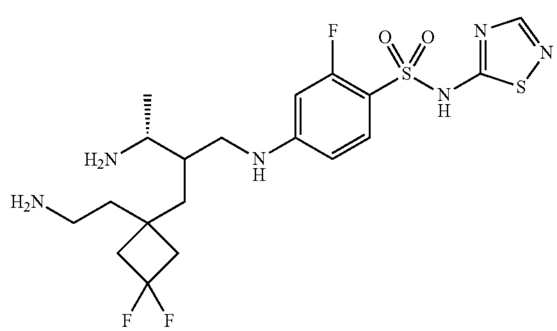 [SMILES: C[C@@H](N)C(CNc1ccc(S(=O)(=O)Nc2ncns2)c(F)c1)CC1(CCN)CC(F)(F)C1] | 2 | 493.3 |

TABLE 2-continued

| EXAMPLE | Structure | Isomer | LCMS (ES, m/z): [M + H]+ |
|---------|-----------|--------|--------------------------|
| 60 | 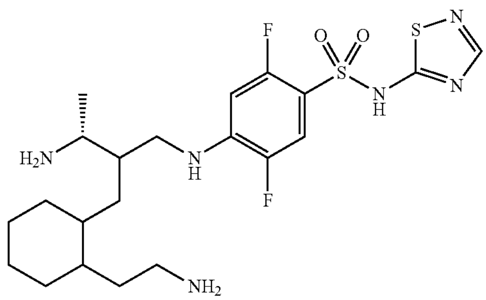 [SMILES: C[C@@H](N)C(CNc1cc(F)c(S(=O)(=O)Nc2ncns2)cc1F)CC1CCCCC1CCN] | 1 | 503.0 |
| 61 | 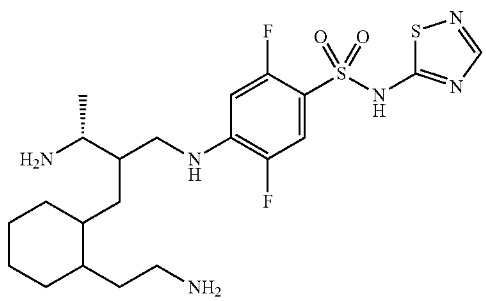 [SMILES: C[C@@H](N)C(CNc1cc(F)c(S(=O)(=O)Nc2ncns2)cc1F)CC1CCCCC1CCN] | 2 | 503.0 |
| 62 | 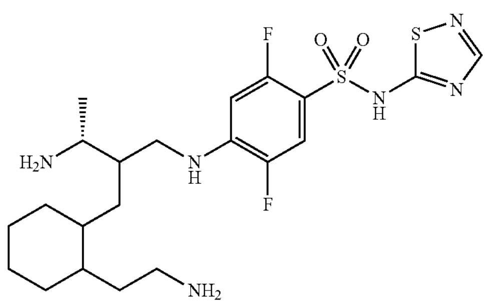 [SMILES: C[C@@H](N)C(CNc1cc(F)c(S(=O)(=O)Nc2ncns2)cc1F)CC1CCCCC1CCN] | 3 | 503.0 |
| 63 | 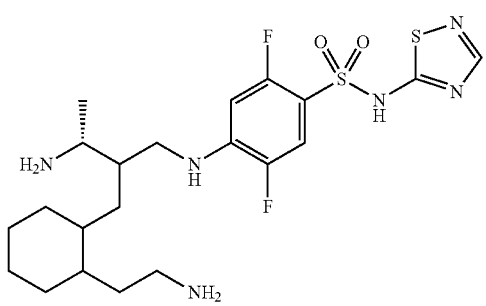 | 4 | 503.0 |
| 64 | 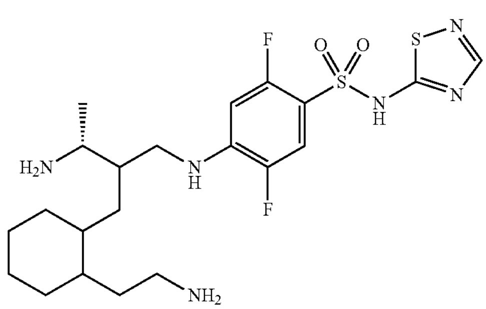 | 5 | 503.0 |

TABLE 2-continued

| EXAMPLE | Structure | Isomer | LCMS (ES, m/z): [M + H]+ |
|---------|-----------|--------|--------------------------|
| 65 | 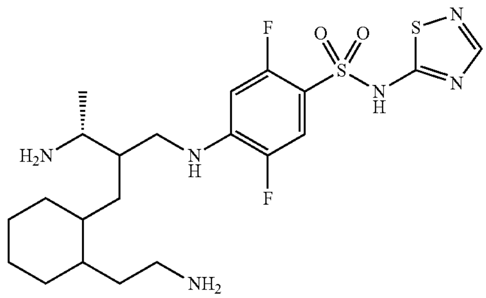 [SMILES: C[C@@H](N)C(CNc1cc(F)c(S(=O)(=O)Nc2ncns2)cc1F)CC1CCCCC1CCN] | 6 | 503.0 |
| 66 | 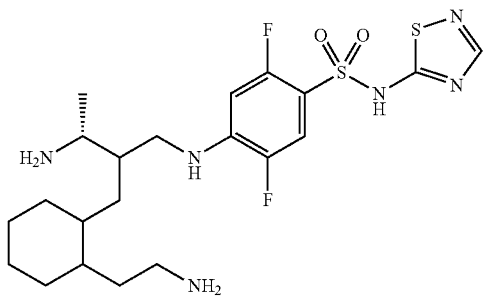 [SMILES: C[C@@H](N)C(CNc1cc(F)c(S(=O)(=O)Nc2ncns2)cc1F)CC1CCCCC1CCN] | 7 | 503.0 |
| 67 | 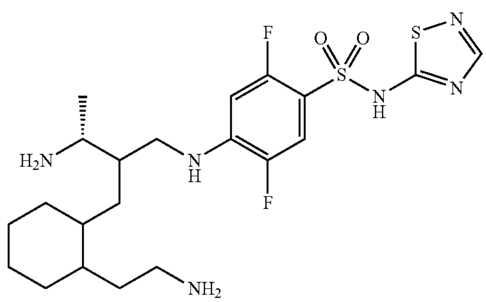 [SMILES: C[C@@H](N)C(CNc1cc(F)c(S(=O)(=O)Nc2ncns2)cc1F)CC1CCCCC1CCN] | 8 | 503.0 |
| 68 | 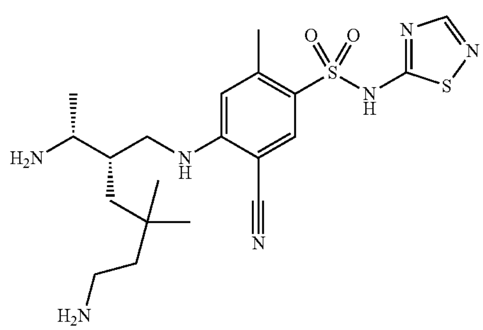 [SMILES: Cc1cc(NC[C@H](CC(C)(C)CCN)[C@@H](C)N)c(C#N)cc1S(=O)(=O)Nc1ncns1] | | 466.0 |
| 69 | 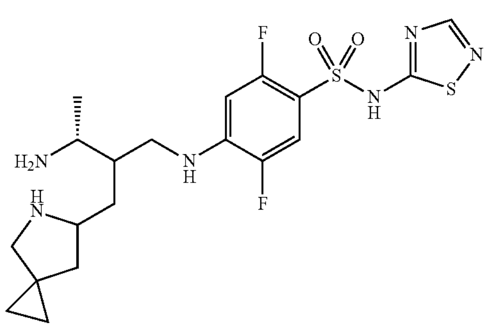 [SMILES: C[C@@H](N)C(CNc1cc(F)c(S(=O)(=O)Nc2ncns2)cc1F)CC1CC2(CC2)CN1] | 1 | 473.3 |

TABLE 2-continued

| EXAMPLE | Structure | Isomer | LCMS (ES, m/z): [M + H]+ |
|---|---|---|---|
| 70 | 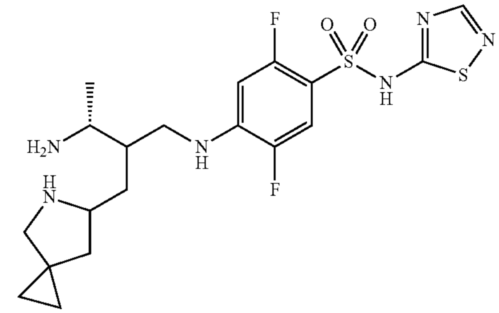 [SMILES: C[C@@H](N)C(CNc1cc(F)c(S(=O)(=O)Nc2ncns2)cc1F)CC1CC2(CC2)CN1] | 2 | 473.3 |
| 71 | 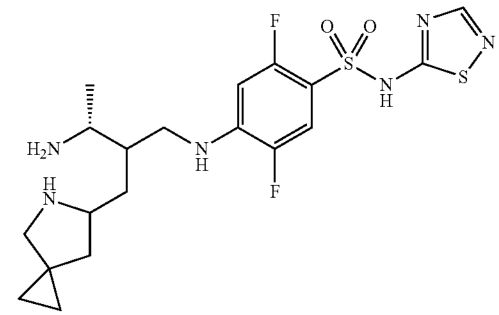 [SMILES: C[C@@H](N)C(CNc1cc(F)c(S(=O)(=O)Nc2ncns2)cc1F)CC1CC2(CC2)CN1] | 3 | 473.3 |
| 72 | 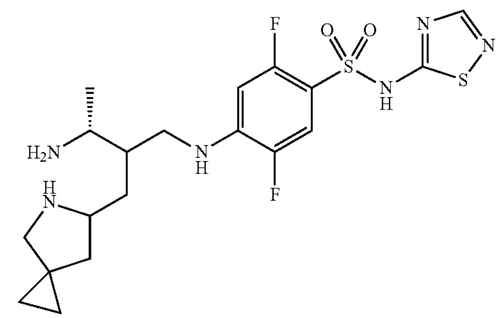 [SMILES: C[C@@H](N)C(CNc1cc(F)c(S(=O)(=O)Nc2ncns2)cc1F)CC1CC2(CC2)CN1] | 4 | 473.3 |
| 73 | 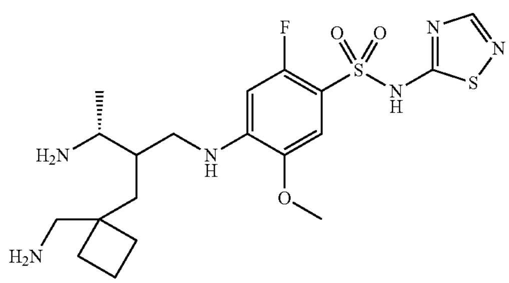 [SMILES: COc1cc(S(=O)(=O)Nc2ncns2)c(F)cc1NCC(CC1(CN)CCC1)[C@@H](C)N] | | 473.3 |
| 74 | 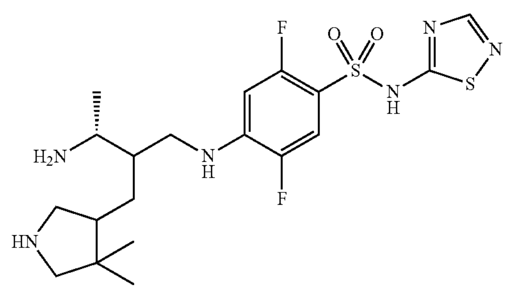 [SMILES: C[C@@H](N)C(CNc1cc(F)c(S(=O)(=O)Nc2ncns2)cc1F)CC1CNCC1(C)C] | 1 | 475.4 |

TABLE 2-continued

| EXAMPLE | Structure | Isomer | LCMS (ES, m/z): [M + H]+ |
|---|---|---|---|
| 75 | 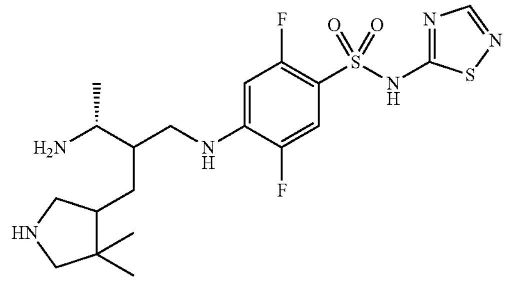 [SMILES: C[C@@H](N)C(CNc1cc(F)c(S(=O)(=O)Nc2ncns2)cc1F)CC1CNCC1(C)C] | 2 | 475.4 |
| 76 | 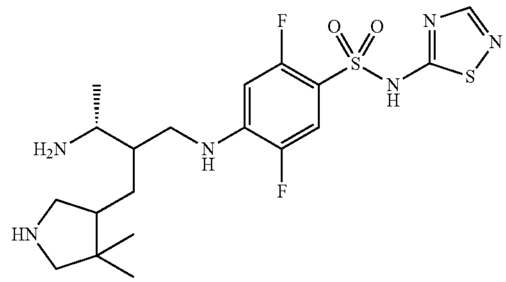 [SMILES: C[C@@H](N)C(CNc1cc(F)c(S(=O)(=O)Nc2ncns2)cc1F)CC1CNCC1(C)C] | 3 | 475.4 |
| 77 | 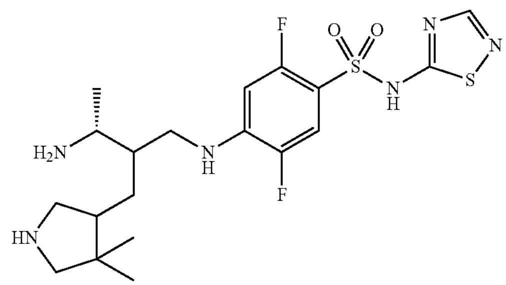 [SMILES: C[C@@H](N)C(CNc1cc(F)c(S(=O)(=O)Nc2ncns2)cc1F)CC1CNCC1(C)C] | 4 | 475.4 |
| 78 | 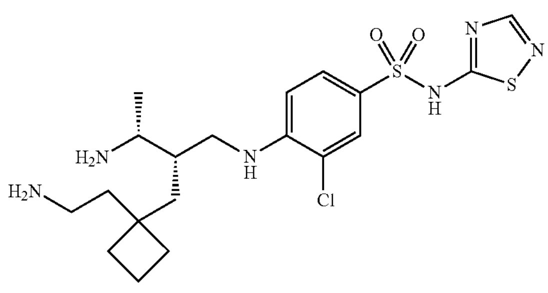 [SMILES: C[C@@H](N)[C@H](CNc1ccc(S(=O)(=O)Nc2ncns2)cc1Cl)CC1(CCN)CCC1] | | 474.0 |
| 79 | 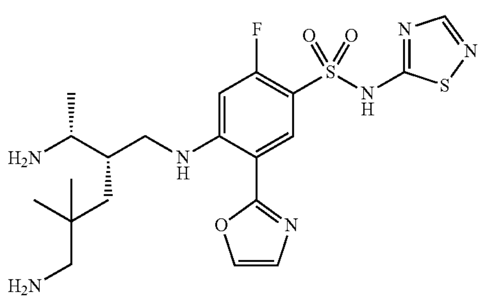 [SMILES: C[C@@H](N)[C@H](CNc1cc(F)c(S(=O)(=O)Nc2ncns2)cc1-c1ncco1)CC(C)(C)CN] | | 512.0 |

TABLE 2-continued

| EXAMPLE | Structure | Isomer | LCMS (ES, m/z): [M + H]+ |
|---|---|---|---|
| 80 | 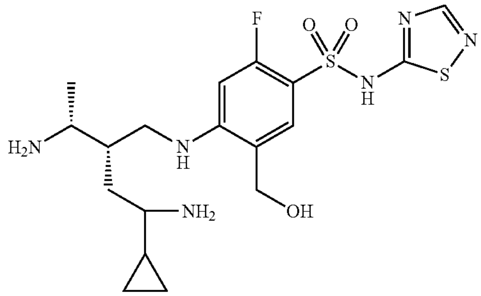 [SMILES: C[C@@H](N)[C@H](CNc1cc(F)c(S(=O)(=O)Nc2ncns2)cc1CO)CC(N)C1CC1] | | 459.2 |
| 81 | 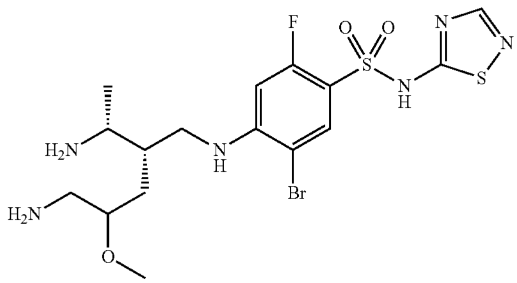 [SMILES: COC(CN)C[C@@H](CNc1cc(F)c(S(=O)(=O)Nc2ncns2)cc1Br)[C@@H](C)N] | 1 | 513.1 |
| 82 | 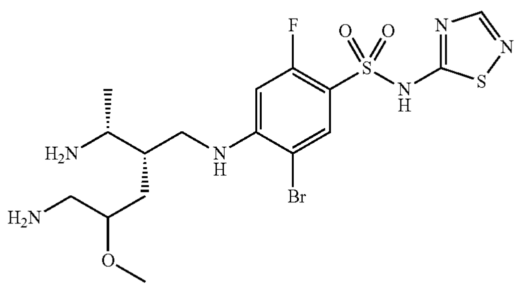 [SMILES: COC(CN)C[C@@H](CNc1cc(F)c(S(=O)(=O)Nc2ncns2)cc1Br)[C@@H](C)N] | 2 | 513.0 |
| 83 | 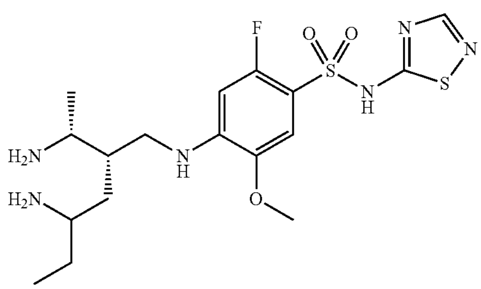 [SMILES: CCC(N)C[C@@H](CNc1cc(F)c(S(=O)(=O)Nc2ncns2)cc1OC)[C@@H](C)N] | | 447.0 |
| 84 | 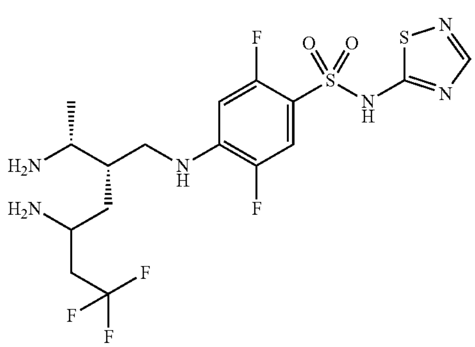 [SMILES: C[C@@H](N)[C@H](CNc1cc(F)c(S(=O)(=O)Nc2ncns2)cc1F)CC(N)CC(F)(F)F] | 1 | 489.2 |

TABLE 2-continued

| EXAMPLE | Structure | Isomer | LCMS (ES, m/z): [M + H]+ |
|---|---|---|---|
| 85 | 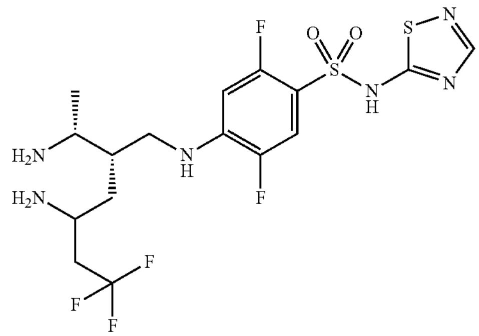 [SMILES: C[C@@H](N)[C@H](CNc1cc(F)c(S(=O)(=O)Nc2ncns2)cc1F)CC(N)CC(F)(F)F] | 2 | 489.2 |
| 86 | 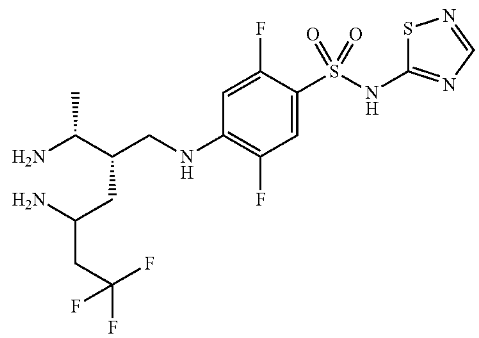 [SMILES: C[C@@H](N)[C@H](CNc1cc(F)c(S(=O)(=O)Nc2ncns2)cc1F)CC(N)CC(F)(F)F] | 3 | 489.2 |
| 87 | 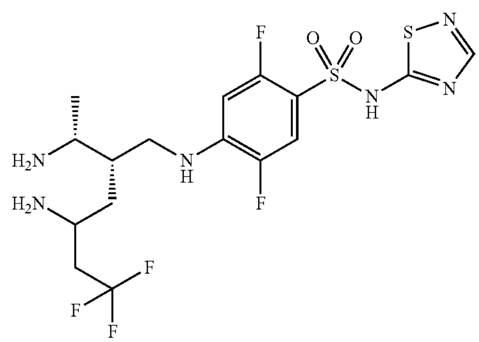 [SMILES: C[C@@H](N)[C@H](CNc1cc(F)c(S(=O)(=O)Nc2ncns2)cc1F)CC(N)CC(F)(F)F] | 4 | 489.2 |
| 88 | 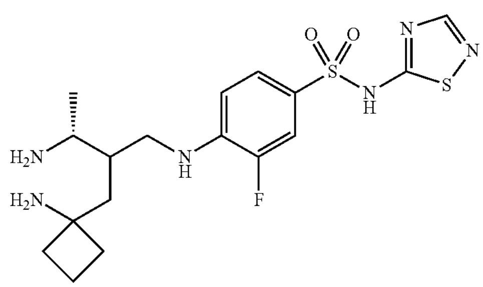 [SMILES: C[C@@H](N)C(CNc1ccc(S(=O)(=O)Nc2ncns2)cc1F)CC1(N)CCC1] | 1 | 429.1 |
| 89 | 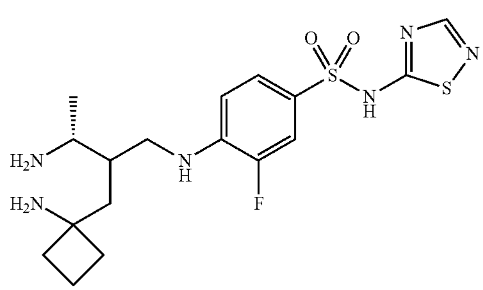 [SMILES: C[C@@H](N)C(CNc1ccc(S(=O)(=O)Nc2ncns2)cc1F)CC1(N)CCC1] | 2 | 429.1 |

TABLE 2-continued

| EXAMPLE | Structure | Isomer | LCMS (ES, m/z): [M + H]⁺ |
|---|---|---|---|
| 90 | 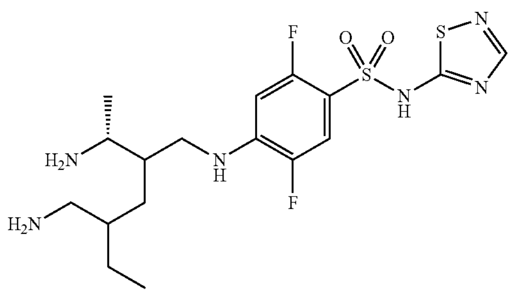 [SMILES: CCC(CN)CC(CNc1cc(F)c(S(=O)(=O)Nc2ncns2)cc1F)[C@@H](C)N] | 1 | 449.2 |
| 91 | 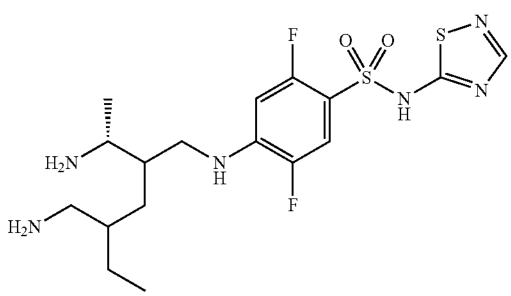 [SMILES: CCC(CN)CC(CNc1cc(F)c(S(=O)(=O)Nc2ncns2)cc1F)[C@@H](C)N] | 2 | 449.1 |
| 92 | 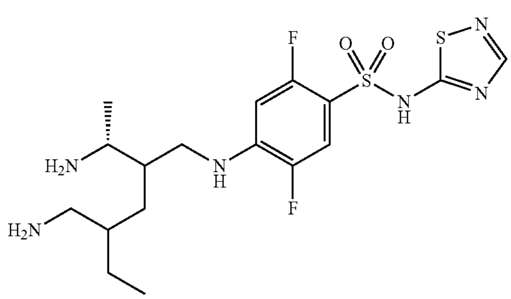 [SMILES: CCC(CN)CC(CNc1cc(F)c(S(=O)(=O)Nc2ncns2)cc1F)[C@@H](C)N] | 3 | 449.2 |
| 93 | 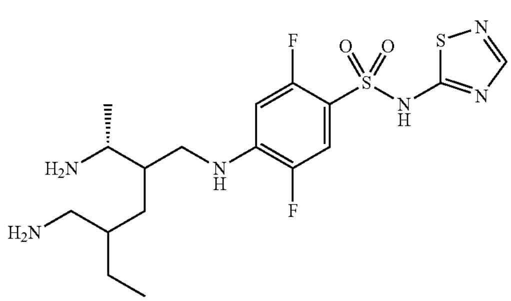 [SMILES: CCC(CN)CC(CNc1cc(F)c(S(=O)(=O)Nc2ncns2)cc1F)[C@@H](C)N] | 4 | 449.2 |
| 94 | 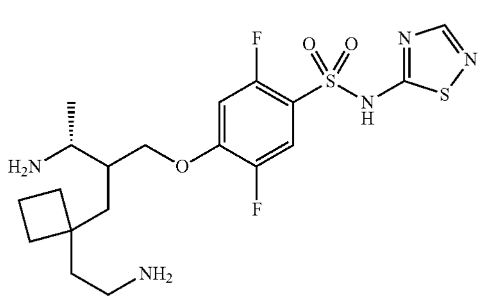 [SMILES: C[C@@H](N)C(COc1cc(F)c(S(=O)(=O)Nc2ncns2)cc1F)CC1(CCN)CCC1] | 1 | 476.2 |

TABLE 2-continued
| EXAMPLE | Structure | Isomer | LCMS (ES, m/z): [M + H]+ |
|---|---|---|---|
| 95 | 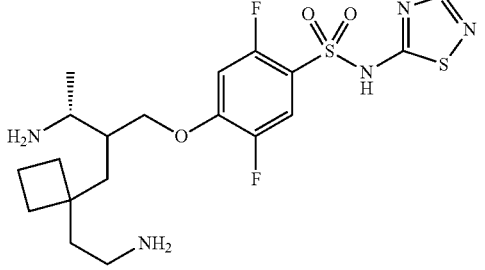 | 2 | 476.2 |
| 96 | 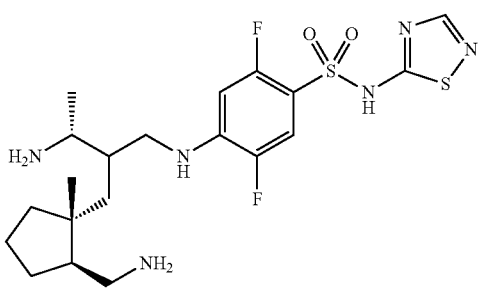 [SMILES: C[C@@H](N)C(CNc1cc(F)c(S(=O)(=O)Nc2ncns2)cc1F)C[C@@]1(C)CCC[C@@H]1CN] | 1 | 489.1 |
| 97 | 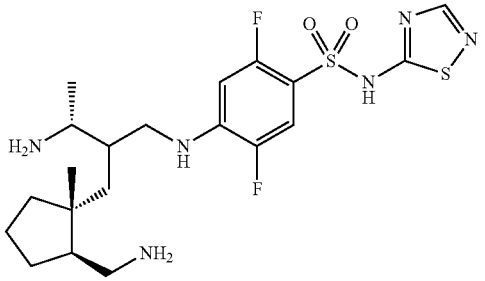 [SMILES: C[C@@H](N)C(CNc1cc(F)c(S(=O)(=O)Nc2ncns2)cc1F)C[C@@]1(C)CCC[C@@H]1CN] | 2 | 489.1 |
| 98 | 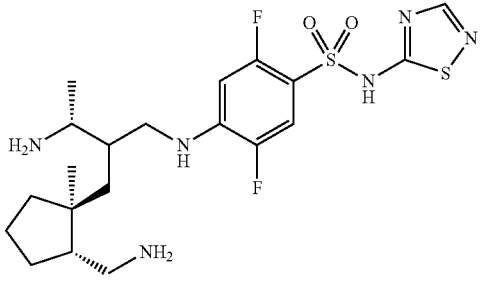 [SMILES: C[C@@H](N)C(CNc1cc(F)c(S(=O)(=O)Nc2ncns2)cc1F)C[C@]1(C)CCC[C@H]1CN] | 3 | 489.1 |
| 99 | 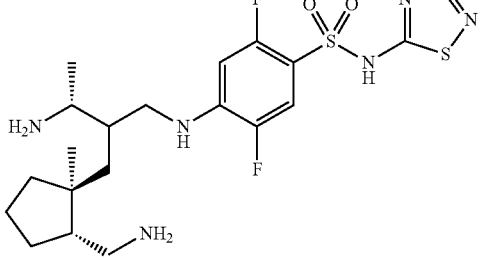 | 4 | 489.1 |

TABLE 2-continued

| EXAMPLE | Structure | Isomer | LCMS (ES, m/z): [M + H]+ |
|---|---|---|---|
| 100 | 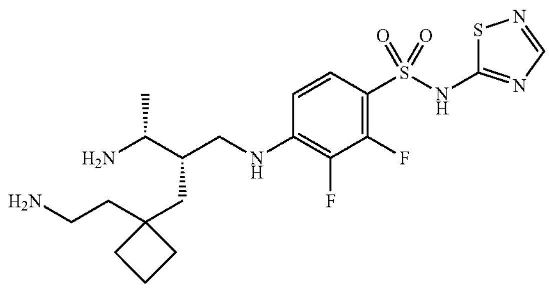 [SMILES: C[C@@H](N)[C@H](CNc1ccc(S(=O)(=O)Nc2ncns2)c(F)c1F)CC1(CCN)CCC1] | | 475.3 |
| 101 | 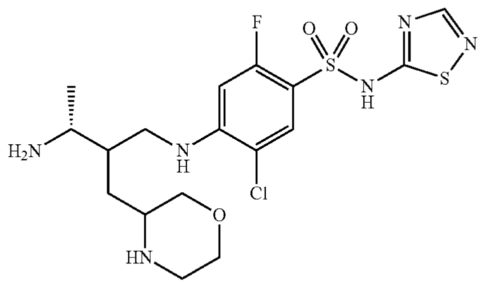 [SMILES: C[C@@H](N)C(CNc1cc(F)c(S(=O)(=O)Nc2ncns2)cc1Cl)CC1COCCN1] | 1 | 479.2 |
| 102 | 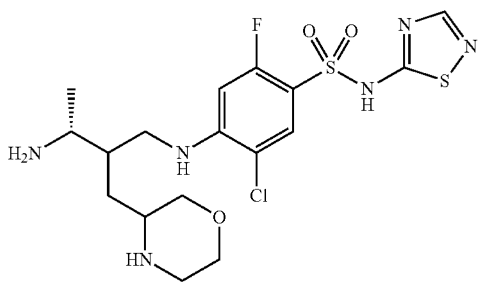 [SMILES: C[C@@H](N)C(CNc1cc(F)c(S(=O)(=O)Nc2ncns2)cc1Cl)CC1COCCN1] | 2 | 479.2 |
| 103 | 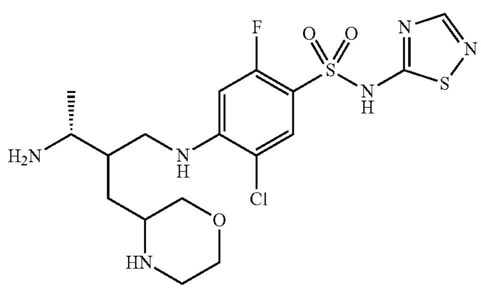 [SMILES: C[C@@H](N)C(CNc1cc(F)c(S(=O)(=O)Nc2ncns2)cc1Cl)CC1COCCN1] | 3 | 479.2 |
| 104 | 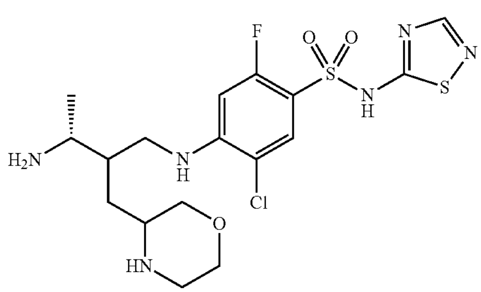 [SMILES: C[C@@H](N)C(CNc1cc(F)c(S(=O)(=O)Nc2ncns2)cc1Cl)CC1COCCN1] | 4 | 479.2 |

TABLE 2-continued

| EXAMPLE | Structure | Isomer | LCMS (ES, m/z): [M + H]+ |
|---|---|---|---|
| 105 | 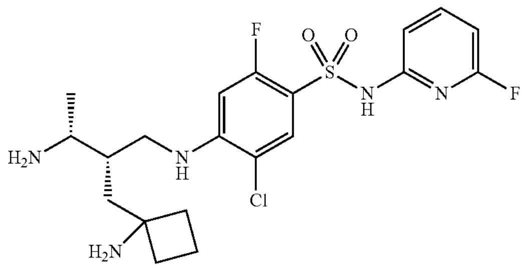 [SMILES: C[C@@H](N)[C@H](CNc1cc(F)c(S(=O)(=O)Nc2cccc(F)n2)cc1Cl)CC1(N)CCC1] | | 474.2 |
| 106 | 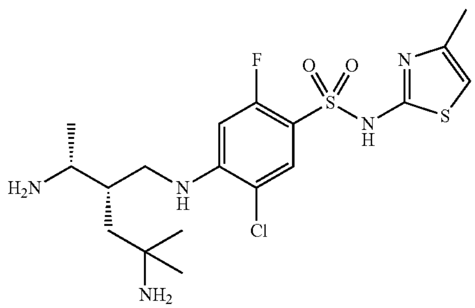 [SMILES: Cc1csc(NS(=O)(=O)c2cc(Cl)c(NC[C@H](CC(C)(C)N)[C@@H](C)N)cc2F)n1] | | 464.2 |
| 107 | 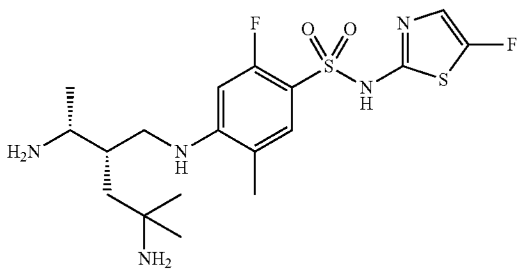 [SMILES: Cc1cc(S(=O)(=O)Nc2ncc(F)s2)c(F)cc1NC[C@H](CC(C)(C)N)[C@@H](C)N] | | 448.2 |
| 108 | 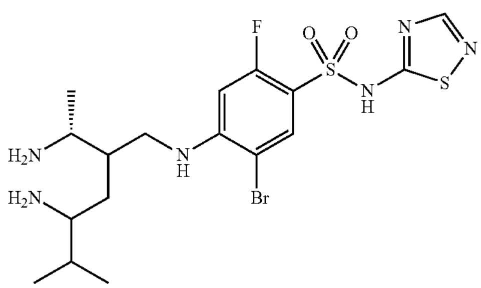 [SMILES: CC(C)C(N)CC(CNc1cc(F)c(S(=O)(=O)Nc2ncns2)cc1Br)[C@@H](C)N] | 1 | 508.9 |
| 109 | 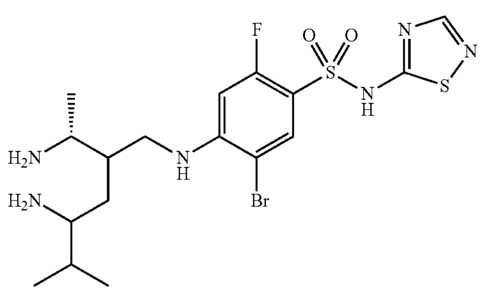 [SMILES: CC(C)C(N)CC(CNc1cc(F)c(S(=O)(=O)Nc2ncns2)cc1Br)[C@@H](C)N] | 2 | 508.9 |

TABLE 2-continued

| EXAMPLE | Structure | Isomer | LCMS (ES, m/z): [M + H]+ |
|---|---|---|---|
| 110 | 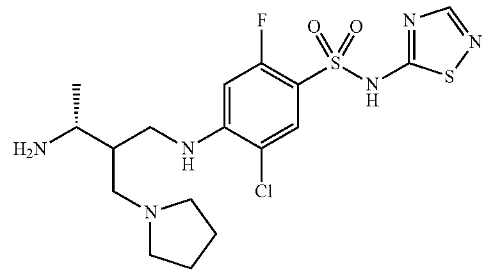 [SMILES: C[C@@H](N)C(CNc1cc(F)c(S(=O)(=O)Nc2ncns2)cc1Cl)CN1CCCC1] | | 463.2 |
| 111 | 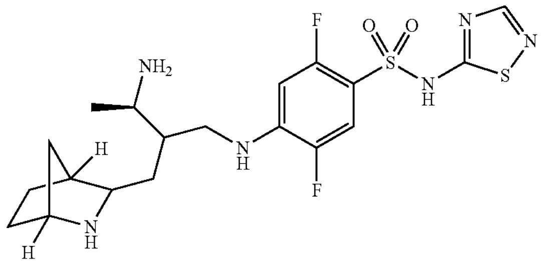 [SMILES: C[C@@H](N)C(CNc1cc(F)c(S(=O)(=O)Nc2ncns2)cc1F)CC1NC2CCC1C2] | 1 | 473.3 |
| 112 | 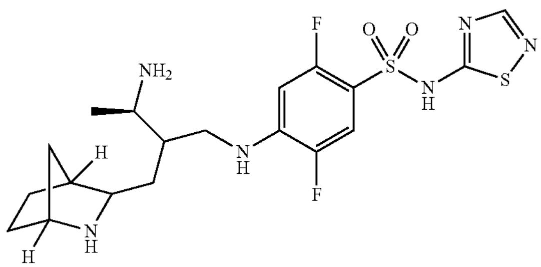 [SMILES: C[C@@H](N)C(CNc1cc(F)c(S(=O)(=O)Nc2ncns2)cc1F)CC1NC2CCC1C2] | 2 | 473.3 |

Qube™ Experimental Procedure:

Compounds were tested on human Nav1.7 and Nav1.6 channels stably expressed in HEK 293 cells. Sodium current measurements on the Qube: An automated patch-clamp assay on the Qube platform (Sophion Bioscience) was used to measure inhibition of human Nav1.7 and 1.6 channels. Cells were sealed on a planar substrate using the multihole technology. Cells expressing human Nav1.7 channels were held at −75 mV or −80 mV. Cells expressing human Nav1.6 channels were held at −65 mV. A train of 6 consecutive test pulses to −10 mV, preceded by 8 s prepulses to −115 mV, was applied at a frequency of 0.1 Hz before and after compound addition. Cells in each Qchip well were incubated in compound for 5 minutes before measuring inhibition. Peak currents were measured in control conditions and after compound addition. The following recording solutions were used (mM). External Nav1.6: 150 NaCl, 2 $CaCl_2$, 5 KCl, 1 Mg $Cl_2$, 10 HEPES, 12 Dextrose; external Nav1.7: 40 NaCl, 120 NMDG, 1 KCl, 0.5 $MgCl_2$, 5 HEPES, 2.7 $CaCl_2$); internal: 120 CsF, 30 CsCl, 10 EGTA, 5 HEPES, 5 NaF, 2 $MgCl_2$. Compounds were prepared as 10 mM stock solutions in DMSO. 10 point compound titrations were generated using the Echo acoustic liquid handling instrument and glass coated 384 well plates. The final DMSO concentration in the assay was 0.3%. For all electrophysiology experiments, offline analysis was used to determine percent inhibition as a function of drug concentration. $IC_{50}$ values were determined by fitting to the Hill equation.

The various compounds in EXAMPLES 1 through 43 and TABLE 2 exemplified above were assayed for activity and selectivity using the foregoing Qube® technique. The results are reported in TABLE 3 in a format expressing the identification of the compound with reference EXAMPLE followed by the observed potency in nM for NaV1.7, NaV1.6 and NaV1.5. NA signifies not applicable and the max concentration tested is 33750 nM. The following results are reported:

TABLE 3

Qube ® Data

| EXAMPLE # | NaV1.7 (nM); −75 mV | NaV1.7 (nM); −80 mV | NaV1.6 (nM); −65 mV | Nav1.5 (nM); −80 mV |
|---|---|---|---|---|
| 1 | 203 | NA | 20410 | NA |
| 2 | 84 | NA | 13750 | >33750 |
| 3 | 41 | NA | >33750 | >33750 |
| 4 | NA | NA | NA | NA |
| 5 | 118 | NA | 20710 | >33750 |
| 6 | 93 | NA | >33750 | NA |
| 7 | NA | NA | NA | NA |
| 8 | 18 | NA | >33750 | NA |
| 9 | NA | NA | NA | NA |
| 10 | 8 | NA | >33750 | >33750 |
| 11 | NA | NA | NA | NA |
| 12 | 133 | NA | >33750 | >33750 |
| 13 | 230 | NA | >33750 | NA |
| 14 | NA | >33750 | NA | NA |

TABLE 3-continued

Qube® Data

| EXAMPLE # | NaV1.7 (nM); −75 mV | NaV1.7 (nM); −80 mV | NaV1.6 (nM); −65 mV | Nav1.5 (nM); −80 mV |
|---|---|---|---|---|
| 15 | NA | NA | NA | NA |
| 16 | NA | NA | NA | NA |
| 17 | NA | 113 | >33750 | >33750 |
| 18 | NA | 149 | >33750 | >33750 |
| 19 | 31 | NA | >33750 | >33750 |
| 20 | NA | 1395 | NA | NA |
| 21 | NA | 916 | NA | NA |
| 22 | NA | 26 | 12110 | >33750 |
| 23 | NA | NA | NA | NA |
| 24 | NA | >33750 | NA | NA |
| 25 | NA | 83 | >33750 | >33750 |
| 26 | NA | NA | NA | NA |
| 27 | 41 | NA | >33750 | >33750 |
| 28 | 34 | NA | >33750 | >33750 |
| 29 | 95 | NA | >33750 | >33750 |
| 30 | 77 | NA | >33750 | >33750 |
| 31 | 205 | NA | >33750 | NA |
| 32 | 19 | NA | >33750 | 20670 |
| 33 | 156 | NA | >33750 | NA |
| 34 | 77 | NA | >33750 | >33750 |
| 35 | NA | NA | NA | NA |
| 36 | 82 | NA | >33750 | >33750 |
| 37 | 6755 | NA | >33750 | NA |
| 38 | 109 | NA | >33750 | >33750 |
| 39 | NA | 210 | >33750 | >33750 |
| 40 | NA | 17 | 11560 | >33750 |
| 41 | NA | 13670 | NA | NA |
| 42 | NA | 306 | >33750 | >33750 |
| 43 | NA | 61 | >33750 | >33750 |
| 44 | NA | NA | NA | NA |
| 45 | NA | NA | NA | NA |
| 46 | NA | 57 | >33750 | >33750 |
| 47 | NA | 3613 | >33750 | NA |
| 48 | NA | NA | NA | NA |
| 49 | NA | NA | NA | NA |
| 50 | NA | NA | NA | NA |
| 51 | NA | NA | NA | NA |
| 52 | NA | 12260 | >33750 | NA |
| 53 | NA | 165 | >33750 | >33750 |
| 54 | NA | NA | NA | NA |
| 55 | NA | 1059 | >33750 | NA |
| 56 | NA | >33750 | NA | NA |
| 57 | NA | 10 | 224 | >33750 |
| 58 | NA | NA | NA | NA |
| 59 | NA | 38 | >33750 | >33750 |
| 60 | NA | 12 | >33750 | 20600 |
| 61 | NA | 16 | >33750 | >33750 |
| 62 | NA | 56 | >33750 | >33750 |
| 63 | NA | 156 | >33750 | >33750 |
| 64 | NA | 14610 | >33750 | NA |
| 65 | NA | 271 | >33750 | >33750 |
| 66 | NA | 12550 | >33750 | NA |
| 67 | NA | >33750 | >33750 | NA |
| 68 | 37 | NA | 10080 | >33750 |
| 69 | NA | NA | NA | NA |
| 70 | NA | NA | NA | NA |
| 71 | NA | NA | NA | NA |
| 72 | NA | 229 | >33750 | >33750 |
| 73 | 23 | NA | >33750 | >33750 |
| 74 | NA | NA | NA | NA |
| 75 | NA | NA | NA | NA |
| 76 | NA | 328 | >33750 | NA |
| 77 | NA | NA | NA | NA |
| 78 | NA | 27 | 10360 | >33750 |
| 79 | NA | 37 | 16880 | >33750 |
| 80 | 71 | NA | >33750 | NA |
| 81 | NA | 87 | >33750 | NA |
| 82 | NA | 1758 | NA | NA |
| 83 | 48 | NA | >33750 | >33750 |
| 84 | NA | NA | NA | NA |
| 85 | 72 | NA | >33750 | >33750 |
| 86 | NA | NA | NA | NA |
| 87 | NA | NA | NA | NA |
| 88 | NA | NA | NA | NA |
| 89 | 274 | NA | >33750 | NA |
| 90 | NA | NA | NA | NA |
| 91 | NA | NA | NA | NA |
| 92 | NA | NA | NA | NA |
| 93 | 16 | NA | >33750 | >33750 |
| 94 | NA | NA | NA | NA |
| 95 | NA | 4127 | >33750 | NA |
| 96 | 618 | NA | >33750 | NA |
| 97 | 7 | 28 | >33750 | >33750 |
| 98 | NA | 2363 | >33750 | NA |
| 99 | NA | 450 | >33750 | NA |
| 100 | NA | 52 | >33750 | >33750 |
| 101 | 84 | NA | >33750 | NA |
| 102 | NA | NA | NA | NA |
| 103 | NA | NA | NA | NA |
| 104 | 305 | NA | >33750 | NA |
| 105 | 14 | NA | 8341 | NA |
| 106 | 133 | NA | >33750 | NA |
| 107 | 17 | NA | 3591 | NA |
| 108 | 17 | NA | >33750 | NA |
| 109 | 3 | NA | 697 | 15640 |
| 110 | 110 | NA | >33750 | >33750 |
| 111 | NA | 65 | >33750 | 13050 |
| 112 | NA | NA | NA | NA |

What is claimed is:

1. A compound, or a pharmaceutically acceptable salt thereof, having the structure of Formula I:

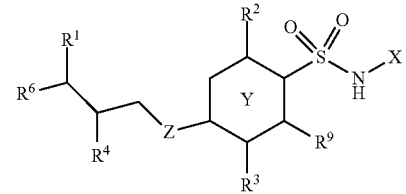

Formula I wherein:

X is selected from the group consisting of thiadiazolyl, pyridyl, thiazolyl, and pyrimidinyl, said thiadiazolyl, pyridyl, thiazolyl, and pyrimidinyl, optionally substituted with 1 to 3 groups selected from halogen and $C_{1-6}$ alkyl;

Y is phenyl;

Z is selected from NH and O;

$R^1$ is selected from $C_{1-6}$ alkyl and $(CH_2)_nC_{3-6}$ cycloalkyl;

$R^2$ and $R^3$ are independently selected from the group consisting of hydrogen, halogen, $OC_{1-6}$ alkyl, $C_{1-6}$ alkyl, $C_{3-10}$ heteroaryl, CN, $C_{1-3}$ haloalkyl, and $(CH_2)_nOH$;

$R^4$ is selected from the group consisting of $CHR^5NR_2$, $CH_2NHCH(C_{1-6}$ alkyl$)_2$, $CH_2R^5$, $CH_2N(R^5)CH_2CHRNR_2$, $CH_2CH(R^5)(CH_2)_pNR_2$, and $(CH_2)_nC(R)_2(CHR)_pNRR^7$, $R^5$ is selected from the group consisting of $C_{1-6}$ alkyl, $(CH_2)_nC_{6-10}$ aryl, $C_{3-6}$ cycloalkyl, $(CH_2)_nC_{3-10}$ heterocyclyl, and $OC_{1-6}$ alkyl, said alkyl, aryl, cycloalkyl and heterocyclyl optionally substituted with 1 to 3 groups of halogen, $CF_3$, $C_{1-6}$ alkyl, $C_{3-6}$ cycloalkyl, and $(CH_2)_pNR_2$;

R is hydrogen or $C_{1-6}$ alkyl, or two adjacent R groups can combine with the carbon atom to which they are attached to form $C_{3-6}$ cycloalkyl optionally substituted with 1 to 3 groups of halogen or $C_{1-6}$ alkyl;

$R^6$ is NHR;

$R^7$ is hydrogen or $C_{1-6}$ alkyl, $R^9$ is hydrogen or halogen;

p is 0, 1, or 2, and n is 0, 1, 2, 3, or 4.

2. The compound of claim 1, or a pharmaceutically acceptable salt thereof, wherein X is selected from the group consisting of unsubstituted or substituted thiadiazolyl, pyridyl, and thiazolyl.

3. The compound of claim 1, or a pharmaceutically acceptable salt thereof, wherein Y is phenyl and Z is O.

4. A compound of claim 1, or a pharmaceutically acceptable salt thereof, wherein $R^1$ is $C_{1-6}$ alkyl selected from methyl, ethyl, butyl, and pentyl, or $(CH_2)_n C_{3-6}$ cycloalkyl selected from cyclopropyl, cyclobutyl, cyclopentyl, and cyclohexyl.

5. A compound of claim 1 or a pharmaceutically acceptable salt thereof, wherein $R^2$ is selected from the group consisting of hydrogen, halogen, and $C_{1-6}$ alkyl.

6. A compound of claim 1, or a pharmaceutically acceptable salt thereof realized wherein $R^3$ is selected from the group consisting of hydrogen, fluorine, chlorine, bromine, $OCH_3$, $OCH_2CH_3$, methyl, ethyl, propyl, butyl, thiazolyl, oxazolyl, $CH_2OH$, OH, CN, $CF_3$, and $CHCF_2$.

7. A compound of claim 1 wherein R is $C_{1-6}$ alkyl.

8. A compound of claim 1 wherein two adjacent R groups combine with the carbon atom to which they are attached to form $C_{3-6}$ cycloalkyl, said cycloalkyl optionally substituted with 1 to 3 groups of halogen or $C_{1-6}$ alkyl.

9. A compound of claim 1 wherein $R^4$ is $CHR^5NR_2$, $CH_2NHCH(C_{1-6}$ alkyl$)_2$, $CH_2R^5$, $CH_2N(R^5)CH_2CHRNR_2$, $CH_2CH(R^5)(CH_2)_p NR_2$, or $(CH_2)_n C(R^x R^x)(CHR)_p NH_2$ where the adjacent $R^x$ groups combine with the carbon atom to which they are attached to form cyclopropyl, cyclobutyl, cyclopentyl, and cyclohexyl optionally substituted with one to three groups selected from $C_{1-6}$ alkyl and halogen and $R^5$ is optionally substituted $C_{1-6}$ alkyl, $(CH_2)_n$phenyl, cyclopropyl, cyclobutyl, cyclopentyl, cyclohexyl, pyridyl, pyrrolidinyl, piperidinyl, morpholinyl, and $OC_{1-6}$ alkyl, said groups optionally substituted with 1 to 3 groups $CF_3$, $C_{1-6}$ alkyl and $(CH_2)_p NH_2$.

10. A compound of claim 1 a pharmaceutically acceptable salt thereof represented by structural Formula A1:

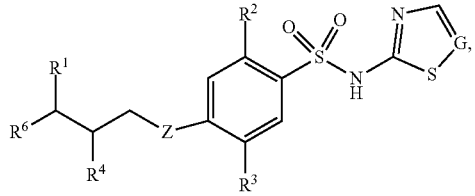

Formula AI wherein G is N or CH.

11. A compound according claim 10 wherein G is N, Z is NH or O, $R^1$ is $CH_3$, $R^2$ is selected from the group consisting of hydrogen and fluorine, $R^3$ is selected from the group consisting of hydrogen, fluorine, chlorine, bromine, methyl, $CH_2OH$, and CN, $R^4$ is selected to the group consisting of $CHR^5NR_2$, $CH_2NHCH(C_{1-6}$ alkyl$)_2$, $CH_2R^5$, $CH_2N(R^5)$ $CH_2CHRNR_2$, $CH_2CH(R^5)(CH_2)_p NR_2$, and $(CH_2)_n C(R^x R^x)$ $(CHR)_p NH_2 R^5$ is selected from the group consisting of optionally substituted $C_{1-6}$ alkyl, $OC_{1-6}$ alkyl, cyclopropyl, cyclobutyl, cyclopentyl, and cyclohexyl, phenyl, pyridyl, pyrrolidinyl, piperidinyl, and morpholinyl and $R^6$ is $NH_2$, and wherein the adjacent $R^x$ groups combine with the carbon atom to which they are attached to form cyclopropyl, cyclobutyl, cyclopentyl, and cyclohexyl optionally substituted with one to three groups selected from $C_{1-6}$ alkyl and halogen.

12. A compound according to claim 10 wherein G is CH, Z is NH or O, $R^1$ is $CH_3$, $R^2$ is selected from the group consisting of hydrogen and fluorine, $R^3$ is selected from the group consisting of hydrogen, fluorine, chlorine, bromine, methyl, $CH_2OH$, and CN, $R^4$ is selected to the group consisting of $CHR^5NR_2$, $CH_2NHCH(C_{1-6}$ alkyl$)_2$, $CH_2R^5$, $CH_2N(R^5)CH_2CHRNR_2$, $CH_2CH(R^5)(CH_2)_p NR_2$, and $(CH_2)_n C(R^x R^x)(CHR)_p NH_2$ $R^5$ is selected from the group consisting of optionally substituted $C_{1-6}$ alkyl, $OC_{1-6}$ alkyl, cyclopropyl, cyclobutyl, cyclopentyl, and cyclohexyl, phenyl, pyridyl, pyrrolidinyl, piperidinyl, and morpholinyl and $R^6$ is $NH_2$, and wherein the adjacent $R^x$ groups combine with the carbon atom to which they are attached to form cyclopropyl, cyclobutyl, cyclopentyl, and cyclohexyl optionally substituted with one to three groups selected from $C_{1-6}$ alkyl and halogen.

13. A compound which is:

4-(((2S)-4-amino-2-((R)-1-aminoethyl)-5,5,5-trifluoropentyl)amino)-5-chloro-2-fluoro-N-(1,2,4-thiadiazol-5-yl)benzenesulfonamide;

4-((5-amino-2-((R)-1-aminoethyl)-4,4-dimethylpentyl)amino)-5-chloro-2-fluoro-N-(1,2,4-thiadiazol-5-yl)benzenesulfonamide;

5-chloro-2-fluoro-N-(1,2,4-thiadiazol-5-yl)-4-(((((5R,6S)-5,8,8-trimethyl-1,4-diazonan-6-yl)methyl)amino)benzenesulfonamide;

4-(((2S,3R)-3-amino-2-((1-(2-aminoethyl)cyclobutyl)methyl)butyl)amino)-2,5-difluoro-N-(1,2,4-thiadiazol-5-yl)benzenesulfonamide;

4-(((2R,3R)-3-amino-2-((1-(2-aminoethyl)cyclobutyl)methyl)butyl)amino)-2,5-difluoro-N-(1,2,4-thiadiazol-5-yl)benzenesulfonamide;

4-(((S)-6-amino-2-((R)-1-aminoethyl)-4,4-dimethylhexyl)amino)-5-chloro-2-fluoro-N-(pyrimidin-4-yl)benzenesulfonamide;

4-(((3R)-3-amino-2-((4,4-dimethylpyrrolidin-2-yl)methyl)butyl)amino)-2,5-difluoro-N-(1,2,4-thiadiazol-5-yl)benzenesulfonamide;

4-(((2S)-4-amino-2-((R)-1-aminoethyl)-4-(1-methylcyclopropyl)butyl)amino)-2,5-difluoro-N-(1,2,4-thiadiazol-5-yl)benzenesulfonamide;

4-(((2S)-6-amino-2-((R)-1-aminoethyl)-4-cyclopropylhexyl)amino)-2-fluoro-N-(1,2,4-thiadiazol-5-yl)benzenesulfonamide;

4-(((3R)-3-amino-2-((1-(2-aminoethyl)cyclobutyl)methyl)pentyl)amino)-2,3,6-trifluoro-N-(1,2,4-thiadiazol-5-yl)benzenesulfonamide;

4-(((3R)-2-((2-azaspiro[3.4]octan-5-yl)methyl)-3-aminobutyl)amino)-2,5-difluoro-N-(1,2,4-thiadiazol-5-yl)benzenesulfonamide;

4-(((S)-6-amino-2-((R)-1-amino-2-methylpropyl)-4,4-dimethylhexyl)amino)-5-chloro-2-fluoro-N-(1,2,4-thiadiazol-5-yl)benzenesulfonamide;

4-(((S)-6-amino-2-((R)-amino(cyclopropyl)methyl)-4,4-dimethylhexyl)amino)-2,5-difluoro-N-(1,2,4-thiadiazol-5-yl)benzenesulfonamide;

4-(((S)-6-amino-2-((R)-1-amino-2-cyclopropylethyl)-4,4-dimethylhexyl)amino)-5-chloro-2-fluoro-N-(1,2,4-thiadiazol-5-yl)benzenesulfonamide;

4-(((S)-6-amino-2-((R)-1-aminoethyl)-4,4-dimethylhexyl)amino)-5-chloro-2-methyl-N-(1,2,4-thiadiazol-5-yl)benzenesulfonamide;

4-(((2S,3R)-3-amino-2-(((1S,2S)-2-(aminomethyl)cyclopropyl)methyl)butyl)amino)-5-chloro-2-fluoro-N-(1,2,4-thiadiazol-5-yl)benzenesulfonamide;

4-(((3R)-3-amino-2-(amino(cyclobutyl)methyl)butyl)amino)-2,5-difluoro-N-(1,2,4-thiadiazol-5-yl)benzenesulfonamide;

4-(((3R)-3-amino-2-((isopropylamino)methyl)butyl)amino)-5-chloro-2-fluoro-N-(1,2,4-thiadiazol-5-yl)benzenesulfonamide;

4-(((3R)-3-amino-2-((((R)-2-aminopropyl)(isopropyl)amino)methyl)butyl)amino)-2,5-difluoro-N-(1,2,4-thiadiazol-5-yl)benzenesulfonamide;

4-(((S)-6-amino-2-((R)-1-aminoethyl)-4,4-dimethylhexyl)amino)-2-fluoro-N-(1,2,4-thiadiazol-5-yl)-5-(thiazol-2-yl)benzenesulfonamide;

2-((2R,3R)-2,7-diamino-5,5-dimethylheptan-3-yl)-7-fluoro-N-(1,2,4-thiadiazol-5-yl)chromane-6-sulfonamide;

4-(((2S,3R)-3-amino-2-((1-(2-(dimethylamino)ethyl)cyclobutyl)methyl)butyl)amino)-2,5-difluoro-N-(1,2,4-thiadiazol-5-yl)benzenesulfonamide;

4-(((3R)-3-amino-2-((2-(aminomethyl)cyclopentyl)methyl)butyl)amino)-2,5-difluoro-N-(1,2,4-thiadiazol-5-yl)benzenesulfonamide;

4-(((3R)-3-amino-2-((2-(aminomethyl)-1-methylcyclobutyl)methyl)butyl)amino)-2,5-difluoro-N-(1,2,4-thiadiazol-5-yl)benzenesulfonamide;

4-(((3R)-3-amino-2-((1-(2-aminoethyl)-3,3-difluorocyclobutyl)methyl)butyl)amino)-5-bromo-2-fluoro-N-(1,2,4-thiadiazol-5-yl)benzenesulfonamide;

4-(((3R)-3-amino-2-((2-(2-aminoethyl)cyclohexyl)methyl)butyl)amino)-2,5-difluoro-N-(1,2,4-thiadiazol-5-yl)benzenesulfonamide;

4-(((S)-6-amino-2-((R)-1-aminoethyl)-4,4-dimethylhexyl)amino)-5-cyano-2-methyl-N-(1,2,4-thiadiazol-5-yl)benzenesulfonamide;

4-(((3R)-2-((5-azaspiro[2.4]heptan-6-yl)methyl)-3-aminobutyl)amino)-2,5-difluoro-N-(1,2,4-thiadiazol-5-yl)benzenesulfonamide;

4-(((3R)-3-amino-2-((1-(aminomethyl)cyclobutyl)methyl)butyl)amino)-2-fluoro-5-methoxy-N-(1,2,4-thiadiazol-5-yl)benzenesulfonamide;

4-(((3R)-3-amino-2-((4,4-dimethylpyrrolidin-3-yl)methyl)butyl)amino)-2,5-difluoro-N-(1,2,4-thiadiazol-5-yl)benzenesulfonamide;

4-(((2S,3R)-3-amino-2-((1-(2-aminoethyl)cyclobutyl)methyl)butyl)amino)-3-chloro-N-(1,2,4-thiadiazol-5-yl)benzenesulfonamide;

4-(((S)-6-amino-2-((R)-1-aminoethyl)-4,4-dimethylhexyl)amino)-2-fluoro-5-(oxazol-2-yl)-N-(1,2,4-thiadiazol-5-yl)benzenesulfonamide;

4-(((2S)-4-amino-2-((R)-1-aminoethyl)-4-cyclopropylbutyl)amino)-2-fluoro-5-(hydroxymethyl)-N-(1,2,4-thiadiazol-5-yl)benzenesulfonamide;

4-(((2S)-5-amino-2-((R)-1-aminoethyl)-4-methoxypentyl)amino)-5-bromo-2-fluoro-N-(1,2,4-thiadiazol-5-yl)benzenesulfonamide;

4-(((2S)-4-amino-2-((R)-1-aminoethyl)hexyl)amino)-2-fluoro-5-methoxy-N-(1,2,4-thiadiazol-5-yl)benzenesulfonamide;

4-(((2S)-4-amino-2-((R)-1-aminoethyl)-6,6,6-trifluorohexyl)amino)-2,5-difluoro-N-(1,2,4-thiadiazol-5-yl)benzenesulfonamide;

4-(((3R)-3-amino-2-((1-aminocyclobutyl)methyl)butyl)amino)-3-fluoro-N-(1,2,4-thiadiazol-5-yl)benzenesulfonamide;

4-((2-((R)-1-aminoethyl)-4-(aminomethyl)hexyl)amino)-2,5-difluoro-N-(1,2,4-thiadiazol-5-yl)benzenesulfonamide;

4-((3R)-3-amino-2-((1-(2-aminoethyl)cyclobutyl)methyl)butoxy)-2,5-difluoro-N-(1,2,4-thiadiazol-5-yl)benzenesulfonamide;

4-(((3R)-3-amino-2-(((1R,2S)-2-(aminomethyl)-1-methylcyclopentyl)methyl)butyl)amino)-2,5-difluoro-N-(1,2,4-thiadiazol-5-yl)benzenesulfonamide;

4-(((3R)-3-amino-2-(((1S,2R)-2-(aminomethyl)-1-methylcyclopentyl)methyl)butyl)amino)-2,5-difluoro-N-(1,2,4-thiadiazol-5-yl)benzenesulfonamide;

4-(((2S,3R)-3-amino-2-((1-(2-aminoethyl)cyclobutyl)methyl)butyl)amino)-2,3-difluoro-N-(1,2,4-thiadiazol-5-yl)benzenesulfonamide;

4-(((3R)-3-amino-2-(morpholin-3-ylmethyl)butyl)amino)-5-chloro-2-fluoro-N-(1,2,4-thiadiazol-5-yl)benzenesulfonamide;

4-(((2S,3R)-3-amino-2-((1-aminocyclobutyl)methyl)butyl)amino)-5-chloro-2-fluoro-N-(6-fluoropyridin-2-yl)benzenesulfonamide;

4-(((S)-4-amino-2-((R)-1-aminoethyl)-4-methylpentyl)amino)-5-chloro-2-fluoro-N-(4-methylthiazol-2-yl)benzenesulfonamide;

4-(((S)-4-amino-2-((R)-1-aminoethyl)-4-methylpentyl)amino)-2-fluoro-N-(5-fluorothiazol-2-yl)-5-methylbenzenesulfonamide;

4-((4-amino-2-((R)-1-aminoethyl)-5-methylhexyl)amino)-5-bromo-2-fluoro-N-(1,2,4-thiadiazol-5-yl)benzenesulfonamide;

4-(((3R)-3-amino-2-(pyrrolidin-1-ylmethyl)butyl)amino)-5-chloro-2-fluoro-N-(1,2,4-thiadiazol-5-yl)benzenesulfonamide;

4-(((3R)-2-(((1R,3R,4S)-2-azabicyclo[2.2.1]heptan-3-yl)methyl)-3-aminobutyl)amino)-2,5-difluoro-N-(1,2,4-thiadiazol-5-yl)benzenesulfonamide;

or a pharmaceutically acceptable salt of any thereof.

14. A composition comprising at least one compound of claim 1, or a pharmaceutically acceptable salt thereof, and at least one pharmaceutically acceptable excipient.

15. A pharmaceutical composition of claim 14 comprising additionally an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an non-steroidal anti-inflammatory drug; or (vi) paracetamol (APAP, acetaminophen), and a pharmaceutically acceptable carrier.

16. A method of treating a pain disorder, or cough, or acute itch or chronic itch disorder comprising administering to a patient in need thereof a therapeutically effective amount of a compound of claim 1.

17. The method of claim 16 wherein said disorder is an acute pain, inflammatory pain or neuropathic pain disorder.

* * * * *